(12) United States Patent
Yoon et al.

(10) Patent No.: US 11,439,677 B2
(45) Date of Patent: Sep. 13, 2022

(54) VIBRIO ANGUILLARUM BACTERIOPHAGE VIB-ANP-1 AND USE THEREOF FOR INHIBITING PROLIFERATION OF VIBRIO ANGUILLARUM BACTERIA

(71) Applicant: INTRON BIOTECHNOLOGY, INC., Gyeonggi-do (KR)

(72) Inventors: Seong Jun Yoon, Seoul (KR); Soo Youn Jun, Seoul (KR); An Sung Kwon, Gyeonggi-do (KR); Soon Hye Hwang, Gyeonggi-do (KR); Hyun Min Song, Seoul (KR); Ji In Jung, Gyeonggi-do (KR); Sang Hyeon Kang, Seoul (KR)

(73) Assignee: INTRON BIOTECHNOLOGY, INC.

( * ) Notice: Subject to any disclaimer, the term of this patent is extended or adjusted under 35 U.S.C. 154(b) by 102 days.

(21) Appl. No.: 16/329,931

(22) PCT Filed: Aug. 21, 2017

(86) PCT No.: PCT/KR2017/009076
§ 371 (c)(1),
(2) Date: Mar. 1, 2019

(87) PCT Pub. No.: WO2018/043972
PCT Pub. Date: Mar. 8, 2018

(65) Prior Publication Data
US 2019/0183945 A1      Jun. 20, 2019

(30) Foreign Application Priority Data
Sep. 2, 2016   (KR) .................... 10-2016-0112908

(51) Int. Cl.
*A61K 35/76* (2015.01)
*C12N 7/00* (2006.01)
*A23K 50/80* (2016.01)
*A23K 10/18* (2016.01)
*A61P 31/04* (2006.01)
*A61K 9/00* (2006.01)
*A23K 20/153* (2016.01)

(52) U.S. Cl.
CPC .............. *A61K 35/76* (2013.01); *A23K 10/18* (2016.05); *A23K 20/153* (2016.05); *A23K 50/80* (2016.05); *A61K 9/0014* (2013.01); *A61P 31/04* (2018.01); *C12N 7/00* (2013.01); *C12N 2795/10321* (2013.01); *C12N 2795/10331* (2013.01); *C12N 2795/10332* (2013.01); *C12N 2795/10333* (2013.01); *C12N 2795/10371* (2013.01)

(58) Field of Classification Search
CPC .... A61K 35/76; A61K 9/0014; A23K 20/153; A23K 50/80; A23K 10/18; A61P 31/04; C12N 7/00; C12N 2795/10331; C12N 2795/10332; C12N 2795/10321; C12N 2795/10333; C12N 2795/10371
See application file for complete search history.

(56) References Cited

U.S. PATENT DOCUMENTS

2014/0105866 A1    4/2014    Torres et al.

FOREIGN PATENT DOCUMENTS

KR          10-1267616 B1          5/2013

OTHER PUBLICATIONS

Letchumanan, V. et al. 2016. Insights into Bacteriophage Application in Controlling *Vibrio* Species. Front Microbiol. 7 (1114). https://doi.org/10.3389/fmicb.2016.01114 (Year: 2016).*
Tan et al., "Vibriophages and Their Interactions with the Fish Pathogen *Vibrio anguillarum*" American Soc for Micro, Applied and Environmental Microbiology, May 2014 vol. 80 No. 10, p. 3128-3140 (Year: 2014).*
PCT, PCT/KR2017/009076, Aug. 21, 2017, Seong Jun Yoon.
Higuera, G. et al., Recently Discovered *Vibrio anguillarum* Phages Can Protect Against Experimentally Induced Vibriosis in Atlanctic Salmon, *Salmo salar*. Aquaculture. 2013; 392-5:128-33.
Tan, D. et al., Vibriophages and Their Interactions with the Fish Pathogen *Vibrio anguillarum*. Appl Environ Microbiol. 2014; 80(10):3128-40.
Tan, D. et al., Vibriophages Differentially Influence Biofilm Formation by *Vibrio anguillarum* Strains. Appl Environ Microbiol. 2015; 81(13):4489-97.
International Search Report dated Feb. 8, 2018 by the International Searching Authority for Patent Application No. PCT/KR2017/009076, which was filed on Aug. 21, 2017 and published as WO 2018/043972 on Mar. 8, 2018 (Inventor—Yoon et al.; Applicant—Intron Biotechnology, Inc.) (Original—4 pages; Translation—2 pages).

* cited by examiner

*Primary Examiner* — Ruth A Davis
(74) *Attorney, Agent, or Firm* — Ballard Spahr LLP

(57) ABSTRACT

The present invention relates to *Siphoviridae* bacteriophage Vib-ANP-1(accession number KCTC 13075BP) having the ability to specifically kill *Vibrio anguillarum* bacteria and a genome represented by SEQ ID NO: 1 and isolated from nature, and a method for prevention or treatment of *Vibrio anguillarum* bacterial infection by using a composition containing the same bacteriophage as an effective ingredient.

3 Claims, 1 Drawing Sheet
Specification includes a Sequence Listing.

[FIG. 1]
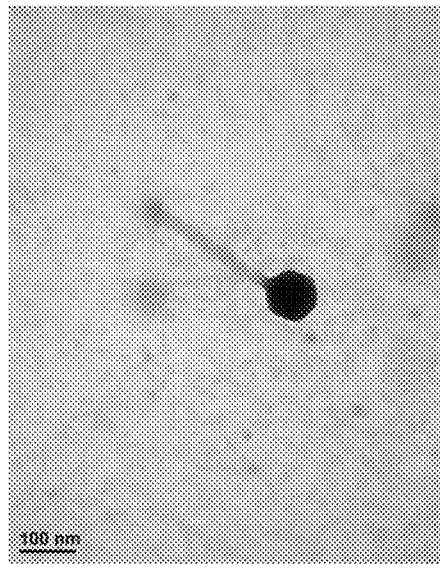
[FIG. 2]
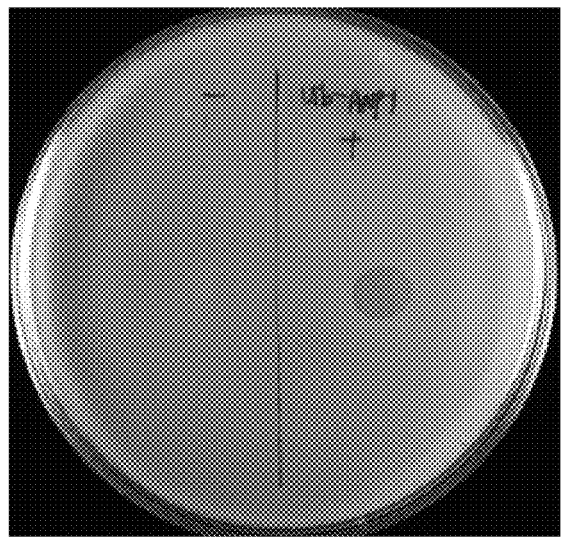

SEQUENCE LISTING

```
<160> NUMBER OF SEQ ID NOS: 1

<210> SEQ ID NO 1
<211> LENGTH: 213970
<212> TYPE: DNA
<213> ORGANISM: Bacteriophage Vib-ANP-1

<400> SEQUENCE: 1
atctgaatat tcatgtctgt gattcttgca atggcagaac gtatactaac tatagcctcg       60
tctgcctctt gtgctttgtt aaccgcttcg attgcagtgt tcttactatc attcatcacc      120
acggaaacag aatgtgcgcc tgattgtaac tgttcgatca tctgcttgat ttcagtagtt      180
gactcttgtg ttcgtttagc aagagttcgc acctcatcag caacaacagc aaaaccacgt      240
ccctgttcac ctgctctagc tgcctcaatg gcggcattaa gtgccagtag gttggtctgg      300
tcagctatct catttatcac ctgaagaact ttttcaatat tgtcagaagc tatagcaaga      360
gattgaactt cttgcacggc ctcatcaatt cgactagcca acacactaat ggtttgggtt      420
gtatgattaa ccaccacatt accatgatta gctgcatcat cagcctcttg agcagccgca      480
gctgcatttt gtgcattggt tgcaacctca gatgacgctg tggccatttc attcatagcc      540
gtggccaact gctccaattc ttctaattgc tttgtcatag ccattgcgga gtttctagca      600
ccagcatcgg attgacttgc acctatttct atctgtccac taatgtcttt tagatggata      660
attaactctt ggagtctctg tgtaaaggtg ttaaagttgt tagcaaggtg tgagaattcc      720
aaatcggtgt tagtgtctaa cctttgagtt aaatcacctt cgcccgaagc aacattctca      780
attgccttgt ttagtaaacc aagtggtttc atcaagaacc cagttaggaa catcataata      840
gggaaactta cgatgatagc aacaatcgaa taaaccaaag acagattccg catattagta      900
acgtcagaaa atgcttttc ttgatttatt gccgaaccaa caaaccaccc attctctttt      960
gtcttagaca aaccaataac gtactcttca ccgccgatgc ttagattctg taatccctct     1020 ctgatttta aaccggtat ggtttcagtt attacgctac cgtttagctt tttattaggg     1080
tgtgcaataa caacaccgtc actggatact ataaagagga aaccaatttt atctaacgag     1140
gtgcctgtga ccagacccgc taattcctca aggctaacat cgtaaaacat agcaccttgg     1200
aagcggctgc cttcgcgtat aggggttgcc acagataca taacttcccc tgttgcagaa     1260
tcgacataag gagcagtagt cactgtttta tttttgctct tggcgtctat gtaccacggc     1320
cttgctctcg catcccaatc tttacctggg tgccagctag gctcattaga aataggatta     1380
ccgtcttttt caaaaccacc gccaacaata agaaacattt ctttcaacgt tggcttgtta     1440
atcacttcgg tgatgttctc taatgacgga ttgctgttga ttaaatcact tgagtattta     1500
accaaagcta tttttttatc gatgttatca tcgacagatt ttcttacggc attgactgtc     1560
tcaccaacgt atgtgtcgac attagtttta acaatccctt caacagtttt atactgttgg     1620
aatgacaata acccgacggt tatcatcaga agcgcagacg cccctgccgt tactttatga     1680
ctgaatttca tttttaatcc tcttctgaat taagattaca aaaaagagg gggatgtctc     1740 cccctcaatt taattacgtt gttagacgcg tttgttgtat taggctgtaa gccatcacaa     1800
```

```
tatcctcgaa gggatactta ctaagttcac caactaaacg attgacgttt tccgtaacct   1860
caaacagctc tcggtcatct tcaataccat acagcgattt aattcttcgg agtgttttct   1920
ttcccgggaa tcgttttcca ttctctatgg tggagtaata agctggctct atgtctaggg   1980
ctttagcggt atcgcttgtg cttctattac tcaataaccg taaggttttt attttagttg   2040
caaatattac tccactttcc acattttgtc cttcagggcc atgacgtact cgttgtagtg   2100
aggttgcagt gccccataaa gagaacgtaa tgtgtctgga tcggaaattc cgcagttaag   2160
cacattacta aacaacggag tgtctttatt gtacaaatct cttgaacgct ccatgagtag   2220
agcgatgtga tgaggatgtc ctttaccacg accacctgtt cccaaatcga agaattgaac   2280
cgagttgttc aaggcaccgg agatcacttt attgacgtca gggtaaagtc cttctagcat   2340
caaacgatgt aagttacgac caaagattga agaatggtg tttgtttcca ggtactctga   2400
gtagtacggt actgaacgct ccagagttag aaatacttca cgcccaagga aactattact   2460
tggtgaactt gaccatgtgt tgctcagctt actaccacgt gacaactcaa catcatactc   2520
gtgttggtta ggaatctgat ttaacatcat gccatgttca ggatagtacg ctgtgtcgaa   2580
aaccggaagg tggtgcactt tgttgcctgt atacaaaacc acaggtttgt agttactatt   2640
ctcaatgaaa ccaaacaagt aattgtcctg tccgttgcgt tggtactcca tgacgaacaa   2700
atccaacttc gcttcggttg tctcgccttt gatacccacc aagtcacgta gctcaacctg   2760
atcaatagac aactcgccac ttgccaatcg ctccaaggtg cgttgattca attcttgtgt   2820
gaattgggta ttgatgaata ctaggttgtc gcgtttcacg tagatgttga aattttccat   2880
ttttgttctc tcttttccga tcgttatttt taacggtgca agtatatatt ttgacactct   2940
agatactaga ggggtagggg ttatatagat caagatatga atcgatcgag gaacgtagtt   3000
tacactacaa gtacttaatc gattcataac atttattttt gtttcatacc aaggttatct   3060
atcaaaagat tttccaaagc atatgctgga tgagcaagac tacgacgtcg tagctgagta   3120
ggtggcttac aacccacgta taagtcttgg gagaaaccat caaaaggaag tagtcccatt   3180
aattcttctt taatgaaagc aaatgtctcc aaagatttct cttctagctc aatagcatca   3240
ggaacattac cgatgaccat atcgttgtat tccgaaacca gttcttcgaa gttagcggag   3300
ttatcggcat aaatccaata ataagctgat agaagaaatg aagccatgcg acggtccact   3360
ttaccgaatg tttctaagtc gtgttcatgg atagcacgga ttgcttcgga tatagttgac   3420
ttgatgtcgt ctaaaccttt gtggaataaa ctaaccttat agtcctctcc ttccagacac   3480
cagcgcattt cagtcaacct tgcccataca cgattatgga acgataggaa agccaaacgc   3540
tgacccggcg agatttcctt ttgaaggaac tcttccttaa tagcgtagat aggatcgatt   3600
tgaattcgtt gctctttgat aagcgattcc aagaatttcc aatcaccctc ttctagtgaa   3660
cgattggcag tgttctctgc aacacgctta tagtgtttgg ccgacacaac acgaaccttg   3720
tcaacgtagg tcatcaattt ctgtttacct tcctcactct caaatgagaa ttctggaaca   3780
gtttgattat cgtggttgtc gatagccgaa tgtgtaacca tgtagtgctt accctcgact   3840
tctttagtaa cgaacttgaa ctcgcttctc atacacacta gcgaaggcca atgactagac   3900
ttcagataat ccgccataag gacgatgtgt tctttgaaca cgtaacccca agccaggctg   3960
ctaacattac cagcattagt aatgtgtgtg atttccccaa attttgaatt taggatagtg   4020
gtgagtgctt gtgccgatga tgttgctcct agcgcatcga ccattttaga gaaagccgca   4080
atgccatcgc cacgattcga gttgttaaca aaacgaggtg ggtaatcgag tttaccattt   4140
```

```
aaaggtaaaa ccaagattaa cagatcacaa tggtctgtat cgaagttatt ggttcgaata      4200
ccaataactt tgttttgata gtccccacct tcaagaaaat catgaaagtc tgccagctta      4260
atgtgtttat ccacgcgcat tttaaatttc ctttaaacta tgattccaag tatcttcagt      4320
gaaaataaca ccgagacgaa atggtacttc gctcgcacat agacgattag ccttaatcca      4380
atcgttcaat ggtggcgctt tatgtaatgg gtgatttggt tcacttaaga ttacttgtct      4440
agtcgagcca cttctagtaa ccttacgatt aacagtcatt ttaaatctgt gtggtgattg      4500
gtaattgtct tcgacataga cgaggttatc ctcgcctaat tcaatcatca aatcatccag      4560
attatcaatc tctggttcaa ccacatctga atacaccaag aacctcccct ccttaatgga      4620
ggagacttct tcgacataca taactttacc catctcacac ctcaggtact tcgtatatct      4680
cgttgtcggc ttttagagtg aagtcagtat gctcttcggt gctgatacct agctccaaac      4740
ctacagtgac ttcgttattg tcgtattcga attcaatacg tgtaatgtcg tcgatatcca      4800
tgatcgattc tttacctgtg attaattcaa atttaacagt gtcgatgtgg tagttgcaaa      4860
gttcttttga aatccccacc atctcttctt tcttcggtgc acgaaaggtt agatggtata      4920
aattattttc tatctgtttg atggaatagg ggatcaaacg tgtttctttt ggaaactgat      4980
agatgaccaa agttttgaaa taacttagtg aaggaacgta accgttttga acttcaatga      5040
ataaatggta gttgttcggg tagatcatcg aaaacactcc ttcttaattt caatttttata      5100 ccaagccaat agataagctt caatggttga acgacactct acacagcaga gagccttctg      5160
accctgacgt aaccaatacg tttgcacagg tggtctgtag acgtacgtgt ttgtacctag      5220
ctcaatgttg ttatcgacac accatgccaa gatatccttt agtgacacta tatgtccgtc      5280
aggaatggtg accattggtt tagtcccatc ggatgcttgg ccactatctg cccaggcaaa      5340
tactgcctct gggataggac cacggtcatc ccaatccaat cgatgaaaaa gttttttgatt     5400 accagtacca gtccatatat ttaacatttt taaaattcct ctcatttaac ctaaaaaata     5460
agagaggtca ctacaacctc tctaacgcat caattaatta cagtagccgt tcttgttagc      5520
gtatccgtag ataagcgctt caacaacact accgtattca actgctgata gttcatcacc      5580
gatggctgca acgaaacgtt cttctttcac gccaccttct tcagtagcag taaccttggc      5640
actaccccgt ggatagtctg ggttatctac tgggtcttta acacgcactg cacgaatgtt      5700
gttatcgtga cagaattgca acacacctgc aaatggttca acatcacctt tacgtacacc      5760
ttcgtccacg tcaccgttgg taatcatcat caacgaaggt aacgcgttat cgatcgtacg      5820
aattaggttt tgactgatga ctttatcttc ttcaagaact aagtcgatga tacgaaaacc      5880
gtctgttgtt aattgaacta cttgatacat tttaattacc tttaactact tttgttgaaa      5940
gattagtcac aaagaccagt ttgattagcc caaccgtaaa tcagggcttc gatcgctgtt      6000
tcgtattcga catcggaagt gtcgttgccg atagcagcaa cgtaacgttc ttcttcttgc      6060
gtgtagacgg taacgctatt gtcaagtgcg ccctgctcca tgaaagacac aatgccgtta      6120
tccaccaact tgatactgac cggacggatt tcattggcat tacagtaacc gagaacttgc      6180
tttagaggaa ccttggaatt ttcagattcg ccggatgggt caactaccac cataaggccc      6240
ggataagcta agtcaagctt ctcaataaag ttagcgtgg ggacaagacc ctcgctaacg       6300
accaaacgaa cattgcgtgt tgttccattt acttcttgaa ttactgggta catagtagaa      6360
tcctcttaag gataaaagta gaaaagtgg caaggtttcc cctgccacgg ttgataggtt       6420
agttaactaa gccgtcttta cgctgcttaa ttgcaatcat aacctgagta gttagcatca      6480
tggtggctac agatgccgca tattccaaag aaccacgtgt cacttttact gggtcaatga      6540
```

```
tacccaattc aatcatgtca tcgtactcct cggtacgtgc atcaaagccg tacgagctat   6600
cgttatttga aagaacgttc atgataacaa cgtctggtgc taccgctgcg ttctcagcga   6660
tttgtcgaat aggtgcttcc atcgctttaa tagcgatatc catacctaaa cgttcactgg   6720
ttgttacatt aacagaagcg aacatatctt ttagtttctt agatagacgc agtagtgtta   6780
caccaccacc tggtacataa ccttcttcca gagcagcacg tgttgcacca acggcgtcgt   6840
ccgcacggtc tttacgctct agcatttcaa tttcactaga ggcactaact tggataactg   6900
caattgctga atttaacttg gccaatcgct cagtcagatt cttcttagca aagtcagtga   6960
tggctggttc ttgcagtttc ttgcggatac catcagcacg cgcttcaatt tctttacgat   7020
cgcccttacc gccgaggatg acagtttctt tactgctaac acgaacttcg tccgcagcgc   7080
cgagaatacc atccatacca gactgttcaa agtcatagcc tgcatcgact actttagcat   7140
tgaccaattt agccaagtcc tgaatcaact cacggcgttt atcaccaaag ctagggctac   7200
gtacagggat agttgacttg tgacgacggt aattgtttaa gaagacttct gtagcatact   7260
ggtcgaagtc atcggccaga atcagaagtt tgctattctt gttctgtgcc agctccagaa   7320
gcggtacgta cttgtcaaag ttggtttcat tgatatcgcc actgacaatc aagacaaaga   7380
cttctttggc aactacggta tcttcgccat ccattaagaa gaatggtgag atgtacccgc   7440
ggctaatggt cacaccatca acaaaacgaa tgtcatcgtc gtaacctgtg gcttctttga   7500
tgtcaacaac accttcgatt cccacacgat ccatcgcttc tgtgataagg ttagctaaac   7560
cttcatcacc attggccgaa atcatcgcaa tgcttctgat gtcgtctttt gttttacatt   7620
cgatggccat ggacttaagt tgtagaatgg ctgcttccac aatacggtca ataccacgtt   7680
tcacctctaa aggattagaa ccgttgttaa cagctttaac accttcattg attaaagcat   7740
gtgcaagcac tgtcgcggta gtagtaccgt caccagcaga gtcacatgca cgaacagccg   7800
cttctttaac catttgcgca cccatatcct ggaatgggtc ttctaagaat acactacggg   7860
ctacagagac accgtcttta gtgatgtgtg gtgaaccagc tagtttctga attacgacat   7920 ttcgacctttt agggcctaag gttgagcgaa ccgcatccgc cagaatattt acacccttaa   7980
ccatttcatc gcgtgcgttc ttgtcaaaga ttagttcgcg tggagtttgt ttagccatgt   8040
ttgaaaattc cttagtatta cttgtttgaa atatggattg ttacggggtg gattttattt   8100
tgattgttta acgattttgt ttaggtactc gaaccattgc gggtggtact tttcaccgtc   8160
tacatcgtta ggcgtcactt tatctttacc aagtacaccg tcaaagtgt gtaggtaaat   8220 tgtgttttct ttacgcgctt cgccgactgt gtagctacgg cttgtgctgc tgttaaacgt   8280
tagtttgttg tagaagctcc gcagtttgac cactggtttc caaacctcac cttcttctaa   8340
atcactcggt ggtgttgtgg tatatgtgtg ttcaggaaac tcttctttca gagctttgct   8400
aattgcctta acgacatcaa cagtgcattc cttgatctct tcgccattcg ctgcgtcagt   8460
gacgtgaata agatgaacct caaaagagtc atcattacac accacaacat gtggtgagtt   8520
tggatttagt ttagatgtct tttcaaattc aacatgaatc tcgacattca ttgcactaag   8580
tgcgatatca gcaaatttac ccatttttaa aattcctcaa aagtaataaa gagaacccta   8640
gcgcctctca tactagggct actagggtta ttttcaagt tgtattaaga aactgttaca   8700
ttgatttcgt aacagtcaat taaagtagtt aacccatctt tacgataagt tacctcgata   8760
gtgcgttcat cgaactggtc tgagatatgg aaatctaatt cgcggattaa atctcctaag   8820
tcttcgtctt ctacaacact attttctttg tttaacttac cagtgttgtt gctagagata   8880
```

```
ctagctgtga tagtttcccc tttagaagtg atgtatttaa tctcttctgg atgatcgaag      8940
gctgaggctt cttaatagc ttgtgctacc aattcagcct ctgtatttat cacatcgatg       9000
tagattttga tgagaggcaa cgacacaaca atattacctt cgttgtcata aacacctgtg      9060
tcgtaactct caccagaatt caaaacagac tctaacgatt ccaaaaactg ataagcagtt      9120
ggattcagtt tatcagacgc catcatatcc atcatggccg aatggtcttg tgtatccttg      9180
aatccaaccg tgtccgcatt tgggactatt ccaattagta ggttaccgta gttgaatgtt     9240
tgacgtaacc cagggttggt tttgagagaa tggattgctt cagcagcgga taacaattct      9300
tcaatttgtt cagggtagat catgttttaa aattcctcat tggtctaagt acacaaagat      9360
aacatatacc taattatttt tagtatcggc cgcaagttta gcagccaact ctatatcgaa      9420
tccaccagag gaaacctcgg tgcgattcgc tacaacgtta tcttcatcaa agacacagtt      9480
atttgcctcg actaataacg cagcccttat gttagagatt gacaactttta agatgtctag    9540
ggaattaggc ccatggggga tagataaaga tactggggtg tttatagaca caaggtcttc     9600
atcaacctca ccttcaccaa tgcttgtttt aagtccagct aaggcattct ttcaagacg     9660
ctcaatcacc gaggtgactt ccgattccac ctcttcgcga gacataccac gtcttaagtt     9720
aagtgccaag ttcccttta attcgtaact tttcatctgt catttctcca ttgagtatat      9780
caaataagga agtatggtt aaacccttag ggatggttaa cccaccaatt attacttcgt      9840
caccaaccac aagaacattt aaatggtcct gaaaagactc cacttctcca cgttcaggg      9900
taccgtatag tttaatgtaa gtggctatgg ttaaagccaa tgaaatattc tttggattta     9960
gagaactgtg gtctatcggc gcaccgtcct taaaacattt tagattccat atggccgtct     10020
ctaaatcata gtccctgggc tctggctcag ttgtttcttc accacaccat tggtttacct     10080
ttttagccac catggcataa tgggccacca gtgatttaga agggtcttta tagaaggaaa     10140
agaactgggt gagtaaatca cccagtgagg tagttatgta aggtcttgtc atcatccaac     10200
cttcgccaa atatgttcct tgaattcgcc attgacaatc gacttggcca agtcaacgtc      10260
catcttagca cgagtcttta tcccactaag ttcacaagct aatagcggac gtccagcttc     10320
gaaaccagtt gtgttgtaaa tacgatttag ataatcgtta acaatctgag tggttaaccg     10380
aggaagctcg attgtgtggt ccgttctacc atccctgaag atagcaccat ccatacgttc     10440
gatgtggttg tcgtcatga atacaagaac atcatctaaa ggtgacacac catcaagaac      10500
atttaagaaa ccttgcaagt cgaccgatag accatccaac aaagaactgg tagagacccc     10560
agtgttttc tctgcctctt tatccttatc tgacttctca acgttgagtt tgtgagtacc      10620
gccacgattt gccgtcgcag ctaaaccatc acagtcttcg aataataggga tgctacgtgg    10680
tggcatttgc gcaataccat taatcaaccc attagtggaa accatcttta agtcgatggt     10740
gcaaatgtta aacttaaact ccgaggcaag tgctctgatg atagaggttt tgccagtacc     10800
gggctcccca tgaagcataa aggttatctt ccacgctaga cccatgtcgt agtatctgtc     10860
tctgttatcc agatagaact gtatctcact acggaagaac tgtttgatgt cttcgctaag     10920
agctagagag tctaaaccac ctgctttaat aacactctgt tcttccacc catcacttgt      10980
taggttaaag aaacgaatgc catcttcgtc ctcatcaggt ttaacatgtt caatcaaagc     11040
ctgcaaagct ttaggtgacc gccctagtgt gtagacaatg atttcttctg caacgtcagc     11100
agtattgcct tctaatcggt tctttcttgc catgtataga acaagaccac gtctgaataa     11160
atgccaacct aatcctaagc cataacgatg ttctcgtagg ccatccagta gattaccccg     11220
gtctttccaa tctgacacaa gagataggct acgtgagaaa ttacctatac ggttttcata     11280
```

```
gatgaaatta ctcaggttgt tgtaaacatc acgagacgca tactgatgtg tacccaattg   11340
aaaactagtt acacattgct ctctgaaaaa cctcgctatt tttgcagggg ccttccatag   11400
aacaaaacca accgcaccag acagtgcaac agtgaccgaa cccatcaagg cagctgcaag   11460
tagctggtta ccatttgata ccgattcgat gtagtgaatt aaatcagtta taagttact    11520 gatgaacaca ggcaatcccc tttcttattt tgtaccaacg atgacaccag tccatgagaa   11580
gtcattagcc tgactaatcg tgttggtggt gatttcttta caggtaggtg gtacgtgttt   11640
gaaatgacga ctgtgttggt agaaccattt gattgacaca atgtgtgtgt cagtgatgta   11700
ggccaatctg atattggaaa tgtttttatc agggttaatc acactacgta aaaggtcagt   11760
tacttcttta gctaaagcaa atgaactttt ttcttttcg tcaccagaga taatctggtc    11820
cagtttgttg ataatttcat tagtgtcttt accttcaggt aattcgaact ctactgctgg   11880
cggggtcaac acagtgtcag tttgtgtagt cacgttaagg taaaaagatt tttggtcaga   11940
cattttgata ttcctctgat aaataatgta ggttgtaatg cataataatt ttcagaggcg   12000
ttaaaaaata aagagagagg ccgaagcctc tctattcgaa acaaccatag agttttaaga   12060
acatactcat ctctaaagcc caaggtgttc cagcaggttt atcatcagta tcaaatgtgt   12120
ttttaaaatg cacaaattga atttgacaat taagagcata ccagctaaac cctgtgatga   12180
taaattcacg acaggtccga taggtataaa ctttatcacc ttcttttagt gtttcaggat   12240
ttatgggttg taggttttct tttaacaaca tggtggtccg ccgtgggaga aattctcaac   12300
atgtagctgt gccatagtca cggcttctgt aaaggagacc gggcctttaa atgccacctg   12360
accactacat acagcagatg aacctgcacc acccatagag acattaccca atagaccaat   12420
agtaggagct tgatagtgg cactattacc ctctactgtc catgtttgcg ctttggcagt    12480
gtaggtcgaa gtgtcaatag cgtagctagt cgccttggct ttataggttt tggtgtttat   12540
gtcgaaggtg tcacattcaa aaccaataaa tttagatttg aacttaatgg tgtctttagc   12600
gtacccgtag atattcgttt tattcatcac aaaggtagtt tctttcgcgt tcttccaccc   12660
gatattggtc tcagcagaat caaaccatcc actattacct atatcatccg aaatcacaaa   12720
acgtccatct ccagtattca gctgtatgct ataacgacaa tactcaccat ttgatttact   12780
ggtgttaaga gtgatatgct tatcatgaga actaatcatt aagtaataag cattactaag   12840
gtcatctttt aaaccattga ctgggtccgc actaaaagcg tagactacgg tttcaaggcg   12900
tttaacgtta gagacattac ggtcctgcca gaaaaacatg tcagtctcac ccaagcgcca   12960
aatcaaaact aaatctttaa ctttgacatc tggggagtg atgcgatttg tgttaaaatc    13020
tatccattga gcagggatag agttacctgt ccgcatagtg acaaagtctt taccttccgc   13080
aatattgtgc tcgactttct ctacgtttaa tccagcctca atcgactctg cttgtgaaa    13140 cctgacctcg actggataaa cttgtatctt gttttcacct cgacctttgt ctttcgcaac   13200
taacccataa ctataaaaag ttaattgtga agttggtcct atcattcatc ccctcgtag    13260 atgaaattct taaacccttc gaattgaaca aggctcagat gtggtttgcg tttacgatga   13320
gtcaatccac gattgttatc gttaaatggc ttaaggaag tatcccaaag acccttgact    13380
cgctgatagt ccgttgtaga caatcgttc ttgtaacgat gtccgagata agtcaacgtt    13440
ccttctttat catttaactg attatcagcc gacatgaata aaaatgggat aagttgcccg   13500
tcggagtcaa tcagcatctc accgtgaaaa tccaagaact ccgtgaggag ataaccatcg   13560
ctgttaatct cattattgac aggggtaaag tgggctgtta aatcaccacg gtaaggtaca   13620
```

```
acaaacgacg ttgggtgatt aagcaactcg gctagagtga tagactcaaa ctcgaaatca    13680
atacagaatt gggtcagatg agcagtggtt ataaataact tctctgctgg aatcttcaac    13740
gattctgttg tgaagacaac atcgttatca ttcttcatat cgagtacagg tttaccgcct    13800
atgaacaaca acatgccaga gtatcctgct tttggatact taatggataa ctcaccctcc    13860
agtgtgacga taaccagctg acttaactgc acaggtaagt cacagtctaa ttctgacata    13920
tccaaagcag ataactgaat accctctttc acaccaccat tgtaaacagc agcatatggg    13980
agatagtagt tgtagtccat tttataactg tagtagaagt acggtccgat agcccagatt    14040
aggttagggt tatcgtactt gtcgcgatta agcaacaaaa tatcggtagc ttcttcttct    14100
aatattggct gactagggtg aacaccaggt ttcacaccac gtgcttcgaa agcgtcatgg    14160
atgtaattga cgtatctcga caagccacta ttgataccag taatcatagg ctttaaaacg    14220
aagacttcgt ttttaattaa cccaaagacc tcttctaatg taagagagga atcaatagcc    14280
accaagtttc tagagagatg atcaaagagc tcaatagagc ctttatcccc atcccaatcg    14340
ataacaggca aatgaatttg acgataatca tttcttaagt ccccgtagga tttagttaac    14400
aattccgcca ctgacgtaga tgtgaaacgt tgggagtgaa tccattcgcc acttcttttc    14460
tctaaatagg ctataccttc gttatagatg gtaatcactt ccgattcctc cgatttatat    14520
gataaattga atcctttaaa ctgcctctaa ggtgacacaa atgatagaat ttgaccccca    14580
taaaactgaa gacagtaata agttttctgc cactggtgtc tcagttggcg gagagttgtc    14640
tagagtgttt cttatcccag aggcacccttt ctattcagac ggttgcgtag taagaataa    14700 cggaactcaa atcttcgaag gtaaagactt tgcatttgtc ctaccctttg ccagatgac    14760 acacaaaacg gcccgccgcg tattcggcgg tatctttctt tttggtaatg gtggcgctaa    14820 tgtcaccttta gatagtcatg ctatcggttc acgttaccag ttagaaccac agagcgtcat    14880
tagtcaattg aatactaaga ctctctctga acttctaaaa acctcctggg aggatatttc    14940
tggcaatccg tacgttccgc ttgtgaatgt gcaattccaa actgatacgt ggttcggtga    15000
agaagaatta gcggcacagc tgaaagcatt agaaaatgca atcgtatctt cagatgttac    15060
agaagaagtc cactatatgt taattaataa ctggctgact cttctagaag catacgtcga    15120
caacccagaa ctaattcaac atctgcaaga aacgggtaac gtgcataacc acactcctga    15180
agaactaggg gctcgtcgta taaatactaa tgccggcaga acaacccgtc tgttcgggcg    15240
tgataaagaa accatgcttg cagatttact gcgcgattta cccaaggtgt ccgacttagc    15300
aaacaatctc cgtaaaactg gtgggctagt cgataacatg acgttgtccg aagcgtttag    15360
tttgatagca aatggtcatt tgttatcga taattacgac ggtcgtttca gctctacttc    15420
ggatgctaaa caaaccatca ccgcaccaca aagcattaat tttaatgttg gtggtcatat    15480
ccttacacta gacggtctta actccaagat tctccttgat ggtaaagaac tcatcactgg    15540
tgaaaacgtt gaccgtgagg cggctaacaa cgccacaatt gaagcggata ttaaaactga    15600
aaataccgca tcagttactt ggactggtaa cggctctact gacacaccgc taaaaccatc    15660
attgtctaaa gagacctttg acggtaacgg tatcgatgta attactaatc agcctacaca    15720
aggtctgtta aaggcagcat cgcctgctgc ggcaaaagtc ctaacagacg aattggcaaa    15780
gaaggccatc aaaggtaaca ccatcgcagg aaaggctttc aatggtaatg tcacactaac    15840
taaagctgat tttcgtggtg ttgagagtgt gcaagattac tccgatgaag acatgccgtt    15900
gtctgatgct gcaaaggaag cttttctcaa gaaggctgtc agtggccacc gccatgacat    15960
ggaggatttc aatatccaac atgcttctga aaacgaaatg ggtatctttc gatactctga    16020
```

```
caatgaagca atgatggtag aggaagtaag agactggttt gaagaactga catcttattc    16080
aaataagaca gatgggatga ttgaaagaga agccatcaat gtcttaagct ttggtgaggg    16140
gcaaggggaa tcggtagaag gaattgttaa aaacggtttt cgcatcacca tccctgcgaa    16200
cgagtatgtg gaaaatggca ttgcgattat gatcccacta aggactattg actttgccac    16260
ggtgagtgat tataaaaatc gttacttcta cgtatctgtc gattctagtg gatacagttt    16320
ctctaaaaca ttagaagatt cgaagtttgt aattggttgg gtgtataccg atagtactgg    16380
tgtgctgtca gttgatattc gtcaagtaac taaactcatt gattctaaaa ccaacgacac    16440
acacatccgt gccgttgtcg acgcccatgc taatcgtgtg tttgacaaaa ccttccttgg    16500
tttggacaat gttgaagatt atccaatggt taatgaccca acgtcggaat cacagggtta    16560
tgcgacaacc ttctcagttg ctgcattgtt ctgccgccat aacacgttct ttaaaaagcg    16620
tggtgtattg acaccagagt tgcgaacagc atctgaaaat ggagtctttt tacaatctct    16680
tcctccattc cttgtcagac aaatgccaca gaaagaccct agtgaaattc cattagagaa    16740
ccaaacatac actttcacta atgacggtgg ttacattgtt tatggttcaa tgccacaaga    16800
tggctatgtg gatgattcaa atcccaacac accaaaccca acgtacccta tcggttctag    16860
atactacact gaacaggact tcaaccctag tagttatctg ggtggtgttt gggagaaggt    16920
catcacaatg gacattcccg aggaacatcg ccagttttat aacacacagg tggggacact    16980
tgtcgagtgg atggatacaa ttccaactag cccgcattat cgctacgtcg tgcttctacc    17040
ggagcagaca tataacgatg gtgtggcaag ggatatcata atctccactg gtcaagacgg    17100
cttagtaatc gacatgccac aatccccagt agttggtgcc gaatacccat ttatgtattc    17160
agaagctggt attaaatcac acatactcat ttggaaagaa gaaggtacat taacacccttt    17220 ggaagatccg aagtatatct gggaacgcgt ggagtaaaga atgagtacac tgccagatta    17280
tctcaaacat atggagtttg acccgaaagg gtcaaatcca aataatttag tagaaatgga    17340
aagtcacttc atttcaagtg aagaagcttc gcatcagatt gtggtcccgt tatatggtcc    17400
ttttttcagt gcaaccttgt tcgatgcaca gggaaaagaa atcgataaag gtgattacat    17460
ctacggtgaa agattaccgg agttgaaagg tgattatgtc gaacgcgatg tttacatttc    17520
tatcctctta accaaaccac gtatgggcga ggtattcgtt agctaccaaa gtgttggtgc    17580
tgaactgacc aacttatcgc acctatttct cagttacctt gtttctaaaa tgaacgagcc    17640
gcgctctacg cattttgaca aggtaacgca caaaccccac agactaccag catttgaaca    17700
tcgccatcat tgggtggatt tcgtaaacaa gactgggtta agttccgcaa tcgctgaatt    17760
taaatcaggg gtagaaaata atcatcttaa caacaagatg agtgaattca ctaagttgca    17820
ggatagagcg acatctgcca cagctcgttt acaaggactg atgatagccg accatatcgg    17880
tgatgtgaac gtggttgcga atccgcatca gaccactgca acggatatcg aagctgagcg    17940
cgttaacaca cccgcaaaga cgccgatag attttttctct atgacgttct acgatttgt     18000 acgcgaattg tacactacag gcctagaccg tgtggacatt gctgactatc ttcgtaagtg    18060
gaactatcac gatcttgaaa acagtctgat agtacgtgtg ttaaactggg gaagaaaccc    18120
aattaacgga gtgattcaag cgactaatct atttagagtt gggtcagatg gtgccgtagt    18180
agaagttggt ccagaaggtg ctaaacttag gctaagtggt tcttcggtaa ccttcaacgg    18240
gcatgagtta ttcgaccgtg agaaagccat cgcttacagc gacgtatcg atggtaagtt     18300 gattgtggca gttgagtcag acgattttgt ggtttcgggt gacactacag aatttaaccc    18360
```

-continued

```
attgcaactg cacatcaaat acactttagc aaatccaaca acaaaagggt tgctcgaat    18420
catcgatttg gctggtgagg agactgacgg ctacgtcatc agttcgttag gggctaaagc   18480
tattgatgat accataccca actatctacc aaagaccaca acggtcaatg gtaaaactat   18540
cgacaaagac attaacatca ccaacgcaga actgggactt ggtaatgttg ataatacagc   18600
tgacttggac aaagagttat ctttcctaga aagacaaaaa ctcggttcaa ttgtccaaga   18660
gaaccataac cataactgga acgagatcga ctttgttaag tcgactaagg tcctttacgg   18720
tattgataaa gctgctttgt cggtggtgga tgaaggtgcg gtttcatcta agttggctaa   18780
ggaatacgtt gatggtatca tcgacttggg tgaggagttt gccacaaagg cattagtctc   18840
taattttttac ttcgtcggtg ttaaagacgt tgtactgagt agtgatggtt cgcaggttaa   18900
tatcctcagc ggtaaaatgt tgacaagtat caacggcgtc gtcacagaaa cagaattgat   18960
ggctggtaac gtacagtacc cgtcagtaga tgcaggtaaa gtaaaaacat acctaatcta   19020
ttacgtcgat aatggtgaga caccaccgca ttatgaaatt cacgacacac tctatccgat   19080
taaatatcaa tcggttttgg ttggtgtagt gaataacggt gcagttttcc agagcactaa   19140
ccaggacccg atttgtgatt ttggtgacga tagctcacta gagacacact tggccgaaga   19200
gatgccacac ggtctcgatg agccaatcga aggtcttact gttgtggaga atgccgatgt   19260
cttcattcaa aacgatggct tcaccagtta catctgggac ggtaatttct acaaccagtt   19320
gatgttaggt gatttcacct atagttctgg aactggccat ctaatccagt cagcgggtgc   19380
aaacccaatg gggtggaaaa cgtttaacgg caaaggattg atttatcaat cttctttcgt   19440
ggttaagagc gaggataatt ctgcggcact ggatgtcacc aaagcccctc atagtgtcgt   19500
ccttggtttg aacaatagtg acagttttag aatgttgtcg tgtactgtag aagcaggtga   19560
aaaaccaaga ttctacgtag agagatggga cgttagactt gtcgacaata agtttgaaat   19620
ctatctaggg gcgtacacac aaatcaacgt cgtttgggat acacaggtca accttccaac   19680
ggatttagaa gagggtaacc attatcgttt ctactacgat gaagttacta atgaaattcg   19740
ctttgagctg actggtaaac aacacatgtt ctataaaggg acggtggttg gtgttactac   19800
cgaggttcag aaagaactcg atatactcct taagaatcct tgtgtgggtg tacgagggag   19860
tgctaaagtc cctatggcag tcggcccttc tatcaggaaa ccgtataaag aagagtatgt   19920
gggtaacgat tatcgctcac tattcagaac ttatgtttcc gctggtgtgc ttgaccgtat   19980
acgtgccaag aacatcaccc aacaaattga tttgactttg actgggtctt atgtgcttgc   20040
agatgatgtt atcgaactag gtaatatctc ctccaagttg ccaacgggct tcactaacct   20100
agagctggat attctgcgtg tcacacgcga tgctggtcca tttgataggg agattgatca   20160
cgaagttctg tctggtgact tgtactacgg cgcagagctg actttaaaca aatgggataa   20220
gggatacggt ttgtctattc gacgtaatga caacatccga ttacctctaa ctcctctcaa   20280
aacttacaat ggtgctgttg tcagcggact catttccgat ggtgatagtt tctcaatccg   20340
agtgcgggtt aaagcctaca acgtcctttg ggggataacc tcagatgact ggcaataccc   20400
ctgccacatt cttgcttaaa agggtaaatg atgactttgg catatgaccc attgggtact   20460
aacccagaga acttaaagag tgagactaaa cgtttgtcag atgcgcccaa taagtggcgc   20520
gtcatcatcc caacgtattc tcctttttat cgttcagacc tagtcattct agatgacgat   20580
ggtaatgaac tctttgaagg cattgactat tacttaggtc attactacaa agagttatca   20640
gaagctctga acgtccagt atacggttct cttattttaa aggatgaatc actcgacgag   20700
gttactttct ctcgttacag agccgtgggc ggcgaccaca tggcggcacc taccgacgtc   20760
```

```
gctaactact tgtcggatcc aaactcccct gaccctcgtt caacggattg ggctgtaata   20820
cgtgtccgta aaattgacat tattgccaac ccacctccta cgaatataac agaggctcgt   20880
gcaaccgacc cagttacaga aagcttatgg cagttaaaag agacaatgaa gtctaacaga   20940
gtgagttcaa accaacaatt ggtggatttg actactcagt taattgacct aacctctctg   21000
attgtcgata ccagttatga gaaacatttg gatgatacag gtcaatatgc gcatcatcta   21060
acatgtgaag ttattggtgc agctaagaaa agcgacacag cgcccgatgt ccagtatttc   21120
cataatctgc cgtacgaaac tttcaaggaa cgtgctagcg attacgcaat gcaacctgtc   21180
gttttagaaa cgctattcaa tcgccttaat gacgagatga aggtgtgat  taaatttaca   21240 ggtgattatc aactagagat ctccggtggt gcacgtttca aagttcgtgg tgaagagttg   21300
gtaattgata ccatcaaacc cacattagaa gtggaagtgg tcggtgacaa tgttaagtcc   21360
ttattgtttg tttcaggtac tggttcgttc acgttaaagt caagtgatgg tgtctgttac   21420
tacaacaata aaccaatcat tacaacggat gaggttaaag aataccttaa cccgtctctt   21480
ggtaaagctg accgtgtaca ttacatcaac aatgccgatg tcagcttttc agggattggc   21540
acagactcat ctaaattaag cgccagtgct aaaatcaaac ttgctacttc aacacagacg   21600
ggtttgtttt acgttgctga taactttgct gctgataaag cggcgacagc agactacctc   21660
tttaagacgc tgaccaagat caatttattg gccgatagtg actttagtat caacggcgtc   21720
cctttctcag agaacatggt ctttaccaaa gacgctcttg ggttagagaa ggtgaataat   21780
actgcacccg ctgaaaaacc gataagtaat aagttgcgga ttgagctgga taaaaaacgt   21840
gatgctgacc acgaccatac gtatgccaat atcaataacc caaaagagc  ttctgttta   21900 gaagctggtc ttgggcaatt cgatacaaac ataagtggta atgaacaacg tctagttcgt   21960
cgaaatcaga tggctacgca gaagagctcc cttgatgcga atgcaaagat catcgacgag   22020
atgctcaatc gcggttatct taagggtac  tatttcaagg attggttat cactgaatct   22080 aatgggacag tgtctgtttc atcatttaag atggtggaga atgggattga gacagcggta   22140
gttggtggaa cgtaccctaa tttcacaggg tatatctctg tacttaacgg tgttttatcc   22200
accagtgcta atggtcgact tgtgtgttct aaggatgtag acgggttata catcgcccct   22260
aattactcct atggaatgac acgtgagtgg ctagagcatt atcatgatac caaagcccat   22320
gatagcgcta aagggaaagg tatctattct ctcatccaaa acttccccgt aatcgtggat   22380
tgggaaaacc cagtgatcaa ccctcttggt agttatcaac gttggtcaca tcagtataac   22440
atcgctgata agcccgcccg tgaggatgag ttgctttatt ggggatggga tggcgaacac   22500
ggtgcagtct tcaatacgga tgaatccgat acctttatct ctatccattc acctttgcaa   22560
gagaactatc aattcaccac actaatcgaa ggtgtgagtg cgagcactgg tgttgctgcc   22620
atagtcctcg cttctaagga tgttagtggt gaagaaaaga ccatggtgct gaccattgcc   22680
aactcagccg ctagtggtaa tagcaaccag ataacctctc ttattcaagt atgggaggat   22740
tacttccaac caacacagcg tttaatcagc acaatcgatg aacgtaccga aatgttgggg   22800
gtttgggatg attcttattg ttacatcaat gtcgtttact ctcagggtat tctaacacta   22860
aacgttatac gagacgtgtt ccccgatggt gacagagaca aagtagtaga attattacca   22920
aacacgatag agaatatcga gtcatggaaa atcacaactc gtgtattcaa tattggtgaa   22980
acagtacctt cgttggtcgg tcctaactcg tatggttacg gtgctcgcaa gctaaaggat   23040
gttaagtttc acatgctgca aagcttccgt gctgagttaa tagagacata tgcagcacag   23100
```

```
agctacttaa gggaaatcgc aaccaaccaa acagagcaag tggaagtcac accgagtaat    23160
ttccaagttg attttgaatt ggttgaggaa ggtttgttta aagggacagt caacacttca    23220
gactttatcg cactgatgga tacctacgac caaccacatg taatcgacta tgattataat    23280
ggtttagttg ttgatattta cgtgcgtttt ttgtttgttg acaccaacgg gactcaatta    23340
tatgagcccc ctacttcact accaacctca gcggttagaa ccatttcgat ggagtttgtg    23400
aagtaaaata aggggagttc tctcccctta tcccttatt taatttaaag gagagcgtaa    23460
tgcttagcca tttgaaatac aggctcgact ggactggtaa gctaccagaa aaccgagtag    23520
agtccaaagt gacaataggg gctactacga atcgcgcttt tgctttaccg atgggtccgt    23580
tctacaccga tgaagttaca atcatcgatg ttaacaaccc gcaagaacca cttgttcgtg    23640
gtgtggatgt cgagtatgtc ctagcctaca ccaagttaag ccgaatggct gaaggtaaag    23700
aaatctgcgg tgttatggta gttaaaaacc ctaacgtcgg aactgatttg gttgtgtatg    23760
ccaaccatgt aggtggacca tacgttaacc aatacgaagc catcattaag gctatcgagg    23820
atctacaact tgacaaccgt gaagttgact tctcccgatt agagggcatc cctgaaaact    23880
gggaagctgc tccgcattta caagacctcg gtgacatctt tggtttcgag tttatcaact    23940
ctatactggc cgagatgttg tcttcaatta ccgctggcaa acacctgaa gttcaggcta    24000 tgattgctgg actgactaat gttgaaaaac gattacagga tgctgttaaa gcacaccgtg    24060
attcactagg taacgttcac caaacaacag cgcatcaaac aggcacttac aacacagaag    24120
aaatcgacac gctatttaac acagtgcgtg atgaaatctc agtagtggct agcgcccttg    24180
gtgatgttaa cgataagatt ggtattctca atgacaagct tgatgcaatc gagcgactct    24240
tcaacgaaaa cactaaaatc atcgcatcgc tatcccagga cttaccaca ttaacggtaa    24300 cttacgtgta tgtcaacaaa gctatcgctg atcagaaaaa ccgtgataaa acccaagacc    24360
aaaaacttgc tactattcaa actgaactgt cacgtatcaa tgttaaggca gatgagttgg    24420
aggcaaaggt taacgaaggt tccgatgacc ttttgactaa aagcggtggt gtagtcgatg    24480
gtccattaac agcagcagcg cttggtgtga ctaacccaca accgactacc gcacgtggtc    24540
ttagtttaat gggtgacgct gatccagatg gtccacctga ttacgggatg tttgtcggtg    24600
ctacagctac ttacaacggc cacggttttg taaatggtga tatggcgaca tatttccaaa    24660
tgctaggtgc aactaatcgt ggatggattt tccgtatggg ttctactaac gtagcgtcca    24720
tttctggaaa tggcgatctt cgactaaacg gtagaatctt tgctgacgag gatatccgag    24780
gatactcaga cgcaagattg aagaccgaca tcaaacgcat cgagaatgcg ctagagaaag    24840
tcttgagtat tagcggttac actttctacc gtgaaggttt gtctgagcgt gaatcgggtg    24900
ttattgcgca agagatcttg aaggtactac ctgaagttgt tcagcccgat gaaggtggtg    24960
atatccttac tgtcgcatat ggtaacatta acgctttgtt gattgaagcc attaaagagc    25020
agacatccaa ggtcaatggt ctagctgaaa agctcggtat tcctttggaa gaagtggatg    25080
ccttagcggc taagttaatg aaagaagggg gtgagtgatg ggtattgaac gcgatctcgc    25140
cgaacttgaa cgccgtacca cagagctgga aaatggcgta aatgggaata aggtaacact    25200
tcaaaccctc caaggtacgt ttaatgattt caaggacacc cttctaaatg ctgagggtga    25260
gatccaactc cttggtgtta aacaagacca gcaagatgta gccattggtg atgccgaaga    25320
ttctgtctcc aacacgtggg ataaggtcaa tggtattgac caagcgctta aggatagaga    25380
agaaaactct ctgaccaata agggtggtgt ggctaacgga ccaattactg caactgcatt    25440
cggcgtacca aatacggatg tgacaaaagc caaagggatt agtttgctag gaggcgctac    25500
```

```
attagctaac ctctcctacg gtgctttcat tggctccaca gttacgtacg gtaaacatgg   25560
ccaagtacag ggcgatatcg ccacgtattt ccaaatgagt ggtgcaagta accgcggttg   25620
gattttccga ttggggaatg acaacgttgc ttcgatctca ggtaatggtg acatgcgact   25680
tgatggtggt ggtctagcca acactgatat gcgtggttac tcagatagac gactaaaacg   25740
tgacattaaa gtcatcccaa atgcactgga taagattaat cgcattggcg gttataccett   25800 tactcgtgtt gataaagact ctgataagcg ttatgcgggt gtcatcgcac aagaggttat   25860
ggaagtatta ccggaagtag ttagtctgga tactgaacgt gaccgctatg ctgtcgccta   25920
cggtaactta gtcgggttat tgattcaagg gatcaaagag caagacgcac gtctaaaagc   25980
actggaaatc ctagcgagtg aaaaacgcta atggggaac ggggaaactg aatactttt   26040 aacgttatcg ttagaatata tgtataggtt ccccgttttg taatcttaaa atatttaggt   26100
gaatgtatgc cattacaaac atcaggacct attagtttag gagatatccg cgattacttt   26160
ggtggttctg gcgaggttag catctctgat ttttatcgag gtggtggcat tgtaccagac   26220
attgctcaaa atagcaaagt gccaactagt ggtcaaattg gtttagggga cttccttggt   26280
gcgtatcgct tatcggtaag aagtgttagt aaaacaacaa gtgctgaggt ttcaaaaacc   26340
accagtatta caacttccta caccgttgca aaacaaacct ttaaacagac ctctatcgcc   26400
aaatcaattg gtaaaagtag aaacacctct tgggtaacca ggtggcgtag ttattggaac   26460
actgcatcgg gcaagtcctc agtgcaaact tacgcagact actcaagaac aacaaccatc   26520
accacatcat ggactagtta ctggaccagt tattggaata catactgaa cactgactat   26580 ccaacttcca aagtcacatc gtggacaact acgtggacct cttcatggac cacaatttgg   26640
aatacacacg tggccgtcta aggccacgtt ttactaaggg ttatttaaaa atgggtatcg   26700
agaaaagagt tgaaaaactt cgtctacgta ttgtagcttg tgaagagaaa tcatcaaaag   26760
caatgagcat tgcctctgaa tctatcgggg catgtaaccg ctttcgtcta gctgtcaaag   26820
aacttatgga gcacaccaaa agtaatggcg aggcgattgt tgaacatatc gcacaactcg   26880
ataccgagaa ggcagaagtt gtaaaagaat accgtgatga gctgaatcaa gtcaaagaag   26940
ggtttgatgc agcagtgaaa aaacttgctg aagagttaga tgctctttcg aacaaagcaa   27000
aagaactgga taagcaggag taagtgatta tggaactcag tcaattctca cgaactggca   27060
cagtgctttc tactgataaa accatcggta gccgtgaact ggccaagtac gcaatggata   27120
aattgaatgt cctgcatcct gaaatgaacg ttttgttcga tatgatgcat aatgatggcg   27180
aagcatacgt tgttcatgaa ttctgtggtg cactcggggg gatttcaatc cgctacctcg   27240
atttgagcat acatcaaacc atccttatgg agtcgattta tggtaagccg actaattttg   27300
tcgattactg tgaattgctt cgcgaggcta ctgttagtga taagtacgta ctccgcgata   27360
cgcaaatcaa agccaagcaa gttgtattcc tttctggctc aaacgtcatg cacgacaaca   27420
ttaattttga agctgttgat tcggctgtgg ctgaaggcgc tatcatcaaa ccgcacccag   27480
tgactcacgc caaagatatt cagtggctaa aaagccgtta tggtgaagac aaagttcttg   27540
ggcctaaagt atccggtgcg actttgttaa agcaggccga aattgtctac atggctaaga   27600
acagcgaatt atggttgcta gctattgcgc atcgtaaaac ggtccgctac gttggtaatg   27660
ctcacttcat ggcagaagtc tatcgtgccc caatcgacgc gatttgggga cacccaatct   27720
acatgccacg tattgccatg aatcgattat tctccgcttc ccaatccggt atctatttct   27780
ctaaagaaga aatcgataat ggtctgcatc tatatgtcaa acgtgtaaag gaactgtcga   27840
```

```
aatgatcact tacaccaaag tggtaagtga agagcaaatt aatcagttct atattttggc    27900
cagtagtttt acttaccatc acccggatag aatcttatat tgccaaagta gattaaccct    27960
gaaagaaata cctggggtgg tctaccttgg tttgtacgat gatgtggaaa cgtttggcga    28020
tacgttctgt tacttatcac cgcatatctg ttttttttgct cctatcgagc acatattaca    28080
aatgaaggtg gatggacaaa tcatccctaa tgacagacct gctgttagaa acgatatgta    28140
cttctacaac aagcaccatc gtgaggtggt gatcgactac ggcaacgatg tatttctgaa    28200
tatgtctttg ccaccattta tcgattgtgg tagtgtcatt ggttatcgcg atttaaccgc    28260
aaaaacaccg atgattaata cacgagaatt taatccgagt atcaaacaac gaaatagtta    28320
caagacattg atcttcccat gggagcgtta cttccaagtg atgatgatgg cgggcggttt    28380
acttgaaaag gagtatatcg actctgtcgt agagaattgc aaaaggcacc cctacatgtt    28440
gtactattac gccaacggat acctacaagg cactgacggg gtataagatg tcgctggaat    28500
tgttagagtt gaagaactca ccgtatctaa atgaggcaat ggaaaaaatt gaccttttgga    28560 aaaagaaagg gttcaataga atgttgttga gtttagagga taatcaacct gggttcatttt    28620 actctaacaa tcgcccagat agccctgtag agtttaacga gtgcattggt agagtgttta    28680
aaaccaaatc atccccaagc gatatgattc cctgtgactt cataggcgtc tcggatggtg    28740 aagtttttggc ttatttccaa tgcattgttg tttacctacc aggtggagtt tctagtgcga    28800
caggtgttaa gatttaccac ttgtcggggt cgcattacaa gataggtaaa ttacagaaga    28860
tgttttacga ctgggccaat cgaaccttcg actatatctc agttcaattc tctgccttaa    28920
atgcttttgc taaaggcgag gcttcttttt ccgaaacaca gacagtcaat gagaatctaa    28980
aaaaggcttt tgataaaaac aaggccatgt acggattccc aaacccaggt gtgattaaac    29040
atcttctgtt aaagtacgat gggtatttta tacttaccac catctacaca taaacttgg    29100 atggtgattt ggatatattg cataatgtgc actggttagg tgaacgtggg attgagaaag    29160
gtcttcctaa gtactctccc cctaaaacaa gaccagagat tataaccaat taccttaaat    29220
cgaatggtat tgaattacca gaggacatta acgatgctac ctaatctcat tgttttaaag    29280
gattccccat acgttggaga aaccatgact aaaatgacg ggtggaaaaa gcaggagttt    29340
gctaagggta cactaactcc tgaaggtaac caaccacagt tcatgatagc ggattgtcgc    29400
ccagacgacc cagaagaatt caacaagctg ctcgggaaac cttttaccta tcgtgagggt    29460
gaccgtgaaa tgaccaccga ccactttgtt ggtttgtcac tcgatgggga ggttaacagc    29520
tatttccatc acaatatcga agagcgtgca aacggtacta agggtgcaac ttgtgtgcat    29580
tgttataacc tcggtgctac ttctttttta tttggcaaat accaaaagga attctacgat    29640
tatctaactg aaacgtttga ttacattgaa atcctaatcc ctgctgattc accgtacagc    29700
aatggagatg tgaatggtaa aggtattgaa ccttcacctg agctaaaagc agttatggaa    29760
cgtcgattca agaaactgg ttaccataac ccacacttaa tcaatcgtgc agtgaagcac    29820
aacggtacgg ttacacctta ctgtatcgac cttccagaca tggacggcaa ccatcgttta    29880
caccacatca ttcgttggct tggaaaaccc ggaattgaaa aagggctacc taaccaccct    29940
gtgttgataa aacgaccaga ttcgctaaag gcggtattgc gtaaactcgg cattaccgaa    30000
tacctttaat ttcaaaaacc ttaacaagag ttatttacaa tgatggagag tacaggtatg    30060 agctgttta tttctatgct gcctaaacta aacaacagct gttttcttga ctgtgactac    30120
tgcatggtag aacacgacga tatggaaatg gtaaaacgaa acggccgacc ttcgaccatg    30180
atgccacttg agatgattga gcagatgtgt gatatggctg ttggctatcg tcgctggttc    30240
```

```
ttctcttatc tgggcggcga gccattgatg aatggtaaag agtatttccg cgaaatgttc    30300
gaaatcatcg aacgtaagtc taagcaatac tacgcacctt acacccaccg tgtaacaact    30360
aacggtctgc tactcgacga tgaatggatc gagttgttcc gtcaatacaa ctgtaagatc    30420
atcttcagct acgatggact tgggtgtggt aaaaaagggt ctaagaaagc acatgacctg    30480
atccgtaaat acgcaaaaga catccacaat gtccaagctg taatcggtgc gttcaactct    30540
caccgtttcc tcgatatcta taagaactg aagaaatcg gcatcaagca gtttaacaca    30600
caattcgata tctacgctaa cgaagacgag tacaaagcat tcggcgacca cactgttgaa    30660
gtgttcaaat acatcgatgg tctgataaaa gtaactacca gcctgtacct ttacaacgac    30720
gcgaagaaca ttgcacgtgg taaattaagt gccatcaatg gtggtgaatt gatgaacact    30780
cgtctagtta cggattacgt cattgactac gacggtgaga ttcgtaacgg tcttccagca    30840
cgtgaaagca aatacgcgta ctacggcaac atcaaccagt tccgtaactg gcacgacttg    30900
atgttcactg ataccgctaa gtacatgatc gaagattacc tgaacgcgat ccatacccca    30960
gacccacaac tacacgcagt atctctactg actcgtggtg gcggttatcc aggcgaccgt    31020
tttggtattc gtcctgaatc tgcaccacac taccctaaac ttcactgctt taagaaaatc    31080
ctaaatcact tcgatatggg tttgtaatta gtagatgcgg ttttgttgg taacgggtgg    31140 actcagttac ctcggagcgc atattgttgt tgaatatatg cgctcctcac acattccaat    31200
attgctagat aacactaaag agacaaataa caatcttagg attatccggt ctttaacggg    31260
attcacccca gaggtacacc gaggaaatct gctaaacgat aagatgatga agcgttatt    31320 ttcaagatac aattttgatg cggtttatca tctagccacc aacaacctag attctcagaa    31380
cacactgagt attattaata acaacgtcaa tggtacaaga aggttgcttc aatacatgca    31440
gcgcttcgat gtaaagaatt tgattttgc atctacaaac aatatctaca acaacggtga    31500
ggttggtctt ttagaccaat ccgccgtacc tcttttaccg tattacagaa gtatccatct    31560
ggctgaggag gctgtgatgg agtggggtgg ggttagaggg aataattata gtatattaag    31620
gttgtttaat tcaatgggtt ttaaatacga tggagctttt atagagtctt cttatgaaag    31680
cttgtgggat tcgttttact cattgtgtaa tttaatgcta aatgaaacca tcgaaccgta    31740
cttcgttcac taccctgatt tagaaagaga ctatgttcac atcagtgact tggtccgtgt    31800
tctaatcggt gctttgttga atgttgagaa gggtaagagt ggtatttaca atgtggggcg    31860
gggtatcggc gtaacgccta agacctctc acaaatttac caagagttga cagacataga    31920
gttaattaaa actccaatgt ttgacaaagg ccttgggttg actcgtctgg tgtctaatgg    31980
tcctttacca tttaacacac aagccgaatt ttccgttaga gacgcattag aagaagcaat    32040
aaaatggtat cctgaacgtg actagctttc atcggctagt cacataccttt tatttatt    32100 tttgtatcta aggaaataag tcatggctgg attcttaaag aaacctaaat tacgccgact    32160
gactgagaaa tggtatcagt tacaaggtga ccttgttttc cactttacgt taaatgaagc    32220
aatggcgggt tataagccaa tgctccgtga tttggttaag aagggaatag ctcccgatga    32280
aacaatctat gtggttgttc ctaagggttt cgtcacagat ttggcatctg tacctaagcg    32340
attacagttc atctttccgc cagatggtga gtatacttat gcagccatcg ttcacgatat    32400
ggcctaccaa tctttgaaag aaaggacttc cattgacaca agttcacatc gataccaccc    32460
aatacatgaa ctgaacaaac accacactcg ttatctcgct gaccgattat ttttaatggg    32520
tatgcgggag cttggtgttg atttgtttac aagaacagcg atgtataacg cggtacgcct    32580
```

```
tggtgggtcg tcttcctatg ggggcatacc gatggacgaa gattacggtc ttgcgattcg    32640
caatcgtttg ttgatggcag actcgtatct catttaccgt gagaaacctt cagttggggt    32700
tgagccatct ctatacgatg atgggtgtgc aggtgatggg gtggctgttt ttgtaaaaca    32760
tcctaacctg aaacgtgcct ttgccttttg attatttaaa ccgtagacga gtggggagag    32820
agttatgtct gtagctccaa ttagcatggc cgttaaaagg ccaaacttta ccgcacacac    32880
cgtctcaccc gaagagaagc aacagatact gtctagaatc aaccaactga atagtgagtt    32940
gatggcggcg ttgaacaatg taaacacgga cttatcacag caactgagtg atgaaatcca    33000
aagtacaatt caacgttttc aggcagtgaa tcaagagtta agtgatatca atagtgcgat    33060
taatagtacg aatagtaacc taagtacaat caacactgca cttactcagt ccattgctaa    33120
cttggatacc aagacagcaa caaatctagc cactcttcgt aaagacagtg aagatgctga    33180
tgcagcctta acggaaagtt tagggtctgc tatcgacgat tacaacaaca agattagtga    33240
actcacctca aacatgaact cgtacatcgg tacgaataat gcacgtgtgg gtgatctgga    33300
agatgagtta gcggcttatg taatctcaaa caacaaagcg ttgaatgatt acaaaaccgc    33360
gaataacttg cgggttaaaa cttagagga taacttcaca gcctttaaga caagcatcac    33420
tactcagctt aaccaggtta acactaatct aactaatgcc attaaccaag tcgcaagtga    33480
cttggctgat tatgagttgt caaatgacac gcgtgtcaag gccattgaag atgacctagc    33540
tgcatacaag tctacaaaca atagctcatt gtccacttac aaaactagta acgacggtcg    33600
tgttaaagct atcgaagatg acctagctgc atttaaaaca actatcacta gtcagttgaa    33660
ttcagcaaag aatacacttc aacagaatat cgattctgtc aactctgctt taaatagcta    33720
tattgctact aacaatgcgc ttgtaacagc aatcgagaaa aagattgatg actacattgc    33780
tagcaataac caagcattga gttcttacca gacttcaaac aatgcgcgag ttaaagctgt    33840
tgaagacgat ttagctgctt ataagactac agcggcgcaa tctcttaata cagcgaaaac    33900
tcaacttcaa gataacatcg atgcaaccaa caccgcatta aatgcttaca agaccagtaa    33960
cgatagtcga gttaaggcag tagaagataa cttgactgcg tataagacat ccaacaacca    34020
agctctgtcg tcctatcaaa cgacgaataa tgcaagggtg aaggctgtcg aagatgacct    34080
gtctgctttt aaaacttcta gcggtaatgc acttacgacc gaagtgaata aactgactca    34140
gagtattaac tctgtctcat cttcactgag ctcgtataag acatctaacg atgcccgtgt    34200
taaatccgtt gaagatgatt tggcagtgca cttggctgct caaaacccac acggtatcac    34260
acctgcaatg attggggctc taactcaagc gcttgctgat gcacgttatg ctagactaac    34320
tggtatgact atgcaaggtg atatcagcat gggacagaga aaaatttctt ggtctgctaa    34380 caccgacgt gccgaaattc gtttcgataa cacaggtgac agtgacctag attcttcttt    34440
gcacatggtt gtgttggata acggtaatga gttcttcaaa tggtcgacac gcagcgctgc    34500
atccgcaggc ggcgttgaaa ccgagtggat gactctgaaa tccgacggtc ttcgaatcaa    34560
agggaatcta gtattccacg atggacgagt tcctactacg acgcaattgg gtattagaag    34620
tgacgctgag aacgacgcac gttttcactt gaagaatgcg aaagttccaa atgcaacgtt    34680
agctgataca gttacggtaa actgggcgac tacgactacg ttctttaacg ccctgtatgc    34740
tgatggtaac aagatcttca acactgatgc tttggtcatt cgtgcttcgg atggttacag    34800
tcgattgaaa catggtgtgt tagcaggcac ttatctctct cacaatgaga atggtcaact    34860
tgttgtctct agcacagcca aacgaagcgc tggtatgtac ggtgtttacg atgccgctaa    34920
gaccgcgcag atttggtcta tgggtgttgc atacaagatt gctgatgacg gctctaactt    34980
```

```
cggtaacttg tacggattgg catacaagca cactaacaac ccagagcaag gcacaatggg    35040
cgcagggcat cagatgttgt ggtgtcagaa cggcgtagtc tacgcttcta tcggtaacga    35100
tatctgggcg aagaacaacg tctatgcaca aggtaacgtc agtggatttt cggatagacg    35160
tctgaagaaa aactttgaag ttattgataa tgctttggaa aaggttttaa ctttaactgg    35220
tctcacttac gatagaatcg atatgaacga tgagcgtcaa gctggcttga ttgcccaaga    35280
tgttcagaag gttctacctg aagttgtttc gcagtacggt aagtacttga ctatctcgta    35340
tggtaattta acggcattgt tggttaatgc tattaaggag ctggcgaaag gtcaggggat    35400
tgctctacct tcaaatgact ttgctaagaa agcagagtaa aaaaaccaat tggaggatgg    35460
tatcgaccat cctccttttt tctattcttt ttggctataa aaggaaacaa gcaaatgaca    35520
gcaacaattc catttgaaga ccttgatccc ggaacacaag aggtgattaa taaattcaaa    35580
ggtaaatcac catctgtcga aggtctacca acaccgtag tattgcgtga caaggagggt    35640
aacgtcttag gtcactatct tttgtcgaaa gctccaaatg ttagtgaggt atctggcgca    35700
gtagctttcc gagttgacaa aaacgatggg cgaatacagt tttgtgataa ccacgaagct    35760
gtaagaaaat tcctaggtct acctaatgtt tttataggaa aagaagcacc agtatccccc    35820
ggagagggtg acttctggat agacgaagga gagtgaaatg gcctcttaca ggattgatta    35880
caaaaaatcc cccaaggata atgtagtcgg tataatcaat gcaaaaaatg aaagacata    35940 ccctgcgaaa agaatactca taagggagt agaggatgat tttagcatcg gtgggtcaga    36000
cacaaaaata aaagtcgact tactcaacaa tgggaaggat acacctaacg agtatgttga    36060
attttgtttt gcaaggataa aactagaaga cgtgtttaaa aacgtggaca tggcaaagct    36120
tgataagatg ctaccgagcc atgtgattga aaacggtttc gtcatggtct cttcatttat    36180
taaagagatg tatcgacgtt ttggttttta cctagatgag actaattacg actatgtggt    36240
cattgacaac attatcactg tccacgcaaa gtcgattaat cctttataca agggattctt    36300
tgaaattacc gtcgaaggta atgtgaaatt agagggcgaa gaagctaata tgatggtcga    36360
ggatttctca ggctatctac tcaaaatcga cgtatttcca gacagtcttt ctgagagaga    36420
ttttgaaggt gctataaagg cacgtagctt tatcagtagt gttgagaata ccgacactat    36480
tgtgggggcg atggtattta aaaacgggga taagttagag tttgtatctg acgtcagagc    36540
aataagacga gcattcaaag ctaacaacat atctgcgtct tcaactgcgc caataaaccc    36600
tatcgaatac gatctttgga tagaggacga ataatggcta tactaaaagt atggaaaaat    36660
gggaagtggg tgactataga cttctcaggc ggtgtgatgg gcaaagagct acttgtcaac    36720
cgcgacatca aaaatgcatt gaacatccgt aactttaacg gtaactggga acttctatct    36780
attggtcagt atgcctacga ccgttggatg aaagcgagtg ctactgagaa agggcaagct    36840
attcctgatg gaacctatgt ccctaacaag aagcacacag ttagttatct tttggatggt    36900
cagcgacata ctgaaactat tatgtctcct gcgggtggta actggttggt gaagttgcct    36960
ttcatcgcgg atgagatgtc tctcagaaag ggtgtgggtt ataccactca tacacctgaa    37020
acagaaagtg aacgtttatc ggcttgtcgt ttctttgctg aaacgcaaac tgttcgagta    37080
tcttggtacg atgtggttta tggtgtttac tataattaca tttatgagca aatgctgtta    37140
tctgacaaac accgttcccc agtcattata ttcgtaaatg gtacaaatcg aatcaatgga    37200
cgggctactg agttaatacc aggcggattt cgttatagca tcactagctt tgatgggaga    37260
gctagcggaa acaaatactt cgaattcatt gcggattcag agattagact agaggagact    37320
```

```
gtgcaatgaa catagaagcg cgctacaccg aagctagaat cggtgagaca ctcccctatt    37380
ctgttagcgt gattggtgag gtcaatgcca aacagttgcc aaggaatcac cccgattggg    37440
taaactgggg aatagatgtt ttagaggcgg aaggtaagat actgccttat atctctaaag    37500
acgccgaacc agaactaacc gaagacgaac tcacgtatcg tcgacgtgaa gatgccaagg    37560
tgacacgtga cttagctatt gaatcaccaa tcaaagtatt tggtgtcagt tatcaagtgc    37620
acgttacccg tgatgaacca cggattaatc gtgccatcaa tactgctacc gaggcgggtt    37680
atccagaaga ctatgcggtg gattggatac tcactgataa cactacaagg ccaaccactg    37740
catccgatct tcgtaaaata ttggtagcaa aagctttgag ggaagaacat atctttgcgc    37800
aatacaaagc ttggctggcc gatggtatga aagacgactt ccttccaata caaaaagagg    37860
attatctcga tgttctatcc tgacccaaaa caattctcgg atagtgaatt actcccccct    37920
gagattttaa agcgatgggg aggtacgggc aagtacctac ttagtccatt gatgttgatt    37980
acactgcaac agcttcgtaa tcgctttggg cgaatcagag ccaactcccc gaagttgggg    38040
ttctatcaac gtatgcttcg aaccgttgat tactacatgg accaaatgaa aagaaagcac    38100
ccagagaaat caggggctga gattttcaaa ttggctagtg aagcttatca acgatactgg    38160
ggacttcaca aagtaggtgc agccgctgat atcgatttcc ttgacgcaga ccgcgaagag    38220
gtaatcgaat acattcgtgc taacccggac gaattcccat tcatcagttt cattgaagtg    38280
gacatcactt ggttccactt tgatgtgcgc aaccagccag ggattacatt ctggtcacct    38340
aacgatggcg tcattgaggt gatagaacaa acccccattg actgggaaaa aattgtggat    38400
atctctggta agaatacgaa gtggaaaaaa taacgaggag ggggcttacc ccctccctat    38460
taggagagtg ctaatatgaa taaacgtatg attaccgtca tcgctatgtc attctgcttc    38520
ttactctttg gtctaacttt tctgtttaca aaaatagaag ggacgcagag taaggctgtg    38580
gcaaagattg tcgtcgaaaa gatggcttac aatatcaacg aagtcgataa gcgtgttagg    38640
gacgtactcg ccaaagttag aacaaacgaa acattggatg cgttaatact cattcaagat    38700
gacttcaatg actctggata tatggttgat gataaagact acatttccta ttctatcaaa    38760
cacgacgggc tggatagagt tctggaagtc aattacaact actatttaga aaacagtggt    38820
tacatgctag ggaggtactt tacagttctc aacgattaca aactaatcgt cgttgatgac    38880
agcactaagg ttaatagaaa ggattttcgt gaatggttag ggttgagcga ccacaactat    38940
ttgtatttct cagaggcact taagtttgac gatggcgcat cgctgtatct agtcggttat    39000
gtaaataaac ccatgctgta ccctatcatt tatccgcaga gtgtgcaaga taggatctat    39060
caattacttt atatcgttct cttattcata ttgtcttaca gcttaatctc caatatgaat    39120
aattactata tgcgtcgtga ggctaggata cgtgatacac tcactgaccc actaactgga    39180
ctttacaatc gacggtatct agataagttt attttcacta atgagctaat agtcgctatg    39240
attgacctag acgactttaa agagataaat gactcaatgg gtcatgttgc tggagaccgt    39300
gcgttaaaga gcttctcaga ggccttaatg agggctacgc gtaacaacga cgttgttgtt    39360
cgaatgggtg gagatgaatt tattatcata cttgaaactt ctgatgtcaa tgtcatggaa    39420
gaggttatta aacgcattaa acgttttacc aacatcggct tcagttgtgg atatgagata    39480
tacgatcaaa aactatcctt tgaagaaaac cttgaagcag tcgatgctcg attgtacgag    39540
gcaaaaaaag aaaagcgtta aaattaaata cctcctagct taaatgctag gaggtttctt    39600
ttttattcgt cgtgtggcag aatctcaatt ctgaaataat taaattcatt tgagaaaccg    39660
ctatcacctg atagacgatg gtcaatctca gacagggaca agtcaagaat gacagtctca    39720
```

```
tcaataaact cttcaccatg tggtaacagt tgatggttga tgtgcttctc tatgtcactt   39780
ttgtaccatt gtaacatatt gcgcatatgt ttactaaccc cgactagatt gtaaatggtc   39840
tctaacccac caatggccat ctccgttaac ttatcgcact tcgggaccag ttcttcgatg   39900
ctctcaataa cgggtgggat tgtcattgtg tattgctggt tagcataggt aacacatagt   39960
tttctcatga ttgtttgtcc tttggctcaa ccttgatgtt gttgattaga gtgtcgtagt   40020
cgttaggaac gaggtcgcgc agtttatggc acatctcgtc catgtcattt tgtttaaggt   40080
cagtggggtg acgaatgccg tattttattt cacctagtag caaagccgct tctaagatgt   40140
catcaggata tcgatagatt ttgtctgtat ctttctctac gatgacagtt cctttcttaa   40200
gggcctctct cgcttcgtca cgaagtcgac cagaagttaa accttctgat gcatccttgg   40260
ttagtaacgc gtacaccaaa tccgcaattt cataaattgc attaactgag attgtttcag   40320
ccatgggtaa ctcattgtct ttttccatta tatatttcct ctttcttact aaacagccat   40380
ggcatattca acagggtaag atttctcaga acctaaatct ttgaagttta taccatccct   40440
agttttaaca actttaatgt tgcttaaacc aatacctaga cgtgctaatt gttgttgggc   40500
gctcttgagt aactcaattg catttgtaaa cacgagtggt ccatctgaag tgtctacgtc   40560
gtccaatagt aagactgttg ggacagtctc tgactctaga gtttcttttg gggttaaaac   40620
cataaagtta tctaggttga tttgcttaga tgtgaagtcc catactactg gtttgatagc   40680
caatgacatt ttatttaatt ccttctaatt aggttaatag aacaagatgc tttatcaccg   40740
taataatata tacctaagtt attttttagag aagaaaata aaaaaagag gggagaggta   40800 acctctcccc ttagtagtta gaataaccgc aaggtatcct caactattaa gcaattctct   40860
ggcatcttga atggctctat gtactccac cattcagaac cgtcatactc accacgttta   40920
agaaaagaac catcaggaaa acctatgatt agatccaaag gtatctcgtt gatcccatat   40980
ccatcgtcgt ataagaaatt tgctcttttt tgaaacgtag cccatgtcat cgttatatta   41040
gtgttagcta atccaatgaa tataggttcc attccagctg cattaacaaa ccccatagtc   41100
tcttctaaga agttaaccat tgtatttacc ttatgttgat tgacaatagt ttagtctcat   41160
caacatggat aaaaataaag tttgtttact agcatagtat taagaaacgc agttattttt   41220
aagggaatgg gaatagtgac gtgatttccc ccaccccgac attaacctgt tgatttattc   41280
acaggctaag actattttgt tcgaatcatc caatgcagcg atgtctcaaa acccaaacgt   41340
tcgtacaatc gtttagctgg attgtttggt actatggtta acatctccac atcggcattt   41400
tcgattagga atgtcgccag ttccgtaccg tatcccttgc cacgatgtgt gtcttcgatg   41460
taaaggttgc tgagggattt tgattcggtg tggagagtca ctaccccaac aacctcttca   41520
cccaaagcgt aaacatacat gttattcaga taagattcaa attgataatc caaatccatt   41580
tcttcgtaat tgtacggctc ggggatatta ccttgtgcca agaggatttt tcttcagcc   41640 atcaaacctt taaagaaacc gattaccttt tcgcggtaaa tgtccttatt taagacagtg   41700
acttgaacta tctcacccctt aggcgattgc tgctgctccg actccaacaa ctgggctagt   41760
tggctgctca ttattttctt ccttcttagc aattttatag aaacgattgt acgtttcttc   41820
attaatggtc tctacaccat tcgcaaaact tggtacgaat ccttcaatga tgacagggat   41880
tttgtacttg gttgttagcc aatggtagat gatgtcacgt tcatcgtacg aacccgtttg   41940
attaatttca gccgactttt catcgtactt attaatcatc gccgttaact tcagggtgat   42000
tttaaaatta cctactggtt cgaatacggc gtctagcatc aaatcacttg catatcgtgt   42060
```

| | |
|---|---|
| gatgccaaca tttcgatat cttgtagaat aacgcgttg atgaagtcag atgggatgtg | 42120 |
| acggtaagtg aaatggatca atcgctctat aggtgtagca cgttcaatct ttgctgtgaa | 42180 |
| taatcccttc tgaccgatgt cccaatgaat gacaccgtca ccctcccccg agaacagttc | 42240 |
| caaaaattta agtcggattg attcttcatc agagaatact ttggttatat ctgccaacga | 42300 |
| atacatgaat ttattttcct tctggctagc acttactttt gtggttcata ctatcggttt | 42360 |
| taaaagttta aaaaaataag gagggggcga accccttcg ttattgttta atgaataacc | 42420 |
| ctagtcttag gttatgcaac ttcaccaaaa gtatgttatc cttgaaccct acgactcgac | 42480 |
| agcgattggc ggtgtaagtc attaaccaaa atactttaaa ctccgactct gttagtttgg | 42540 |
| agataaattg tgctaccttc ctgagctttt gatgctgaac tttagacaat ccagggaaga | 42600 |
| gtacgtggtg cggcaaagaa ccttcgtaaa cttgatcacg gtggattgtc acatatggcc | 42660 |
| acgattcatc tctgaatgct tgcatttctt tatactgcgg taacaagtcc atagtggcgc | 42720 |
| tcaggaactc tctgagacac gatataacac gaacatattc atttgtatta agttcataaa | 42780 |
| gatacctag aaacgactta gggttataat caatatggtc caggttaccg atagaatctt | 42840 |
| cgatgtagat agatttgaac ccgaacatat tcaataggcc ttttcctcg atagttaact | 42900 |
| ctgtgaagca gctgtcttct gttaacttct ctagagcgtc gcgtatgttg ggatatcgtt | 42960 |
| caatcaaatc gatatagttg tttttctcgt tggtgctgta atacttacga ttcattttaa | 43020 |
| ggttcctct agtcaaccca aaacaaacca cctattcaaa aactgctacg ttgagtggt | 43080 |
| gccttggtat attcgaatcc atcatccatg ggactgaata gacaaatact ttcggagcaa | 43140 |
| cttccactgc ccccttcttg atgttttcat cggttaccca ataatccaat tcttcacgag | 43200 |
| atctctttgt gatagcaggg actaaaactg acaccgttaa gcaactaggt gcgatgtcaa | 43260 |
| actctttatc cgctatccac ataggtggtg cctcgatgaa aatagaatct acatatccag | 43320 |
| ggatttgctt ggatagaaga ttggcaatct cgacaatatt catacgttta aaaattcctc | 43380 |
| gattaaaata aaaaatagca gggagcgaac tccctgctaa ggtctaattt acccgatatt | 43440 |
| agaatgggcc gaattcacga tcgttgtagc gttggttgta accgaccaat ttcactttag | 43500 |
| aaccttgtag tgtttctagt tcagccagag tgatgaattt gttgttctca acattctggt | 43560 |
| agtagctaca gcagtaatgg ccaaagttac cacgttcgcc ttctttaaca tggtctttgt | 43620 |
| tgaactgttc acgttcaaag tgccagttgt acaaatcacc tgcttcaatt tcaagtggct | 43680 |
| tcggatcagt ttgttcttca acccaagctt ccaagtcagt tgcagggac aggatttcga | 43740 |
| ttgaagagct cttgttgtgc cagccacaag tgttaccaac ccaaactttg tcctcaccac | 43800 |
| ccactgcatc agcgatgata gatttcacat tgtccaggtc ttctacagat gatttctcaa | 43860 |
| cgtgctcgtt gtatgcattc accagaacat ccagctcttc tgtgtaaggg atatcttgag | 43920 |
| cgaaggccga gtcgtagtaa gccgcacaca gtgtacgaag agaacgtttg aagctgttag | 43980 |
| tacccatacg gtgcattggt tggatagcac ctagttcttt ttgacgagca acgtagattg | 44040 |
| aactgatcaa gctgttttgg aacaaacgt cgatttcgtt aagcaatacg cgacgttgag | 44100 |
| atttgttctt ggttacagcg ttcgccaatg ttttcatttc acgagatgac gctttagccg | 44160 |
| cagcaacaac aagagcagaa gcaagtactt taatagtgat catgggtcat agttcctttg | 44220 |
| tttaaggtat ttgtagagtc ttctaaacca ataggtgac atcctaagaa tatggatagt | 44280 |
| cttagagtgc cgtattcctt ttccttaaa agacagtcga tagactctgg gatacaagtg | 44340 |
| tgattgatga gctcgatttc ctcgtcagaa acatcaccga ttatcacacc catagtatcc | 44400 |
| tcttgagcgt tagaaattgt tgcgatggtt aagctgttag cgtcaccacc tccttcaacg | 44460 |

```
tattcgtcaa tggtctcttt caccgaaaga cgaacgtatt ttaagtaatc aagtaggtct   44520
ccacccatag aatcaatttc ctacgtaaat aaaaactcac ttttcttcca ttacctccag   44580
ggacattcta gaggctacac ttttgactat acccggatag tcgtgttccc taagagcgaa   44640
accagttcca gcctttaaat cttccaactt gattaggtgc ttatgttgat gttcaatata   44700
gtcccaatct tcaaccatgc gtttacagca ccagtcgaaa gtttcatctg agcaaattcc   44760
ccgtgcttct ggatgcaggt aataaagata gcttgaagtt aagaagcagg ctataaatga   44820
ctctgtcttc tccagctcgg cgcgagtcca gtcattagat gacttaacac caattttacg   44880
attgacgtgt aactcatcgt gtaaaaaaga ctcggctaat tcactacgct tctttaaagc   44940
ttcttcaagg gtatccctca aatacacagt catcttgtat ttagatttct ctgtatgatt   45000
tgcctgcatc acagttgaac ggaaacgtcc attctttaac tgtgtttcaa actcttcctt   45060
tagcacctcg gcatccttcc caataccgag gtagaagtgt ccactggaag tattcttaaa   45120
actgtagacc tcgaatgtca tacagtgaac gggtattgaa tcttcggatg tgggttatag   45180
tccactaact cgaagtcttc gcgtgggtgg acccaggtac gtagatcttt cagggtcttg   45240
atttccgggt taatcaacaa ccgtggcatt gggcgtggct cacgttccat ctcttcttta   45300
aagagttcca actgattttc gtatacgtgg taattcgaat gggtatgtaa agcactgcca   45360
cccttattac ccgtgatttg ggccatcagt cgacctagga cataaacctg tggtagattg   45420
gaaacgacgc caagtggtgc atcggatgag cgctgtgtac tgttgagata caaagtctta   45480
tccaacaatg tgaagtggtg tgagtgcaaa cacggacgca gacaccctag atggaacata   45540
ccagggttcc agaaagtcca gatttcacta ccatcatctt tacccgcttt aagattgttg   45600
taaatcttat ctagcaggtc gatagaatca ctgtgcacga agtctccact taacccataa   45660
ggtgcatcga gcttaggcca gttgttgcct acagcaccat agacaatacc catgtcgtta   45720
tcgcctttac gattcgggtt atttaaccac gcttcgtttt tattggcatt ggcgtgccaa   45780
ctaggtgcca tgaagtcttc aagtacctta gaatccgttt caccgcgtat ataacacaga   45840
agttcaccaa tacccagttt aatcggtgac tcgcgagttg tgttgagtgg cacgtactcg   45900
gtgcttaaat cgatgttaaa caccacattc gggatggtta aacgtcgagc gttatttcgc   45960
tcaaccgtga accacttacc ttcttttaat agacgcttac cagcatcctg atactgtgta   46020
tcaatcattg ttccaatgct ccctgagttt tactaaagtt tacttcaccc ctggctttca   46080
aaagcgcaac ggtgttttct gtgattttga tggccacgtc aacatactgg atgagtacct   46140
cggctttgtc ttgattcgtc ggtgtgtaaa caaacgttga caaaatgtgg gtctcgaccg   46200
ttgtcgggat ttgatttaga ttaagttgga cgtctgctat cgcattaccc agttctttaa   46260
agaactcgcc ttccaattcc ttattaatat caagatgata ataataatgg tcaacatcac   46320
caggtaactc ttgaagaaac ttattcacct tgtcacctga tgaataagaa ccgtcaaaga   46380
gtagaagaga cgaaggatgt tgttgaatgt agtttgcgac gaatgctaga cagtcagccc   46440
gtgtcatgct tggagtagcc attgcgagtc ctcagctaga cgtaaacaat cacgcttgtt   46500
agccacggca ataccttggg ttaactcgtc gatggttccc gtactgatat aacctagttc   46560
cttatataga gctaggtgat cagagattac ctttggtaga gaggggggttt ctttaattaa   46620 ttcgttaacc acacggggttg gtaggaaaca tagaggactt ttatccgcta atgttttcag   46680
atagtgtggg ggttgaatat ggcctgcaat gatattcaat cgtgaattaa tcatacccte   46740 gataccgaaa ccgaacatgc cgcgaatttg cgccatcact ttagtaccaa aacggttctc   46800
```

```
caaggtgtgt tcgttatggg ccataatctc cagaataaag aatgaacgaa tctgttcttc    46860
tctcaattca ccggagtcaa tgaagtcacg ttgaatgaag caactagtca cttcctcacg    46920
caccgtcttt agacgaacgt atcccgtgga tggatcgtaa acgaagttac gtgtctctaa    46980
cttgatactg attcccggcg tgtgacgggc aacgttaaca agcatgatgc gtagcgcttt    47040
acaatactcg tgaatttctt taccgtagtg tttgataaag gctttgtgta acgccttata    47100
actggtgcct ggtttaaggt tctcgtataa gaacaaagca gcttcacgca atgcctttgc    47160
tgttgttaac ttgtacgtct ggttattttt ttccacgcgt tcaaaggctt tgttgatacc    47220
gtcttcgata acactcggtg gggttaaact atctactaag accattgttt tactttgtcc    47280
ttatctgatt aggtcgtaag cttctttagg gagataacct tcaacagcaa tatcatgcac    47340
tagctctttt gcacgaatca agtccccgcc atgtagtaag ccagcgcgga aaaggatttc    47400
aatttctttt ctagcaactg ccactaagcg attattcaca tggggtttgt tgtaggttga    47460
gagttgaatc aggcaacgaa tgaacgttgg cgggagacca gaataaccat ctgtgtcttc    47520
cggtttaaac aaacgcatac cagactcata ctttgccaca attttactgc ggcgattaaa    47580
atgcggacct tctttgaaaa agccaaagat atgatccaca tagctaggtt cgcgatagaa    47640
tcggaatact ttatcttcgt gctgatttaa agcagctttg aatatttctg ttttggtagc    47700
cgtactagtg gggtgggtgg agcacattag actgtccatt acatcacact tgaaacggaa    47760
atcactaccg catactttga cttcgcccgt gatagggtaa atagtgaaag cgtgtcgtga    47820
acgaatagag acatgtcttg acatctcatc gttattacac gttcgaaata atcgcatcat    47880
ctcatggtat tttgcgcggt aaagaatcgg gtctttgtgg cattcgacat agagagcttc    47940
ttgcaattct tcgaaacttt taataccatc aagtagtttc agatagtaag cgtgttcttc    48000
accaaagtta ctgataggcg accaagcgcg ttccaccatc tgtttaaaga aatcaagcat    48060
acgcgccccc attgcgttca cggaaagatt taagctccaa ccattcttct ggtgggaggt    48120
tgagtagatt actttggtta aacacatcga taagatgatc gatgctttgc gacacatcca    48180
ttgtggtatg tggtgctatt acccagaacc atgagcattc attaccatcg gcgcattctt    48240
cgataaagaa gcgcatcatc tcaggaatga actcattcat aaactttgaa gtgactttcg    48300
gtacaacacc ggattcgaag ttgtaataaa cttcatcatt cgttttgtgt aagacacaaa    48360
ccgtatactg ccaatcccgt tcgatggtct tcaggttctc aacgaataaa tcggccaact    48420
catctttctg cttttttattt ttgcaacgct cgaataccaa ttccatattg aatgtaatcg    48480
taccagattg tttagaagaa ccgatgtagt aatcacgtag agtgcgggcg atagcattac    48540
ggtataaaat tttcatattt aaaattcctt ggttgttgtt aaacgatgac attaattaaa    48600
ggtgtacggt atgtgcgttt tacctttctg attttgtttg gtgatttgca tccacctatc    48660
acacgctccc caactggagc agcacgtaac ttgagaatag ttttcaactc ttccacattc    48720
acaaacattt aaaatttcct catggtgtat taccattagg ataatatata actgttttga    48780
attcgagttc gtctactcca tgtgaaagcc acggaacgta aaaaagaaa aaaaataag     48840 gaacccgatt gggttcctta cattcactac aattgcttag caacctttcg gtttcacaat    48900
tgtagttggg tcgatgcctt gcttctcagc gtctttcact tgttggcgat acattgtaca    48960
tttaccaatg ctgatattgt acgcgccaga ttctgccccg gcgttaccac ccattgctgc    49020
tgttgcttga gatgcgaatg cgattgctga tactgctgct acgatagcga tgatgttttt    49080 catgaatgt tccttctaat tactttgttt gatttaagat tactttgttt ggtattaagt    49140
ttgtttgtta actactgact tagcagccag caggtttcac gattgttgaa gtgtcttggc    49200
```

```
cagcttgttc tgctgttttg acttgttgtt tgtagattgt gcatttgcct acgcttacgt    49260
taacagcgcc tgagtctgca cctgggttgc caccaagtgt gccgcctgct gttgcgtttg    49320
ctgcgaatgc gatagttgcg attgcgattg ctttagtgat agtgttcata gtgtgttctc    49380
tctatattaa gattaaattt aattaagtat tttgattata aggaatgatt catcacacct    49440
tattcactaa aataatatat atctgaaatt atttggaatc aacctttaac ccatataggc    49500
caaagtaggg cctttgcagt aatacgtcgt aaacccacat tagggtactt acaatatatc    49560
accacccaag cccaaacaaa taccacgaag taaaagattg acaataccccc tagtacaaac    49620 ttaaataaca tttttactct ttggtttaca tgcaacaatt aaagaacagt aaaaaggttt    49680
ggctagattt ttcacccatc taccttccac cattttactg tgacttagga cccatagtaa    49740
aaacttctct agcttagttt cagggatgag gaggtattga ttttcctcct ctctaaagtc    49800
atttaaattg acgatacgca ttatccaaag aagctttcca ttggaccgat gccaggcatg    49860
tgatcggcgt atagtttcga ataacgctct gctcttactt tcgatttgaa tgcacgtaga    49920
tggcactggt tagggtcgaa gtaagtggat tggaaatggt ggatatttag aacaccgtgc    49980
atgttagcga tttctagcat cacacccttt gttgggaaat ggtatttggt aacaacaacc    50040
caacgtgggt ttttgcattt tggtcgatga tgaccgaagc ctaacttctc catcagctct    50100
tcgctgtatg gtaggatgtc ataatcaccg tgttcacttt cccactttgg tttcttttcg    50160
ccttcgtaga aatgcacacc aactgcttca gtggaggtat tatagaaccc cttcactttg    50220
gcttccatca caggcatacc tggttcggtt atatagatta cacgaccatt gaacaaatct    50280
ttaaagccga gacgaatatt tttagttttc attgaaatga tttccttttc ttaattagga    50340
atatgggttg atgatttcga ctttgaaagc aatttcctca gtctcgtttt tgattctgaa    50400
agagtaggat tcgtgaccca ttaccttctc attcatggtg gccagttcct tactaagctc    50460
ttcaccgaac tcttttgaac actcggttag ttgaaccatc gttaattcgc tgaagtaagc    50520
cattacgttt tctgttggtc caacaaaaga catctcaaaa tcgtcttgtg cttttcttgt    50580
ccccaatacc attccaagta cattggagtg gaagtccatg attaacttgg ttctcattac    50640
gactccgtct tcaggatttc ttcaccacaa cattcgaagg agccttcatc atacttctgt    50700
ttcaagaaga taaccatatc catagagtag tcttttacctg cgacaaaacc cggatcgtta    50760
gttgcttcat ttggattgtc agttaaagac caaacatcta cttttttggcc acttcttatt    50820 tcatcgacgt ggttacgtat gtacttgccc gttttgttg aacgcatgaa catcttattc    50880 attttttctat cttgtaaact aatacattgg tggccttcac attgtagtgt atgccattat    50940
agagacagct aacaaatgca ccgtaagagt tgatgaatgg tttcaccttc tctattgatg    51000
cacccgcagg gatatctggg gttttcttag ctatcgctgt agcaatatca gaatcgttac    51060
atcgctccac tacagtaaat gtgcagtcgg ccagaacatc tttggtccat cgaccatttg    51120
cgaataatgt acctaaaggt gacatatcac tcttctccca tttcggcata aagaataatt    51180
gcagagactt cgaataaggt ctcgccacat ttgtaagaaa actcagcagc gttgtgttgt    51240
ttaatccctt cttttatctt actcaaacct tcgttgatta gctcgactat ggatgggggc    51300
gtatcgacat cgaaagcaac gttaatgcgt tccactaaac atcgtaactc aaccaaattc    51360
ttcgagtggt aatgaacatc caaataagag atagggaatc catcgctatg aatgaactta    51420
acaaagttac tgttaagttt tagcatgaga cgaagattat ccattaaaca actccttcaa    51480
tgtcatgttg ttcttagggt cgaaggtttc atcgtaccca tccataccag gtaaaagatt    51540
```

```
tttgttatct ggtagaatga tgcgcactaa tttaagtttc tcgatgtcgc caaaggtatt   51600
gatatcgtag aactcatggt tttcaggtag agtgtcaggg acaatgcgta cacgacatgc   51660
ccccaccata ccacgtaatc ctgcgttcct aacaaagact tcttttggct cagtgatgct   51720
gttgatgtcc acattatcga gtacgtattt aaatattgtc gcaatggcac caacaccaac   51780
aaatttgctg acaagtacca catcagtatt attaaacaac gagcctgtaa aactgaacat   51840
gaaattctga gtaactaaca tggtgagttt agggtcagtg tcatgcataa gtatctgttg   51900
gcgagtctct tctctccaac gggcaatatt gtgagctgtc ttgcactcat cgcaaattag   51960
tatctctgtg ccaatagcca atttgaagac tgaaacgtct gtcatatctt ccaccaacac   52020
gacattacag atcgggctga tattgtcccc ggtttgcaaa tctttgatgt gcttgcaaac   52080
caacgcacca gggtatgctg ctttcttcat tttaaaattc ctctataagt atttactgga   52140
aaggtttcca acatatggt aaacccatca caccaagttc tttgaagtcc ctgatagaca    52200
taggaccttc gacatcttct aattcttcaa ctgagaatat gattttagc tcagggtttt    52260 ctggtagggg ttcggtatca cgccatgcaa aatccacgac ttctttattg tcatctaata   52320
gagattcatt agcgcgttga acaccacagt cgttcatttt taaaatctta cctcgactat   52380
ctaaacgtct atcgccgagt ttgaacagta ccccattgcg cttccatgtt tctacagtag   52440
ccatcgtatc ctctaatcga ataaaaaata aagggagca gaagccccct taacccttac    52500 cttttgccagc tagtttcaac agtaacatcg gaccccagat ataaatatgg cgtatccatt   52560
gatgtttact cttcggctca cttaatagta tcaccagtaa tgcttccgct aaaccagcat   52620
agatatacca ctcgagtagc ttagcaaacg caagcatcgg tatacaccca atcttgagaa   52680
agtacgaagg cttttacttc ttcgaggttt aggtttggcg aagaaagctc catggttttc   52740
tgtggtttga tgattaggtt cttttccgtca actactactt cgccaacgta gagtaccaac   52800
tcaccgattc cgtgtttggc tttaagcttt gtcagttctt tttcgattgg tttaaaatca   52860
gaacgttcaa agctggaggt tggctccagg attagatgtg cttttggcat atccacaatc   52920
caacgaatgt tttcaccatt gtagtaagcg atgtcgtttc catatactgc tttgttcatt   52980
ttaagttttc cttattactt aactaggttg tagagttttt gtacgatgat tgcttcttcg   53040
gtggctaacc agcaacgtcc attttctgtg tagacgtttg ctatcagccc ccagatttta   53100
aacttcatca aagccatgtc atttgacttt gagccgacca cgttgacacg tgcaatatca   53160
cgcaccttgt aacgatttgt ggcgatgtcg attagatact cgacgttctc cacggtgaga   53220
ttggataata tgctatggta cttggcaata tcaactgcgg taaggtccaa accagtagct   53280
tcgttaatct ctttacgaga cttatcctta agtccactga tcccatcttt aattttcgat   53340
tcacccaacc acatagagga ttcgatatcc agagctacag tatcgtcatt tgaagaaaca   53400
ataaccttga ataactcaat gtgagtttcg ttacgttgca tgtaattaag gcggcaaagt   53460
aaggtatcaa tgaataccttt agcggggtta aatttggtga attgcataaa cagcattttc   53520
tttttccaat caaccaacgc tgtgtttact tctaggtcac aattcttttcc gcagagaaca   53580 atccaatcat tcattcgcaa accgactatt ttgtcgacta tttgagaatt aattcggatt   53640
ggtgattggt cttcaatacc aagctctaag cggattgtgt taatatccaa cgattgtgtt   53700
gtttgcataa ttcaaaattc ctcttcatgt ttacagtagg gtttagtttt taaacttggc   53760
gtatcgcgat gccactttac gttttgtttc tgttaactca tcttttaaaa ttaaagttac   53820
acggttggct aatattccat ccagcaacac atcgtaattg tcgaacttttt cctcgtcaga   53880 gataagaagc tgtaatccgc caaccaccga aaccttttca tcagcggtga cgacttcttc   53940
```

```
taacagctct tcaattaaat taacatcatc aatagcgata ataatacgtt ccataaataa   54000
ctacttatgt tttccaggtg tgaaagttaa ggggccatcg tcgacaacag taatcgaatt   54060
gattccgaca atatctagct cgtgggcgag taggagatta ttctttcttg taaggtactc   54120
gttggaatcg acagctaatg tgtcaccttc gaaatccaac atattgtata gcttccagtg   54180
gattcgtgat aactcttctg cgaactcttc aattttccaa cttcttttga tgttggtgtt   54240
tagcgcagta gagctcggtt tgattttctc tattaaggaa agatacgtgt caaattcagt   54300
attgtttaac tccaccgttt ctcgtttacc aacgaggtgc caacaagcag tttcaataat   54360
gaataactct ttggctaacc cttcccctaa caaacccaca taacgataac tcgcgcctaa   54420
catgtggttt ggtccgacga tcatcgccat ttcttttaat gtgagttctt taccattcgc   54480
tttattcttt aaagcaaact cgatcgtttc tttaacagtg taacgtccat cgccgtatttt   54540 ctgatattgt tccatagtct ctacctcccc ctgtataaga attgttcggg gcgttaaata   54600
aaagaaaccc cctatcctct accgaagtaa aggagagagg gagagagtcc atatagaataa   54660 catatacccg atattattta gaaccctgaa caccaagacg cagatcttta aacattgctt   54720
tggcgatatc ttgcaatgtg taatcatcgt tagagtcaat aggttcaacc tgattaatgg   54780
ataagtatcg catggccatc agaagtatga atcgagaatt agcacgtagg ccgtcaccga   54840
catctatacc agtctgttta attggttcct ctaactcatt aagataagtc agaagggcgt   54900
cgtcgaaggc tgtttgtgcc accttgagtt tttcaatcac cccggctgat ggaggaagat   54960
tatcacgctc agggtctaac atacacctca cttcataatc acacatctcg ccaacaccga   55020
tctcgtttaa gaggacagcc gatgtcaatt cgacgttcat taatccaact aaagccttttt   55080 cgaattcccc agggtcatcg acatcaggtc tttcacttga atctattaaa ggccaatact   55140
tcatcgctat tgcggtgtat atatcgccac tagactcacc gtctcgaaca tactggtcca   55200
tatcgagctg atctaaatca aataaagttc ttgctgtggt agttttttggc ataacaccc   55260 ctattgaaat tgtaggtgct gatttcgtca caataacgaa acacactcgg ttaattcaac   55320
cgcatcagct tcttccttag tcaatataaa accaatgacc tgtgatgggt tgttaaactt   55380
ggcggttctt tcaagggcat caaggttata gtagttcctt ggcagtggta gtacttcgac   55440
gccatatggt ttcaaatact cacgatactc ccaaggttcg gaactgtaaa ccaagtctat   55500
tttagactca ataataaaac gaagatatcg gtctctatct tttttatact cctcaaccac   55560
ccaaactttg aatttccctt gttgcatgga gaccctcgat aaaataaaga agaagggtgg   55620
agaatgaact ccaccctcta acctagagt taatcgaaca tttcattgaa ggtatctaga   55680
acttcatcga ccaagtcgtc tttgtcctca tcaccctcgt aatgaattaa ttcgatatcg   55740
tgttcatcgg caagttcttc acaagctatt tcgtaacgcc tattcagttt ttcccaatta   55800
ccgcggttac gatgcttatc agtttctgtt ttatcccaat catcaccacg ctctttatga   55860
cgacgtaaca tggttttatg atctaaggta agtagaatag tgatatctgg aatcatgaaa   55920
tcaacatcag aaatgtcgat gatgtggtct tggtgcgcgc gggttgtagc aacataacgg   55980
tcgagcaaaa ctacgacatt atcatcctca ccatatgcct cgtttaaaga gatagatttc   56040
tctttgaaat tcagctctag atggtgtgat actttgtagc tcgggtcacc ctttgctaaa   56100
ccttcacgtg ccaatttacc atggccatca ttcgaaggga aaggttgtac aactacagtg   56160
taatcctctt cttcgaaagc ggctttgagt ttttgatta gggtggactt accggagtag   56220
tctacacctt ctacgctgat gattcgcatt gaacattacc taccttgatg atgacagaac   56280
```

```
gacccagttt cttgccgacc gtgcgctgaa tttctttgat tttactttcg ctcaacggtg   56340
agggtgcctg ttcgattgta aatacatacg gttgttttt agcacgcggt ttttgcttac    56400
ggtgctcatt caacttatcg atgtcagttg taccatctgg atttagacca accacttcga   56460
tatccaaacc caagctgacc aggtaacaca taatcgtgtt cttagtacgg aaatcgttat   56520
tgaccaaaac caagtcgatt tcttttaatt ctttgcgcat gtattccgca gggggggattg   56580 tcactttccc attgcgtgaa atgatcgctt ccaacgcctg tgtaaccaat ggtgagataa   56640
ccccggttag ttctttgaat gggaactgct ccattccaac taaagcaata ccacgggatt   56700
catggttgat tggacgctgt gcattttttc ttagtgatgc tttgtacgcg aagatctttt   56760
ctagttcttc ttctgttggt ttgtttagat caccaacttc aacaccgttc tcttccatag   56820
ctaggcgaat accagcgtac agtgatgatt tacggaaacg gaatggtccg atacggaact   56880
ggtctttggc ctttagattg acaggatttt gagtatcctg actatattgt ttcaaaagca   56940
tatttagcga tggcattatg ctatttcctc atttctgatg taattgtaat tggaggtgtc   57000
taacttaaac cgtagcccgt cttcactacg gtatccagtg aaataaatgt tagacagatc   57060
ctcacacgaa tcaatactta ttagtgactt actaccctcg agtttcacta aatgggcccc   57120
cgccctcgaa ccttcttttt taggaaagat aggtttcggt attggccgaa taattaactt   57180
agcgccgtcg aagtagaacc cgtccgtcac ccatccggtg tacccaacta ggttttctcc   57240
tcttggtatc aattctgtga tgtattttc ttcaccctca acaagatgtg ttgaaaaccg   57300
ttccgggtgc ttcaaaatct ggtacacaag ctcttcttca aagaaccca tgaatcttcc    57360 acagatgata tatcggcaaa gtaaattatt gttgttttta acattaacga gactaacgtg   57420
gttaccgagt aaccttccgc agttatcgcc tctatcaacc caatccttta aatccttaac   57480
aggaaattta ccacggtccc agatatgcaa ttcatttcga gttgatagca acccaatcgg   57540
atatctgtag ccgtaatatt ctccttcagg tctctttaag agaggggaga taggtttaag   57600
taatttggca tcacctagcc gaatcttctt gatgaacgca ggtatagtga caacccttttg  57660 cctacgttca gcttgaacct caattaacgt gtcaccgagt gcaggggcgt ggtagaataa   57720
cccacatccc ttcaggatag catcaactga tttcgggtgt ttaatagcca tggttaaatc   57780
cttaatagcc aagagatgtt tatccggcta catttgcgat cttcagcgt aatccaaaag    57840 tactttaatc gaccgcttga tgcaagagt catagcatct tccacatcca acatagcctt    57900
taattgttta gccgtgattc gcttatcctt ctgagatagt ccctcatctt tcattttctc   57960
atacaaatcg ttaatggcgt tagataatgc gcctccttct tttaggcgct tgctgtaacc   58020
gctaataaaa tcagataagg cttctttcac ctttttgtat tcttctttag ttagcgctgg   58080
aatagtcata tcgattgaat gttttgggta aaacttttta aatgggatat ccattatatc   58140 ctgaaccta ctggttggcg ttgcgccgaa cttaacggtt tgtgtaccgt cacggttcat     58200
atcgatacaa actaggacac ccgatggtaa tataaaggct gtaatatctt ttccgatata   58260
tagacttagt ttaccagcga gtatcagggc acgagcatca gtcacattga cttcccgtcg   58320
acttagcccg tctacttcca aagcagacat ccgtgttggg gaactaaagt cataactgat   58380
tatctctcgt cttgctgaac cttctaatgt tttaggttca tgtgcgaatt ttaaaatatg   58440
gtccaggtca accttaccct tgaataaag aggaatagac catccgaagg ctttaatctc    58500
agcttcgttt aaaagtgggg tgtctgggag tttatcgtaa cgtcgcttaa acccctctaa   58560
accttgggaa taacgtttgt attctctccc aagtttggcc attctctctg cgaaccaaga   58620
cttcatatcg tccatcagac cttcactggt aatgtaacga tgacccatc gattggcaag    58680
```

```
ttcattcatt accaattcct ttgctggatt atctgattga gactctatgt cacagagtaa    58740
ctcatgatcc tcacaaagga tatcaaaatc actatctaag ctattcatta ctgatttctc    58800
ctattgtgtc tataggaaaa gccaaaaaaa acaggggacg gggacaaccc cgtccgttaa    58860
cctaagttaa caatacgaga acgaatctcg tttgccaaca ttaggtgtag agcagatacc    58920
tttttatcta cgatagtttt agcaaggtat tctgcacggt ctgctttttt ctttaagaat    58980
tccatcacgt ctacaagtgc attaccgtaa cggtagatag cttcttcaac aatgtggttt    59040
actttagttt ctagagttaa tgttttcatt ttaaaatttc cttggtgtta tcaaatttga    59100
gaggaccctc gtttggaggg tccttgtaaa ctagtgttta gtttacttcg tcgtcgtggc    59160
gagtggtttt ttctttaact agattttga acagatgttc gtgtttagcc gagatctctt    59220
ttaactgtgc tttgaactga ccacgagtca gtgacatgaa tagtgcatac actgaatcca    59280
tcacaggcat gacggtttcg aagatagcca tttcatattc gcagatggca gccagtagtt    59340
ccggtgatag ctcgatgcta aggtcgaact ccatggtgtc tttgattttc aaagcgtagc    59400
ccaggttgtg gaaagagttt gtagctttgc agttaatttc cacataggag aatagtttct    59460
ctaccatctt gtaatcgtct tcatcgacca tcgcacccat gttaggcaat gccttgacaa    59520
agtcattttt ggcatttagt acagatttaa gatgtgcgat ttcttgtgcg tcgataacta    59580
gtttggttgt tagtttcatt atagatttcc tctttgacag ttaaagtatt tgtactacat    59640
tcactaagat aatatatatc tgaaaaaaat tttattgaga cttgagtaaa aaataaaaaa    59700
agagagaccg aagtctctca gttattatct attcttcgta gtccaacttg ccttcgacta    59760
gcgaattaat ccacaggcca aagacatcgt tttggaataa ctcgatgtct aactcgtccc    59820
actcatggtt aatgtgaaga cctagcaaag tatttatttc aacttcgata tctaccttgt    59880
ctaaatcaaa atcgtatgta agggggaacat agcgctcata attaacataa ctcattgcgg    59940
ccatgcgtct aagaagaaca tgctcaactt catgaaatgc agttttgtcg acagcgaata    60000
gggtttcacg aataccttcg atgaaatcca taatgctttt cgctgtgctt ttaatgcccg    60060
ctgttgcttc aaacaacgat gaatcagata accaatacat ccgagtgtct tcatgagaat    60120
accatgacag tgcatgattg acagcaatgt gaaagttttg acgcttagcg catgttagtc    60180
tatcactccg agcatataac tcgacgatct tttctgattt atctaggaaa ccccagacac    60240
gtaatgaact atctcctttg attaactcgc ctacaaacgg tgtgaggttt atttcgggaa    60300
tggtacgctt ctctttccag cttgagagga gtagtgggtc ttcgtcgttc ttttgtatct    60360
cggccaaacg acctgttgag aaaacaattt tctctatttg gtgttcacga acttgaatag    60420
ttggtagggt agctatactc aatttcattg tttaaaattc cttgttataa aaaagaaagg    60480
ggcgtttttc agcccaaga gagaacaccc cttatgcgtt aggggtaatg gtaaagaaag    60540
cctcgccatc acgttcgact gtgaacattg gcaccacttc tttcgtaggt ttatcaaaga    60600
cagcaaacga aatacgatta atcgttacca gcgtttcatc gtagatatag ttggtgtcgt    60660
ctatagtgac gcgattagta ccgtggtcgt aatcacggta atcgattaga aacgaactct    60720
ttgtcatgaa tgtggagaag ccatcgtaag gtaacccgtt acttgggaac accaagtgag    60780
tttccacagt ccgcaagttc tgataatctt cacgcccaaa caagtaaacg atgctgttaa    60840
tgcgagcttg gactttatcg ctaacagcca ccttgttctt gtagagacct gggttatcgt    60900
tgaaagcagg tgaccaaaca aaacaacaat cggtattttg tgtcatctgc tcaagttcgg    60960
ccaagtattt acgtagccaa attgcccggg tgatatcttc cattgttaac ccggtgtttg    61020
```

```
ctaatcctaa ccatccttt t  gcgcgcttaa cttt gagggc tgtgccaagt tctggaataa    61080
gagtagggag gtctcgattg cct tttgttg acacgatcga ggaacgtaac cacgat ttga    61140
tttcgtcact gtgattagat tcttcgatct cattagtaag aatctttttc gattcgttac    61200
caccacgcca aacattgatg tcgtcagaga aatcataagt cacgtcgaag ttaaaacaat    61260
ccaaaaacag ttgtgggcat tcggtgttga gtagtgtttt ctcttctggg gtaagaatat    61320
gcataataga catttaaagt ttcctt ttgt gtaattaatt cattaagata atatatatct    61380
gaatagggtt gggttgtacg atcgt tat tt ttaacttcgt agact tatat tttgaccaaa    61440
tagacagggt acggggga aa gggggttata tgagat tacc ctatatcctg ttatacccgt    61500
accatct tat ctgattaaga aagtacctta cccaact tag agtaattgag tttaggcaaa    61560
gtacct ttct ccacatacac gt tctcttct aaccacttat aaaccttagc ggtgtggggg    61620
ttaagaacag gtaaccctgc ccaaatttcg atctccaatg gaagagtttc ccaaggtttc    61680
ttacacttga gtgactctgc accgtaaagg tcgtagacta ctcgcttgat ataagggcga    61740
atgaatgacc cacaatcatt aacaagcaac caacgctcag cagcatctgt aaat ttagtt    61800
tcgtcaccga ccgcgt tatg taggtactgt ggtat tgtcc acttccaacg catcgcatag    61860
cgcattttta ggatgacaac gaatctctcg aatttcttgt tttgtaatgc gtactgtaag    61920
atatcttggt acttgctcag ctgtagcaaa tccatttggt aatctgccat ttttaaaatt    61980
cctcttagtt ttgatgtact gt ttgtacat taatgtaggc tttggtttca cggtaatgtt    62040
tgaccgagcc tattaaataa cccaagtcca aatactcctg gacctgttcc tgtctaatcg    62100
cttt ccaat t acgactat tt cggttttcac gccatgggtt atgcatcacg ggtttgccgt    62160
aagct ttgac tcgaagatat cgaagatcgg gtatctcgat ataatagtag ccgttgctca    62220
ggtaagctgt tctccaaaca gtgggcatca ttggaaaatt gaactttgct agtgcataat    62280
ctgtcatttt caattcaact aat tcatgct tgctgttagc taagactcta cggaat ttac    62340
tctctgtgat tagacacatg tcttgttttt taggtctata cgacattacc ctat tcct ta    62400
tttat ttacc agacgatgtt tcactctaaa cagtgtttga agtttgtcgt tgtctacttt    62460
attccaaagc tctggtggaa ttcttccgac cggggtcccc tcaaaatcta acttccctag    62520
gttgtatgat ttgtcaagat gctccgcttc ttcagataag acgacataag agtttgggcc    62580
gatgtaacca tcgacaaata aacgtttggt taaatcacca aacggactcc tagttagatt    62640
taaagttctt agagcattag actccttccc tttataacct gatacaggta ggaaccacca    62700
gtaatccaac cactcattac tat tggttaa tttctcgtta tcataaaccc accctagcat    62760
cttaccagat agtgaaagaa aatgaacagc t tccggct ta cttaagtcgt aatcaatttt    62820
ggatagtgtc caagagccac tgataacgtt aacaaataca gcaatgggtc ccgggagata    62880
ccaaaggtgt tgtt tggaac gttcagcgaa agtctttcca ctgtagattg ggtgaggttt    62940
agt tacagtg tgccgttt ct tccaaagt tt ct taaactcc tcccagtgtc t tttt tggacg    63000
atacattat t ccacccct tc taaaaggacc agccaatcca catcgtactc aaacactgca    63060
ccgacagatg aaccttctgt catcttcacg tagatggggt aacgactacc cggatacaac    63120
ccacgtgttg cctcat tcaa acgatggacg acaccgatgt gatctgtgcc tttcacactc    63180
acact tttac caacgt tggt ttcaaaccat aaacgctgcg caggagacgg accaccttct    63240
tcctcgccac cctttaggaa atcaaccacg ccttccacat tacccgtttc ttttatagcc    63300
gccaaacaaa ttccggctgt tgctgaatca atcattt ctt tactcct tcc atagctgtgt    63360
tgataaggca cttaaggtta agtgcgcatt cgactgtagc ttctttgaca aat tcctcta    63420
```

```
ccgtctttcc tgattttgtt gccgcctgtg tgatggcggt aaattcttct tcgctaaaat    63480
caacaagata atctttgtta gccatcacac actcgtagtt tttattagcc acttcactta    63540
cccctttgta ccttaccttt tagtttgtaa agtactatca ctgtgattac gtacaatact    63600
gttgctgttc caataacagt acttttattt tctaacccac caaagaactc gactatctcg    63660
ggattgtgtg cataaatctg aaccgagata agtatataa tcgatggtgg gtatatgaag    63720
aagggattca aattacttta ccttaatgtg ttttgtttct ttcaaccact tatcaagttt    63780
ctcttcatcc catctcggcg atttaccgat gaataaagtt ggcttcataa agttgattgt    63840
tcgaatacgc tcaaatgtct ttctagaaat agaaaggttt ttacagacac catttatagt    63900
cagcagtttc attaccaccc tcgtcttttc ttccttgcct tccgagcacc cttacctcgc    63960
gacactcggt tatcatgggg gcgcggcaat gtagtcaact gattcagagg gtgtgggtta    64020
accacatcat ctaaactgat aataccattg tcttgaatgt tctgaccaat gttacaaagg    64080
ttacccgagt atttttcatt ggtctccaat atcactctta atacttctgg actaagagca    64140
gccaacccgc taccaattac accaaccta atcatcttaa acctctacgt tgatataaat    64200
gtttcttact aagatcactt tgttggatag caggcttaaa taatctcccg cgtagataac    64260
gttgatcttc tctgtgacct aatacagatt gtatcgctga ttgcagagtt gatttaccat    64320
gatcaacatg cccgatagtg ccaacattaa cccgatgatt taatgccaat tgtggtcgtg    64380
taaacattgt cttgtatgct ctgaccttgc acttagtggt gagagtttct ttagacataa    64440
cccaactcct cgatgtcttc tttgattagt tcttccattt ctggagccgt cattgtttcg    64500
accttttcac gaatcaactt catctcttcc ttgtagaact taaagtatag cggtggtaat    64560
ttagctgtac cattcttgcc aaatttacta cggatgtgtt ccaagccatg tagaagtgct    64620
tcctcactag acttaccgag ttttgtcaag ccgtataagt aacttcgcag gtagtacttc    64680
ttaaggtctg gtcgacctct atcagccaca gcaattatct cagcaaatag attataatac    64740
ccacctaccc acgaagcacg atgcgagagt gctccttgtg aagcccaggt gtatttccat    64800
cgattctcgt taaactcacc taggaacccc aatgtagtaa actcatccga gacaagatac    64860
ttggctgcac gatgatggtg gtcttcacga aaaacagtaa acatgtcatg cgcgtaacct    64920
gacacaatgg ctattgggat ccatccatct ttccctaacg cttcacagat gtggattgcg    64980
ttgtctacga cgtcgtcagc gtggttgatg aggtgagcag catcgttctt tgtgtagtaa    65040
cctacgaaat gctctcttac catagcgcgg aattcttcgt atttcttctt atccatctta    65100
cttattccca atcccaaaca tcttttactt ttacgttttg tggtttagtt aaggttctat    65160
ttagaacctc gtcaattgtt aagccaagaa cttggtgctc tgcaaaatca accgcttcat    65220
tatacggcat ctttctgag tacttgacaa cactctcttg ataaagccta ttgattgcgc    65280
caccaagggt cttatgtgga atgatagagt tccagtcata cttcttaact ctggaccatt    65340
cccaaatgtt tttgcagcgc atgtatttct tatcagggtg ccatttgacg cccttagcaa    65400
aaacgacctg attgatgttt ctaaatttgt cagtgtgtaa agtagcttct ttcatgagtt    65460
ctaatggtaa aactataatt agattaccgt ctttgccatg gtcccaattc atatcctcca    65520
gcatcttaaa aagtgctttt ggtttaatcc cgcaaaaggt agcggtggga ttgatgtatat   65580 cgttatcgtt aaaagatatc cgacatggca tagctgagta acaacgctc attataaatt     65640 tcctcttttct tatctaaatt aagatgttgg taattccact actataacat ctacctgttt    65700
tacctttgaa tacattagcg ataaaaaaag aagagggta gtaggaaatc ctactaccct     65760
```

```
agtcttcaag ctttctttga ctcaatacgt gaaacagctt cacgacttgt ttcaggtaga   65820
acaaagtaca aacacatgtg agcatttgct tcttcattag tgtaaccagc tgtatcttgt   65880
ttaagaacag gagttataat ggaagaggca taatgactaa tgcttggaga atctacgatt   65940
ttgacatctt tgtttttagc atcatgtggt aacaactccc actctttagg ggtaatcacg   66000
taataacgct caaacactga ggccactatt ttcttaatga agtccgatgg atcatcacaa   66060
agcacaaatg cagcatggca aatcttagac aaggcactgt aagcagcagc actgacacga   66120
atctttcgac ccttagttaa tagacgaatg atttcatcta agacaggtga gtctggagaa   66180
tgacgcaaat aatcgcgcca acgtgacatg tcattgttct tgactttagt gatgttgaca   66240
gttaaggtgc ttttatcgta gtagtcacga atacgtgttt ccacgtcttc taatcctacc   66300
actatgtcac cagttgcagt ctcaaaagaa taaggttgca aaacaatagt caacagttga   66360
ttgagtcgac gagcacccaa atcctcttct gcctgattta actcgtatgc cattgaagcc   66420
actgcggtaa tggcctcatc tgtcaatgtc aagttaatac catcagtccc tagaagctgc   66480
tgtatggcga gcaatggtga cttggctgac ttagtaagga tatcctccaa atgcttagca   66540
gagagcgaat gaaggcgtat ttgaataggt aaacgcccac gcatctccga gataagagaa   66600
gattcaccaa cgttagcaaa agcacccgcc gcaatgaaca aaatgttact ggtgttcata   66660
cggcccatac ctttctctag accagagtta ttttggtcta ggtcaatgtt accaccttca   66720
atcaccttca gtagctcgta ttgaacctcc acaccattta ctttaccacc gccttgatca   66780
accagtttat cgatttcatc aataaacacc accccgtagt tttcagctaa tgccaacggt   66840
gtgcggattt cagcaggtag gttaaccgtt ttatcgtcag agagtaaagc aaggatgtat   66900
ttatcgatgt cgttttcgta ctcgtcaaaa ttaaacggct cgctattatc gagtccttca   66960
aaattactta gagccttacg aatccactca ttagtttgga agaagccacc ttcatcccaa   67020
gtcttaactt tctttaagga aagcttggtt tttccttcgg ctacttccgc aataacttta   67080
tcaacgatac cttgtagctc tttcttagag gaagctttgg tgaaacttga cacaatgctt   67140
ttatcaccgc cccaaaagaa cataaccaga cgaaagattt gtcgtatggt taacccttcc   67200
tttatcttgc cgtaattagc cacgcaccca tgtgtagtca tagagtgagg tattggtatt   67260
ttgaccatgg gtggtaatac cataacatcg tccaaggttt tgttatcctt gatcgctgca   67320
cggattaatt tctcatgttc accaatggct ttccttacaa caccaccatt atggttcttt   67380
ctcaggactg taaacaagtt acgaagaatc ttattttcaa atcctggttt aaactcaata   67440
ctggcagagt tttccaattt gtagttttca actaccttttg gatgaatttt ttctgcttcc   67500
tttaatagct gtttaaggaa atcagttacg ttaccaccaa cataaccacg tgaagtgaat   67560
gaggtcgctt ctgtttgcac aaaggggaag tcacataacg ctgccacctg tctagctagt   67620
tctgttttag ccgtaccaga tggaccctta attaaaacat tacgaaccgg aacccacttt   67680
ttatctttgg ctggaagctg ctgtctccgc caacgatcac gaaatgagac ggcgatagaa   67740
gccttagctt cttcttgtcc tatgatagtt ttatcaagga acgccacaat ctctgaaggt   67800
tttagattcc gcatatttat atatcccttg ctttttctaa ttgtgtcata ctaatgtctc   67860
tacggttaaa aataaaagta ggtgtatgac ctaagccata cacctacaat tactacacac   67920
gaatagcttc acgcaattcg ttcttcacat cttccagcga agggagttct aacttggcaa   67980
cgtagtagaa tttcttctgg ggccaacgaa cttccatacc aaccactagg ccattttcgt   68040
agtagtgtgt tacaatagca tcaccactgt taggaccagc gccagcttca cgttttgccg   68100
cttctttgac tgctgtttta aactcagctt cgctcactag gcgataattt ggagctgcaa   68160
```

```
tcaagtccaa tttagtttcg agtagcgcaa ctcgttcaag tacttcatca cgtaggcgac  68220
cgatgacgat gttagctaga gataactcgt tatcttatc gattaacagt tcctctgctg  68280
tctttgtcac cttctcgatt gtgtcggttg cactttaac ttcttcggca acgtgctcta  68340 cttttcaac cgcagtttcg actttatcaa cgacattgtt gatggcttct gaacctttgg  68400
ttaatttact agctaattta tcaaaccagc ccatgacata ctccttagtt aactattatt  68460
agtcataaaa aaggaagcta aggagacaga gtattttct gtctccttat taacctgtca  68520
taggacaagg cactataact cttcccttaa atcactttcc tgtttcattt ccaaataact  68580
cctttgtgat aagttaacct agagtgtttt tagcgcagta atagttgtag ttaacactca  68640
tgacattctc ttagacgttc aagtatcact tctttatact cgtctttgag attggtagat  68700
aggtaaagtt tccaataccc tctttgttca tggttaccaa gtacgaaagc aacgagttgc  68760
tccgacaaca aaggattgaa ctcaatgtct ttgtaaacta gctccaacgc aatagctaac  68820
aaatcattag ctaagcgctc atcaacatca ctccgttcca aaagtgaggt tatgacggca  68880
gcttgggttt ttggttcaaa gttactcatg acacttagat ggtaaccttg tggagaatca  68940
atcactttca gtaaggcatc catatctgga atcttaacga ttggattgta ctctgattcc  69000
ccttcccaca aatcgaaact tgtgaagtct cgattcaacc ctagattaac gattacattg  69060
gcccccactg tgacgtcgtc tgggatgttt atttctcccc aacgctcctc cgggaggttg  69120
cttaatagta acgaagcgac acgtggatat tttgagtaat cactcattag tttttgtatt  69180
gcttcctcat ctagtaccaa agcatcgtag tagtaatgtg gtagtcgatt cggtaacaaa  69240
atcgccagct ctgccaagtt agtggcagaa gtgatacgag tcaacatctt tgttatttca  69300
aacaaccgat acggcgattc atctttaatg cgttttagca cttgatgaaa tatttcgggt  69360
gtaactcgat gaagacgtag tttgtggtaa tcttccgtaa ttacgtcggc caacttctcc  69420
ttagttgcca gtatgcgctc ccatcggttt atcaagacac tggatttatc accatagtgt  69480
tcaatcaaaa cggaatgtgg gattgccttg ttgtgaaaac acatagtcaa attacgtgtg  69540
ctaatatcac tcatcttttt cggcaaatct tgaatagtaa gattcttgtt aaaacgataa  69600
gtgttctcaa acccaaataa tctgatcgaa cgttccactg gaatatctaa agtgatgttc  69660
acgaaagccc gtaaagaaag ttttaattcc ttcactaaag caacgttagc ttcattaacg  69720
cacagcataa atttttgct cccctacaga aacaagttca aaaagacgaa taatgtcctc  69780
agggtcgctt atgtttaaaa actctatgct ttcacgtcga gcagctccct ttagacaacg  69840
gtactcgtta gtatcatcgt ttatgtctcc agcatacacc accacatcgg atggctcttt  69900
aaggtctggg cctaacacag cacaaatgtg tgcacccagt ctttcgcggt tgataaagtc  69960
tttactaacc attgattcta acacgtcaga gtacggacgt ttatagaagt ctacaacatc  70020
ttccattacg taatcttcga ttatgaatgg aattcgatcg agggtagctg ataagcttc  70080 gagctcaata tcctcacctt caatcaaagc acgctccaca gcggcgtagg ttgcttcata  70140
accaccacgt ctacctaaca caatacgaat gtcgtgttgc gggataaggt aagcagtgat  70200
accgaatagc agtctttgca ggtctgatgg aatgtgggtg ttaccaacaa gtgttataat  70260
catggtgatt ctccttagta gatctgccac cacattgata atatataact gtttaattat  70320
caaatgtatg acattgtatt gattgttaga tctagccagg tgacgtcatt tttataatat  70380
tttctaacgg gtcgtgtact acattaagtg taggtatgcc caaagactcg gcatatcgta  70440
ctcccattgc tgtccctccc tttactttt tagacataca accatatacc actaagtcaa  70500
```

```
cgtggtcatc taaatcgacg ccagcaataa tacttagatt tctacaatga agagggtaat    70560
ggtcttcctt tagtgcatcc ggataactgt gtaactcacg aactatcctt ctgcgttctt    70620
cttccaactc cgggtttcca tataggcaat actcgtagtc gtaagaactt ctggtgagtt    70680
gccttggcgg ataaatttca atatccactt tccgcttctc tataatagct tgctctaaaa    70740
caacacttac tactttatct ggccccttt gacagcgacc tgaccgaatc aggtgcatgt     70800
atgaccaatg agttactaaa ccaaatagta atctgttata tcggatttcc gtttctcttg    70860
atccaataac ggcaatcttc ataaccacct cggaatatgt tattattctc ccattatatt    70920
aaaagtgttt agcgttaaaa aataagtaag ggacgcagca agcgctgcgt ccaatacaat    70980
caccggggtg attatgcgtc gtctgatgga tccatgtcga cgttctcttg tgtaaagcct    71040
tccatagatg gagtagcgat acgagtacga agagcagcat ctacagcaaa cgtaacttca    71100
ccagtgtaag ccaagttgcc tgcaacagca gtaactttga tttggcttgc agttggcatt    71160
tcgaacgtgt aatcagtttc gttaaatgcg aaaccgtatt tacgttgtac ttccgcgatg    71220
aagtcagcga caacaagttg gccttgttcg tcgattgctt cgatttcacg gatgttgttc    71280
ttagaggcag caacgattgc agagaatacg tttgatacat ccatacggtc aaagtagaat    71340
gtaacaaagt caccaactac ttcagaaggc tcaaccagaa ggtcgatgtc tacagaagag    71400
tttttaccag atgcgtgacc tgatagaaca gttaggtttt gaatatcaac gtcagcaggg    71460
ccgtagcctt tgttgttgtc gttgttaatc aggcccaaaa gcagaagctt aggagccaac    71520
gcgaagttcg gagtataagt agccatactt ctctatttcc tttttctagg gattcaaaat    71580
ttagtcggta ttagaaatgg cagttcttta ctgccattgg ctattactca actacagacg    71640
cagctgcgat tggttcgtaa acgaaaccgt tcagttcagt aactgtgatt tcttcgctga    71700
agtggcgagg catcacgtac tcaactgctg gttgccacac gtaagacgtg atagcaaatt    71760
gcagtttgta acggttaagt tcagcgtcga aaacgcgtga agcttgaaca gagtcagcgc    71820
cttggtcaag gtcaactttc tgacgaacag cggcagcttt aagagcagta accgcagcag    71880
caggagaagt ctcagcatcc cataggtctg gttcgtacca tgtgaagtca ccagcagctt    71940
cgtccatgtc gacgatgaag cttagttgca gacggaagta gtctacatct acgaagtcag    72000
atggaaccgg agtgttcaca agacggacgc cagttttacc agtagcagcg tcaagaacag    72060
acaggttaga cagtgtagtg ctcgctagtg tcagcggagt accaactgaa gattggttgt    72120
agtggttcac catgttcagc aactgctgac ggtgtgacgc acgagggtta agaatataag    72180
cactcatatt cacatttcct tagttgattg tggatggaca cagtgtgttc atataaagaa    72240
atgaaaaaag gacctcggct cgaaagccaa agcccttgct acgcctacat cggtgagtaa    72300
aaaaattatt ctacacgttt ccaacggtat tctggatcat ccacattcgc caaataacct    72360
ttgcgtttcc aaatgatcat gtaagtttta atgccagttg tcatctcatc acgccttact    72420
tctttaacga attcacccctt tagcggtgag tcttccaaag taatctccca tgagtcggaa    72480
acctttcttg ccaaccctgt gttgtaagtc tcagagccag ggtttaagca atgacccttt    72540
aagtcattag cctgcaccca ttcacttaac cattcgaaac ttgtagcgat gggcatacgc    72600
attaaatcat aaacatcacc gcttagaatc aacggtgtgt cctgttccca tcgtccccag    72660
atatcaccat tagggtcata atcagggtct gatgtgtaca agaacccatt aatagggtaa    72720
gggttaattg gtgtaagact ataatagcct ttaaacttaa ccacatcgaa tccagtaatt    72780
agattaatgg gtaaagtgtt gaatagagaa tcgaagatgt gtaatttggt tctaccgtgg    72840
tacagataag aatcttcaag tgcttctacc caccattgcc cttcgacaga aatcaaacgg    72900
```

```
atatgtgtat ttaaatcgac accgtacaac ttagctgttt ctgtgaagaa acggctggta    72960
agtctcggtt tagtttcggc ctggtcaaac caatcaatct taccacgccg taaggataga    73020
aaggtagtgc caaataaaat gtttaaatcg attcggttgt atgtcacttc atgatcagtt    73080
ccatctgtgt ggtagagtgt ggctgatgta ttacccaaac tgccattaat gagttggatg    73140
ttctccaagt gatctatagc atcaagtttg acgtagctgg aagaagcaga ttcttttaat    73200
agcgtagcta gtacgcttat tttatctaga gtaagattga acatatggtt tctctcaaca    73260
aaaaaaatag gagagatttc tctctcctat atgtctttac aatcggcgca gtgctatata    73320
cggaatatgt ttcacataat ctattaatag actgaggcct tcgaatggcg gggttgcgtg    73380
caataacttc agtaaacgta tcttgaaatc aaaggaggat tggtaaggtc ctggctcttt    73440
gtttgcgacg tagttataat ggtacattgc gaaattctca acagagttaa ggaactcttt    73500
tttatcttcc gcccggaact catccgcgta attaaagttt cttagataaa caacacactc    73560
tggtggttgg atacctacca ctctatcacg tgggttttt ggtgttagtt cagataatcc    73620
atcattgaac ttactcacca agaacggttc actcacttcc acaacttcta cgtcttcacc    73680
aaaacaagat ggattcatag caatctcctt agggaaaata ccagtggttt tgttttact    73740 aaagaaacca cctaactcgc gtttaattac atatgttact ctacaaccta atttattctt    73800
aattgacaat ttaattttc ctcttttgaa attaactatt ttggtagggt gtcttattta    73860
tcccaagttg agtcttttag cccattctct tcccgagtac ggtcctcgta catcttgctg    73920
gcaagggtcg ctaaatcggt tctggactta caggcattca ccttctcttc taccaaattt    73980
agagggaata atttactccc tttcgctgag gattttttag tcaactctat caagtctttc    74040
tttgccttat ctaaatcaaa catatacaat attccattag cgataatatc actacgataa    74100
tatatatctg aattaaattt tactcaacct tataaatcaa ttggtagcga ttcgaccatc    74160
ataccatctt ccacccaaga tttagcaact tcagttaaca cctcaccaaa ccgaacttct    74220
tcgacaagtt tgcagtgttt aaagttaacg tatggtttat tatcaccgtc accatcatct    74280
agagggtgat accatccaac tggtgagaag ttacatttag cgaacagagc tatggcttta    74340
aagttactag gatggcaaca agcactatct acacgattag aatttataag ggcattgatg    74400
tgctctgtca tgtggccatt acgtcgagct tctgtggtcg tatagcagaa aataatacgg    74460
cgatttagta accaaatacc tgtaactatt aactcatcct cgatgccaaa ttccacttcg    74520
acacctgggt agcgttcatc aagtcgtcta gccaagtctt ttatctcttt ggctttgggt    74580
gggagggaaa cgtaatacat ttcaagaatc cttattttatt tttagaacc aagttcacat    74640 tttccaaaag tttatttttg gcatagttga tagtttaga ctcaacgtac tcttctaagt    74700
tttcaccgag atactttatt gtttcagatt tcaatagtgc ctctttggtg ttaggaatgt    74760
gcgggttgat tctctcctct gacacatacc ccacaagctt cttaaatagc ttgtaaacac    74820
cgtaagtcct tttagctagg ttgatgtact tcttaggacc ataaaccatt atagcttgtt    74880
taacgaccca ccttgcagca tcccttgcag tcaattgact ctctgagatc aatctgcctt    74940
cgtagatacc actaatcgta aacacagcat accaacgaac cccgctaagt tttttactct    75000 ttggttaaa ctcacacagt tctatttcta gatcttcata gtccaagtca gtgttgatta    75060
acgttattcg ttttctatca tcgagtaacg ggagccgatg ctgctctatt atattccata    75120
gtagaagtgt aagttgattg gagaagtctg tatcgcatcc tggtcttta ggataacata    75180 acccatcaga atcagagaaa gtcaattctt cgatcttctt agagatagtg cttttaatgt    75240
```

```
cggagtcgga ggtgtttatc tgaaataaat aatacttcat agccaccatt aaacttttcg    75300
ctatcagctc tgtggcgaaa ataccggata agccagagta acgtcctata agacggcaat    75360
tctgattaac cagttgtatg gtttcttttc tcaactgagt aacgtccacc aatcgtgcct    75420
gtttggcctt gtagtatgtt tgctctgcca tgttcttatc caagtttagt taagctataa    75480
aaagtccaag atgcgttaaa aataaaaggg gaacacccct tgcattagca agaagtgtcc    75540
tcaatcagtt ttagaatttc tttatcgata tcgacatcgt gcctatcgat tttgctaggg    75600
gtgtaaatac gatgtagttc ttcccttaac tcttcaccag tcatctcacc gtaaacttcc    75660
gcttggtcta cagtagtgaa tttagataag aataaacgac caatattagt cgagttaatc    75720
ttcttaccag cgtgatgttc tacaatagta cttatcttca tttcttctta cctttacgac    75780
gacgtcttct ttttcttgca ttcccactcg ttggtttctt ctcccttatg aataatggag    75840
gtaattccaa caactcaaaa cgccagaaat aatgtccgac agcaatagag tcaatagagt    75900
gctcgtcaag taaagttaga tcaatctctg tactttcccc aaatagagat aagaccgctt    75960
gtctaacttc ttctttacca gtacctatat gatccacgcc gacgtaatgt ttaactgaaa    76020 ttggattttat accataaacc tttgtagtga gtgtcaggct acgtacagcg tcatgaatca    76080
tagtttgtag ctctacacca gattcatacg ccgacatctt tccccttcta aagaatggtg    76140
tttcagtgat aaaaaacgta ggttgggcaa attcaatcac ctcaatcatt tgttttttgta   76200 tctcttccat tctccagcga cgaccaccat caatcaaaaa aagactgtct tcaacctttg    76260
ggttttttac gccaacggta tctgaccaga cgacaacagg taacttatta aagtcttcta    76320
tgtctacttc tagtatggaa agacccagtg tcacagtgcc tgggtcacat gccataattc    76380
taattctgtt atcaggtgga ggcggcggta gactaaccat tcgatgtgcg gagtttcatc    76440
ggtttagttt ggcccacttc aacttcataa gccacgcgtt ggttagtttg agctaagtta    76500
tggtaacagc taatgaagat acccggctgt aaaccaatca cctcgtcgaa cacgatttgt    76560
gaaccgtcac cttttggaac ttggacagtt ttatcaacac ctgtacagag gatgatttca    76620
gacatcactg cttttagtgg gttaccgcgc atgactctag ctacattaat gtactcttgt    76680
gtgtcgaatt cattgaattc aacgttgcgc atgactgtac tgtgtacgta ctcaccgtcg    76740
ggcaaagtcg atacaaggtt actaccatct tcttcgagag atagcgaagg gacacgtagt    76800
ggttttggat aaagatcttg gtcggtgtat tcgaactctt tagttgagct cttaccatca    76860
acaaccgtag tcttatacaa aatcgccttc tgggtttgct taggaagacg tttgcagtag    76920
taagcaaaat aacgaatacc accatactgt acttcgcgac gtagaccata gtttgcacgt    76980
tgtgcctcgg tcagatcatt atcgagttcc cggataacca tgggtactag caagaatggg    77040
gcagaatcgg ttgggttgtg tgcaactggt acggtccaca tcaactcatc agaatcagtt    77100
tgtccctcat gaccctttg accgacgact aagtattcaa gaagcggtcg ttggtccggt     77160
gttggtttca catctttaag aatgtttatg ttctcattga tggtagattt ttcttcatat    77220
tcgatgggtg cacctgtaat aagactagcc tgaatcttca tatacgataa agaaggcgtt    77280
gtcaatgcac catcaaaaac tgactgatcg ctcattgcga aaactcctta atggtttaat    77340
cgagtggaaa ctcgaaacta cctaaacttc taattcttat ccgtgaagcc aatgtgttat    77400
tgggttcggg atccgtccca cccaccatct tgcgatagc gcttgagtcg taaataacac     77460
gtgtaaagat ttcttcgtta accacactgt tggcataaat agccgtatct accttgactc    77520
gctggatggc gttgtcatag gccgtggttt ttaacatatc aaagccgtct actttaactt    77580
ttgctccgag ctcgatagcg ttaactacta accccgattc agtaaaagat tgaagcttcg    77640
```

```
attccgattc cgagccaatg tgttgcacca agccacagt tggttcagtc gacaatttat    77700
cagagctggt aaattgtgta gagaactgta tagagtaact cgacaactta ctaaataacc    77760
caactaagtt actttgtata tcatcgaaac ctatcacatt atcagggtcg taatcggttg    77820
ttaatttaag aaggtctttg gttaaatccc gccacatcgt atcgctgtat ttgctaggat    77880
caataccaag ctcgtacagg aactctgtgt agtccttgtt caccaactgg tgtgttagtg    77940
tatggtcacg ataagtgtaa ttaaataacc actcaacctc acgacgtgtt ctatcatcac    78000
gttgactacc taaataacgc tcacgacgtg ttttgattgc gattcgacga gtaacacgat    78060
cataaaaatc atttctgttg taaataacag aagtatcccc gtccgtggtc tcattaaaga    78120
aatcgatgta agtgtctaag ttcagagtat gtggggtgat tagacccctta gtgaattcct    78180 ccttagtata ccacacccct tcttcagtac tgaccacgtt aaagatagga atccacttca    78240
gctccaagcc atgataacct ttataatagg catagagata aagtgcgaat gattgtagcg    78300
gtgtcacacg gaaagagtta ccagattgtg gatcaataac atcggcattg ttccgcatta    78360
aatcttttgc agaatgatag gcccattcat taatcacacg agtcagtgtc ttctctgaat    78420
taaatgaact ggggtcgata ccagaaactt ccagtaactt ggttggcatt gaacctgtac    78480
cagaacgaat caataaatca ccggaagtct gaatatactc gtctatcatt cttccatgtt    78540
ctttacccgc atcgtattct ttaccaatca cttcttctat tggtaacgtg tcgatatctc    78600
ggccacggga acgttcttta aagttaactg gttctttaac acctatgggg tgtttgtaca    78660
atccaccact tttaacctcg gtgtaattct cagcaagcaa gaacttatcc agagggatat    78720
ctcgcttagt caagagattc tcgactaaga aatcaaaagt gtcctgttta cccgcatgtc    78780
tttcaatgta ccggatatta cggtacaaga ataacatttg ttcaatagtt aaataaggaa    78840
catactcgtg gagatttttgg tgtgagcgta aaaactctgt gatgtggtac gagtgggttt    78900
cgcttgtatg gatggcacgt aatcgaagtt ctttgatttt acctggaagt agtgcataaa    78960
tgcggcctat gtgatccgcc acactaaagt tatatgcagc attccacgac tccatcacat    79020
attggtgatg gtatgccttt atccacttct ctatgttaag aatgagtgtg gcttcctggg    79080
cctctacaag gtctttgtta tagcttatga tagaaccatc ttccagtggc acagttattt    79140
ctggcggtac tgggttgaaa acaccctcta tatataacgg cataaaagga tatctatcgt    79200
gaatcttttc cctgttttct gggtctcgat agaaagtgta tgttttctta tgattcttaa    79260
gcatatcttt cgttaagacg acggtttcac ctgtgtctaa cgattcaatt tcaactgtct    79320
cgtcgatgcc ttcaagatat tccccgttga ggtgttttaaa ataacgccac tcactttta    79380 tatcgggaat agtctgacca agctctttca atggctggtt catggcaaac gccgaccaaa    79440
tagatttaaa ggttatgctt cgcgctaacc gcataacctg attattgtaa atcattagga    79500
gtcctcatga tatcagaatt ggatccacta gctgaggtgt tttattctaa actcacctca    79560
ccgacagaac gacaaaggca ttctagtggt gatgaacaaa ccccatcacg atgggaatta    79620
agcccaatca accgagccct gatgcaacgt cgtctagacg ctgagcgaat tttcgacacc    79680
ttaccagaca tggagaccat cattagtgtg gccgtgtcta gtatgctctg tacaaaggac    79740
ctggtaactt caacattagt ctataactgc cctgttccgg agaatgaaat cccgctgtca    79800
gttaaagaga atatgttaga tgttttgagg gaatatttca gcaatgagct aaaactccct    79860
caaaaacttt acgagtggtt gtacgaggct atgtcagtag ctggagcagt accattacta    79920
atcctacctg aatcatcttt tgataagatg tttcaactac gtcgtgaagg catcgcgaaa    79980
```

```
tcaacaacgc tacctggtct atcatcttca ttaaagtctt accttgataa ccaagaaggt    80040
tactggggag acccagaagg aagaccaaga ctttataccg aatcgtatca gaaaccggaa    80100
cgtggtactg gtgccagaga aatcgaaatc ggtgttgaag aaagcaaact cgaaggtaag    80160
attatactaa ctgataacat tgactttatg aaagtcaaga agaatcagcg tgtggccttg    80220
caacgcgaat cttccgcga aaaggcatta agtggcctga atagcttggc atcgtcatat    80280
aaagaccctg cgacgttaa taaagataag acggctgctt ctatgggtaa acgcatcaac    80340
ccaacatacg aagataagcc gaactcagca ccgcacttaa ccataccaac cgctaaagaa    80400
gcaggtcgtt ctaaaacgca tccttctttg caaccatatc catctgaagc agtcatccca    80460
gtaaccattc cgggtaatga actagatcct atcggatacc ttatctctca cgatatgagt    80520
ggtaacccac tttcgctacg tagtgtcggt agcttagaca atgctctatt tactaacacc    80580
tcgggcggct cagatttgat atcttcttct gcacgtgcac ttggtttaac tgacaatgaa    80640
gtagcaccgc cgattaagaa aatcatgtct aagtatggtg aaatggtaga gaagaagttc    80700
ttagcttcac tggaaaatgg tatgttgggt gaaggcattg cactaggtaa gaacgaagag    80760
ttctatcgtg tgatgtatgc acgccatctg gccaaacgtg acacagcggt cgtctattgc    80820
ccggctgaac aattggcata tctggctgtt gacttcgact ccaatggtat cggtcgtagt    80880
ttaattgatc gttctaaagt tattagtaca gtgcgtatgg tgcatttgtt tgctactatg    80940
aataccatgg tacaaaactc tgcacgaaac attcaatatg aaatcactgt tcctgaggaa    81000
gaacgcgatc caaaaacagc aattgctttg gcaaagagtg catcgtacg ttcgcataat    81060 tcattccagc cagtttgggg tgatgtagat gacgtttatg cacaaacagc caatgctggc    81120
atcgtcttta aagttattgg taacgaattc tacccaactg ccaatattga caaaccgac    81180 atcacaccag atttcaaagt ccctgataag gaactcgatg aaaactttgt gcgtcgcatc    81240
tgtcaattag cacgagtgga ccctgacctc atccttcaac ctgagaactt ggaatttgct    81300
tcgcagattt attccaagtc gttaatctca actaaacaaa ttatcatgaa gcagcaaggt    81360
attaacaaga cggtaactaa ccttgttagt aactatacac tgtcttcagg tattttgtta    81420
gataagttgt tgaggccat taaaggttca gatggttatg actcagaaca cccagaacta    81480
atcccacgtt atgtacgttt gctgctagaa tacttgaatg tgcaaatccc accaccagat    81540
acatctttta ccaaatctca gatggaacag tatgatgaga agatgactat cgtagataag    81600
attcttgaag atactatcac tgacgacgta gcggatgctg ttggtgtaga tggtactaaa    81660
ttacgtgcca tcattaaaag ctggtatagc attcagtggt tgcgtaacaa cggtgtggaa    81720
acagatttgg ttgatacaat cttaactgag acagaccatg cagcgatggt taaagatatc    81780
acagacagac actccaccat tggtaaatta attgccatgg ttaacaagcg tctggaaggt    81840
aaacttgaaa ctattgctaa gaactacggt acaccggatg acggtggtgg ttttggggt    81900 gacatggatg gtgatggttt atctgatgat atcggtgggg atttgggtgg agacgacgat    81960
attctatccg acgacttaga tattgacggt gacactgata atgatgccga gggtcctgaa    82020
gaaatcgact tggattctga tactgattct actgacgaag tagaagaaga tgaggatgaa    82080
gagaaaggac ctgaagaaat cgacctcgac taaaaaaata aagaaaaaaa tagggactcg    82140
caagagtccc tataattctt ttttactttt tctacattaa aacgagtaac gtttgttaac    82200
gtagaacttg gcagagctag cttctctga gataatcatc gcagcattgc cagcagcagt    82260
atcagccaga atgacaggca tgataccatg atcactccaa gcatcgccga atacagtatc    82320
gcgaatttcc aatgcggcgg tagccacagt atcaagttca ggatgatact catcattaat    82380
```

```
gcgaagtagt ttagcatcgc ctgctgcttc tacagagcga cagaaagccc ctgttgattt    82440
cacagcgagt gatagagtgg aaatttcaat acaaccgtct ttatcacttt tatcgatagc    82500
aatcaacgaa cgcaccatgc cattgtatac cgcacggaac tgtgattcga taccgttatc    82560
aaatacatct gggttagaga acattgtttg tgtttcttcc cattcgacca gtgcatcatt    82620
tgtgacgtag tccatcttaa cacgagagta agattggct gtaatctcaa gtgctgctac     82680
aagacggtat ttaatcactt cacagaaacg aatagtagat ggattgtcag agttacgaag    82740
atcggccacc atctgcatca tctgttgaag tggttcacca ccacgattga gattaagagc    82800
atcttcaatc tctgggttgg acaggaactt acgacgtttc tgaataacgc ctacttctaa    82860
agaatcatct ggtgtgcagc aaacaaaatc ttcgaagtta tcgaagatag gaagctcttt    82920
acgaacttca tgtgctggac gtgagatgaa ttcgatacga cgactttcga ctttaggttt    82980
gtcgtaagaa ggttcgaccg acgataagct atgttcttcg aatgtttcca cgagaactcc    83040
tttcactagt ttgaatttac gtgggtcgaa tacactaggt ttccctttga attctttagc    83100
caccacttcc acttcttctt ccacttcgat acgatcacgg cggcctttc cgaaaccacg      83160 cgtacgttca cgtttggttt catcatcacg ctcacgtgta cgctcacgag tattacgacg    83220
gctattacgt tcactgcggt catcacgatc acgatcgcga cggctattac gatcgcgacg    83280
actgccacgg tcgcgtccac caccgcggcg ttcacgacgt tccagttctt tcaagtcagc    83340
gatgtattct gatgctcggc ggcgagaacc atcggcactt gaaggaatgc gtgcactcaa    83400
ctctgactta caccaacctg atagaaaggc gatgtagaag tcttccagaa tcaaatcgaa    83460
ggagtcttct ggtttgagat gatcgtctac tgcttcagcg tgttcgtaag cctccacacg    83520
aagtgcgtct aactctttac cggagttgtc atcctccatc atcatggcta agttataagc    83580
caaatctgaa ctgtcttcga ttgcttgaca ggctttaatt gcattacgtg acatgaagat    83640
tcctctttat aaataatact gtagggataa ttgaaaatta gttagcaaga cggccacgat    83700
gacgtaagtc ttcttgggtc ttgtcggtga tttctttgaa tttaggattt tgttgtaact    83760
catagttacg acctaaaatt gcatagacgt ttagtgtacc tgggccaaag ggctgtgctt    83820
ttgtcacata cccgtaacta ccaccttcca aacgagaagc atgtctgaag ttaactgggt    83880
catcgatgtt gatggtttta ccagacttct tactttacc tcgattgttt ttagtggcat      83940
cagtttgatc aatagcgtgt gtagtcacac caatcacagg acattacaa gtactggaaa      84000 gatgtgatac ttcaccatgg cctgaagtaa tcttggtcaa tacactcaca aatagtttat    84060
tgttaactac acgcgcaatg gaggtaggtt ttacaatgcg tgtaccagtt aactcatact    84120
ccttatctgc taaagtagtt agtttccaac gaatctcatt gatggctaca gcgagacctt    84180
tttcaccact aaataagtaa tctacggttt taaggcattt tccataaatg ttacttagtt    84240
cggaacgagg tatgttgtgc acatctatag tggaacgaat gacgtggaat aagaaatccc    84300
aaatcgtttc gacatcgtcc acaccagatt caagtagttc atgtttaaaa cgggcacagc    84360
aataacgttc aatctcaatg aagttttct ccatctcctt gtagagttgt gcttcgttgt      84420
ctgccgctga acggccttct aagctataac ctagaattct cgtccagaca tctgggtcat    84480
taatgatatc cgctgagaga tgatcaggct gcgcttgctg cgcatagaac aatgccgaaa    84540
tcaaacttaa tgcttgtttc tgcgctggtg ttctttttgc aatatcgtgc cccatctgct    84600
cacgtggtac agtaacgatg aagttctcaa caccacgacg aatacgttta gactgaataa    84660
cagttacttc gtccagattt agttcattgc catttctgaa ttctgtatca taaacgtcga    84720
```

```
catcgatgcc agtataacgt ttgatagctc cacggaatcc gtatttagca aatagccaat    84780
acgcaaccat aggcatgttc gttttaccgc tgccattgcg actcttgaga gtttctgtag    84840
tggtgaggta acaccgttca tccataccgt gtacagatat cgtgtaagat tcgaatttaa    84900
aagtaattcg ttttgagaaa ggaaagtgta cgaaaaagcc atcgttcaca taccctaacc    84960
ctggctgatg ccaaacggcc gaaatcaaac gcgaaccacc attaacattt acaatgttat    85020
aagggttcac atatggaaca agtagcggtc gaactatatc agcttcgcca ccacggtcat    85080
ctcgcatttt aaagttgaag tcgaccatgt agtaatcgct acgtgataca tccacacccg    85140
gtgacttatt acttttttgta ctcgactgcc aaccaaacat ctcttcaggt gtctttaagc    85200
tatatccgct ataatagaaa ccttcaggta gttgtttgtt atttcgacct aattcgcgct    85260
taagtaaaga gtgaattgtc aggtgtagat tgtctccgat ttggtggaat gccaaacctt    85320
cggcaatctg cggattcatc tttgcaattc ttccgcgctc atcaagtgct gctaatgcat    85380
cagcaaacat accgcttttc cctcttcgtt attatattac cttggccaaa cttgtcaaca    85440
aggttgaggt tgtcttaacg ttctcagtaa cgagtttaga ctcttcacta agcaagtttc    85500
gtgtagtctt aacttcactc tcgtaatctt tacgcatgaa gtcccttgct ttaaagcctt    85560
cctcaatttc tgaatccact ctcgctaagc aacagaaac tctgttgtta agaccatcaa    85620
gatgtttatt gaatagacca acatctatac cttttatttc tttattgcct ttttctttct    85680
ccaccttctc agataattta tttaattcgt atatgttatt tgccactatt gggtcagcgt    85740
caactaactc cactctggct gacacaccat cgttcacaat gacataaagt ccattatcca    85800
tatcgttata atgtttcaca tcaatctcag taggtttacc atttagactt acggcaacat    85860
aacttcgatt aagcccttcg caattgtaga agtactggaa gaccgagggg gtgccttcct    85920
ccactattac attactgaag gaatcctcgg gaaattcaag ttgtgagtac aaagtaccga    85980
taacaatatc taactccttg atgtaaatgc ctttctttgc atctaggata gtttctattg    86040
gtatctcacc ctgcactaca taatgctcac cgatatctgt cagtgcttct tgaatatcat    86100
cacgagttgt gaaattagaa cgtgcggaat aatcgtaccc tataccaact aatacatgct    86160
tcgtgctaag atgctttgta ttaactgttg gtaataacgc acttgtcccc agtctatcga    86220
taaaacgcaa ggtatgtgtt gtgggattcc aaatccccca cgacttacta aaggttgcat    86280
taaaccccaa acgttttggt ttatgtacct ttaattcgta actatcatgg ttcataccag    86340
tttacctcca acaagataac atatactcaa aaaagttgg agtttgacat agtataaaag    86400
aagggcgtta aaaataaaag aacctagggc cgaagcccta ggtctttatt ccttccacga    86460
acttattggt tcaaatctga atccattcag tatcgtggtt atggtgccgg gtttgggtct    86520
gttgcgtcaa ctgtcgccgc taccttcact tcgtcagcaa tttgaattgc cagagactta    86580
cggatcttca tccagttgtc tagaccagtt acatggatta gaccagtaac aggacagtta    86640
acaacgtgta ggttacgtgg ttgaacagtc agctcttgtg caacaccgcc ttcacgttga    86700
atttgagtgt tagacactag aggtggaacc cataggtgag taccccagtt gtagatttgg    86760
tagttatcac cgtcgccatc tacagttaga acccattgca gacgacgctt gtaaccgcct    86820
tctggcattt ctgggtagta acgtaggtcg ttggttgtaa cgatcttgca ctcgatgtcg    86880
tcgccaagaa gcttagtgtt gccccatagt tgcagaaggt cagctgtaac tgtatcacaa    86940
gtgataagta cagttggttt cttatctgcg caaccagaag tagcacgtag agcagttagg    87000
taacgagaac gttgtagagc cacagaaacc tgtgcacgca gcaggttaac cagtgcagaa    87060
cgagcgttct taacgtcatt tacagactca aggctttgta caactttcgc caagtcgaag    87120
```

```
ctatcttctt ccatccaagg acggatgaag tgacgcgcga tgccagagat aggtgctggt    87180
tcgttgtcga aatcgttacg gatagtttta acaacttcac gaagagtgtc tgtgtactca    87240
agagtacgag taacagccag gttttcgtta cggatgttaa ccagcgagat caagtcttca    87300
agacgagaag agtcatctac ttggataccg tttggcggag tcttagtagt gatcgggtcg    87360
ccaaggcgga tcttgtagtt ttcttcgaac cagaacgcgt ctgcaagaag accatggtta    87420
cgtttgtttt cgttagtaaa cgtcgccgcg tattcgtagc cttcaacagt gaattcaatg    87480
ttgtcaacta gagtcttcac agaacctttg ttgtggctta ctacttgacc ttcagcatcg    87540
tacacacgct taaccataac ttgtggttgt gtcatgcgct cgatagagtc gttggtagtc    87600
acgtaagagt tcaggatgat ttcgaagttc agctggtact tcattggctc aagaggagcc    87660
gcagcagcga ttacattacc ttcccagtct tggtcgcag catcaagtgc gaacaggttc    87720
ttacggaatg aaagttgagt ttcacgaccg tcgccctgtg gtgttttgtc gaagccagag    87780
aaagacatgt tcagaacatt aagctccatg aactgtttcg cagagtcagc ttcgcctttc    87840
ttcttaacag aaaccaggat agacttcaga gccataccct cagcgatttc atcagattcg    87900
ttcagcaggt tgttaccgat cagcagtggg tttgaagcca acgccatcag gttacgctct    87960
gactgtttga agttcaggta agaagtacgt actttgtgac cagctacttc aacttcgcgt    88020
gccgggaata catttggatc aacgaaatgt tcgtcagcag aaccatcttc aggcatgaac    88080
gggataagag ccaggtcatc gccagttagg atagttgggt cagtcagtgc atcgattgcg    88140
ttacgtggtt cgaacttacg tgctttgtca gcaaacagag tgtgacgtgc accacggtgt    88200
gtacgcagtt ttttcgcacg gaacgttgca cctgtgtctg aagggtcgat gatcattgtg    88260
cgatacatgc tttcagcgta aggtgtttgt tcagcaacct gaacgttcag tacgatagat    88320
ttgttgatgt gcttagccag gtcttggtca gagaagtatt ctgttgccag aacgctatta    88380
gaaccgtagc cattttcgtt cgcccactca gttttgcttg agaagttctc agtagccaga    88440
gtacgcgcat aagccattgg gtcagctacc gctgctgcaa caacacgtgc cgcttctttc    88500
tgtgcaggag taagtttacc tagcttgtcg atttcaccgt tgatggtggt ggtagccttt    88560
ttaaggccag cttggtcgct gattgattca gttgtcagta cgcgtttgct gtactcgttc    88620
aatgaaccgc cttcacggcc aatagaggta accatctttt cggctttctc cattgcttga    88680
agcacggctg gagaagaatg aatatcattc aatttcatct taattttcct tattacttaa    88740
gtaatttaga actattgagt attatacgtt tacccaaagt acatggctta taaaccataa    88800
gaaatgtaat aactgaacag accagcaaaa tttgggtgat ttgcaaatag tactcgtcca    88860 ttaccttaa gtccattgac agctacaaac ttgtcacgaa tgtaacatag taactcttca    88920
atcaaactcg ctcggaactt tgcgtggtcg ctcaggtcta acgctaccga ccccggcaca    88980
ggttcattac tcatattaat aaagatttta tcttcatcag cagtgtgaga gaaccttaca    89040 tgcttttaa ggcatgaact ctgcataata taagcctccg cagagtctgt catagtatac    89100
aaaggtcttt ctgaattttc agcattttgc tcatcgttaa ggatggcagt ttgtatggtc    89160
atgcgagcag ggatagtttt ggtatcgatg agttcatgta cctccaccat ctcacctttt    89220
gacataagca atttaaacac attggtgatg ttcgaaacac ccatatgttc agctaatggt    89280
aaaggtagtt ggaaattttg gctatccaac ataagaagct ctctgaaaaa gctgtactgc    89340
atttccaaat aattattaac gtcgtgagct gttactatag actcagacaa atctttggta    89400
ctccctgatt caaaagaatc attcatccac tcagggacat actcaatttt gatattcata    89460
```

```
ggatcgaccc catatgttat acgatattaa aatagcactt aacacttcat tggcacttct    89520
atacctcgcg catagacaag aagccatcga tccagaccaa gaacttattc gttcagctct    89580
tgatacaatt cgtgccaacg accaagcagg tgacgatgac gaagcatctg caattagcta    89640
tataaaaggt ctaattgaag aacaaatccg ttctaaagac ttcgataaga aatctattat    89700
gcgtcgagtg aaggttgcgt gctcactttt tcctgacgtt tacgagaatc ttgaaaccta    89760
tctggaagaa gaaatcggtg acccagaaga agctcgtaaa acagcacaat cgcataaaca    89820
atggttgcgt cgattcgtaa accagaataa actaaagaca aacgttgggc gtctatacgg    89880
tgcattgacc cgtggggatg gtaaactagt agaagaagaa ctagcctcac taaaaaagac    89940
aatcgatagc ggacgcagtg ttgagaatag aaaaatccca tccttagtag ggagcctaag    90000
aacatcacaa ccagaaggct ttggtattgt tattcgtaaa agtcgtgaga ttctaggtgg    90060
agcatgtttc cgtacaggct tccgtggtat aaaccgtatg cttggtgcac agggtggtat    90120
tcgaatgagc gaattagctc ttatgcctgc tcttccattc aatggtaaaa ctcttttctc    90180
acaatcgtta tttcttagcg ttggtgtggt gaataaagca gaagacttcc gtgaattcat    90240
cccaggtgat aagacgccag cgttcctaga cctctctttt gagaatacac aagatatcaa    90300
tgtaccccaa gcattcgata tgctctatgg taacttagag agaaaaaaag caccgaccga    90360
acaatggtac gaagaagctt tggctactgt tatcacaaag gctggtatcg ctattccaga    90420
tggcgttaaa gaaaagaaca aaaccacaga gtggttaaag tcagaacata agccttata    90480 tgacgaagta gagactatag tgtctaatcg tactggtaac tatatttgta atccctgaa    90540 taaaaatggt tgggaataca ttatggacca gcacataaac actgacttcg agattcaata    90600
tctcccagat atcattgcag attacgagtc gcaaggtcta cacatcatgg gtgtgcgtgg    90660
tgactaccta ggtacgatta agaagaaagg tcttggtaac ggtgtggctg gtacagacat    90720
taaagaatct tatcgtattg cacgtaatgt aacggcgatg aaagataagt tcgctctctt    90780
accacatcag ctatccccag acgcaaagcg ttttaaagct ctcaatccta caggtttatgt    90840 tcgtaaccta ccaggtaaag gattctacga gggttgtacc tctcttgaca acgaggctga    90900
tttagagttc tatttcggcg taactgaaca agaaggtaaa aactacctag aagttcaacg    90960
tggtaaacac cgtggcggta ctaagacagc aatcaaagac cactactgtg taattccttt    91020
tgatgatgta cgcatcctac catgggatat gttagacgac gctgagatgt ctaaagactc    91080
tctgtctaaa ttctcttctg gttcgggtgc actaatggag tggtaatatg catgacggtg    91140
agttactgta tgagatgagt atctcttcta ttgatggtcg taagttattg gttgactgcg    91200
aggttcttta tacctcgccc gataacctct acagactgtt cttttataag gaagatgaat    91260
ttggttttcg agccaaggct gtggagtggt gttctagttc accgggtcaa aaggatcact    91320
gggaaaatga aacttctatg gtggaggaac tattcactct gacagcaaga aaagacggcg    91380
caagacatct tgaatttaac cggagtagtg acatggctgg ttatatttat tgtcctagtc    91440
tcttagcctt aaaagagatg atggaaatcc tcatcgagaa agagaaagag cattgtcctg    91500
ataagtgata aaaaaataaa aaagaagtag cctcattgcg aggctacctt ttaatttta    91560 ttcgtcttaa caacgaacct cataagcttt gagagcttga taaacgactt tcttgatgta    91620
acggtcttga ccggactcaa aacgttgtag ggcaatcagg gcatcttcag aatcgaatgt    91680
accaaaatga ccagccaaga atgggatgat agaagcatcg acactaatga caggtttaga    91740
acctctgacg tagaaggctg tggttacttt aataccactt gcgttgcctg gaaccagcgc    91800
agacaacgca actttcgatt gcgctgttac agaatcacca cggtagaaga ttaagccatc    91860
```

```
tggtagatta ccatttgctt ctacaggttt ctttgcttgg ttcatgattt gcaataattt    91920
actaactttt ttcattttct aatatttcct tgtttatttt gattgcttac atttaacgtg    91980
agcagctaca cggtggtgtt taaggtacac cacaaacctt tcaaacttat ttctcgtaat    92040
ccaaaacagc gtatgtagca tgatgtaatt caaagctaaa gagtggagag aatatcacag    92100
gtgtctcttt accaataact agaattttat tattctttgg ttggagtaac tcttcgtaat    92160
aagtcatcca gttcttcacc atctctaccg cttcaaactt atagatcaag tcccctttt    92220 tgtttcggat gaatttgtct aaagttttga agtcgtcgtt cattttacgc atcacacaat    92280
tcacaaattc ctcagtggcg tattttggaa acttaactcc taaagaaaat ccgaggaatt    92340
ggtttgtcgg taatacaccg taagtgaatc cgttttcttt atgacatatc cagtaatcat    92400
ggccatcgag aacgactact tgtgtactgt gctctttaga cacagctttc tgatacacct    92460
ctagagcgtg tggggtacaa ctacgattgt acattagtcg acctaatcta ggtgactcag    92520
ggagaaggtt gaactccttt gcatatatgt aggttgtagc cgtcatagta caaagtattt    92580
ctcttctaac ttctgatgcc aaatcgattt ggtggaatag tacactacca gccactagcc    92640
caagacggtc aactagaaca gatgttcctc ttttaaaccg gaagtagttt tggaatttac    92700
ctgtcgtctt gacacccag aataaaaaca gtttctttag atcaagtgct gctgaatgta    92760
gaggtaacca tttgttgtac tgaccacaaa tgtaatgaat gaatgcaggc gggtatttat    92820
ttctttcacg attgagatct cccataccca tatactcgtg aatccagtcg atggtttctt    92880
tggtaatctt tacgtagtca aggctaatct tacactctct tcctctgact gtgtcgtatg    92940
ttctcacagt ccaacgtgtc aattctccat ctctgaagaa cttagcgttg ttgtcgtaaa    93000
catccttcga taccaaagta cctaagtaat cccctgaata cacagactgg ccgtcagccg    93060
caagtgtatt tttatttttt cttaaaatcc atttaaggtt ggttagttcg tcgcgttcat    93120
tgaaatgtct taacattgtt tcttttcctta tagtttggct gtggagttat tttagcccct    93180
cccgcaaagg cttgtttgga ttaaaatccc attttcttaa gtaatgcttg tgaagctttt    93240
acttgttctt cttcttttccg cacagctttc tgtggggttt ttgtgaatac acttcgttta    93300
ttatcgtaag tgtaaaagtc atctgttacg tcaatacctg ttttttggttc ttgaactaca    93360 ggtaaacagt agctgctact gaaccatccc gacccattga tcattttttc aatcggtgtt    93420
tctttgatct gatttaccca ccaataacga tatgtgtcta cacgcccatt agaagtgggg    93480
caagtgcacc ctgttggcgg cttttcttta gtgccgactt taaacttatg ggtaggtttg    93540
ttgttaggtg aaacacccctt atctaaccaa cacgcacaat tgtatttact gctggcactt    93600
gtaaatacga aatagagttt accatcgggc ttttaacga ttatagcgta gcggttttt    93660 atagcctcgc gtatttgccg ttcgcgtttg ataaacccctt tgattgcttc ttttcaatt    93720 ctcatcttta aatattccct gctaacttaa acaacccacc gtcgtatttc ttcagtaact    93780
tatctatttc tgtttagcc aaaagacgta gttcttttt ctcgttagtg ttgaggtatt    93840
tcatcatcca cttgacggag tcttcattac accgcccat agttttaagt agttctttgt    93900
ccatcaaacc aaatacatgt atgttttgaca gcggtattct gggcttagcc cttttcaata    93960
cttctcccac taactccaat tcccaaactt tcacattgcc tactctgaaa gctggtgtta    94020
ggcttctatt cttagtggcc tctgtaatcc gataaccaaa tactctttgg atgtcgttat    94080
tggtcacata accacccaat cgcatcaatt tccttaatct ccaagagacc ttggttatag    94140
agacgcgttt atagacgtca tcgaaattgc tctttctctc tggtggatga tcgatgagca    94200
```

```
attcgaatac atcacttatg taatagaata tacgattgta aaccacatgg tagggtaacg    94260
ttatcaagtg ttcgtctgac gtgtatagat tgtataattt ctcgtaaatt tcgccagtca    94320
ccacactatc taaatcgcaa gtgttcgtta ataggtaatc ttcgaataga tgatgtagat    94380
tatcccaccg tactatcttt ggttccgtta gaccattgat cattttaagt atcctctgag    94440
ttatcaaatt gaacatgttc actaaaataa tatataaccg aaaaatatta gaggaggcta    94500
ccgaggatta actcggtagc agattattaa taactgtgta gcacaacatc acggctcgtc    94560
acagcttcca gatcttcgtg cgggttaaac ttctgttgac gatgtggcat cggaatgata    94620
gcgttaaagg cgtaatatgg tccgctgata acgaatgggt gaatacgccc atatccttca    94680
tcgccttcaa ctgcacatgt gtcgaagtat agacgctcta ccgctgttct tggtaagcga    94740
atctcgttag acgcttcacc ttgaagatac agagggttaa ccacggtgat ttcataatcc    94800
ggatcgaaat gctctggggt gaaacgctct acaaacgaca tggtgtcgaa tcgacgagtg    94860
atgtaactga atacgtagta acgataccac tcaggttgat ttgccagagc atggtacgtt    94920
ggaccaccac aacaaaccat cttgattagt ttagcgatga actggtcagt atcgtcccat    94980
tcagcttcat catggtctag aacaaacaca atgttttcta gatttgggtt tttcaaaacc    95040
actacgagtt gtagtgagtc agggtcagct tggaagaact taatctcatt agccgatacg    95100
cctgtgattt tctcaatgcc agcttccatc gtctcactgc gacgaagatc gaacaaggtt    95160
gcttcgtatt cagcaatggc tgttagagtt tccattggag caacgtatgc cttcattcta    95220
cttccttttt ttaactattt acagggtctg cataaaaaga cagaaccctg taatttttta    95280
cccatgtgga aatactagca aagttaagct aatggtattt cggtgttgtt tctccataat    95340
accaccacct tcaacttcac taaactcgga ggaggccaat agcgtccctt ttacacgttt    95400
aatggtattt gattgtgggt atatcaattc aatgcccata ccgggcttga gagcgtcgta    95460
gagaccgttt tcccattgaa ctgtaacaac cgcaccccct cttctaaaaa gctctgagga    95520
agcttttaga ggattatccg tgtagcgttc tgctaacata ggggcattcg tcatattctc    95580
tctggggtta gtgttaacct cagtcaaata tttcctaggg tcgatgttgt tactatcccc    95640
aataccacga ttctctaatg aacgaatatc ggcaaatcga ataccctgtcc cctcgtttac    95700 agcaacgtca tcgatagagt taatgacttt actgtcaccc gtagcagcga tgtaataaac    95760
gtcaccttcg cgatagaagt ttctatcggg tgacatcatt tcatcagttg ggacgttata    95820
gatgactaaa cgttcaccac cttcgtcgaa ctttgttggg ttgtagggtt caaacagttc    95880
ccatgttttg t tatatagga aaatacctaa cccttt gggg taaataccat atcggttttg    95940
aaggaagtcg aatacttcta ggaaccgctt cccttcctcg attatgatac actcgtagtt    96000
tttcggggtc ttgtcaacat agttgataga gtagttgaaa tcactggttg ataacgtgtc    96060
gtctaattga ttcttttttta gtaggtaacg tgcgacatcc agagcgttgg tttcgtgaaa    96120
tggaccacca acggatcttg tacgcaattg ccatgctaat ttatcaagta gctcaaccac    96180
caccacagcg atagtttcat tatccatacg ttcggcatta gccatctcac gagaaatggc    96240
acccatgtca acgtcctcgg tgtttgttgc ttttgccaca taagtctttg tggagatgac    96300
tttgccatta actcgttttg ttaaggacaa ggtcatgtct tcataaccga gcctcatggc    96360
atatacagca accgaggcag ggactaagag catcatcttt gttatctcga acatattcga    96420
gtcgtagttg ccctctttgg aaaaagcttt taccgtgtat acttttttgat aagcaccacg    96480 tattgataaa acgccctcgt actggtattg gggcgcacaca atacatttttt ccaaatgtcc    96540 ctcgaggatg ttattaaaaa cgccttttct caaactcccc tccttctaat cgactttgcc    96600
```

```
tacctcttga ttttcgtctt ctgtattcag attcaataaa ctcaatcatg ttttcattat    96660
acacttcaag tttatcctta tacgtttcgc cgcgcagact agcgaagaat gattttctaa    96720
cgcgtagttt ggtgtggtaa ttatccagcc tagctaaacg aataagctca gaactcagtt    96780
tagaaaattg tcgcagccct tcaatcggta tatctctttc aatcaacctt tctttcttaa    96840
ggtagttggc ccagtcgatg atgtggtctg tcaccacttg gaaagttata attgccgttt    96900
ccttatccgc aggtcgaata cggtgacctt cgtctaacac ctcagcgact tgtgaggtga    96960
agacgtgtac cggaatcatg tcactggcaa tctttctatc tgtgtctagg ttacctgttg    97020
aacggcgacc tatcactgta gcgtattgtt ggttatcgac taggtagttt ggaacgtacc    97080
acaaacgtgg tactttaaat aaccatgtag cgttactaca tttcagtttg ttttcatcgg    97140
acataatgca acaacaacaa aacaataggt gagaagtaaa actgttctag tggctctagt    97200
tcaaacagtt tatcataaag tcctattaac ttatcgacat caatagtttc tttacgaaca    97260
tactgtaaaa ccattcgctc tagttcagtc tctggcattt cattgtaaaa accttcagaa    97320
aacacataag gtttcaacgt gaccttttg aatggtggta attgattttc ggctaattca    97380
ccccagtcat attcacggtc tgggttctca cgtcgtaaga ttgactggga tggcgtatac    97440
ctcaccgttg accccatagt cttcatatca ccagaccaca tagtcatgaa gtattgtgag    97500
tagccgatgt tattgatgta ccgcttacca cggaatggtg caatatcaac caaacccatt    97560
tctttcgcca acattttgaa agtgtggcga tgtggcttca ttaacaaaga ccaaagagtt    97620
ggtacttcat caagtttaaa cggtggatag ttgtaaacac ttttccgttc aatgccaacg    97680
aatggtaaga aggtttctat aaaaccatcg ttcattggtc tagattgctc tggtaaacta    97740
tacccatcag tcggaagata catccaggtg tggaaataca cttcttgtaa gtaacgaata    97800
tcgtctttga ttttaattaa ccgattgtaa ctatcctcgg ttatcaaaga ttcgccagtt    97860
ctttccagat actctggtga gtaaaccatt gattctgata tcttagaatt gatgatgttc    97920
atcaacgcat catcaatcac ttgtttaagc tgatactcga tacgatagga agcttcttta    97980
cgatgagaca tcctctctga gttagtcacc aaaaacagac ctaattgacc atcaccaata    98040
tcagcaacaa aaacatcgtt attgttgggg attaaaccat gatcaatata accttcacct    98100
tgaacagtaa aggtcttatc gtcggtattc tgtgtgcttg tcaatggact aacgacacgg    98160
ataatcaacc ttttgatctc acggtattgc tgcgatgggc ctttgatgta tgtgtcaaag    98220
tcggttgaga tattgtcact gcctacacgc attgaaagat aagatgggat agtccactta    98280
gcaccttcag catgttgtat tagacgagac ggggatagac gttctgtatc tatctcaatt    98340
cgacgagctg gttcactact cgtctccacc acccctgtgt tatcttgggg tactggtttg    98400
ttagttgcgg gtctaccaat aagcatttct taaccctctg ctttcttaac taagatagag    98460
ttgttgtgaa tggtaatcat cccaatctta gtaggttctt tactaacggc cttggtgaca    98520
tcatcaagaa cagaaacagg cactctgtct ttggtgatga tgttttccca atcgatgaca    98580
ttgtcattgt tgccgcacga tggtctctgt cctgggtacg aaggtaaagt agaaccatta    98640
ccagaaccgt tcggttgtgt taacgatggc gcaatagcat caatgtactg ccataatacc    98700
ttaggaaact cccttaggct atcgattgtc ttattggcat cgtagcttaa ctctgtcact    98760
aactccagtg tgaactgatt acgtttccac acacggtatg gtgcatcaga ccaaactaac    98820
agattctcat ccaaccagac attgagtggt tctacacgta gaccggatac atggaatcct    98880
accttgaaaa tagaattcaa catgtgcttg tctttaacag ccacgtactt taaatactcg    98940
```

```
atgaattctg gagtgaagcc aaatggtaac tcgttaagat cgatgataca gtacggttct   99000
ggattattct catcgtaact ttctggtgca cagtcagaag agaagaagat gactgtatct   99060
ttaccacttc cgccctcgta gtccactgtg aaatgccacg gtagtttcag aacatagtca   99120
tcgatatatt gttctgattc tatcaaaggg tttttgtaac ctgttctttg aacaatccaa   99180
ggtgggtcca actctggcca ataatcttct ggcatgggtg aacctgccac cactacaggg   99240
tattctatcc gtaattccga tggtctctct aaacggaagg atacggagaa tgaagtggta   99300
tagttggttt ctcgtttatc aaaggtaggt tcttcatggt cataaatcaa atggatgcct   99360
gagatttgtt ttctcgcgat gaactgagca cccttgccat tttgttttgt gccgactgtt   99420
acccacttgg ccagattctt caagaagaac tcatcaactg gacccgcacc caattcgtct   99480
ttttcacaag cagtggtgtg taagtcgatg atgacttgta atgcttcgtg gggaataggg   99540
taactgaact ccccaccagt catgatggca ccttcaccag aattgattct ggttcttagt   99600
ctctgaacaa gacgtttagc ttcatctttt gaagtggtgc gaaaagacaa agttagtttt   99660
gtattgaatg tttcacagat aggtgttatc ttcaatccat atcgggaatc aaagaagata   99720
tcctcttcaa gattgatatc cacactacga acactagcag agtgggcatc tggttcttca   99780
tctacctgta cagtgattgt tttaatatca ccaaagtcaa ccgatgtttt aaagccttca   99840
gttgacagtg gttgaaagtt attctctagg tcgccttcgt actttattga tgttttaggg   99900
tcgagaccga caccactaat caaattacga acaacgctat catagagagt cttacgaaga   99960
acgttatcta cgcttgataa cgatgtgatg atacgcatgt ctcaactccc aatttaaagt  100020
cagtcataca aacagttatt gatggaaaaa ataaagttta aaagcccaa ccgtttggtt  100080 gggcttttat atcgcttatt agtaaagtat tactctttac cgtaagcgcc gatagcagta  100140
cggatgtagc cagatagacc ttttgcaagg ttaacgcgac acttgttctg taccgattcc  100200
atctgaccga tggaagtgat gatcatggta acgccacgtt tgatgtcacg tgcagcagct  100260
ttatcttcag aagtttcagc gcctttacca gcatcgtttt tgatcttctc aagatcttta  100320
agtgccttag cacgagaaga ttcaacctta cggaacttgt tgatgtaagt ttccaggtct  100380
ttaccgaagt cacccatcat gtcgttcagt tcagaaagaa cgccgatttc aggagtgtcg  100440
acttcagatt tcagatcaga tttgtcaacg gctttgatat cgaatgcgac agatactgtg  100500
ccttcttttt cagtcaaagt tacgcgcgct tcttcaccgc caagataccg tctttaacg  100560 ataagtttct taacgccttc ttcaacagac tcagatgcag acttagtcat gctctgtgct  100620
actgccttaa ccttagacgc ttcgccttca gccgattcaa tcatcttgat tgcatcttcg  100680
gttgcttttt caatagcacc gacgtcagta cactcagcac cgatttttc tagcgctgct  100740 acgttgttac cagcgaactc tttaccgata gatagttgct tgatgaaagc acctttgata  100800
gtgtctttct tcttgctacc cagggtatcg atgatcttag cgttggtttc agattgactg  100860
cgtagtgact taccagcgtt aacgtatttc ttccaggttt cgcgagcttt gtcccacaga  100920
gctttaatcc actcaatgaa cgcttcccac atacccttca gagtatcaga aacaccttcg  100980
cgtgctagaa cgcggttgtc tttacggtca cggccgaagt tttcacgaga cagcttacga  101040
gaaggctgta caccccaacg acgagcgatc gattcagttg cgatttggat ggtttcggct  101100
tcatcttctg aaacttctgc atcttcatct tcaagcttgt cttcaacctg ctcaagagtt  101160
tcagtatctt ctgcaagaac ttcaccctct caacgatttt gaatttcgcc atcaacttgt  101220
ttttcaagcg ccgcaagatc tgagtcagtc tcagcgtatg gtgcgatgat tgtttggccg  101280
tcattctcta gacggatatc agcatccatg tttttcgcgag ctagttgacg tttacggaag  101340
```

```
ttgctcatta cactttcctt ctaaatgttt tacagatgtt tgaaaaggca gttgaacaat 101400
caactgccta atcgtacggt ttcaaaagac gtgattaagc gtctttcttg tatgctgcga 101460
taccagcgtt aacaagacca gacagaccag cgccgacagt tttgtaaacg taagtaacag 101520
ctttagaagt gtgctgtgca gaagtagcag cttcacgagc aactttctgt gcaacacgcg 101580
cttggtcttt cgcttcacct ttttcagctt tgccaactgc tttctcagct ttcttagctt 101640
cgtccatcag ttttttcaga ccgttacgag ttttagtaaa gccttgctct actttctcga 101700
atgctttacc gatgtcttcc atcgcgtcgt tgcactcttc aagtacagct acggttggag 101760
tatcgatttc ttttcttca gttgagtctt cgcctgggtg tagacgaact gcaacgattt 101820
gcgctttcac cgcagaatct tcacgaggtt tgtactcgta agaagcagac tgtaggtagc 101880
cgttaccagg cagagcgtaa acagtttgtg actcaccaga gtctttaccg ccaagagatt 101940
gaagtttctt agaaactttc tcaccgaaca gctcacgagt tttctcgccg tcagttacgc 102000
ggttgaactt agcagaatcg ctgtcttggg tagtagcgat cttaaccagt tcgccagcag 102060
cgtcaacgaa ttttcagag gccgcaagtg cagacttagc tttaccgtcg atagacagtg 102120
caagttgaat tgctttctta gcgtcgtatt taccttcgat agaaagttta gtaacgaagc 102180
tacctttgat cttgtctttt gacttggtgc cgagtttgtc aaggatcttc gcgttttct 102240 tcgcacgaga ttgcattgac ttaccagcgt taacgtattt cttgaacgtg tcgatcattt 102300
tgtcgaccat ttcgctcaac cattcgatga aggttttcca catgtctgcc aggcggtctt 102360
tgatagactc gcgaaccagt tttgtgtcgc cacggcggcc agagaaactt tcgaatgcca 102420
gtttacgagt gcttgcttta ccaaggctcc aacgcgtgc gattgattca gttgcaattt 102480
gcagtgtttc ggcgtgctca ggagtgatct cttcgccatc ttcttcgatg tcttcgacct 102540
ggtcttccat cttctctaga gtctcggtat cttgctctag aacttcgcct tcgttaagaa 102600
gtgcgtagac ttcttgatcg tcttttgtcga cttcgccaac ctgagcttct actgactctt 102660
caactggctc tacaacattc agaacgtcag cttcgcccat gttttcgcgt gccatacggc 102720 ggttttcat aaatgacata atgtcttttt cctatcgtt aacgatttac tactttcaat 102780
tgaaaggttc ctgcctagcc gttatgatca ttcgaccagg caagacattg ctaataaact 102840
gttcaccatg tcattaacag catttggatt gttcatgatg cggctaatga aagggtggtg 102900
ttgtgcatat aataaatcct gaactggatt tacacgcttg tcatgcttac cgtaataacg 102960
ctctgtaccc tctgggacga aggtaattcg acctgtggtt gacagagaat ctactttaag 103020
aacttgacgc tgagacgatt ctagatgacc taccgagttt ttaattaact catagcggat 103080
tcttgattcg accaattttt tcttatcctg aagaacgctc ccaacgaatt cgttaaagaa 103140
ctcataatat aaggttgcga taggaccgta cttatcatgg agcatgatag cggactcttc 103200
agtactcaac tccacccata ccgggtaaag ggcagcaatg gaacggtaga gcttggccag 103260
agtacgtggg tggtctgctt tagcactccc acgtttctgt aagctacggt actcgcccaa 103320
cactgctaag tggtgagata gtaacatagc tcttatcctc gctcacgtaa accgtactgc 103380
tcttccgtct tgataagttt gcgctgtaac tgagatagac gttcttcttg caaagaaatt 103440 tcttttctcaa tgttggcatc gccttcacca gactcctgtt tgcgcttcag tgccacgaca 103500
cgatactgca caagtttgga ggttgcttcg agacgctcaa gacgatccat ctgccagttt 103560
gcaatcacca tctgcggata gaagatgata gacagaggga atggaggcac agacaagttt 103620
agagggtcag cgttaccgtg acctactact tcaactagct tgttatactt ctcgctatcg 103680
```

```
gcaagaagcg ccgggatttt accgtaagcc gctttgatgc tactcaaatc acggtgcagg   103740
atatccatcc caataacaaa gctaaaacga tgaatgctta ggtagtcttc ctgtgtcggt   103800
gttaacttac cgaccttttg attcgaaccc gggatgctat tcaattcgta gaaagatgac   103860
acgttcaaga actctgtcat gtaacgaaca gtgaactcga ctaagtcaac catttgcaca   103920
agattagatt gtctcagctc catcccttca acgtggatgc tacgggctga aaactgattg   103980
cctaaccaag gcaagatgtt taggaggtta cgaagtagtg atacttggta atccagaatt   104040
gttgggttgt tgattcgttt aaggaagatt ttttcattct taaattcgtc aaggaagtac   104100
ttgttgtact cacccataaa ctcagagttg aagttgccat ccaagacttc gctcagactt   104160
acgaaagctg gaagaagctc tcggctaatt tcactctcta agttggatag gttgttctta   104220
acatcgctgg tgttaataga acctttcagt ttattcttcc attcgtctaa attgaacatc   104280
tatttcccct taacgaccca ttggtgcact gccagcgtta tatgcacgga tgatctcatc   104340
cacatccata ttattaccgc ctttagagcg acgcaggtct ttaaatggaa cttctgttgc   104400
atcgtcaaga ccacggtgat aaatagtcac ctgctcccaa cgttgatcaa caaccaaaat   104460
aagcatggtc aaagtgtctt taaatacacg agagcgaatc tcgaaatcag acaaaggccc   104520
acccaattct acttctaggt catcgactgt ctcttgtgag gcaacgatga tagaagaggc   104580
attgttcact gaccagttca tgcttagtag accagccagc cagttattag aacggcggct   104640
catcactttc tggtaatacc cggttttatc acggtgtcga ttcttacgca tctcatcaat   104700
gatgtcacga gagaacacga tatcacgtag ccacttcagg tcaccagctt cgctttaat    104760 gatacgttct tcaaacatca tcgacatgcc accgacaccg agaacggatt tcagtgactc   104820
tgggtcgatt aaactaacgg ccaaagctac tgtcaaattt actggtactt tgttaccgtc   104880
acgttcaatg atgaattcga attgtttacc cgtactaagg tcgtcattgg ttgacaacac   104940
tttaccgtaa tcgcctttac cgaaagcagc accagtagcg ccaccgttcg agaacgattc   105000
agccatcagg tatgaagcaa agttcccagg ggcacctaat gtcccaccaa tcgactcggc   105060
accaaggtaa cgcataagac caaggccacc tgccactgca cctttaacag ggtcacgctt   105120
aacggcaact ttatccagtg tgcgaccaat gttaacaccg gggataccga tgatttgact   105180
tagcgagctc aaatagtatg aggacacaag ggtattagcc acgcctagga tgtcgcgcat   105240
ctctggcaga tcggcaattc ttgtttcgac taaggtaatg aaatcgttgc gagtgtttga   105300
attaaattca ggcaaggagt cggctttgtc ctgccataaa tcaccgaatt tagtgactag   105360
gtccactatt gtattagctt cgctcataat cttaaattaa cctctttta  aaaggacact    105420 tatacaaatg gctatgttag aaaaaagaac tgttgatggt gttaccaaat acaaagtaga   105480
tggtgtcccg gtctccaaag aaatctacga aaaaactcaa gcagaccaag atgctgcctt   105540
cgccaagttc aaagaagaac acggtcttag agaaactgat atggataggg ctactgcaca   105600
ggcacgttca gcgactgagc catcaccagc accgaaccaa gccccagtag tcgaattaaa   105660
gatggacaca gccccagtgg tgattaatca agttaatccc gcacagagac ctggtacatc   105720
gcaagcaagt atgccaatcc tagatactgg aacggtatct aacaccacca cggactcatc   105780
aggtaacgaa caagttctct cttccgcagc ttctgattct gccaatgcga aaggtactgc   105840
acctcttagg gtagacaaca cacgtgaccc taatcagatt tggaagaacc gaatcggact   105900
gtcactaggc aaaggtttgc caaatgagtt actaaccaac gcattaagcg gtttaatca    105960 taggatagtg acgcagagcc taccacaaca tcgtgagtta caaggttatg tctttattac   106020
acgtcccgat attaacttgt cagaagagaa tatagccaac tcacgtttct ttagttggct   106080
```

```
ggcttcgaag cctgtggaca gtgttgaatt tagtatctta gctgctttag accccgagtg 106140
cccattgact aatccacata aaagaagggg tatgccaact gacgccagaa tcccttttga 106200
caacttacag gctttcactc cgatactgac aacacaactt cgttctttat ctggtttccc 106260
tgaccagacg ttggatgtct ggatgagtcc tgaaggtgct ttccgtgaac agtatgggat 106320
ggtggattct gtttacgaag ttaacaacgc tttcactta aatgccacat ttaacaactg 106380
cattggtgat ccagtgatgt tgtatgttcg tggaattatg gaatactctt ccggtgtgcg 106440
acgtggttta tttaaaccga agacatacaa tcaggtctca cgaagaattg attaccagtc 106500
tagaatttat gtctttaaat tcgacccaac tggtagacgt gtaattaact ggggtgcggc 106560
tatggtagcc tggccaatga atgataacga aggttcattg ttaaactatc aagcagacag 106620
aactatcgta gacgatactc gtgaaatcaa tatacagttt caatgcatcg gtgctcgtta 106680
cagagacccg ttgttattcg agactttcaa cgagacagtt gcgatgttca accctgacct 106740
tattcctgac tatggtgccc cgctaccaag taacggctct gaagattctt tacagtataa 106800
ttcatattcc ccaattgggg gtgatgggtt agtagagatt ggtgaagagt tactaccaat 106860
ttttaactgg tacggttatc ctattgttga cccagacaca aatgcttttc gatggtttgt 106920
ttccatcgaa cagtacaatc gaattttaag agaaggaggc gtccgtgtct aaaacgattc 106980
agaccttggg tgctgatatg gtatccgttg ggcagaaccc acaagctatg gctagaatca 107040
tgctcaactc gttgtccgac agagggttgg aactagcttc tccagtagac ccaattgtgt 107100
attcagccga atgttctcta atgagtggac acgctacact tttggccaca gataatgtat 107160
tatcaaaaat ctatagtagc atggcgacat cgtgggccga tttgtacaga cacatgtctg 107220
acaaagatgc cgttgactta ttctatcagc caaccagaaa tcaattcatc tggtcttatg 107280
atttagaaga gttgcgcgat gcagctattg aaatcgatga tacaggtaca aagaaaatcg 107340
tcattccggt agacacaatc taccaagcaa aggacaggcg ttacgctcaa ccgtacccta 107400
ttgagattcg tttcttaagc aatgaatgga ttcaagtccg ttgggataca tcggtcgaga 107460
acccagtgac taatatccct gctaatgaaa ttgaatggca gaaacgccct tactccaaag 107520
ataacattca gcgaactttg ctgactatta ctgtcccagt agaacaatac gaaattaggc 107580
atcaaaagtc acaggtctta cctagactag gatgggaaga gacctatact atcgacgata 107640
attatttcac cactcgtatg tggtacagaa aagataatcg ttgggctgag atgaagattc 107700
accacagcat agatgtcatc gatccacttg agccaacagc tgttatcacg gtcgctgaca 107760
aaagaatcac cctctccatc cctgaagtct acatcaacac gggtttggtt tctggtgatg 107820
ttaaaatgtc tatttactcg acacgtggtg ctgaggtaat caatctttca aactacccgg 107880
tctctgactt tagttgggta tataaagatc atcttggtgt aactgactct gtttactaca 107940
atgctcttaa aaaggtagag accatctctc taatctccat cggtacaagt acaggtggtc 108000
gtgatggttt aacttttgat gaagcaagaa acgcgttat tgccaacaca ctaggcgata 108060
gacaaaaccc cattaccgac gctcaactaa tcgataactt ggctgaccag ggttacgaca 108120
tctataaagc tgtcgatgta ctcacgagtc gtatttatct tgcggctttg gctatgccta 108180
agccgggtgc tgcaaatatc tccggtgcaa tcggtacggt aaatgaccct gttactttaa 108240
ccatctctga tttggatgac caccctgcca ttttgaagaa tggtaatcgt tggacattga 108300
ctgatgaatg tttgttttaag caatggtctg gtaatgttgg tttattcaaa gatatcactt 108360
tggcccaatt gaagtacctc aaaccagtcg atcgaatcga ttacttaagg gacttacagt 108420
```

```
tgcttaattt accccttccat gttgttcttg atattaataa cgacattgtt gatgggagag 108480
cttacgcgat taagaaacct tcgttagttt ctcgcgtaca tcgaatgagt aacgataact 108540
tacaattgga ggttagtaca caactaatcg atgttgttaa aaagggtaca aactacgaaa 108600
tcacagccgt tactcgctcc gatgcaaact acaaatcaat acctgttagt caacgctccg 108660
cttatctaag cttcgacaac gacggtgatg ttgtatatct tggtggtgag cgtattggct 108720
catatggtga tggtgaggac cgttggctat ttcgtgttga gaccaatcta gatattgaca 108780
ggaacgacaa actcattgtt aataacttta acgagagtaa tgggcaaggt tacccaatgg 108840
cttgtccatt gactgttgac tttaacttgg tttatgcact cgatggtaac tacaacgaca 108900
ccgaccttac cgatatcgac aattacatcc cagggtgggg tagtggcata ggtgcctcat 108960
tggacactgt cacaatcgag tttggtaaac cacttagtaa cttgtgggtg aatgcaagag 109020
ctatgccggg tgcgattaaa cacaaggtct acgaggagga tgtccctaag gtctatctga 109080
aagatgaaat tatgactgac ccggaaacag gtggttataa atataacatc gtcgatggtg 109140
atattcagtt tgtttacgca catcgcaaag gtgaccctat ctataaagac ggtattgtac 109200
aacttcgatt taagaagggc gagactgttt ttgaaaatgg ccaagctgtt gttgaggtgg 109260
atcgcaaaat ggacctagag tctaatttgt ggttggtgga tgttcgctat cttgtaacag 109320
atgacacaac cgtggctgag tacaacagct actggtatga ttacgttatc gagaatgcga 109380
tgaatgttct accgtcattg gctaaatccg cgttagaaaa cacagacttc ttcttaactg 109440
ctaaaaatac agtagcgaga atcaaagtca aacttggtaa tgagacagtt aactacatcc 109500
ctgctgaaca aaaattcggt attgattact acgttactga caacgttaga caaaaccaag 109560
agttactggc gcagattaag gcaaccacca atactgttat tgagaactat ctaactagtg 109620
ccttaactat ttctacgaca gacatcacta agcaattacg cgaaacccta ggcgataaca 109680
tcaagggtgt ggagatgcgc ggttttgaaa atgcacaaga tacacgtatt ttcacaatcc 109740
ttgatcagaa tgcacgtgcc accatcgcta acgtttgat tatgtcggcc gaaggtaagg 109800
ttggactaga gaacgatatc tcaatcagtt ataaccgtta ccgataaaaa aaagaaagag 109860
tacaggcttc ggcctgtact ctactttatt ttttacagat ttttgtggat tttgtaataa 109920
tcattaacga ccgcattcaa caacttccaa gatgtaaatg agtccttgat tgttctcaga 109980
acaccttcga tgtgtttacc cactggtatg ttgaacgcca cgttcttgaa tttaccatcc 110040
ttctgcaatg caccaacttc aataccctttg attggaatat cgtaaacaaa gaaatccttc 110100
cctttgtttt tttccctatc acgtgataat tccttaatga cgctgtaata ggtatcgtat 110160
cgcttctcta gttcacgcag tgcgccgtcg atgttttgt aatcatcggc gtataactgg 110220
ctgattcctt caagtcgcaa ttggatattg tttcttggat tgtactcgcc gtgttgctca 110280
tagaacgctt tagcgtaagc ggctggacca tcctcaccct caagactatc gaagtagctt 110340
cttaccgcga agtacgcttc acgaccaaca gattcgattt tgacaggttc tctatcaaaa 110400
cctataacgc catctaactc tttacgagta agcgattgcg gtttggtgtt ttttgttggt 110460
ttggttaatg ggttggttgc tttgacaatt tggaagtcac tgttctcacc taactgggtg 110520
acaacatgat cgatgatact ttgggcatct tgtctattaa gatcaacctt attccataga 110580
tagaagtttg caagagtagc gtagcttttg ccgaactcgc gaacggtcaa ctccgtccca 110640
aggaagtcgc tcaatttctg acctagattc tcaaggtttg tgatgttacc atgtaaatca 110700
taaatgcatt gttcagaaac aaaacgaacc cggtcgtttt tgaactcgtc agaattcaac 110760
catgctcttc tttgcgggct accttcctcg atgtcgatca aaccagctaa ggtactcacc 110820
```

```
atcggtgaca acggtcctct gtaaccacct tgcacaaagt tgatgaagtc acgtgcaact   110880 cttttttcgca tagagtctgt ccatgcgaaa tgtccaagag gtacattgtt atcaatgaaa   110940
gtaaagatga tagcaaaacc accacgaagc agttcttctt tcttcttaac atccatatct   111000
aacgtgttga cataatcaac catctctgct gcaacttctg cggcacaacc agatgtgttg   111060
ctacccggtg ttcttaagtt acctggagac gcgtagttgt aaagacgaat catctcttct   111120
ttgatgatgt cagagaatac accgtacttt tgttcaaccc actctttcgc agcatcgttt   111180
gctagtgctg acaactcttc attgattttc ttttggcgtt cagtaggtgc tctgttacga   111240
ccaccgccct ttccacccat acccttagaa ccttcgatac taagagaaat caacttcaag   111300
atggcaccaa tgataagagc cataacagcg taacgaatac gttcaccca gttttctgtg   111360 gctaatagta tctcgtcttt atagccttta ctgctagtcc cctcgaccat gaatgacttt   111420
ggttcaattg cagtgtcgtc gatgctgagt agtgtttcca tggcttgttt atcggacatc   111480
ttgtcgatat tagccactag gtcatcggct cttcgcatta gaccgtcgta ctcagttagt   111540
tgagtttcta ccaaagtcac cgttctatcc cacgcctcat caagggaatc gccttccccc   111600
aaagattcac gagaaagact gcgctcaagc aatttctcaa cctcatcgat gtaactctta   111660
cgatgctttc ttttcgattg ggctaaacct agtgtgatag cactaagttc cattacgcca   111720
cctcgttgta ctctttgatg tagttgttaa ctactggaat accacgttcc agccaaccat   111780
aaataaagtc agctgcccca tcacattcat gttcaataaa tgctttaacc gacggttgct   111840
caaacgacac gataggacaa acaaagttct cccaacgtga ggcgtagatt ttatctgcat   111900
ctcggaggac tttctgagac ggtaagtaca tcgcctcacc tgcttcacta acgagtttga   111960
taacagcgtt gcggttatca gccattacag cttcttcgct gttatgacaa cctacgacca   112020 tgggttaat gtcacgatag cctacaaatg tagcgatggc tagtgcaact aactcagaac   112080
gtttggttaa cacagtcgag ttatctgagc caccgttctt aaggtagcta cccgctgctt   112140
catttagctc tgttaccaga gttttcaatt gatagtgatg tgacatgatt aaccttccaa   112200
tacgctttta acaacgaata gttcatttgc agagagttct tccaattctt ccatgtaatc   112260
gcggagttgg ctatcttctt tgcttttgcc gagatattta ccagacataa tccgacccat   112320
gattgtagtc acgtctggtt tctctttgat attttctaac agcccacgaa caacactaag   112380
gtcttcttgg ataccctctt gttcttcttt ggatatgttt ttgactttta ggcgatcgat   112440
gataccgcgt tcaatggcct ttaaacgacg ctctggggta tcgtggtctt ggaacgtctc   112500
atcgttcaag ttaccataca aacttgctaa tacagccatc acagggacaa atacgctagg   112560
tgccaaagaa ctacccagaa taattccaat gactttcaca gattgtgtga tgtagtggaa   112620
tgtattaggg gtgtaatcac tactgcgtag aatagcaggc agttctttat ctttcttaac   112680
taacgctgtg gctaacgctg caccaccacc cattctggtc actatcatat ccgataaacg   112740
ttcccatgaa tgattggcgt aagtgactga acctgtttca gcgcgtcttg ctttggcagt   112800
ctcagtcact agaaccttgt agagagtgtt cttggagcta gcatcggcaa taacgtcgct   112860
actttggaat tcaacaccaa tgacttcacc gacttcttca attaactgga cacgttttac   112920
tttgtcctcg acaccaagaa tacggtcaac actggcacta atcagatagt tgtaagagac   112980
aacgtctgca atagctgcaa agtacgacag tatgtgacca acctcatggg ttatggcttc   113040
tgccaactca cgtgcagtcc aaatctttga gccgaacata gagatagaga tgcacaagcg   113100
acaattgatt tcgctgaaaa tgccatccac ccgtgcattg actaagtcta cgctaccaag   113160
```

```
taaaggtttt cctttcttga tagacttaag agcatcgtgg tcgatgtttg caaggaactt  113220
gcgtttgtaa tttgcaatga ctggattgtt ctttgtaagt gtgggtgcaa agatagcaat  113280
ttggtagtaa tcgtcatcac caccgattga agaccatggc accatactca ctgacaaatt  113340
gtggttgtca ttaagaacag caggaatttt tgaatgtctg tatcccttct cagagaaatc  113400
acccgcatcc ataaattctt gaactgcttc agtcaaagca tctagtcttc catcagccgc  113460
catggctttg aaagcttcgg cacttaaccg tcttttgttc atgaacatgt gtttaccttt  113520
tttaactgcg aaagtatata ctatagcata agaattgcaa cgaattactt cgagaggaaa  113580
tatgagtatt aaaccacctg tagagatagc gggatacgaa tgtaagaaca ttgcttacca  113640
gaaggcaata gacggtagta ttgacgatgc tatgttcgtt aaagagattg tccactacac  113700
ggacggtagt acagaacctc gtactcgtct cgttgagaac ttcgaacgac cattctacat  113760
cactttaccg catctaagaa atcaccaaga aaagaaagaa tttgaaccag aagagaatct  113820
tcaaaagttc atgtcgacgg attctaactt atctaatgct atacagctag cattgggtag  113880
ctcgttcccc aatccacaca agcaactaag acagatttgt gatagcccat atatctatta  113940
tgctgacttc actgcgccga tgtatcttaa atcacgctac atgatgaaat ggcctgaact  114000
aaagaccatg aataaggtgg cggttctcga catcgaaaca aacgaatatg aaaaaacaaa  114060
agaagttttg atgtgttcag ttgtggtcga taataaatgt tatttggcga tcactaagaa  114120
gtactacgat gagatgtgtc ttaaacaacc agactacaag aaacgtatta caaatttgct  114180
tagtcgtgta ccttttgttg ataagaagac aggggaaatc aaaacaagga atctcattga  114240
cgagttcgac ctagatgttg agttcatcat tgaacctaag atatccgtag cactagctag  114300
aatgatgcgt caggttcata agcatctacc agacttcttg gctatctgga acatggactt  114360
cgatatgtcc aagattctag aggtgcttaa gaaagagaag atggcacctg aagatgtttt  114420
ctgtcacccc gacgttccgc caaaatatcg taaggtcaat tatcgtcgtg atgttgcttc  114480
acgtatcacg aataatggta caaataagac caaggctcca caagaccagt ggcatgtctt  114540
tgaagtcatg gcttcgttct atgttatcga tgcgatgtca ctctataaaa agattcgtgt  114600
tgcgaatggt aacatgccta actataaatt ggctactata cttaagcacg aaatcggcgt  114660
tggcaaacta gatattgagg agatgcctta caccgaggat ttgaaatggc acatcgatat  114720
gcagaaggac tacaaagctg aatattgtgc atacaacatc atggatgact tgttaatcct  114780
cttattagat aagaagactt acgatatgca atctgcggtg agtgtcttat cggaatggtc  114840
accttttctct atctttgctt cgttacctaa gcgattgtgt gcagcactaa ctgtttatct  114900
tgaaaaggat aaatgtatca ttggaacagc tggtactaaa attaagaacc ttaatgatga  114960
agaggtgatt ggtttagata actggattgt aacgttacca gcacacaaca cgatggaaaa  115020
tggggcaaaa gtcgtctctg aggtgaagag tctggtcaca gctatacgga acaggtagc   115080
ggatgctgac ttaacacagg cgtacccgct tggttcctct atacttaacc agtcacgtga  115140
aacacgaatc atggaattgt gccgtgtgcg tgatggagaa gaatgggaca gacgacgggc  115200
tggtattaac ctaacctcgg gtaaagttaa ctcaattgaa atcgccaaca ctttcctaaa  115260
gatgccagat attgatgtgg tattggaagc gtttgaagaa cgtaataatg tagactacag  115320
attggagttt atgagaaggc gacgagaaga agaagagttg gccaaagccg aaagagaaga  115380
gaaagcggca taaagaaaaa aaccctaaga ccatttggtc ttagggtaat cttttttttat  115440
tttcttactt agatgggaaa aggtccatta gacgcttagc cacatctttg tcagaaatac  115500
tttcaaacac acgcgaaaca tttgcttctt tgtggatttg tgctttgtct ttaagacgac  115560
```

```
cgtacttcga catcagcgtc aagaattcgg caaggaacac acgctcacct ttgtcttgaa   115620
tctgtttagg gttggtcaag tgcttaacga tggtaggtag ttggtactca ccgttcttag   115680
agtcggccac acgttgaaca aatgcaccaa acatcatacg ttgtactttt ggagatgctt   115740
tcaccagagc gcgtaccgcg gcatgtagtt tttggtgtgc tgctagatcg tcagctggtt   115800
gtgctggttt acggatatag cgtgctgcat attcgtccag ttgttgcgtg aaagctttaa   115860
cttctagctt ttcatgcaaa gcgatgtctt cttcgacatt ttgttctaga gtggccgtta   115920
gttgtttctc accctcagct gtttcctgag tgatgacttc atccaactgc tcttcttgct   115980
gaccagccgc ctgctgctct agagcctcac cctgctcaac cgtggtattt tgttgagttt   116040
gagttagttg attatttcca cgtttagaca ttatcgtctc cttagctaat atggtatttc   116100
ggaataaagt ctgctacttc taagtcagag gcgtgcatag cactcattgc accgtacata   116160
gtatatgaac cgatggatgc ctcttcgttc gcaatagcat ggggttcacg agcatagtac   116220
tcgttagcac aagtactaca agtgtcgatg tggtcttgct tacacaagaa tgctcgacgt   116280
aatgggattg ttttaccgat ggactctttt gctaaatcat cgtcaaatgg cactatttta   116340
ccgttgattt tcgcattgag gccaatatag agtttgtagt tctcttctgt gatgtcctgt   116400
ggtaaagctt ctgcgccaca atcaccaaaa cgaactacgt ggttctggaa ggtggattgc   116460
aagaatgtta ccttctcacc gccttttgct gtctctgagc cacgttggta agaaccttca   116520
cgtgtttcgt tgttttagc aaccagttct tctttcttcc agccatccat taaagggct    116580 gattgtagaa taaagaacc atcctctcgg aaagccgatg aagcaccttc tataacgtag    116640
agcttgcgac gacggttacg agccttaggt gagtcgtagt attcgataga ggcgtcttga   116700
gataaccatt ctctatccag tgcatctagc tcatctatga tcttcgccac cacagaaggt   116760
ttatgtaatt cgtgcgcgtg ctctttcaat agccgttcac gggtctcctt cattttaggg   116820
tgggtgccaa gagttatctc agtacctgtt ggggtgatgt aagttgataa agcttttacc   116880
tcaaccacgc cctgaatgaa acgacctaat tctgttgagg taaagtattc tccagacgag   116940
ggtgctttgt catcatccac acctaagtgt aaatggtcat caagccactt atctggaagc   117000
acattaacat tgacgaactc aaatcgtgga ccaaacgcat aataccaaac agtaaagttt   117060
gcaattactc gccccggtga ggttttgatt tctttactat caggaccca catacctgct    117120 ggcaatgtcc accactcatt gactctgaat aagccctggt tttggatagc atcttctatc   117180
ttaatccatt cgccatcttg gtagtaatgc gccaccccat cgagataatt taggtcatag   117240
tcttttggct tgtagtcttc gggtagcaag gccacgttaa agacgcctaa tcgccagtgg   117300
agacttctcc atctttcttt acggagagct gttacaaaat aatcgttacg attcatcttc   117360
ctctacctct gcgttaaagt agcgaatcac accttcacgg atatcgtagt aatcaccaat   117420
accaaagatt tcattttggt ctaggatagt aactacctttt tcagcattac tcattgcttc   117480
gttttcagaa tcagtagttc ccaccaatac cccaatagat agagtagcaa tcatgctttc   117540
cgtcatctcc acagggtttt catcaaagtc aaaggcgttg accatacttt ctggtgttgt   117600
gaaagacata aagctttcaa atacgctata gaaaggcacc tctggattat ccagtaggaa   117660
attaagaagt cgcttaccac gttcagcaaa gtaaacttca ttgtccatat cttttctttct   117720 accaatgatg ttttctttga tgttattaat aaatcgaggt tcgagatgtt caaaaccacc   117780
tgtgtagtca tacgtctcat ccgggaagat gaatagactt aggttattaa ggattatgaa   117840
ttcgtcttct tccgatgacg caatcgccaa taacccatcg atatcctcga acgtttcaat   117900
```

```
agcatccaaa agcttaaaca gaccgacaat cgacaacaac tcattattaa tgaaatcgta   117960
atcgaaatgc gcacctagtc ttgctaggaa ctcatcagtt agtttaagga tatgatcttc   118020
aaactgtcga taagcatcaa cagcagagtc attctgatcg gcgatggagt aaagatagaa   118080
caggtcttca ccgacatcgg tatccgatag gattttaact aagtaatgga atgcttctcg   118140
tctactttct gttctcaccg aaaggactgt gtctattaac tcttccatct ctactccaaa   118200
aaataattag tgtattctct catacaaaac caccccaact tattttttaa cgatcatcac   118260
tattatatag aagggtgaga tcacctttaa catatttact tttatacttt ttttcacggt   118320
aaagtcttta catatggaag atttacccat caataaagga ttcaaaaatg tctcgcaaaa   118380
agaaaatttc aaaaggtgac cctcgccgca agttccactt taaaacacca aaagatcgta   118440
agatggctga actgcgcgct taccgtcatt cgatgcgaga actaaaactc gaatctacgg   118500
ctgtcattca attcgccgaa cacgataaac gtttaactga accgaaatta ctgacggctt   118560
ggaaacctga aacaaaggcc gagcatcaga agttatcga  tagttgtagc aacatgatcg   118620
agttagcaga agccacactt ctagttacag agaagtacgt tcttctaaac cgtgaaatcg   118680
ccgctacatt aaccgattat gatgattcac gtttgtacga tctggaagaa ttacgtgaat   118740
tggtaatcaa atcccaagaa gagctgcgtg tggtagttcg tcaatacggt cttaatgaac   118800
tgaccgcaat tagtgcttaa aagaggtagt agaaatgcca gtaagtaaaa aacgtgtaaa   118860
gaaagtcaaa aaacaaggtg gtaatctacg tgcggacttc cgtcgtgatg cacgacgcac   118920
catgcgcaca actatcgcta ctcttcaggg tgttacgcaa atgcgtgaac atgtagccaa   118980
aaactttaag aatttcccta aagaagttct agcttctgta gaaagtaagg aacatgctat   119040
ccttgcagaa atccagttga tggagggtaa agctgaatcc atcattgaac agtgcaatcc   119100
tgactctaaa acaatgcaag agtgggaagt tgatgatatg ccaagtgtcg ttgtgttatc   119160
acaagaactt gaatcgaaat ccgatacgct gatcgctcaa tgtatcgaag ctggcgctga   119220
actacaaatt taacgagat agaaatgtct gaagttgata accaaggggc aaatgttgcc   119280
cctgaatcaa ttgctgaaga gcaaaagaaa gtaactattg aacgcaatgc tgtggactat   119340
cgtagcattt atgagaacag tgctgcattt actggtggtg tgtaccagtc gtttaaaaca   119400
ccattaccag catacagcct gtctgatatg gtggaacacg ttgcccgctg gaaagtttct   119460
gatgagagcg atgctcgtct tgaagaactg acaatgtttg ccacacctga agatattggt   119520
tctcgtatct ctaaacgcga caatgctttg tggggacagt cactacccgg acctaacggt   119580
gaaatgggca ttcgtccaag aaacacttcg aagaatggtg cgttgtccgt tcttaccagt   119640
ttgactggtg gcggtacgca agttaagatg cttatgcctg cctctggttt ctacatcacc   119700
ttctcagccc caacagagtt ggagatgtgt gacttcgatt tctctagtgc attagagaca   119760
tcaattgtgg gtatggacac agctggtcta ctaatgaatg catcgtcagg tgtctacatt   119820
cgcaaccagg ttaacttcgc tattaactac gcagttgata cctcactagt gcataaccgt   119880
gagaacatca gaactgtcat cttaaatcgt ctgaatgagc gtgactatgg tcttgttctt   119940
ctcggcccta tgattgctaa gttcctcggc ggtttccctt acacgttgac ttgttcagtt   120000
gattcgtgtg attacgaaga agataagcgt gttaacctag gtcgtctaat tcactacgac   120060
cgtaaagcac tcaccaaccg acagttagaa attcttgata cctataccga tagcagctca   120120
ttaactgaga agttgtacgc agagtatcac gaagagtttg tgcgggttaa aggctcttct   120180
accactatcg gtaacgatga acaaggtaag ttgattctca attactatca tcctagtatt   120240
caacgttact tctacttcac ggataaatgg gtaaatgatg tcgagtcgag caacaacgtc   120300
```

```
atcatgacaa ccatggctac cgaagaccaa cgtcgccgcc atctacaaac acgtgcagaa   120360
gcgcgtcgta tgttgcgtta tcagcatcta atccaaagta tcgaaagtgt tgcacctacc   120420
ggggaaacag aagtagttac tgaagaagaa gacattgctg agattttgcg tggtctttgt   120480
gcaaaccctg agttggttaa aatggtagag gtggatatcc aagagttcat tgtcaactca   120540
tccatcacac taatcggtta ccgtgctcaa gagtgcccta agtgtaaaac aaaaccaact   120600
gctggtaatg agttcatctc catgagtccg gactcggttt tttttatgct tgttcaattg   120660
gtatcagaaa cttacaaggg tctagcaaat ccagacgtgt agtcgctcac cttggtgaag   120720
accacactga agaccttcat cgtttgatta gtgtagatac gaggaaacta tttactggtg   120780
aatcggatat accaatctct cacgttgaag gtcgtctctc actcagacaa tgttacgatg   120840
cctcatatgg tttagacact ggcccattcg gtatcgagat gactgatgaa gagtcccctg   120900
caaaattcag tttgtacgag tactgggctg aaatacatgc aagagaacga atcttccatc   120960
actacggttt ggatttggat cagttttctaa atcgacctag atacaaaata gaaatattag   121020
ttgataaggt taaaccgctg aacaaatctg aagagacgac agctgctaag attcaagatg   121080
agataaaacg ccaacttgaa cagaactcaa aaaataataa gatttaggct agcattgcta   121140
gcctaatttc ttttttttagt gtggtactgc caaacgacct gcttctaacg attttgttat   121200
aaactcaata gttaaagacg ggttatcttc tacgttggtt ggtgtatcat ctttaataag   121260
atgataattg aagatttcgt agccgtgtgt tccacgtatt gtactgccgc gtgttacaat   121320
gtatttcatg ccacgttgct ctacttggaa gctaaatatt ttagccttag tggaatggtc   121380
tagaagcgaa gctaggtttg gtgtagatgg ctctacaagc ttctcaagcg attcttctaa   121440
actagggtac agtttcagct tttcagataa gaactggtag aagctttctc tgagagcttt   121500
aatatcacgt ccagggacca ttatccttct cctaattcaa gtacaaaaaa agaaggtgat   121560
ttctcacctc cttcccttct tacgcctatt gtttctggca ttgtcacgtc tattcttcca   121620
ctcgcgtctt gcctgcttat gtttaaaacg tttcaatgct ttagttgcct tagacctatc   121680
tggaagtttc ccacctgcta cctctggcga tagcttgtag tttaccttct cattaccttc   121740
gatctgatac ccaccattaa ctatgtttag acttttcgct acgtggctta agctatccat   121800
acgttcctta agataagtat tatgcttatc cagttcacga caatgtaaga ataagacttt   121860
tggcgtcact ccttcccatt gcgtaacagt tctagggcgt ccagcaatct gttcgttctt   121920
ttgtctgtca ctaatagctg gtgttactag tgctagaaca agaccgggta agtctatcgc   121980
tgtgcctgct ttctctggtg acgagacacc aatatcggct gattgcaaat cctcaaactt   122040
atctttatct acataccgca caatattgaa ttcaccttcc atttctaaag cgacgcgttt   122100
ctttaaaaac tcagtgaagt ctgtacaagt ttgtatcatg gagaaaaaga ctaatgactt   122160
ttgtcccttc tgataattat tgaagtaagc acgtttcatt aaatcgtaaa ccatttcaaa   122220
gtaatcgttt atcatctcgt gttgataaag atactgctca aaggtcttat gattgtacat   122280
cgacatgcca ttgacacgat tacgcatttt cttaacgaga atgctataat agatgaaggc   122340
aatatcacac acacgaatgt atggtacatc cacacgatta tgttgaggga aacgttcagc   122400
gtaacgaagt ctatggaact cttttcttggc tgatggtttt aacgtcgctg acatctctac   122460 caatttttggt gggtttaaga taacaccact caaatatacc gttaggaagt gttcatggat   122520
ttcgtcataa ccgacaagcc ccgcaccgat atattcgtaa aacttatgaa gctctacacc   122580
attacgatgc acacgattgg agaattcctc taaccacaac attaatgagg ttgttgggat   122640
```

```
gatgattgtc gatatatttt ttctatctaa ttcaccactt ctcccatctt cgattaggtt 122700
atcgatacca gctacgcctg acacaacacg tactctaggc gatggttcat acaaaccacc 122760
ctcatcatca acacaatcgt atttccattt cttaacatac gctggtctaa cgatgataac 122820
ggttcgtctt ccaaaacgaa cctgcacttt ctggaacgtt ttagttttac cacgacccgt 122880
ttgaatctca aaaattgttt gattgttccc gggctgcaat gctgtgtcac tgacctcatt 122940
ctggaagaag aaacgtgact cctcgccatg tacacgcaaa tcgaacttat agttcttgta 123000
agtgacttct gcaccttctg ctcttggtgc ttcgacaatc tcaacctcac ccatcctccc 123060
ggcttgttga gttgcctgca cacacatttt aacttgttct aaaaaagaac ggtggtaata 123120
atagctgttg gcttgcttgt cgatgtagaa gtatggtctt ccattaccga cttgccattg 123180
attgtaattt ctctctagta ctggctcata gagtgtattg ttgattttgt ttgaaagctg 123240
attagctaaa taagggcaag ggtcatgtac aatcaaccct tggcttaaca atgtaattct 123300
ttgtttggac atctaatccc cccaatatcc tgtaggtaca catatggtcc taaagggggg 123360
acgaatcccc catgtttaga cttcggtat ataaaccgcg ttatcaagaa gtgaattgtg 123420
tctatacggc gtaacgaatg tacgcggcct gtaatagata tcattctgtt cttggtagac 123480
caaatatgga cccaaagaac gttcttccat tagcgtggtg tgtttatcaa accgcgcttg 123540
ggaattacca aaaccaccaa ccaatgatgg gtctgattca ctcgaacgac gcaaagatgc 123600
gagaatagtc gcaatgtgcg taatcggtgt acctggaagt ttacgttcca aatacgtgtg 123660
aacagccaac atggcttctg cacaaccgtc tgctgtcgag ccatcgtaat cagttatcat 123720
gctataacga ctgttagatt tgctagaacg cagaatgttc tcaaggttag ttacgtagac 123780
tggcatactt tcgtgacgtt gttggtattc aaacaacgct acgtttcgca gcttaccatc 123840
ttgtgtttta ttgaatccat ctagagaaaa ctcaataaat ttttcgttgg tatcgtctat 123900
aataaaatct ggattacggc gcaagaagcg gaagaattcc actgttagcg aggctggaac 123960
accagaaaatt atccttcga actcatctga cactacacat tcaccatcag gggaatagta 124020
atcaacccag tattttgtaa tgctggatat ctcaccaatc tccaacaact tgagattgtt 124080
tgtgtatgaa agacgcgtga agtttggaag ctcttcacgt agaacgcgaa gacgtgcaaa 124140
ttgtaaatct gctttcgctt ttacgtgaat acggtttggt tcttttggta cgacttcaaa 124200
tattcttgat tgttgttggt ttaggacaac acggaatagg aagataatga agtctaggtg 124260
cttaactgat aagatactct gagaagctcg ctcagtcacc gtgatacaag aaacatgtcc 124320
tggtgaatcg atgtcaggga tattgtaggc caagtcaccg taacacttt cacatatacc 124380
ttgtttcgat agatgattac atcctaagga agttctaagt ttaatcgtct gaccgataag 124440
atgaactgag tctttctcta tcaactccca ttttttatct ttgtttaagt ggtaactgcc 124500
aacacagcgt tcgaataaaa ctttacctgc tttgttgtta gctaagttta tctccaatac 124560
ttcacgacta ccacaatcac ctttgtataa cgtagtgata gccgatgtta gtagctgcat 124620
ctttctcgag aagtattctg agaaggcaat gtaaccatcg ttgtaaacga atgacttagt 124680
cgcagaagta cattctttaa caaagtcagc aatagtacta aaaccagtac cgaacccgcg 124740
tttaattgcg cggtcaaaga taactgagtt tacctctgtc gtacggccac gcaacgccat 124800
ctgcaacgat tggttcattg aacagatttt gttattcgtg gttacactga taccgttgtg 124860
tggatacttc ttagtactta tgacatttcg gattgtgttg tgagcatggt ctatactttc 124920
aacattatct gttaccttgg acagagcttt cttaatctct gggtcttcca gtagctgttc 124980
tatgtcgtca aagtcgatgg tgttggcata ttgtggtaac tcagccactg ccaggttgta 125040
```

```
cgccttattg taaatgtaac ggtacgcgat agcccaaaca tcatacttgt caatctccgg 125100
gtaatcacgt gtcaccttaa ttgctaagct aatgagctct ttgtgtgtat cgtcgtttat 125160
ctctcgatgg taatcgtagc agaggtcaga tggtattttc acctgattat aatgacgatg 125220
gatagcccag taaggccaac ttagcaatat gtgtgatgcg tgaaggggtt tttcaacccc 125280
atcactaaac ttaaccaaat acttggtttt gttttgtaca acttcttcat agctaaaatt 125340
agccaattca tggatactga ttttctccac tcttttattc ctcttattat tccattaact 125400
attaatagct tgggtctgat acatctactt cttccaagcg tagtttctgg agttcaagcc 125460
cggcaatatg tgtgagtgtgt tgtaggattt gatgtggtcg tgaatcacct aaaggatata 125520
gttcacgatc aaccgcacat tcaatattca tgggggtagg gtgagttaat accatgtaat 125580
cttgcattcg tgcaacaata gggttattgg ctctatcatg acattctgct gcaagttcac 125640
cagcaccgtg ttcagccagt aaacgctcct ctgattctga aatccactta catgctttgg 125700
ttggtgcagg acgtaagctg atttcatcag agttggtttt ggcgattgta ccaaatgggt 125760
caaagcgaca agaagaaata ctggagaatt cacggccagt tttgtttaga cgtatggtat 125820
acacgtcacc gatataaaat tcttttttcag tccaaacttt ctcaccattt ggtttggtga 125880
taagcaattt agatttacgg actttgtact tctcttttaa gaggcgagct atttcataaa 125940
agcttttctc gtaatcattt ggtatccagg cacggaaacg aacatcacgg atttcctcat 126000
aaaggatttc acgttgttcg cgcttactgt gagtgtcttc tagtacatcg gcccactcag 126060
ggttgaaatc tcttgctaac tcaaccatca aaggccaagc tgcatcaatt cccccttcct 126120
cgtatgcctt cactatttcc tgactcacaa cctcgcgggc agtgtgcgac atgaatatta 126180
cgtagatcgg taaataagtc gaacgacgta aggttgcatc agctgcacgc atacagtgaa 126240
cacgattacc aaattcatca attggcatat cttcaactgg cattatttta gaaacaatac 126300
ccttagtacc acttaagtca gaaatcttac cactctttgt tagagggata ggatagcgga 126360
ctgtaacttc gattcgataa gtttcgattc tttcgaatgc gtagttttta ttgtagttca 126420
aggtttgaag atgacgagag aaatatttcg atttctttcc cttgcccatc aagacatgag 126480
cagccatagc gatagcttca taaatgaaac gtgtcgcttt acgagtgtaa gggatgtttt 126540
cctcaccgcc gtattctttt gctaactcga tatggtaacc gagaatattt tcataatact 126600
ctcttgtttt gaatgcgtgc tggtctaact caagctgaac acgatctggg atgttgaact 126660
ttggtaatgg tgacgtatca aagttctttt ggtcattacg tataaccttt acatccacaa 126720
ctcgtgcacc cgattcacct gaggcatcac catcattgtg ttggattta ttgtaatagg 126780
caatggggtc gaataggtca ccatcagata attctaatgc tgcatcctcc tcactccact 126840
cgataacacc aattacttt ccgttttcac cgatggaatc accgacacga ggaacatatt 126900
gtggttcagt cgccgtgccc attatgttag ccaacgtttg accattcttc aggctagtca 126960
catatttctt gtaaccgtat gccatgaatt ccccggcagc ttcatttgac atggtgtatg 127020
agtcctcaat tagactcggg tcagaaatca ctactgttgg tatacaacga ccaaaagcaa 127080
actcaccgtc tttaaactgt ggtgggtgat ttaagttcat ccccttatat acaccgccac 127140
ctgatgagcg caaagcttgt ttaccatcat cagtcaaagt taattctgag gcaaagacat 127200
cgtcgtgttt aatacgatta tgaatttcta atacatcaat tgcctcacca tcatcactaa 127260
aacttctgac gaaaattgct tgttctaaag cttgatagtt acctggacta actcgtttga 127320
agacgcgtag ggttgttcca tcaactaacg atttatcatt gaaaaggtat ttgccatatt 127380
```

```
ccaattcatt accagttggc cattgtacta cttctggatt tatgataggt gcagtttgtt   127440
taatatgacc gcccaccata ctcacacgca taccagaaat ttcatctggc tttgaaatca   127500
ggttagtggc tgtacccact aactccggtt ttagttcggt cgacattgat atttcctctt   127560
tatttctaag tcaccattga tataacatat aacttaatat tttttgcagg ggttttgtat   127620
gttagaaaaa ttctacacca aaagaatgga tatgtttcct ctggagccag acgtatattg   127680
gcgacttatg agacaacaca agttatctct aatagaagcc tctcaggagc aagtgctaac   127740
tgaaggacta tttaccccct caaagtatag cttctaccgt tattttttaa atattgagtt   127800
agatgctaaa ttatggatac ctactttggt ggcttctggg attgataata tagaagacta   127860
cgttgatatt aatcaggtta ttaaaatacc ggatatttca gtggtcgagt ctattatctc   127920
ctcagtgaat taaaaaaaga aagtagggcc gaggccctac taatctttat tttttatcgg   127980
cgaccccaac gggaagcgcg ttcgttacga ccatgtcgat catcgttgtc acgtgagaag   128040
gatagatatc ctccacgacg atctcggcta cggcgtcgac caccacgacc atagtcatca   128100
tcatcgtaat catcacgacg ggatggacga cgctcatctg tatacaggcg cttgtctagc   128160
ggattgccag ttgaacgtgg tttatcatca cgaccgccac gatattcaga acgttgacca   128220
aagatagcca aaccctgtgg ttcatcatct tcgtcttcgc gttcatcaac atacttatca   128280
cggcggcgat tacgcaattg ctcttcacga acttcttcga catcaaaagg aatgtcttct   128340
ttctcctttt tcttctcgat ggttgaacgg ccagtgttac caggtagtgg tggaatacga   128400
ccacggtaac tgctgacttt atccatgtgt tcagcaaaac ccaattcgat aactggtaac   128460
ttgatgtcct tttgcaccat cgcagccagt ttattgtact gatttgcgaa cttaatgtag   128520
aaggacatca atgcttcgaa gtttggagca tcaccattgc taccgaacat gtgggaatcg   128580
gagccctcat gcatcagtaa ttcgcgcatg actgcaacga taccgcgttt acgtgcttta   128640
ctactcattt gaacacccat taggaaggcg tcatctagat caacgtcgaa ccagctagaa   128700
gtgtagtaca aaacacggag ataatcctca ccagcaatct tttggttacg atcgacaaac   128760
aagcggaccc agtctttcac atctgcgtgc tcagtaagtt ttgtccagtc tttgattgtt   128820
ttatcatcga catcgttttc gaacttagcc aagaactttg cataggtgga tttcttttta   128880
tccgcagaag cgcgaagttt aaagaatgct tcagctaaaa gaattgattt ctcaataatg   128940
ttagctttga ccattttggt cagccattta aaaacttctg actgatctgc tgttacagac   129000
tcacataacg ggaagtatgc atacttatcc ccccagtcat tatcatccaa aactgcatta   129060
gttggtaaaa ccaacttgtg ctcgtcgata gttacaggtt tctcaccacc gggtaataga   129120
accgcttgtc cgtctacaac acaacctagt gactctaggt tgctagttag aaattcaagt   129180
accttcactg tttatttttcc ttattcttaa atttgattaa tcgcgctcta gtaggcggcg   129240
accgaaactt ttcttagaga agatgtcatc taaagttgtg gtagcacgac gtgggctacg   129300
atcactgcta gggaaacctt cttcaaactc ttttgcattt cgttgtaaga ttgctgtgtc   129360
aatctcttcc cgaacattat ggtattcctt aacagtatta acaaatgaac gactgcgtgt   129420
tttggttagg tgtgttgcca atcgaccttc aaggaaggag ccaaatgtga aggcaatgac   129480
ttcaccctca tcatcataat cgatttcaac gcgcgtcaaa cctgacaacg tagagtaaac   129540
agtgatctca accgggattt caccgttacg ggttaatgga atgaaaactt catcgacgaa   129600
actatcttcg aatcgatcga ggaagaattc tgggacatca ccattcgctg ttagagtttc   129660
aatgttgtaa ctatcttcgt cgtgtgcgtt agcatcttgg aagaattgaa actctggttc   129720
aacacgccca gttgaacgcg acgagtaaag attcgataca cggaacccac aacctttgat   129780
```

```
gaggttattc atcattagct ctggaatacg atgacacaaa tcatacacgt ctagcgttac 129840
ttgacgagcc gattcccaac gttcagaatc ataatcagtg ttgtcaaact catacacttc 129900
gattagattc attgcttcgc gttggctacc agaagttact tcaatgatat cttctagagt 129960
aaatgcattt tcgcggcgca gatcttcgaa actctccaag tctgcatctt tgagtgcaag 130020
tacaaagtca ttatcagcaa cgcttgactc attaccttta gatttgaaac gggaagaaac 130080
gaaagagtta cgggatgcgt ccatgtttag accaccgtaa gttgcttctt tatcttcctt 130140
acccatcata tctgcgtagg ccaatgttct gaagtagtta tctggtaaag acaaattatg 130200
tcggacaacc ttggcagtgt tgccatcttc accaaccaca attgagtctt cctcaacatc 130260
gtgtccatct gcatagtcat caacataatc agcaaaggat acgggtgtag agaacttctc 130320
gtttttacgt gagtggcggt ctggtaagat taccagtcca ttactaacca ctgaatactc 130380
atcctgcatt cggccaccgc gtgtttcacg tgtagttaca cgtaaagtca acagcgaatt 130440
gatgtgcatt acagtgtcca aggtaggttt accacggtct aactcggcac ggtctgtgta 130500
gccacaaacg atcatttgca atctagagtt tgaacgaagg tttggattct cctgttcaaa 130560
cacagccacg taacgataaa tgcggtcacc accacgaagg taacgcgtac cagaatctgt 130620 attcccagg atgatgtttg gatcgtaacc ctcaacatca aaactagcca tacgacgaaa 130680 cacacccttta gcttctggtc cgtcgaaata gttacgaccg cgatcacgta caccgtcgcg 130740
cacatcacgc aaatcgtgta cgtttgaacc ggatgtattg atcttcaaat tacgacggat 130800
ttgttttggt aggttaccta cttcgaaaaa gtcaattgaa actaaatcta gcatgtttta 130860
aattcctctt actgatcaaa attatttagc aggtgcggtc atggctaata gctgaccaag 130920 ttcattttg aaatcttcag ttgggctaaa tttaccgttt tcggttccta ataagccaca 130980
gatttctttt gaagctttct gctcccaaaa gtactggtta aggtagttcg tcattgcgtc 131040
aatagacaga acgtagggtt ttacccaact agaacctctt ggattaggga tagagtttgt 131100
gtaataacga tccaaaaact ctattgtgtt tttgtctagc ggttttacat taattcgatt 131160
gtattcaatc tggtcaccgc tacttttcac atctttcaca tcggaactca acaatcgcgc 131220
taaacctatt aatttatgct cgattagata aatctgagtt aatccaacta agtgtgtgat 131280
taaatcaaaa gatatatctt gtattgtttg atgcatgaca tagcgacgaa gtgctgcacg 131340
gatgatgaag cgatggactg gtgtaaattg gctatatgga ttcttttgtg cggaatcgat 131400
agctgcttta ataagagatg gtttagattc aatacctaaa gcatgtcgtg ctttacgata 131460
gtctaaagcc cacacaccat tcatcattgg tatcatatct gggacttctt gacgtgattg 131520
atacgtctcg aaataccca tcttactgtc ttcacccatt gccatttttct caccagggcg 131580 ttcatctgtg atattgaaac gacgaataat tttttttcgtc agctcatcac tgatttatt 131640 attgaccgcc tttgcgaggt tggtttggtt actagttatt gatgttggaa taacacctaa 131700
aatgataccg acacccatca ggtattgtgg aagatcagca gaaccgatgc catcaagaat 131760
actaccgatt acattagaac gcttattctc aagtatcttt tgagatgtag cttcgatata 131820
aatttgtagt ctctcaaaac catcggagtt acttatttca caatcgtcta acttcgccat 131880
gaaagctaat gccttaaaca tgaccgaagc accttgtcca gttttctggt gttggaacat 131940
accttccatt gccaagattg gcataagagc acgcagacga actgctaata tagccagttg 132000
tctatattct ccacgggtat atgtttcctc aaccgtatag tgtttatgtg ggatgaacac 132060
ctcggttgca tttttaggat atgcgatatg gtcgatgtgg tcgatgatgt gttcttcagg 132120
```

```
atgcatttca tctaaaatgg tgcggtaaat tttcgcatcg atttcgatat tgcacattac  132180
taattcgtgg acttgtttgt aaatgtcaaa cagactctgg gcttctgttt cagacagtga  132240
actccaatac gaatttattt ctttaaaagt accttcggtg cgtggtccgc ggaattcacc  132300
acagtataat tcttcaccag cgtttgatac aatcaaagaa gaactttgga taactatctc  132360
catttaagaa tcctctttta tttcgtttta ccactaagat aacatatatc cgttattatt  132420
ttaaagggga ggagtgtttc cactcctccc tttattact ttttgtatct actgcttaga   132480
aatagttatc tacgctagta gttggagctt gtggttgtgg ttgataaccg ccgccattac  132540
cgccgccata attaccgccg ttgccgccac cgtaattacc gccgccatta ccgccatttg  132600
gattgaatgg ttcatacatt tctgccaaac ggtcaattag gcgatgttgc tgagatgccc  132660
atgcacgtgc atttcgctct gagctttcag ctactgacat ctgaccaccg ccacgtttca  132720
ttgggtattg tttcagtggc atccaacgaa cttcgacaga tttaccttgc gattcaagga  132780
ttgctacgac ataccttct tggttacgct gcacagttag tgtggcgtgg atagcacctt    132840
tacgctcttc tgcaatagtc agtggcacga actcacgaga ggctgcacat tctttaacag  132900
catctacgaa tgtttggaat tcaacagtcg gaagagacat attgatccat tgttgtttgc  132960
caaccatcat cgataaatcg atagtgttac aaccacggcc gcggttctga acagcctttt  133020
tcaaaccttg ctgttggcct tgtgaattgg ctacagtttt tggtttcatt gtacgatcgt  133080
tcagaaagtt ttcttgtttt actaaatcta ccatttggtt aaatccttac taagcttagt  133140
cttcccacaa gatatgttcg gggcgttatt ttttaagttc tcgaagtagt tttactaaat  133200
gtggctcgta agcacgctta acagcctcaa taattcgagt gtcagaggtt ttataattcc  133260
acttatactt cttggctaat tcaagaatca tcttgcggaa cttaattggt tgtggtgcaa  133320
ataccacgcc atcaccaaat aaggtgaggg tcattttact gaatggaatc atttcaggtt  133380
taccagtcaa cttactagtc cactcagatg gaccctttgac tttacctgtg tgagactcca  133440
gcaatgaaag cgaagggaag ttttcaacgc taagtaaatc aattggatgg tgggttaata  133500
acaccgttgg tttacttgca ctgatatcga tctcatattc agttacttcg tggatatcac  133560
cgatgacctt ctccatattt ttgaagaagt cttcttctaa tgcacgatag gcttttgtt   133620
tgtctgtcgt ggcattatag aaatttgctt tttggtagcg gtcgttgatt tcttgtacg   133680
tacagtaata gaaactcacc acacaatctg gttcgacgga tttaagagtg cttaaaatcc  133740
catccatgtc ttcacgcaca ctatcgatta atggaccaat agtcatccga ttttgaagtt  133800
cagtggggaa cgcattcatt gcgtttcgaa acagagtgcg aagattaacc atcagcaact  133860
tattgcgcaa agggaaatct tttgcattgg catcttcata ctctcctgtg tgagtagcac  133920
cttctatcgc caacgatgtg gcgatagaga tgttatagat gccgaagtta cggtcgtatg  133980
actttatcat agtcgttcct cgatctcttt aataatgcca ttagcgatag gcgaattgct  134040
atttattctt tctagcagga ttcgactgat ggtatcttta tctaaatgga taccctcgtc  134100
tgcttttcg ctaagagctt tattgatttt gatgatgcgg tctttattaa ctaagcgttg   134160
tggttttatt tcaataccgt aacgttcaga tagactgcgt aaagtaactc gaatatcact  134220
atcgtgtggg taagttactc tcaacttacc atgtttgctg tggggtgatt tctcaatctc  134280
cttaacagct aactccacac cttttgatgat ttcctcgtct gttttgtttt caccattcac  134340
ggtaatgtaa gggcatgggt gagggttatg gacaaaccaa ccctctgcgt agtcgtcgta  134400
aaaatctaca acgtgtacac cttttgtacc aacctcacca tggctcaaac aatcaggaga  134460
accagtgact ctgattatac cctttttgttt tgatttatga tcgtgaccaa tcataatagc  134520
```

```
caaacgaaca aatgacatcc attcgtactc gtcgaagttt gcctttgcta caatatgtgg    134580
gatttggaat ttaaacatcc catgcatacc agccaagtcg attttactgt acccttcga     134640 tttcatcaaa gacttaaaga gttttgttgt ttctgctgca tcatctcgat attcgtcagg    134700
aactaaacca accactttgt ttatcttctc atctttgaat acagtgatat catcgaagta    134760
ttttaaatca accccaaact ttttattaag ttctaaaata acacggctct gtttacggtc    134820
gtgttttggt gtcccttcta aaacccgcaa tgccacatct ttcttttac aaagttcgag     134880 taattcgttt aagaaaccaa ttgccttgat cagatcatcg ttttccaacg tatctctttc    134940
atcaaacaaa tcacccaata tatagatagc atctaatggt gtctccaaaa catacttaat    135000
taacaacatt aggttgaaaa ttataacaga cgttggagtt tgtttatgca atagatggac    135060
atcgctaaag aacaacactc tagaagcgtg tgctgattta tgtggtaaag tgttagatga    135120
ggtcaccgtc cacgcgttga tcttcattct taacttctac cttatcttct gttgtgtttg    135180
agactaccgc cttgttacca tctaccagtg ttttatcgaa aacggtaaag ccattctcgg    135240
agaaaacata gttgatttga tcaataaagg tatcgtcaac accagtgtca ggtagacgca    135300
ttgaaatcag ttcttggatc atggagtcaa aagaatccgg gttatcttgt cggttcaaag    135360
ataactctgc gtgttgtgaa ctgaacccag ggaattctgg atcgtctgtg ccaacgttg     135420 gttgtggtgc atgtagtggt ggaatcttga tgtagacttt gtcaccttgc ataacatgca    135480
tttcaaggtt ttcaccgcca caataagtaa tccagtgacc cgggtgaatt tcttccttca    135540
ttacaccgtg taacaatggt agaccgacac gaatgaaatt atcgtagtcc atctccacat    135600
ggttttcgtt taaaaaacgt aacatttctt tttcactccg tcgaacgtaa tcagttagag    135660
ggtgtccatc ttgtaaacta gccatgagat aagctcctta gaatttaaat tcgtagtacg    135720
tttgttcgta gtcattaaaa aagtcttcag cgttagtttt taggatcgtg gccagatcat    135780
aacttttgtt attgacgcga atttcagctg agataaatgt actataacgc ccatcatcat    135840
cttcaacata ttcacattta actctcacat ccttcccaaa cgaatatgag aacaaacgcc    135900
ctaagtcgtc ttgtacccga ttacagaact ggtccgggtc atggttagtc tcttgatagg    135960
ttttaccaag agagataatg ttgtctttaa aaataatgct ttggtcagcg ttaactgcgc    136020
gatacgccat cattatttct ttgactttat cttcaacaga tgtggcccat ccattataac    136080
ccatgcttcc aactacctt tttaccatta tagtaccctc acaaagaata aaaataaag     136140 cacgcccaca aatggggcgt gcactgatgt taccctctca tagcattata cgtagaggtg    136200
acagcatcat cagtttccat catcacgcgg atttgttcac gccatgtggc ttgaatatcc    136260
aaacgttctg aacggctaag tgatccttc tcttcgctat ccagtacgta tgagtggaat    136320
ttattttctt cagtatcgag ataaccgtcc atgacgatac gatagtttac atcggtatgt    136380
ttcactgcgg ttccacgcca acggtcacgt ttagagaaac catcttcata acccggctcc    136440
atatatcgat tataatttcg acgtacaact gggttagcga ctaggtaact ttccataact    136500
gaaggtgcga attgcaattc accaatacca aacaaacgac gtactgaatt tgacttacgc    136560
gaatgtctta aacgacgtaa agcagataca gagttacgat acagagagtt tgctcggatt    136620
gaacgactag tttcggcaac gccagctaag aactcttcag agaagtttct ttcgctatag    136680
cgtcgtttca aatgactagc gctgtggcca gacaaccgcc ctgaagctat gccgctaccc    136740
gtaccaacat cccaaggatg tgttcctgta gtcatatttta ttactatcct cttcctttaa   136800
atattaatca tcccactcac tgtctgtcac cgttgcattg atgaatccag attgtaaaga    136860
```

```
gatgatttcg gcatgtaagg ttaacttttc actaactgcg ttagttttac tgcgagacat    136920
gatacttaac gcacctttta atcggttagc taatcgtctc atcagattat cacgtggcat    136980
cataacctga atttggtcac cgtcgtaatc agcgttagcc tgcttgataa ttaacggtga    137040
taggtcaata gaaccatcat tgacatctgt cttcacatct gtgatgtaaa gcacccatac    137100
tgatagacgt accaatgtag ggttacgtaa tggtacaatc atgataccatg gaccaggagc    137160 ttcctcaatc agttctttaa tgacatcatg aatgaatggg tcatatgtca ccaaagctcg    137220
atctattgtc ttgattgttt ctatcggtgt aagattatgg gtgtggagta gtttattggc    137280
aatgtctaag taaagtaaat ttacagtcca acgccagggt gttttagagt ggtcgaattc    137340
atggacacca gtttccgaag aaattgttgc acggccagaa tacgatacac gcgtactatt    137400
gttctttgaa cgtgcaatgc cctctttagg gaaaacgaca tcacgacgaa actcaaagtt    137460
aaagaacgca tgggttctgt tagcggtaac cattctagat tgaattatgc ggattcgatt    137520
ctttctagat gtatggtagt acgcggacag gattgttta gctgcatcaa tcatacccac    137580
gtagattcta tcgacgtttc gttttgattc agcctgccct tcctcacaca aaaccaattg    137640
gtctgaaatg atcggtaact tagttgggaa aaacttacca cggtgccact ttatgaatcg    137700
aatccaatct tggcgttcta tttcaacttc agtggtttcc ttttttcggt tcaacatctt    137760
gctggataat tgaatcgcat gaaaggtatc gggttcaagt aaccgttcaa ataaccaatc    137820
gaagttctca atgaagctat ttaacccgcg ctcatatccc caactaagaa ttagatcctg    137880
tagggctacg ttaccacgcg aaggttgttt ctcaggtttg tatcgtgggt ctgtcaacca    137940
cgcgaccaaa tcataagact tcatcgggtt attcttaggt agtgtgaaac ttgaaaaggt    138000
acttaggata ttcatccata atgttggatg aataaatcca cgcattgggt aaatggaacc    138060
tatccaacta cgtattctga ttggttgctc taaagctttt acacaaacag tattgcactt    138120
ttcacaaacc gcaccgatgt cggcgtcgta ttgggttgat agatgaccac acgaacaacg    138180
aggtgtggtg ttaaaactgt cgctagatac ttctgtcttt aatatctttg aagcatagct    138240
cgcagcatca ggctgattta gagtttgtgc aatctcatta atcagtattg tttccttttg    138300
ctccgaatac aacttatcta ggtcgacgag agtcatggac acgccataat atccctcagt    138360
gtgcattcaa aaaccctctt tacttttgaa acaaaaaata aaggtcggga aattcccgac    138420
ctttactaac cagctatcta tgtcgattaa cgacgtagac ggccgaaacc acgatctgaa    138480
cggtcacggt aagtgcgacc agaacgttgt gagcgtagag aaccacgtag ttcaccacgt    138540
acacgttgtt tacggtcttc acgtacacgg cagtcagagt aaccagccat ttcaacttcg    138600
tcaaagttgt cttcgattac cttgtatagg aactcgatga actctgggtt gatttggtat    138660
tcgttaccga taccgtcgat ttgaacagaa gttgctacgt tgcttagaag ttcaatcaag    138720
aactctttag aactttctag gttcatctcg cggttttcta ggctggttgc agccaggtat    138780
tcaccgtaga catcttcgtc acccgcagca atagttgcga tgcgcgctag gtcgaagtct    138840
tcgagagtac gtagttgacc atttgctttg taagtaccga agacgtgtgg tacgatgttt    138900
tgtacgatgt cttcacatgt gatgctggat acacctaggt gttttccag agctgcttcg    138960 aaaccttctt caaggttttc accagccgcc atcaatgctt ccaggtagtc ggtgtcaccg    139020
ttaccgattt tagccagaca gtgaacgata ccatttgcag tttcaccatc gcggtgtaga    139080
acagtcacgt aagtttcgcg agtcatagcc atttctagct gttcgcggat cttgttcgca    139140
ttgtccaatt taccaacttt gattgcgact ggtagccaca tcttatcgat aaccgcacct    139200
aggttacgag acgcatctgc tgcaaggtct tgagtcagta catccatcca gctgttacgg    139260
```

```
ctgtggactg ggtataccgc accaagtgca agaagaccgc gctcgtagat attttcttcg  139320
gaagaagaag tatcaactgc gttgatttgt actttagcag caaactgctc aggtttgaac  139380
ttagctggat caccttcgta atcatctggg ttttttctcag gaccgacata gtccatacct  139440
acgaagccga agatttcggt gcgaccagca tctgtttcaa cgccttcttt taccaggctg  139500
cgagagaatt tcttgcgacc gttaccagaa gcttggttta cttcgatgcg gaagtctgca  139560
cgatgcagag ttgaagtttc ttcgatttca ccgacttggg ttttgaaggt tgcgctgaag  139620
ttagggaacg cgttgaagtc gaactcttct tcagaagaac cagataggtt ccatgccagt  139680
gtagccaggg cgtaagtaag atgacgcact gaatcttcag taacgttgaa gtcacggttc  139740
aggatttgcg catcgatcag gtaaacgtca gattcgttac agttcaggtc ttcggagatt  139800
ttctcacgac acaagatatc gaactcttgg tcaagcatgt cgtaagtgaa gactggtttg  139860
tcgttgttat ctaggcggta accaccgctg ttgttttcga agataaccgc tacagcgtac  139920
ttttctttgt caccgttttc gataccgatg tagttgatag acgcagagcg tagatcttgc  139980
acgtgaccga aaatcaaatc accgcgattg tctttggtga tttcagccag gattttgttg  140040
aaggtagcag aacgagtagt gtcaccttcc atacctagta cgtttgagat acggcgagca  140100
ggacgacgag tctcacggcg ttcttcgcga cggtcgtcac gttgttcagt ttcgcggcca  140160
gttttgttag ctttgttgtc gtcgatttgt ggcatgattt ttttccttaa tttgcaaatt  140220
taaagttgac atagaacagc ttttgtcacc attctcacaa ggataatata tacccttagt  140280
ttttttggaat cggtgccatg gatacatttc tatgtaaaga catataggag aggaataatg  140340
tctaatttat taaacatcga tactgtatcc aagggcaggg tcacagaccc ctccttcata  140400
gtattgcgca acaacgtaaa aaagtacagt aacctttttc gcaatcgtat cgcggatcag  140460
aaccgttta tcccgaaaga ccatatcctt tacaaagtat tgcttgaact aggtcttcaa  140520
ccttatatgg atgacgaatt cctacattat cggattcgtg ataaagcaaa acagttagct  140580
actagcttcc gttttaccta ctacaactcc tttggggagt taagttatgg taactttata  140640
ccagatacaa aagaagtatt gattcttaca acagatgaaa aaggaccaat gactcgaatt  140700
ttgtaccaca atcatttcaa tttaaacttt gaacttggcg aaaagaactt tcacgatggt  140760
ttagctttca tcgaattgaa catctacgcc ttagccaaag cttatttcaa atgggttaaa  140820
gaacgtgggg aaaatgatac aactcataaa ttcctgtaca tggaaggagt ttatcgttta  140880
ctaccagaat atatggactt ggcgttaatt aatagacact tctataatct ggaagaaatt  140940
gacctcccga tggaatcaaa gaacaaggag ttcgcaaccc cccacatagg ggagagtgtt  141000
actacacata taaatactat agaaaaattc tacaccagtc gagactttga catcggtggt  141060
tttttagata atatcccttg tgtgtttaaa gaaactgctt taagttatgt tccaaccatc  141120
ccatcatggg ggactgacca gatacgttgg gcatacgagt tggcaagatt gcaattcatt  141180
aatagttccc tacactattt gatgaaacgt gagcttggta agaaggaaaa gaatcacttg  141240
taccaattcc agcgcttcgt taaaaacttt aaccaatcta gacagcttag cagaattaag  141300
aaagaagatc ggacttacct ttcgccgatt atcaacgaaa ccgatcttct actctctaaa  141360
ctactttagg ctgtgtaata gtctgataac agacgagtac ggttgtcatc tatcatgaag  141420
acaccaaata cttctaagat gtggtaatat ggttccacca tcgcaaaaac tgtgcggcgg  141480
gtattaacca catctaaaag ttcttttggt acaccgtggt ctgtcactag gctatccgga  141540
atgatgattt gtttgtaggt acgtttacga tcgtcaaacc aggattgaa cgaggctgcg  141600
```

```
agtcttctat cctccatcga atccaaccat tctttgattt caactttggt gtccaggtct 141660
accggaatac gcatagcgtg atacggtggt tctggcacca ttccatattt tgtccctaat 141720
gtagcattgt acattaagtg gtaatggtag ttggattcag tctggtatga ttcttttgag 141780
ttgatatcca gtgttttaag ataaacacct tcaccagcac ggatagagcg ttcaacctct 141840
aactcaattt cagccacgcg tttcattact ggtaaaagct gaacatcttc accattcgca 141900
atctgcttag aaagacgttt aacagtggct ttgtactcat ccatgatttc gttagggatg 141960
ttagaagtac gtaatgcaac acctttaat tccagttctg ggtctgatcg tagagttcct 142020
tcttgcgatg tgataagtgc aaagtagtgt ttagcttttg tagttaagcc aaacgaatcg 142080
aatttaaatt cattcttcat cgagtactta aacaacttct catctgatac acctaattgc 142140
ttagacatcg aagccatcaa atgggcgatg ttttgcacta ccaagtatac cattgtatct 142200
gcaacacgag atgcttctac accagtatct ttaccacagt accactttga ccaccattgc 142260
gctgaaccca ttgttgagtc agtatccgaa accacaccaa ccgcacgaat tacttctggc 142320
attcgggcta tagtaggtgg cacgttttta gttgtcaaaa tagaacggat tagtaaagca 142380
tatgaaccaa tagtgttttg tagatggttc acggtagtca ttagtttacg ataatcgtct 142440
gggcgattat ctcgggcatc ttttaggtta ctgccaacac caactaaatc cgggcgcaat 142500
tgtgagacaa ggatacccat atcaccatcc atgcccttcg ccacacgttt aagctcttca 142560
tcactaattt cagattcttc aactggtgta atgattttct gaatgaacgt tcgcataaac 142620
tcatcgttgt atttagcaag gtggtacaaa tcacccatgt aaacaaacgc tgcacgttca 142680
tgaggtttag ctttagacaa tatctttttg attcgtctat cggctgctgg atttttgtag 142740
tagtcgcgtg tagagtgctg ataaacttcg aaggtttctt caactgtcgg aatgtgtaga 142800
ttgtattcgc taatacagcg cttaaacaat ttccagtcag ttaaagtaca aatgcttaag 142860
aagtgattga ctacaatacc aggtgcccaa taatggcgac gtccacctaa taaacgttcg 142920
ttagcagcat taccgtaaga ggttgcggta cggcaagttg acgttagagc cgaatgtgaa 142980
gacatgttaa acaagatagt aaatggcgaa gagaagccac cagaacctgc gttgttcaaa 143040
gtcttcttag agttttgttc gttctttttg ttgatggcta gaacggtatt cttagcagct 143100
tgagcagcga acatttcttg cttgatacgt gcgcgctcgt taacgttgtg ctcaaagaag 143160
ctagctagtt ttgatttctt catcgactct ggcatgtaga ataccatcga tggtgcaaca 143220
atcaaatctt tctcttgggt agtcttaata actttatcca tcgggataag tttcttagtt 143280
cggtctttag tggttgggtc ttgcactaaa aactcaccga ctgggaaatc ttgtttaaac 143340
atcccatctt caccgaactc tttctgcatc catgcttcta cttcttcatg agatgcgtct 143400
gtcatcatct ggatatagtg tattacttgt tcttcgtaac cttggatgat atcaatctca 143460
cgaacgtatt ctgatttttg taaacggaaa ggtgattggt acacaccttc ttctgtgaaa 143520
gctttaattt gaccaatagg atcatcgctt tccgttgttg tcaataaagt atcggtcatc 143580
gtacaacttt ccaattaatt cctgtcacac gatcgccagt taccgtaaaa aaagaattgt 143640
ccctaggact acaactgtag tcctaggtct atcgagaatg gctttaaacc aaagctggta 143700
taaagaccga gtgcagcctc attattcact tcagtagtga cggataaatt agtacaaccc 143760
aatcgctttg cttcactcat tatggattgt atcaattgtt taccgtatcc acgtcgacga 143820
tactctgaat ccacacaaac cagacgtatg ccaagtacct cctcccattg ttgggttaaa 143880
gagaaaccac aaagatacc attctctaag atcaggtgta atgcacaatc acctgagtcg 143940
atgtcttttc tcagatcgtt ttgcatctct tctgttgttc tctctaattc catgctccac 144000
```

```
gagtcccaca caaaccctgt cttcttattg tgttcgtaag agttaaggct tagttgcttt   144060
actaactcac ccaatcgatt gatgtgatta ttcaatatcg gatcatcgtt gttgtagcaa   144120
atgtgtatca tgattgttac tccaatttcc tcttctcata ccaattggaa taagggttta   144180
ttttcttgat cgtttttttt tacggcggtg gtattataat atgcacaaaa ctgtcaggct   144240
ccggaaggag ggggaaaggg gctttctgta atacccctata atacgctata atttaccttt   144300
ggggaaaagc ggtataagag gttaggagag tacaagtaag aagactaaag gtaaaggatc   144360
gaaataagaa gatagaaaag gatcgatcga tccaaaaacc tttttttat tttttgatc     144420 aaaatttaca gagtaagatt ttgctatgtg aaaacgtata tagagggata tacaacatgg   144480
ctatgaaaat cttagactgg gaacaaagtc gagactatac cgatgaagaa tggagcaaag   144540
tcattcaatg ttggcacacc cttcactccc atctaccaga gatgaaaaga ctctgttata   144600
aactcgcagt cgataatttc gaattaccag atgaagacga attccaagta ctgaccgtag   144660
acactaaaga agaaagagaa gattctttag cttacgtgac agatgatggt attagcttca   144720
ctcacgattc aaaacgaatt gaaccgttca cactacacaa aaccgtacaa cacccccatg   144780
aaaggaatat caaaacccgt tatcacttct attgtgatgt agcacaaata ctaatggtaa   144840
tgtgtgagaa ggttgttcca ggtgtgttgg gcgactttga agaagacgaa ttatatcctg   144900
agctattagc tttgggtgag caattaatta gtgcggttaa tgaaccatcg gactacaaca   144960
tcgtaaaagg agaggaataa tggaaaatgt aatggagaag tataatttca cattccattt   145020
ttattcaaat cgtttttaa ctgaaggatt aaaagggaac gaggacttttt caaaaatcga   145080 agagtcttac gatggcgtgg tcattgatag taaattacac cttatcaaaa ccagacaaat   145140
ggaagggcgt gtctggttca taaatggtga ggaggaagac ttcaagttaa aaatcgtcga   145200
ctcactcatc atggtaaatc gattacgtac ttgggaaaag ttacgtatta tggtcatcgg   145260
tgatattaat acattcgtaa aactcgcccc gtatttcaac actatcacag tacttggcgg   145320
attaagtcag gctgaaatag ataagtacac tgacttcatt gcaaaacaca caagagagaa   145380
tgatgaacaa ctgcaagaac caagctccac ccgtgttcgt gtaaggcaaa ataatcagta   145440
ctctactgtg ttcaatatga tgataccaga accttggata attgaccacg tctacgcaat   145500
ggattggact tttggttttg tacctgatac taccacaacg atttgttccg gtagcctatt   145560
attgaaccca aggtatggga attacacatt aggtagtgtg atggaaacat caaagccgtc   145620
gactaccttt aatagcgaac ttggtaaaaa atacgccttg gaaaaactat tgtctcgtac   145680
actagagaac gtcggaagta tctttgctta cacagaacac acacaatcaa agataccacc   145740
tttgtacgat atgcgcccat accaccttcg ggtaaaaaaa taaaaaaaga aagtaccctc   145800
gtaacgaggg tactcttta cttttttaacc acgtccatgt ctattacgtc ggcgagtttc   145860
actactaaac gtgcaatact cacgacgctg actgatagag ggatgacggc ggtcttcgaa   145920
accttctgtt agaaagccaa accgattact tctgctcctc ccagttacag agcttacaat   145980
gtcttcgaca ctatcgaggt gtgtattggt gttgtaacgt cgcagctcac cgtcttgtaa   146040
gtaatagata cattctagac cacctgcgat catctcatta attagagcaa atgtctctgc   146100
tggttcatca aaggtcacaa tggcacctgt cgcacccgct agactacaac gctcattaac   146160
ttctaccacc acatgaccag gtacattgat tagagtatct gtgaaattta agaatatggg   146220 ctttttcattt tcttccaatt ccaactctaa tgctaacacc gcttgtggct cttcttgctt   146280
aatctcttct acttccacta cttctacctt gttttcagcc atgacaccca catccttaac   146340
```

```
ataatccaaa acaacagtcc aaccgttcaa ctccgataaa atataatttt gtagagcttc 146400
tttgagctgt gttaacttat ccacatcgaa tacttcggtt acaattagtt tgatgtacaa 146460
ttgtttatta acacatcgac cgaataattc aatttcacca atttccagag tgtcgtaaaa 146520
caaactgtat gttttacggg cacttaacat atccctagtt atgtacttca ccccaccaaa 146580
gagaaaccat agttgttttt gggtatattc actacgtttt ccaagctcta atttgtaaac 146640
gaaatccgtt ttaataggta cgatacatgg gtggagtagt ttaaagaact cgtccaagtt 146700
tgcacctgta tcggctgaat aagatatgtt gtccatgtcc atgactatcg aggtattgtg 146760
aaccacccct tccttatctt tgataccaaa tacatcaaca gtcttaaacg cctctctgta 146820
gatgttcaat atcgcccgtt tattcccacg tgctatacgc tgtaatgccg cttcttcgta 146880
ctggtaacgt ctgaataaac cagatagtag tctgattaca tttccctcat cgccgtgtaa 146940
cacaatacca gttaatttt cgctacactt actatacacg atcgaacaag agaagtccaa 147000
tgccacgacc aagacttctt catcattcag ggatataaaa ttagcgctga agttacccac 147060
atcatcaaca aggttatctg ttgtgtattc ataaggttca gataatacga ttggaatctt 147120
tctgttaatg cgtttacctt caacatagtc tttggtcact acgatgttta gatcttctag 147180
tactttcatt ataaatttcc tcttttctaa ttaaaaataa aaagtcagtt acagggacca 147240
atccctgtaa cctatatcac ttactgttta agatatcata aaccagctct tgactaaaac 147300 cttttgatcag cttaaccgtc tcgtcggttg ataaatccac acctgccagt atacaactat 147360
ctgaaagact accacgtagt tgcgactgtc catccagtgt atatacctcg ctgaggtact 147420
ttggtagaaa ctccatacgc ttctcattta taaccacagg aaccgcccac tcattatcat 147480
gggttaagat gtgcttcgat agaaatacaa aactccctac attgcgtttt agtgagataa 147540
cgactaaagc aaactcaggt acttccaccg caggtaaaaa gcgttcttcg cttggtagaa 147600
aatatttgat ggcacctgct cgaccatcta gaaattgttt tttatccacg accagtacat 147660
tgcccccatg agtgacctgc ttccatacat ttaccttctt gcgcatcgag gtacatactc 147720
gcaccgaata gtgatacgat tagtcccgct aagccaagac gtttgatagt gttgcgttgg 147780
aatacattca gtgattaaa catttaaat ttcctctcgt tagaatttat ttaatagctg 147840
cttcaacttt ggcgataagg ttagcacctt tgcgattgat tttgaattga acaaattgtg 147900 cgtcttttg tttcaacgcg taaccttctt tagccaatac attcaagata cgaccaactg 147960
ccccatacga ccacttacct ttcaaaccca actcttgtcc agtactgtgg aagtaagcgt 148020
gagattcgcc gatgtaaagc caagtcccct tttggttatt taggatagtt agtgcaacgt 148080
atgcaggtaa tgttaaacca gatagtttaa tagcgatgat aaatttaaca agattttgca 148140
ttttaaaatt cctcggatgt tatcaaatta taagttgttt ttacagtgcg ttagaagctt 148200
tgccagcttc gtagatttca gagacggtct tgattgatag tttatgctta actgccaact 148260
tgacgatttc tttgtagtca ggagtatcag tatcaaaagt agaacgaata cataaccact 148320
catcctcaag acttagtgat agtacgattt ttgcatcatt aattcgatcg gctcttgtca 148380
gaagctcatc gtaatgtccg ttatcatcaa aggtcgaatc ggtgactaag acgttgtgat 148440
aatcgattgc acccttagct tcgtacttac cccagtgacc tttgtcgaca aagtcaatga 148500
gtgaatatgg cttggtcgag gcattgacga tatatagctt agggagttta tcacctggta 148560
acttcatgat ggccacaagt aaatttgtgt acatcacatc tttagttgaa agtagaaccg 148620
ctggtgagat gacatttgaa tcatcattac ccttgtggac aacggcaatg atttgtccag 148680
caactaagtc ttggtagata acctcattcg gtaatagcat ttaaaaactc ctctgtataa 148740
```

```
ttgaattgaa tgcagcatac accaagataa tatatacctg aaaaaaattt tattgagagt   148800
tagcaaaaaa taataaagtg agaggccgaa gcctctcaac actagagcaa tacttaaacc   148860
agtaagcaat gggtctggct aacggtttgt ctaggatact ttattaacat tgccttaaat   148920
agcgcactaa gataatgtgg gtgtgtgggg ttaccatacc attctgtagt ggtgatagta   148980
atcccacgtt cacgctccag tttttctttc tgtgagttca taacgcccct tgaaaccata   149040
gttattgaga atcttagtca agtcactgta ttccttggtc gatagcgaag ttaacttcaa   149100
agtgtaatct tcagtatcgt gacgtgtaaa ctcctctacc cagttgtcag caatggcaac   149160
acgtgtattg tcagccaaag attcgagaat ggtatagttt aataactccg cactctttgg   149220
agtgtcttct ggtagatagg ataagttaga tgcatgaatc ccatccacat cactgtagtt   149280
tttagcaatc tcgtaacctg tgcgagtcgc taagaccttg tactttgcat cggaagggat   149340 acgcccttg attgacagca caaggctaat tgtctcatgt aagacgagtg tgttcatatc   149400
agcactcata actccacctc tattctgtgt cggcatttac catacacttc accagtccat   149460
ttgaaatcct ctaaagaaat ctcaaactga gtatcaactt caactttctc gaagttgtac   149520
cactcttgta tagtgttgat tcgtcgacta attaattcga attttgacgc gtcaacgtta   149580
gctaagtatt ccgccaacat ttgactccac tgatctaaat caaggaactt accttcagtt   149640
ttaagtatac tcgaggtaag gatataatcg taattagcta caccttcgca atcagtatca   149700
cattccatcc ccaataacag atctgaaccg atatcctgaa ttttatcacg aagtcgtttt   149760
agcacagcct ctccatctgt acattcttct gtttcaccta ctggaacacc aaaaagatgt   149820
tccatcacca agtattcgat cagtaggata agttcacgct tttctttctt ttcgatagtg   149880
atgtgggtta ggcaaaagtt gacaaatgac aaataggcgt tgtggctcca caagttaggt   149940
aatttgacta ctgcaaacat tcccacacct ctaatcaagt aatctgtaat aaacgattta   150000
ctagttttga aacctgtctt tcgacagtat cgtaatcgtc gtttgtaatt tcaaggactt   150060
gtctatcctt ctttagaaaa agactgactg tccctgtttc tggataggaa cgcgtgctcg   150120
ttaaacggta agtgtaaata aaccactggc ttctatcttg taatccagca attatgatat   150180
ctaacaactg agctgcgttt tctctcatag tatcaataac tgaatcggta actatacgtt   150240
cgtagttgtc gacagcagcg gcgagtgtta acttatatgg ttcaatccac acatcgctat   150300
caacttccct tacattgtcg gttagagtac cgcagactgc ttcgatgatg ttatttacat   150360
cgtctattgc tgcctcgatt atggcttggt cctttaagaa tttgttactc ttagatgacg   150420
ttatactgaa ttctctattc cgcattttaa gattcctcga ataaaataaa ttgaagcacac  150480 gtgctttcat tagatagaag gcacgtgtat atttttaattg aaaattagga tagggttacc   150540
taattgatca ccgctggtga attcgaaatt acaaatgacg atatccatca aatcatcttc   150600
gatgttacac tccttagcat aactctcagc taaagacatc attatcatat cgtactggtc   150660
accgccgatg tcgaagatgc tatcaaataa ctcttctaga ctaccataaa ttgaacagta   150720
atcttcccat tcaacacatg tactggttcc cggtagcagt ggaatgaaat acacaccgcc   150780
atcatcctca cactcctcta tacagttcga tataaaggaa attcttagat tctcagcctg   150840
agtagtacca gcatagtgtt taatcaatat aacacaaaac catacaaaga ccagagcatc   150900
gccaacaaca tcttcgacgt catcaccgat tatttctttta gcagcacgta ctaagatgtc   150960
tttcagttca tcgtaagttt cttcgtcatt ctcaatcaga tgcctaacga tgtgcctagt   151020
ctttatatac tgtttcattc tttcttagcc ttattaacaa ttacaactac aagtcttgac   151080
```

```
aaagcttcga ttacttcttc ttttggtcga actggttcga ttactgagaa ttcaacagat    151140
aatgtttcat tatctctgtc gggataaatc cccacagtta tcttcttaat ctcgcagccg    151200
agaagaatgt ccggtataat ctcaagcata tcaagagcaa gtaacctaga atcgtcaggt    151260
aacttattga tacttaagag aacatcggac aaatcgttat tattttttaat agaacgatag    151320 acgacttctt tcaaagcctc tatagcaagc tccgccaatt ctataatgta ctcgtttagg    151380
tcatctgtta gaccaggtaa tgaaggatac ttattccaaa gattattgat tgttagtctt    151440 cttttttcgaa gtttctcaga aactcctctt ctagttcgtc ttgacataca cacctctcta    151500
ttataaagaa acgtccgcta gtatccattg ttagaaaagt acccatgaga tagtaatctt    151560
cgagtaactc ataagcaact cgtactatct cacgaatatt actctgcata aaaatgcgag    151620
tatcggcaca atctggcaac gcatcactga catcactttc gtcatagtta ggtctatgtt    151680
tgcaaaatac gacccagttg actaagtcac aaacatcata gtcatttacc cctcttaacc    151740
taaatatcct ttttggaatc agaagtttca tacactacac cgaatggaat gtcaccatcg    151800
tttgaattgg taaagtctaa atcgatcttc gaaatttctt catcgacaga ttccctgtaa    151860
tgtgaagcca ttcttttacc aacgtcccca tacaacatag agaaaccagg atcatcatat    151920
accaaacggg atgaagttaa accacgccca ttgctttgag gttgaatgct aacatccacca    151980 ctgggtaatg acataatgaa cccctcagga tagtcatctc taagggtatc tattaaacca    152040
ctgcattcgt ttagtatacc tttcggtata tcttcccgat cattgtggta gattacttga    152100
cctagcttat aatgcatagc tggtcctctt ttcccctcaa caaactggat gtggtctgtg    152160
atgggtttta agttattagg tctaactctg gtggtagaca taattcctct cctcgttgca    152220
atcttttcag agcaatgaat tcatcggtgg gtataacacc aatgtattta tctgaaagta    152280
ccacatcgtt gtatcgacca actaaacctt cgtgcttcaa tagagaaact acctctctga    152340
cttttgtctc agcaacaata gcaaagggta ttttgatacc atgtaccgtg tattgaaatg    152400
gtttggtttg acgattgtaa taaatgtggt tgataaacga accatacatc tgtaacttta    152460
gcatgttttc gtcagggtat ttgaattccg taagagggtc gcgtttaaca catggccaac    152520
cctctacaga aggaatcaag tgcaagtcat cgtaatcatt actgatttta ttcattacac    152580
ttattaggac tctgtgaatg tcgattctac aggtagcagt gacaatagtc cttctcttcg    152640
attgattcag catcttttaat actacacgtc cctaaatcaa aaacttgacg gaatactatt    152700
tcttccaagg tttcagatga tttgaaaatg tagaagaaac aatccttttt gtaaatttca    152760
acgaccgtgg acgggtgat acccatcgtc tcataaatca tacccatggc tacttctata    152820
gcctcgaagt attcttcgaa tgtgaaagct agaagatcgt ctagactatc ttcttcatac    152880
ttttcattgt tatcttggtt gattgaatat gctaactcca ccaattgatg cttttccaaag    152940 tatgttagta gcgggtgctc tttagggggtt ataaaaccca tgagtgttga ttttaaatgg    153000
tgcgtaaaca tcgaaatgct tatatctaga aaatcactat cgtctagata tttttgcaaac    153060 ctcaaatgtg ccttagtcaa atcgaccaat aaccccgctt gtacttttcc aattaacttg    153120
aaccccggtg cacatcttgg atctttattg aggtaaggga tagtcaagta accatccttg    153180
taacgcattt caaaattgta atcgcgcttt ttctcgtgct cttccatggt atcgaaaaaa    153240
ccattgatta tgtaatcttc gatatcacga acccatttat cttttgggtt aacaccaaca    153300
gattcccata gagccgacac actagtcact tcttcataga tgtcgaaata ttttcaata    153360 gcactgcgca ttaagtatc aaagattctt tttgcaggta gctcagcgcg ttcttcggga    153420
atcattcgaa taacttcgat taacccctcg ttaaaatcaa ttaccgccat ttttattat    153480
```

```
ccctagtatt tcaccgtcgt gataggtgaa gtgtacttgt tcattagaac acatcaccaa  153540
ctcgccaatc ttgaaccata aatcggagcc aaacatttcc tcgccagctt ctaagtcata  153600
tttgtttaga cagtaggccg cctcatacce gagaccaggg actattagtt cggctataga  153660
agcaaccaat tttatacgtg ctgaaataga agctctgtcc tctataacat ctataaaaaa  153720
ttgatcgctg atatagtagg tgagaatgat accaccagtt tccatataga caacctcgtt  153780
taatatttcc tcttcagact tataacatat atttgaaaag tcttagggtg tatagtctca  153840
taggaaactc tctggcgtga ttttttgcag ttggtatggg gtactattta taaaggagaa  153900
aaaatcgtga atattatcac acaggctctc cgacatgtaa ctggtgtaat cgaccgccga  153960
cttttgaccg atgcattcct cgatgaggat gaacgcgaca tgagaggtac acagttacta  154020
gagcagtcga tttatgaaaa ggtcattaag caatatgtcg tacctaattt atccacaatg  154080
ggtggtatcg aattagaaat cgaccttagc ggtattgatt acgtcagtat cgatagatgg  154140
acacgaagtt acgccatccc agtagaacgt cggatgggta aaatattgt ggcggcacat  154200 tatgcaggtc gttctttgca tggtggatca acggcaatag taccaaacta ttacgaccat  154260 tatgacgta agactggttt actccaccaa ggtgctcgta tgagtgccaa ccatcaaccc  154320
atctatcaaa cacaaacagc cgatgtcact atcgttgctc caaacgtagt tgaggttaga  154380
gacttcaata ctgttgcaac aactttgca ctagtggtta ctcttgagtt atcagaccaa  154440
cttgaagaga ttcgacaacc ttactggtca gaattcaact tgttggttga gcaggctgtt  154500
cgtcgtttta tttggactac acttcgagta gaactaaacg tcagtaaatt agaggctggt  154560
cgtgaattag atcaatataa tgccgccttg aagaatgtg ccgatggtaa agtagcttac  154620
gaagaagaat tgaaaagtg gccaaagtat ttgattctta atgatcgtcg ctcgcagcaa  154680
gcagtctacc gacatgctgg caagtaccac aactaaaaaa taaaccctct ctatcgtttg  154740
atagagagga gcttttattt aatgcatttt gtggaatgct gaacccgaag atgaatagtg  154800
ctcaacaaga taagcatgta accatccgct taacaccatg taattacata acccaagttc  154860
agcattgtta aagtgattag ttatgtaagc tctcatgaca cctttggtga acaatgggtc  154920
atggtggttc tcaagcatat ttaaataatg ttgaacgtat ggttcagtta catcaacttc  154980
gaaagtggca tactctgaga caggagagta atattctcgt gaaacgaatc tatagtaaag  155040
atgacctatg ttgtttaggc cactgaggat ttcttccgtg atgttttttt cgatgttgaa  155100
tctttgctgt gattcttctc ttttatttcc caccattttt cacttatcac ctcgttaagt  155160
ttggaaagcg cctgctcgta ttcaatacca gctagttctt ctggtacttt gatttctaat  155220
cttccacctg agtgaaaggc atggctctta agtctttgat taggatgctt tgaaaaacat  155280
gcatgtctca gcgcacgatt aaaatcattt ttggtgctaa ttgtatggat ggatatagtg  155340
tcccgccata cctcttttt aaggaattga tcgaatgtca caataaccct cctacaataa  155400
atgataacag ttccccatag taaaatccta acatcgttaa aaagtacata tagtatgtag  155460
agatgccatt gtacagcaaa aaaaatattt gcttattata tggacagaat ttattcgcct  155520
gattagaaag atgaactgta gcagtttcct cctttcagct ttttggttaa tcgttagttc  155580
cgtgtacaga gttagcttga tagcgagcaa tactgtgact acgttctgac atcttcatca  155640
ggcgaatata cctaatcttc tgaagctaac gacggttgtt ccggcatgat attcctcttc  155700
cgagctaaag aagcaaaatc ctcaagtggt gagatgtagg gttcgaccct cttgaggtga  155760
cgttgaaacg cgtccaacgt ccaacagggg tgggtaagat gacgcgccgc atccaccccc  155820
```

```
gtaactatttt tgaaaggtag ataaatccct taaccaattt acagattcgc tatgtgttga   155880
tgtctgcctt tcaattcttt atttgcatgt tagtgcaaac aggtccttcc tcagctcgca   155940
actaagttat ggacctgacc ctattcgagg agtgtgctct cctgtgtcgt ccggttgtat   156000
atcccatgtt tcctgtatcg ccaccgcaca ctcctcgagc caactttggc cgccagctaa   156060
agtgaaccac tgctttgagt ttattttaaa cttctcccct cttaggattc taagaggggt   156120
ttttgttatt tttttcttct cggcaaaaaa agaaggtagg ggtcgaaacc cctacaattt   156180
agatttttgc tttgatagga acgggttcaa gtacaacact tccatcatct tgtaccaaca   156240
cacgattacc ttcgatcatc ccataacctt ccacttcgtt ctcgtagtac aaaccaaata   156300
aatgtatttg taaacccgaa gcgtaaaaca tagtgttgcc cataatgctt ttgatgtaat   156360
cgtcactatt ggcatcgaga gtcgctttag tgattactgt gtacgggtaa aaacgttcac   156420
gttcatgatc atctactcga actggtccaa gtaatataac cggagagatg ttctttaatc   156480
caagtgccag tttcatcaat gggcgacctt ggttatgtag aacatactct ttgatgcttg   156540
aaccattgac ttcaacagtt gttgtgtcga tggtggcact ttcaatttgt cgtttactta   156600
gcaacataat tagtcctcct ccgacttaat ttcatgtacg actgctgatg ttaaattatt   156660
taaacagttt gtgtaggtag actcagtgta cttgacccga accactgtac ccacaacact   156720
ctccggagaa gagccctcgt acttcgcacg aattggtcta acaccttgtg gtaattcgac   156780
atggactact agagtctttc catctacagc aactaccaaa ccattgcaac tacgacttgg   156840
taatatgtgg tattcattat caccatcaac cacatacaac ccatcgtact ctcgatcttt   156900
tgaacgcgta gtatttagat ggatgacatt accagccttc actgttgtcg ctgacacact   156960
acggcaagca aaaggcaaat caccatctgg caaatcccca aaggtaaata ctgtcaaggt   157020
atctaaccaa gaaccgcctt cggagttatt gctgatttgg taagttaacc aacgtgatat   157080
cgccactgga ggcatatcgc gatatataac gattctacct tcgtaccctg cctttgttag   157140
agctgtggcg attggctcgt ctaagaagat acgatggtag ttgtcaagga cagcagcccc   157200
atcttcagaa agatagacgt ggcagaatat ccctcttggt ttagagaaga cacgaacatc   157260
cttttccata gggtctgata gtgatgagag aaactcattc cacatcactt ttgttttggg   157320
tttttcgata gaagcaatca ttataaattt cctcttaaat agcatttcca gaattgcatt   157380
tcttcaatat gataatatat atctgttaat tattagagtt aatatgagct gagtattaag   157440
ggaatcatta tgtttgaaga gtacttgaac ttacttcaac ctagaaagct ttcaaccgag   157500
aagcttaagg aaggtgagtt aaaaatgaag caagctctag cagaagctgc tcccaacttt   157560
acagttgata aaaaactctg caataggata ctgtctttct atcaacgaat taaaagttcc   157620
gagtggaaca ttaactggtt tggtggatgc taccttggaa ctgaacttat ccgctttaca   157680
caacaagaca gggacagatg gtttgatgaa gttcttgaag tagacgaaga ttacttagag   157740
aatatcttag agagaacagg tattcgtagt gactggaatg tttcatcaga tgcttttggt   157800
atcattaacg ggtacgtgtt gcataaagcc tatctagcct caccgggctt taaagacaaa   157860
cttatctacg acgcaatgcg tgcattgtta tctgtgtggc agtttcgcta ttatagctcg   157920
ctttatagca ttcgttttaa aagaaatctg gttgacagac ctgctgccga agcagcatat   157980
gctgccctca ccatgaagtt cactattaag caacttggta actggggtgc tgctatagag   158040
taccgtgctg aacgtttctt agataagtct tcaccccatg ctaacacgta caaaacatac   158100
gacgatatca acgatgttgt ttacatcgcc acgatctat ctacacgatg taatcgaaca   158160
ttctacgatt actacaatag tctggataag gtgaggaaga ataactcacg tattggagtc   158220
```

```
tacgaggaga tagcaacggt tgagggtgag caaatactca aagatagaac gagtatacaa  158280
accctagcta ttgagtattt gttaagttct tcaacttcaa catcctcgtt cgtaactaac  158340
caatatcttg atcttgtcaa tgaactcatc actacgtcgt caccaacggc ggttaaagat  158400
actctcattg ccatttctaa tttaccactg ggtaaagaaa gagatgagat agaagatgtg  158460
atgagacgag tcttgatata tacgtttaac tacgttatgg aaaacagact caagttcaca  158520
caggtgtctt tgttattaac caaaatccgt gcaatcatca ccgcatctaa gaacaaagag  158580
gacgatgtgg tgtttatgcg tgaacgcaca gaaaaattca tcactaagca cacacacctt  158640
aaacatgaca ccacagtagc ctcatgtcgt accgcagtgc tcctgtactt cattgtgaag  158700
ggtttgtctg ccaacaaaca gtaaaggtat ctagtatgga agtaaagggc tacagaaccc  158760
cggaggagtg ctttgcggcc tacttcggtt tagactctgt tgaagaactg aaagaagtcg  158820
attgcatcaa tgctattgat gagaaaggtg agttggtcaa ggtcaacgaa gaagacctct  158880
ttgcaggaat acgaaccttg ggtatttggg ggtgggtgga tgacaatagt actatacact  158940
attggcgtgg cgaagacgtt gactcaccaa ctgtgataca tttcctagga catgaaatcg  159000
ggcacttgac cggagactgt cacgaagacg agtataaaga agagttgcgt gctgaagaat  159060
tcggcctcgt ggcttctaaa gcttttgagt tactgacaaa gattattcct gtctaagtcg  159120
ataaaaaaga aagatgttac ccacctatgg tgggtaacga ttcttttatt tttctccaat  159180
cccattcgtt aaacattcca aaaatgttcc gacagggcac caacccaaaa gagaccagta  159240
ttatagactc aataatttcc gatttggcgg attgggggag aagtacctct ttcgagggtg  159300
cgtcccagtc aatcaccatg tcgcccgtgt aaacaaacat gataaaccaa cctagatgca  159360
aagtatatat tagaggaata cccctgctaa tcattgactt accttcaaag tgacagtgct  159420
ctccatatta tagctacgcg cagttttaaa aagttgttcc ttttcaaaag cttgtgcaga  159480
taaggttaca gttgcccta accaacccac accaacagaa aaacttagtg ccacgaatac  159540
agcaacgcga acaaaaagct tacaatgttt tttagaaaag gataatgtgg caatccagtc  159600
catcagctca aataacatcc aaccgagtcc taggactata ccaccattaa cgaacacact  159660
tcccatcatc tgcctaacct ccttctaaag cgttcagctt taataagttc cttataatca  159720
cttagagtgt tagcagcccc tggtttaatg gaagtcttag taaccagatt tttcaatttg  159780
gtttctaatc gcatcttagt gacgatatca cgtgtagtcg acaaagtctc atagagaact  159840
tcaatttcgt ctagaatgcg aagttgttcc tcgttttcat taacgattct ttcttcttca  159900
tctagtgtga tatccccacc gaagtcagct ttaagacgtg cacgttttg atcaacaccg  159960 taaaaacgtg tattcttagc aaggaagata aaccagaatg ccaataacca agccaccacc  160020
atatcgtcgt gcccagagtt gatgtggtca atacgttccc ttttgacaac aagagcaagt  160080
aactgatcaa tcaatatttc cgaacgtgca actttcttag cagtagctat agcactaccg  160140
aatacctcgc cgtataacgt tttacgttta ccaccatctg ttttgaaacc gatttcttta  160200
cgaaactcca tccagaaatc ttcagcgcga ccagacggtc cgcgtacgta cttcttgtat  160260
gttgggtcag acgtgtcttt aaactgagta atgttacagt aaagacgatg gtgtaaatct  160320
tttaccaccc cgcttagttt ctcaagaaga gcatcgacga taacaccgcc agtagacttc  160380
ctctcgatca ctaatactgt cttagggtat tttaataata actcacccaa ccagtcagcg  160440
taacgaataa tgttggtttc attaatctcc gaatcagcag aggtctccag agtttctgaa  160500
ttaaccatac ataggctaag agaatctcga ccaaacaccct cagaagtatc taaaccaata  160560
```

```
acatgcattg tttctgacat tcttttttct acatcttctc ttggaatgta ccagttaaga   160620
atgtagcgat tggaaaatat ctccttccat aaaggtttga ccttatgctc ttttagagtc   160680
ttggcatcgg cctctgacag aggagaagac attcgaccag cggtccaacg accaccgtag   160740
tctcgtgcga tttgttcagg tgtgccggac gcatttcgaa tcatatcgaa taactcgtcg   160800
tcggtagtac ccaattgatt atgattaaat ttgatgtaga agatacgtcg tggaaccttt   160860
gcagctgagt ttttatcaat cagctccaga agttccttac gtgttggtaa gtcaatgaag   160920
cgttcatccc atttgatacc tgaagtcatc aggttgtaca tgtacgcacc ttctggtgaa   160980
tctaactcac ccggcgtagt tacaaagaag ttggcgtaag gtacaccttc tgcctcattt   161040
gccttacgcg ctgcaacacc cgaaccaaat gccgcaggaa gaatgatgtg gatgtatggt   161100
gtaaagggac cctcatccga accaagtctt cccgcagtta acccacgtcc ctggagttg    161160
gcacttgccg ggttgttttg accgatggcg gtgatgagct ttgtgtttct agcaacgcta   161220
ccaaaagtct cttggttatc agggtctttt ggatctggaa cccatatacc tggaggaaga   161280
tggtcacgca tgtgctttaa cttctcaatg gtctcggcac gcagcttagg gtctttggta   161340
attaggattg aacgagcgtt ttctaatatc cttgttagat acaagaataa tccactgata   161400
ccgacagttt taccgtgctg gcgcagaaac tccagcgccg catcgatgtt cgagaagaaa   161460
caccaatata gtgcaaaagt accacggtta attttgaaag gtactgggtc accaccatcg   161520
ataggtactt tgatacattc gcggaatgcg taccatgggt tgaacagaa ctcctttgcg    161580
attcgaagaa catactcttc gctaagagta tcgtcaaagg ggtccacacc gatcaatttt   161640
tgatcgtgta atgctagcgg tagataccag ttttttttgaa cacccactct ccgtagaatc   161700
tcagccatct caataaaact tttattggtc gtagtgaaat ccggacgggc ttctgggtat   161760
agtctccaat cggtaggttt taagatcatt caaatactag gtggggttac ccccaccccc   161820
ctcaactgat gtcacggtgt acaatcatac cacaaatagc taattctaaa tcatccttag   161880
cttcacgacg aatccaacgc aattcgactg ttgaaccctg tgtgatttcc gatgggacgt   161940
caatagtctg ataccagttg gatactggtg cttcgtatgt cttagtccca atacgcactt   162000
ggaagtgcgt aggggttaaa ggaccacttt ccgcgattct atcgtaaagt ggataagttg   162060
tgtagtacaa cttatttaac cactcggtca aactattaca cccgcacgaa acatcgagcg   162120
tcgactgtga aacgttgttg tagtcgtaca ctgcaaaagt atcagtgccg aatgactcct   162180
caccatgaac atattcgagg atgaagttcg tcccacgaat agaaccttca cgaacaagtg   162240
taatgttgaa actttgtgcg tgttggtgtg gtttatagga agcattaacg gcattggcat   162300
ccacactgac gtttagcttt tgtttaaccc catacagtgt tgggtcaaaa gcatcaagtc   162360
cagtcgctgg tcgcacataa gcagtggcat cgtaaatatt accacgtcgt aaatcgtaga   162420
ggtagtagcg taaacgataa ccagctgttg cattgaccca ctcgggaaca acaaatagtt   162480
ttagcgagta tgcgccatcg actacttccg tgactgcaaa gtaatctttc acgattgttc   162540
cgccaaccaa atcttgtccg gtgtagattt cattttttacc taagcggtat gtgaacaaca   162600
aatccaattc ttgccctgcg ttggtcgaca agtagaacgt gtcatgtgta ccagcattac   162660
gtaaaccaat tagactagct cttgcttcgt ccaatgggat ttcgactta ccgtcattgt    162720
aaataacctc cacacttagc aagatatcat cgtatggaat gttgataggt aaacgaagga   162780
tgttcgaggt tggggtagtc aaccacggag atttaagacg gacgtctttc acaacacgtt   162840
gtggggcttc tgcttttgaa atatacgctg tcttaataag ctgcgcactt tcaactaccg   162900
agacaatacc agctgaatca tagacaacgt agaatacttc tagatggtcg ccatcaatcg   162960
```

```
gtttagttaa aacgccagtg agaggcacct tcaccaaatc atcgctttcc gaattcgtca  163020
gtggaatatc cgtacttacc aattccccac ctttctgata accagagatg atgtttttgt  163080
catcaccgat atcattggtt aagaatacac gaatgctttc cgcacccggg atgttgaaac  163140
cgaagcgtgg atcgaagcgt aatgtaggtg gtgattttgt ctcatcgaca tagatgcggg  163200
agaatttact gttatagtaa ttcaccgcac ccttcaccac gttaccaccg atatcattac  163260
cattgatgcc ccagatacga tgctcatact ggtagttggt gtaatcgacg gatgtaaaca  163320
cccgtctttg atcaacacca ttcatcaata catgatcacc cacgttagga acaaatcgtc  163380
cattttcgtg ccaaccataa atgtcatttt cgttgaagtc acgatgtggc gagtctcgat  163440
cgatcaacgg agccttaatt gaagacatta gtcattcctt atcgtcaagt aacgatttaa  163500
atctacacgc tttttataaa aacgcgaatt gattctttcc aacacagtgt aaagtaacgc  163560
acttacttcc actgtcccaa atccccagtg tgggtcaaca acaacgaacc aatcattcac  163620
acctaggtag gccgggtctg tgctaagtag atggtcgtat cgtccaacaa tctcatcgag  163680
ttgttttgtg gtaactttgt aatcgtcatc atcttcgaca attaccaaat caccatttt  163740 ccaatcagtg ataatcttgt taaacagagg actgtataga ggatagcgat actgtagcgg  163800
ctgctccata gttagaacag gacgaggata gtgtatcgta agaaaatcct ccactaattt  163860 atctcttct aaagcagcca gtctgcggtc atcgtaatga ccttctaaca aatcaccagc  163920
aggaatcgca accgaatcaa ccgagtaagg taacccgttt aactcactat caaccacagc  163980
tgcttcatcc tcacggaatt tcacagagtc ttgtgtgaag attgacccac cgacgacaat  164040
acgattgacc ttgtcatctt taatgtcata atggtcattt tcagaaagca accctccgac  164100
aacaaacccg gtcttgggtg ccactagttc cttagcgggt acgcgcgctc gcaccacaac  164160
cgtctggtct ttgcctggca ataagtgggt tttattcgtc accgttaccg atggccaatc  164220
aacaagatag tcgattccat aaactagagg tcgtttattt aaaaagactt ctagcgtcgc  164280
aaacttaaat ggacatggga ccaacgtgcc atcttgtagg ctatgtttca caccaacacg  164340 aatcaaccc tcagattcac tgatagtctc ttcataaacc aagtgacgct tatctgataa  164400
tgcaatactg cgatatcttt cagtatcata attccaaaca agctttaacc catcatcaat  164460
ctccactgtg tcgcggtcgt ctgtaacgtc gatgaactct tgtactggaa caccgtcttt  164520
taatcgttgt aagtagaaac gataagattg gtaacgtgaa acaagtaagt tatcagcccc  164580
ccaaactaca tcaagatcca caccaccaaa ccccgggatt ccctcgatga ttttagtgtt  164640
gttacgccga caaatataga taccttgttg atgcgtccac catccactta aatggccttc  164700
ttcatcatac tcgtaaatag tcgactgttc ttcaagtaaa ggcggcaatg tggcataact  164760
acgaccgtcg tcaccttgtt ctgtagccat aggggtattc gcagagtaga atagcgcagc  164820
attgtacccg tatgcatcag aagctagttt gtggtcaata cctctgaagt cacacgttct  164880
caaacggttt atctgagatt gctctagatt agctgcccgc cagaaatcca atgcgctatt  164940
taatccagtc atcacattga tgatctcttc atcatttaga cgatagagtt cgtggattct  165000
gtaatcgtta taaagcatag ttcgattaaa accagacttt ttaacaaaga acagaagttc  165060
taaattggat gacttaagaa cctcggtgta ctcttccacc tgcttacaag acatggcgaa  165120
gtcgccgtgc gttagctgcg tgaaactact tctgaagtgt tgttgtaat agcgtccttc  165180 ctcaccattc caaacgtaga gtcgatgtc atcgtggaaa tcaaaatctt ttgtcttagg  165240
aaaatgaaca agaaactttt tcatattgtc gagtgttgac ataaaacttc tcatgtcaga  165300
```

```
cactgggatt ctaacaacgc gcttaatact tttatcgata tagaactcta ccacgtcacc   165360
gatgttgaca ttagtggttt ttaagccttc gcgataaata ccatttacga aacatcttaa   165420
tgacggttct tggtatcgta gattgtggta ataatccgcc aattgtgaaa tttgataact   165480
atcctttggt ctctggatag tcacagtcaa cccattaccc acgccttctg ggctatcgtg   165540
tttgatataa tggtcataga cgcgtaagta gagttgcgcc acatgtacat ctaagtaacg   165600
gctatctttt ttgatggcta agactaaacc gtcactcatc aaacgacgca caaacactaa   165660
atctgaaggt tgacgtttac catcgatgtc gtaaacgaaa atcatagcac ctgtgcgatt   165720
aatgatttcg tttagtggaa cccaaccgtg gtgatagttt atgttcaact ggccacgttt   165780
agcgtggaga aaccccacgt tataaacagc gtagaaatcg gactctgttg gtagtccgat   165840
ggattcacca tgcacattta taatgttct atcgagatat ttggaactaa cccgtgacaa    165900
tttaacattc aattgtccat cgataccagg tttagcccaa acattctctt cagcatgttt   165960
gattaaccaa gttcgcatca ttgctcctta gtgtactcca cacgacgttg gatgattgca   166020
ggaagttttt cacgaacttt actgtcttta taaagttgtg ccccaagagc agacttctta   166080
agaaaagagt tctctaggat agtgtagacc attgccagaa aagctggtgg gtgacgcaga   166140
ccaagctcaa tgcagatttt aacctgaccg atgccgaata ctgtacgtga catcacgtta   166200
cctaacataa gtgcattgaa agagttcaat tgtaaattga tattggcgtt aaccacgaac   166260
ttacagaact cttcgactgt tctagggaag ttgacttcct ggtcagcaga acaaatgag    166320 atagattcat cgttagtaat cacatgttta gtcaataaac gatgtaattg ggtttcctgc   166380
atccccggct ctacatggct gtggaacata ccaatgtagt atagaccaac acacgtctct   166440
agacgcattt tctcgctcca gtccatacgt tggtcatgtg caatattctg cccaatccac   166500
tccgcaaaat gcttaagtgc atcagaacaa gcatagagca actcatcttt attttcaaa    166560 ttaatccagt ctagttctag ataggctaag gtatcaaaat acatagccgt gatttcgtta   166620
cggattttta tggagacttt gtctttacca actgtggtaa aaccacgagc atcgacataa   166680
atttctttac catcagatga cacaattggg aagtcgaaag gtgcgatgtt acttgcttct   166740
tctgtgatat agattagacg gggcgaacgt ttaaataaac ctttgcctga aattttagcc   166800
aattcaatct ctgaacgcaa ggtgttgatg agataaccat catccaattt taactcttct   166860
aatgttcttg acattttcat ttgcctcttt actttaaaaa attacgttca ttactatgag   166920
ccactgctta atggcgtttt agtaaataaa ggagctcttt atgtttacac cgcgtaacgg   166980
tgttccatat aaccaaaagc taggtatgca ggacaactct gttcagcgtg cagtagctgc   167040
ggctatcggg gacccgattc acaagccact gatttttaca ttcagtgcaa agggtgacac   167100
caacgaggct tatccagtcg caggtggtaa cctgaccaat aagttcggcg ctgagatgtt   167160
ggacccgcgt tcaaaatacg caacattcaa cacccattc gctcaattgt ttaactctct    167220
cggtaacgag atgatggtgc aacgtctgga aacaccagat ggtaaaacag catctgctcg   167280
tgcagaaatc gaagtcattg aaacgacggt tgatatctac gagaaagacg catccggtga   167340
cgttgtcatt ggtgccgatg gtaaccctaa gattgcttcg caacgtgaag gtcttaagat   167400
cattcatcgt atcgttccaa tcgatgatag caagggtgaa ttcggtcagg gtaaaaagta   167460
cgatggtaca attactggta cttctggtaa aacctctcgt atctacccac tgtacgacgt   167520
agttgcacct tactacggcg aagcagcaaa ccgtttcggt tggaccattg aagtgatgca   167580
tagcgaatca gccagcccgg ttgacgcaga tatgcaaaac tctgtaggta gtcgtatcta   167640
ccgcttcgaa gctttcgagc aattagaaga cggtgctaag ccagttaact ggcctatgtt   167700
```

```
gaacggcggt cgcgaattca aatttgcact taaagaaggt gcatactacg acgaactacg  167760
tctagatttg gattaccgcg agttactacc tggtgcttac cgtaacatga cacctgttat  167820
cggcatgttg ccagaagatg gtatcttcaa agatttccac ttctaccacg acaacttcgc  167880
tgaagtcgtt gctctgatgc aacagcatgg tgctgatggc gcaaatccga tgccagcaga  167940
cgcatacatg atcgatattt tcggtggtgt aaacgttcat ggccaaccat atgatgggat  168000
cgtagttaac ccttctgacg caacaaacgt agcgaattac actgcaaagt ctgttcacta  168060
catgaagggt ggtgctgacg gcaccatgac taatgaagtc tatgactctc ttgttcgtca  168120
agagatgact gtctttggtt ggggtaaagt caagtacgac aatgaactga aatacggtct  168180
gggtatcctg tacgactctg gctttagttt cgacactaaa gaaaaactgg ttaacttcat  168240
ccttaaccag aagggtacgt tccttgtatt gtctactcac ctgtggggta acataacga  168300 tgagcaagaa gaagaagcgg caaaagtagc tgtggcggct atgttgtcta ttgcccctga  168360
gtctatcttc tacggtactg gtgcgggtgc acgtgcgatg ttggtgagcc aagcttacaa  168420
actgaacaac agcacttaca aaccacttgt cccgctgacc tacacattgg cgcgactact  168480
gtcaaactac gctggttcaa aagaccctcg ctttaacccet actaagggct ttagccgtgg  168540
tgagcataca atcattaccg aaggtactga tctgaatctt acctataaac cgatgagtac  168600
ttactcaacg gactgggact tgggtgttat tgcggcacgt aacttcgatt accaccgtta  168660
cttcttgcca gcggtttcaa ctgcttttgc tgatggccgt tcagttcttc gtaatggtct  168720
attcactttc gcaatgtctt gggttgaacg tgtttctaac caagtttggg cagagtgttc  168780
cggtgaaagc acattgagcg acagccaata cgcaaaactt gtggaagata agatcatcga  168840
taagattcaa ggtcgcttgg atactatcgc gactatccgc ccatacgtct acttcactga  168900
agaagatgtg cgtaatggta acacagctac agttgacctg tatgctgaag gtcagccgct  168960
taaaacacaa cataagacga cgatcaaagt atctcgtcct agcgaggagt gatgaagaat  169020
ggctggtgaa tctaaagctg catttatcga caagagtgtc ggttaccatc agaatggtgg  169080
tcttcaaact attatcgatg catcacaagg cggacagaat ggtccggcgc tgcaacctgg  169140
taagtacgtc cagaacgcag ctgacgtcat tcgtagctgg caggtgcgtg ttatcgattt  169200
cccacgctgg acctacttca tggagaaccc tgctgcatgg caacgtgcaa tcaaggcctt  169260
cgttgaaact cacaccatcc acactggtat tgagttcggt ctaagcgcag agtacctaga  169320
aacacaaatt ggtcactctg ataaaatcca atacgacgct ggccgtgttg tagaagcttc  169380
ttctaatatc aacatgacca cgccggataa gtacggtgca tacttccaac gtatgctttc  169440
aacctggttg aaactttcag ttggtgaccc tgcaacagga cgtccgtcta ttgcggctat  169500
caacaaagac gtgaaagacc acctacctga tatgtacagt atgtccctgc tgtattaccg  169560
taccgatgca tacaacaaag aagtgctgga cgccgtttac attgtgaaca tggctccacg  169620
ttctgatggc gcagctgctg gtttccgtga ccacactgct gcaccacagt tgaatgaaat  169680
gtccatcgac tggacaggcc ttcaaacgac tggttggggt attatgaaga tggcacagga  169740
cgacctagag cgttctaagc tattcggatt acgtcctgat cttcgtaaag cgtggattga  169800
cggcgcaaca cctgatgtta attctactac tggtggtgtt agcacagttg tagacgacat  169860
cgctaaaaac ctagttaaat aggtgaaaaa aagagagaga ggcctcggcc tctcttttt  169920 ttatttttta tctctgtctt gtggcgcgtt caatctcttt gtgatttact aagatgatat  169980
ggcgagccgt aaagatagtg aggtagtaca taaaagacac gagttgattt ttgtctaact  170040
```

```
cgtatacttc tttgtcaaca tctttctctg taaagatagc ttcttttaca tcaatatcat   170100
ttgctttaat gatactcaga gctaacttaa cataggcttt gatgacccgc aattcatcct   170160
cacccagata aaggttagaa agacaagagt ttgcaaattg ctcaacaacc tcgacattgc   170220
cgaccttttc aaaggtttct ttgaagcgct ctataccagc gatggtaaat aggtcaatgt   170280
ggtttctttt actgattaca gagtacacgc tagtatcgcc tttggtgacg atatcggcga   170340
caacatagtt atgcaatgac tcagaggtca ttgtagtaaa accaaccagt ttatctttt    170400 cttcagacat aactaatccc aataaaaaaa taatggaggg cgaaccctcc attgatgaat   170460
ctacaaccaa cgattagtcg taaaggttac cgatacgtga acgtacgtca gacaacagac   170520
cttcttcagc atcgactgag caacgaagag agaatgagtt aacacgatct tctttgcttg   170580
catcttcagc tgtaggacgt gcataatcca gagcgtaggt ggcgaacggc gttttgaatt   170640
ctactgtggc attgtctaca ttcggatttg ccttcgtgta gtttgccaaa ggttcagctg   170700
cgaaacggtg gaagttgtta ccccattcct tttcgtgaga cgctaccttt caacagtct    170760 cacggtcaac accttctggt agggttgcaa agtactgttc actaagaccg tcttggtcga   170820
cgataatagc tttaccttct tcagcgcgga ttgcttctgc tacaagtttt gcatatacag   170880
catttgccat ggtgatgatt tccttttac aataaattaa atgaatacga ttttgagata    170940
agaagaatgt gcatctctct cactatgata atatataccc gtattttttt aggctgttac   171000
ttccaataga tgcatctgtt caattgcatc atcgatgcgt ttacacacat cgctcgaatt   171060
gtattcgtta gcacgcacgt gaatcgcaaa gccacctgct tcagtgaaac gctcacaatt   171120
aacacgccag tcgtccacaa gaatattgtg tgggttcgca taattaatct tggcagcact   171180 ggtagggta acaattatct tgtttgcacc tatcccccac tcgcgttcaa accataggat    171240
ttttgattct tttgctttta ggaaagatgg gtgcgcttca cccgcagctg tacagatcat   171300
ccaacgttca ccagagcgtt cacaatgttc gatgatgtca atgaactgct cgatctttgg   171360
tagcgtgtta aagaagttag aatctttcgt aaaaacatca actaagaaat tatgctgctc   171420
tgcatcattc atagctgaga aatctgacca tgggatgtat tttgccaatc ctgctttaaa   171480
attagcagct aaaccatctg agtctaatag tatcattttg ttagttcctt taagtttaat   171540
aatgaaagta ggttttctta catataaaat cctgttgtgt aaaataaagc tgtaccctga   171600
catttgtcag ggtacgctat ttattaatca caaatcaaag taacacgggt cctatctcga   171660
cgaaagggca acacttttgc ctctttcacc tcccccaccg cagatactat ttcatcgtgg   171720
atgaaattaa ggtcggcttc attaacgcga ttagcgattg atttagccac ccgtcgttga   171780
ttagggtatc ttctctcaac tagagaaacg atggtatctt tggacaagac cgttttggcg   171840
gactctttaa agataaaccc tacctcctca tcactcagtg aatacagtga atctggaacc   171900
tctacatttg ttgttacact cataaatcga tggttctctt atcttaatgg tagtcttgca   171960
caacgccacc ctagttaagt aaaatgaaca tcgaatttac cttctgatta tcttagaaaa   172020
tcgcctttgg ccacaggagt gatttcgatt gtcttgccga taacgttacc atcttcccaa   172080
tcaacttgaa ctgttgcacg ataacattca cccggattac cttcgtaacc ctccttaaga   172140
aaggcgtagt cattcaaact gatgtgtgcg tcaaaaatgg tttttgtccc atcgcgacta   172200
ttcaacacat ccttaatgac aatttttaccc caaacccaac tttggtaatc tgactgtgtt   172260
ggatcgtaat taactatcca acgttcgttt aaattagcag aattaggtag gggtttcttt   172320
gttggtttta acgagatggc tggctcaaag ccataaatcg tcaaagtgat ttcttcgtca   172380
ctgatgatac gctcaatctg cgtgtctatc ataccgatag tagcatccaa tacattattc   172440
```

```
gatgtgcaga ttctagcaat tgtgttgtct tcaccaggct ttacaaaatt tggaatcttt   172500
ggaaagaact ttctgattgt ggaagatggc gatacgtgga atagacgctc gcgctccttg   172560
atagtgaagg agttaacgta ctcgttcttt tgtaacttaa accaatagtc tataaaacga   172620
cgtttcgcct caagactttg ctttcttaat tctgcctcag tgatcaacat acaggttacc   172680
agtcagttga aaatacacct ttagatttaa cttgcacgcc cggagtcgta ccgcagattt   172740
ctttgatgcg acgcgatacg taagattctg ttgcgagctt acgaccagat gtcacttcaa   172800
tgttttcaca ttgtagaaca cgctcagcca agttagaggt gagtccaata gaaacagatt   172860
cacgtgccat ggtacgttca ttcgtaatct catagcccgc ttctgcataa aatttgtttg   172920
cctttgaaac acccggttca ataacccagt cgaaagtgat gacttcatca atcatcaaga   172980
atttctggcc accgacccat ttttcacgta cccaacagcg gatagagaag caaacatttt   173040
gatgtgggtt gtcaagcgca gctttcaagt actcaccgcg cattttatcc ggtttaaccc   173100
atccccagat ttcccaaaca ggcagaccat tgcaagtttg tttagttgga acgaattcca   173160
tctcacggat atgacaagca atgcggtcgg tgtcgatatc ctcgttgcga agtaggaatt   173220
gctcttcggt catccaacct tcccatacag gatggttgtc ctcgccgtaa aggttcccac   173280
catgcatctt acgtttgaat tttgttgagt cgtcaaacgc tggtagagat gcttcgtatt   173340
cgtaaaagtg gccttctgag ttaaagatat tcagagcccc taagcaaacc caatagtaat   173400
caccatcacg ttttactttt gaggggtctg taataccatc caaagccaca catcgatagc   173460
ttaaattaga catatagttt caataccctt gttactctac ttcatgaaga gactttctaa   173520
aggctcctcc cgaacaggtt cattcaacat agcggcacgt aaaccacgct ttaactcact   173580
gttggcaacc aaagacaagt tagaagaacg gttcaatgca ccattacgta aaggaacagt   173640
ggtggctggt ttcttacaac ctgccaaaga tttatcagca tgtcgtgcga atcgtttgat   173700
atcacctggg tcacgacaaa tctgactagc taaaacatcc aacgtgattt gcgaattgtg   173760
gatctttagc ccgttgaagt acttggtgcg ggaaagaagc tcagctaagt ctacacgact   173820
catccaccaa ggtgaatggc cataaccata gaagtaatca aaacaatcat tcactttacc   173880
aagtatcttt ttaggtttac ggtcagcaac aacaacagag cctttaggga agaagaaacg   173940
atagaactcc tcttcatcca ccaccactgt gtccactttt gttggactta agtcgagcat   174000
cgttgtacaa caactaaccc cgtaggaaac attatcggtg gtgaatagca acacaccgat   174060
aacactgacg ttggagctta cgtaagccaa acctttggaa gagtacttaa tgggggcata   174120
gacccacata tcagacttag tagatatact atcgcctgtt tcgaatagcg acgaaataac   174180
cttagcatcg tcacgtatca tctttgaagg aatcaagtta gcccctagg tattactcgt   174240 taatggtgat ttgtgcgacc atccaatcga agaagatggt caaggtggct tgctctagag   174300
ccttctcttt cggcatacct tctttaatgt tgaagtcaac caaacgaagg aactccacag   174360
tcatttcacc cttgaagaga atcgcttcac aagcgtccat gatgatacct tcgatatcat   174420
caatcatgtg taattgtaca tgatcgtaaa cgtatttacg gaactctgtg attttgttag   174480
aagcttctac atcgtcagca accaaatcag gttgtgcagt tagggcatcc ataaaaccac   174540
gaataagagc agcacgaaca gcttcgatcc actgttggtt gtcttctct tttgtgatag   174600 ttacatgacg ttcccaaacc gaaacataac gttccagatt tgacaagatg tcatcctttt   174660
ggaacagagt agtttgacgc ggatcatcgt cttgtaacag gaacatgcct tgtagggctt   174720
ctaccgtacc accttgcgat tggaattgct gcatcacagg tgcgtatacg tagattaacg   174780
```

```
taatttgatc gatgaaacca ataccgccaa tcaactgacc ttcttgaagc gccatctgat   174840
agttagccag gtattcgcga acccacgatg ccaaaatgtt agtgttctta gacattaatg   174900
cagcgtaagc atcaagactt aacttggtat tttcccaagg gcgttcttct gtagcagcac   174960
agattagtag aactgccaac agacgatcaa atgaaacaaa ggcttctgat gaatccacac   175020
gcgggaaacg tgtctctgac gcgtatttga agagatcagc aaaggagtag ttgtatttct   175080
ccaacacttc tttaatgatt tcatcgtatc gctcgtgacc agtgataatg acggtttctt   175140
gatcgatgtg tggataaact agagcagagt catcatggtt aaagtcaaac tccaccacat   175200
cagacaatgc tgtcaacatc ttcccaacaa tcgggtcatt ccaacgctca tcaaaagcca   175260
ctggtacaac ttcgtacaat gagtcaatga tatctttacg tgttggaatt tcttcagccg   175320
atttcagcac ttggccaatg aatggtttaa cttggttacg tgaacgatca agaataccag   175380
aaaccagact gcgaatcttg tttttacaga acaccagggt ctcttcatgt tctgcaattg   175440
gaattagctc atcgccatca gttacatgcg cattggttaa accagtacca agtccacgct   175500
caagagaagc tttgtatttt tcaataaaag tctccgggtt ttcttgtgac atttctgcca   175560
atggtgtgta accagctgca actacgacgc tagcagcaga gccatcaaca gtaccaagac   175620
gtaggccagc tgtgttcaca ttggccgcta aaagaccaat cgcatcaaat gtaccttgct   175680
gaatcatgct agcgttctcc cagttttgtt ctcgattgtt ttaccaagtt ttgctgtgaa   175740
taaaccacga acttgttcgc gttgacgttt accactgcct tccttagttg aatgaagatt   175800
tggatcaccg tttagtaaat ccatcgccac ctctgtggct aattccgtca cattcgcaag   175860
aatgatgata ttgttcaatt tacttccgct attcatcttt ttaacctcta aaaagcccat   175920
aagtgcatga tggttctcat gtaaaaaggg gtaaatgtat atttacccct aatagtacaa   175980
cttacgagtc tcgaatttcc cttgcccctt cggcaagacc catgctgaaa cgtgtaccca   176040
aacccattcg atataaacta ccaacgatac ggttatccac accctcgcga ccaaacttca   176100
aatgaacttg acgaccagtg actgtctcgt tcttcccaac catacgtcct cgcaccaccg   176160
acttcatctg gttcgcaaca acaattttat caccaccgat catctcatgt tcacctgtga   176220
tgtaaaaacg aatcagaact tgcccttcta ctaatgcaga accaccagtt ctaaattcct   176280
catcaactcg cccagtctct gcttttggaa catgggaagc cttagcttct tttcttctac   176340
gtctgtcacc tttacgaatg atggcctgaa gtgtttccga cattaaatcg atttcaccgt   176400
tgtagatgat ttcaattttg tcaatgatac cttttgcacc agcccgtggt gagttagtag   176460
aaagatcttg aagtgtctca attgcatcag aactgaaacc gccgtaatcg ttagtgtcgt   176520
cgattaaaca caatgttgtg tcatactcaa ccacggttcc ttcattaaga agctccaata   176580
tagactggtc tgagttaaca acaacatctt taattttggt agttcttgtt gtgagttctt   176640
tcgccttgtc ttcagagatc tcatccgagt cctcgtagac ctcttcacca ttaattagcg   176700
ctacgttaca ataacaccg tttctccagt taacctgggt tgggttcatg atgtccggtt   176760
caaaagattc agagcaatag gctaggacgt ctcctttact aaatttctga cctttcttaa   176820
catgcggtac tttgtcgtgc ggatagttag tcccttcgta agacccatac cagcgaccta   176880
aagaatagac ttcttcagta ccatcagcat attttacccg tacaccatgt tcatccaagt   176940
caataacttt accatcgtcc ttagcaacgt tggcgtagta atcggaagca cggtgagcaa   177000
ctaatttttc actacctgtt cgatatggtg ggcatttgcc atgcaaagct tgtgtggctg   177060
aacccatttg aatgttaacg aagttaccac gcttggaatc atcaacgttg acatctggtg   177120
ccaatgagtt atagaaactc aataactgcc cgaattcaag ttttgataaa tcctcttcaa   177180
```

```
cctttaccat cccatcgata tcgagaatgt tagggtcatt agaagccaag gctgtgatac   177240
ccacgtcggc gttatccacg gtgtcacctg agattatacc gagttctttg gcatcgtact   177300
cacgtgtatg tttcaccata ctacggcggc tacgtccatt gctaccaccc atcgttataa   177360
catcttgctc tttgatagac tggatagcgt tagcgtcttg tgccgttaga acagatggat   177420
cactatctat acgtgcccat actgcctttg gtttaacatc caacttacga gtagttggtg   177480
gcgagttgtg gtagcgtcgc attgctttag ccacttcggt gtagaggtga ccagctaagc   177540
ggtgattaga gaagatatgc atgtattcga tatctgtctc acgagggtgg tcgtgggaga   177600
caagtaacga gttagcacga atgaggagtt tcttaaagcc agtaggctca ccaatcttcc   177660
taagtaactt ctcatgaatc gcatcaacga aacctttctc taacaaatct aattctgtta   177720
gatactctgt gccaagtttg ttcttttgta acaacaaagc ataagctgat ttcgtttcca   177780
tgtctctcaa caacagagtc ttcagctggt ctttgtatct tataaagcag ttgtataaga   177840
gctcctcctc gtaactctta ggatagattt caagtttacc ttcttttaag gataggataa   177900
taccatcacc ccttggtttt tcacctggtg ggtagaactg atactcagta ccagtctctt   177960
tcattagacc cttcaggcca agatagtaag acaagataat cccaagagga atagcttac    178020 ctagaatatc gacgtcagta tgaggtctcg gttccttgtt tgtcggtaaa tctaattgct   178080
caatcaaacg ttcagttgga gtaatcttac cattctctaa cttatacaaa gctgaacgct   178140
cgtccattgc aagagtagtc gttcttgatt tggccactgg aaccagattt tccttggtaa   178200
gtagcttgac ttcttttttcg tcaaagacat caccaatctt agagtggtcg aaattgtaat  178260
ggtaaccttt agagtcgaaa gaagaaatct tcatagcgac tgtggtgtaa tcgcgcggta   178320
acttaacctt gtgatcgaag acatttgaaa aactaacatt cgtgatggtt gggttatcca   178380
tatccacacc acgtgcagta atttcattac gaacccactc gccccaattg accacggatt   178440
gctcagaggt agagacaaac aacttaccat aaaagcttgt tagagcaact tcactcggac   178500
taaccttacg gattggtaaa tcaacacgtt gtttacgcat tgtgtattta acaccgttgg   178560
atgtccagta gccatctttg tctacctttg gtaagatgaa agggatcgtt gcttgtgtac   178620
cgtctaacaa ctgaacacgt aatttatgct cttcgcggtg accacctgca tcaagtttct   178680
cttgcatctc atgagctgta atcaccatgc caaacttctg taaggagttg gtgattttaa   178740
taacgtcagt tttaaggcgc ttggtgttgt actcttctgt gtagatttta gtgcgtgagc   178800
cattccaaga atcttcaatg attgttgggt cgtcgatgaa tttctctttt tcaatgagaa   178860 tttcttttc tgcgtttctt agttcctcac cgtagctacc accataagga gattccagat    178920
tatcaacctc gccaaataga cgcaggaatt tatcatggcg tttaggtgac acctgcttga   178980
tttgctcaag atcgcgtttg ataatatccg aaacagatga gtcatcttca gtatttacaa   179040
tgatttcgtc ttctgttact tcttcaacaa ccaactcctc atcttcaatt tcttttcctt   179100
cgaagcgttg aatttcatct tcgatcaatt catcgtcgtc ttggaaatca acatcatcct   179160
catcaacttc tgaattgatg tcaacatctt taccctcagg tgcagccttg aagccagtag   179220
aaaccgcagg tgtttccatc aagatacgaa tggtttcacg gaaacgttta accatctgat   179280
ctggcgggac tttaccttca cgaccttctt tacgccaacc gtccaactca ccaaggttga   179340
tgttgatgaa gttaccgttg aattgcaata agaagttaac atggcgtgcc ttgcgagaat   179400
caatctcact aaacatactg ttgtttctat catccgacaa ccattggaaa agttctacaa   179460
gaactaacat ctcatactgg gtatttcctt cccacacggt ttcagtgtga gtgttcgcca   179520
```

```
ttttgataaa acgtttacga ctaggtaaga acttaggaag gttcagtggg atgtagtgct   179580
ggcgttcagg gtattctgaa attgaatcca aaacaccacg gattaaggta ttcagcaagt   179640
tgtgcgcttt gtcgtaccac acgttgattt tgtcattgta acggtagcga cgcaggattg   179700
gtgtgtagtt ctcaacaaga actattttat tgtcggttga taaaagacgc ggatctttca   179760
atcgtttgat tttttttccac ttacgatggt aagacagaat gtcgtctttt atctcacgtt   179820
tgatttcaat aggtagaccg acagaattct cagcacgcat ctctaagtga tgacgcatac   179880
gtgcgggttt ctctaggtcg ctaagatgat ataatgttgc aggtggacca aactccagac   179940
actctgggtc tagataatgt aatacagtac cgcgtgcaaa ctctaattta gcaagacctc   180000
tgacttcagg ctcaccaaat tgagttagac gtctgaccgt aaaacgacgg ttgaagtctt   180060
ttaagagaat cattgtggaa cagctcccat gttttttttac ttaacctact cagggtcttt   180120
cattagtgat ttaaatgttc gtttagctgt gccatcgatg agctcaattt tgagtttgtt   180180
gttcacgtca acccaataac tgatttcgcc cattcgcttc ttctgttcct ttaacgactc   180240
ttcggtgtag accgagttac cagaaccagt atcgccatcg tagtcacctt gcaaacccgc   180300
aatacgcgta gagtgtggtg ccatcgcaga gatgaactct tccacatctt ttctagggta   180360
agatatggca ggtacttctc gcactgtttc ccaatcgtcg ttgtattcgt agacaacgtc   180420
tgatttaacc gttgtctcta cacgtatagt agaaggatat gtactaccag agcctgctac   180480
cgggtaacgt gtaacgaaca tgaagtagtt accccaaatg tcataacccg acaagtagag   180540
taactcagct aatgtgatgg gttcgacata cttcctatca aagccatcag gtaaatcacg   180600
aatatcgcaa aatactttaa atctatcgtc tttacgatac actaatgcaa tgtaacggtc   180660
tgctacttta agaggagcat gtcgttttttg tggaaccctg aaactgtgta atagtttctc   180720
aataccttcg tcggtagtat ataagtcgta gtctttaacc ccgactttaa catactctga   180780
ctcaagagtt ttaggattga tgagattcat atgaccttga cccgcatcag cacggctcaa   180840
gtatcggttt cgaacgtaat gttgtgtaac tggtaaaatg gagcgtagac cctgatgtaa   180900
accaactaaa gtatctgtcg gtctgtattc atcaggcgca cccatttcag ttgaactggc   180960
gatgagtgga cttagtacgt tacgtgtacc atcggtcaaa cgacgggaag taactttacc   181020
acgagtaaat ccctttttttac cgtcgataaa attaaagaaa tactcgtata catcgatgaa   181080 ggcttttttga agtttccatc gagggatatc catcaatggt gaatcaacac cgcgctctgg   181140
tattgttttt gcaaccgtca taacggaacg atataatggt gttaactcat gctccttctc   181200
tccgttctcg tctatctgca tatcgcgtag accagcaggg aaaacgagca cataagggct   181260
gagtgcgaac tctctaaact tatagaagaa gtcaatagac tgctgtcggt tttgagagtg   181320
gttctcttta ggggtcagtt cgtggaaatg cttaataaaa aagctataac cagtatttgc   181380
tccagggtca ccctgctttg cgctgtcgaa gtcttttgtc tcttcgttcc aggtagcaaa   181440
tgcagtaccc gacattactc ccttgtatag ttgctttaac tcaaaaagag ttagagcaat   181500
gataggtgag atgatactcg ctttggcgtc tatgtaagag aagttttttgt cgcggttggg   181560 tgagccaaca ggaccaaaga tttcaggtga ataaaaacca tcggggtgaa agttttttgt   181620
ggcacctacg tatgtgtcta acgtcgtaac aggacgtaac ttagacacca tggtcttatt   181680
cacgtttaat agataaatgt ctaataacac aacttgttcc ttaggtggca cttatgagtg   181740
atgatatgga cgatttggat aaactgcttg gggatttaga tgatgatttt tcatcagaac   181800
ctcatggtga ctttaagtca gatgaccgaa aggcagttac taaggcagtg aaaggtgccg   181860
cttcttcggc attttcacgt atccttccaa aacgcaaaaa acaagaaata atcctcaagg   181920
```

```
cactcccaaa aaattatggt gaagctgccg acaatatgcg ggatattaaa tacacggcag  181980
acgatttata ttctcataca aaagaggaat tgcttgagac taaacgccaa atgaagcgta  182040
agactcaagt attaatgcca acacttagaa agtacctacc aactccaatt tccgaacgtg  182100
tggacaaatg gagtaaacca gaagagcgtg gttaccgtgg tgagtacgat gaagaacagg  182160
ctaaaattga ttcagcgatg gcaagtgtgt ttaatagcac acgtgagagt gttgttccaa  182220
cagacacacc gcaagccaaa cgtgcccgta acaagagggc gacgaagaa ttacaacaac  182280 gtaccgaaga agaaattaaa gagttttcta gcgatcaacg acagttacaa atagtcgagt  182340
ccaccaaacg catcgagcgt ggtgtagaag ctattgttcg tcaagagcaa ttagtaggga  182400
catcgtggaa gagaaaaact ttagaagtta gtcttcgcca gatgtttgca ttgcaagaaa  182460
tctcagcatt aattaagatg cagaacgata gaaatattcc agcgatggaa gctatcgtta  182520
aaaacactgc tttgcctgat tacgctaaag agcaatttag tgaagttgca gcagcaatga  182580
tgcaacgcaa aatcattgag tcaattaacc caatggaata ttcacgaaac ttcttaagcc  182640
gctttgcaga taatgcgaag aagaaggtga gtgaaacact tggtgaagtt cgtagtttga  182700
tggatttggc tgataccatg gccgatgaca cagactttga ctcgggcgat actgaagtta  182760
gtgaagacca acgtaaaagt aacttacgtg accttacctc aaatcagtta gcagcttgga  182820
ttgcagaacg tgtagctgtt ccagtacgcg acaaggtact taagcgtgta cgtaaagcgg  182880
cagaaggtaa tgacaaggtc gttgagttcg gtgagaaact acgttattac agcgggaacg  182940
ttgctcaaat ctataacact gagttgacag atgaaactga cgactctatg ttaaagacca  183000
ttgttagtta cttagaagaa attcaaagtg gttacaatgg cgagttaaca aagctacgtg  183060
aacgtgatga gtcctggttg aacgaatccg ctaagaacga taaccgtaaa tatatcacga  183120
taacagaaat catcccggca tggctagccc gtatcagtgg aggtattgat aagttaaacg  183180
gtggtaatgg cgacgatgta gaatacgata ttcaaactcg taaattcgtt aagcgttcag  183240
tcatcaatga ccgtgttcgt gatgtcgttg gtttacaaga taagaaagat gttctaaagc  183300
aaggtttgga tggtctcgtt aaaatgttcg attcgaacaa tgagctgtct gaacaaggtc  183360
gtaaggaact gcgcgattac ttctacgacc gtgttagaaa gaatagaaca tttgacatca  183420
aagatctagc agcaagaccg ggtatgcaaa gaattgtcac agagcaagct gacgatgagt  183480
ttttcaataa gcgtattcaa gaacttgctg gtgataatct ttataccaac atgaataagt  183540
acgcatctcg ctttggtgcg ctacgtggtg cggcgggtgg atatcagaat gccattaatc  183600
agatgtctgg gttatatggc gataaagctc tagttgatgc aggtatcttt aaaggtgatg  183660
ataaaggtcg ccttaaagtt gacgaatctt tgtttgattt agataaagag tatgtcggca  183720
gtgcgactaa aaatgatcgt gctatgagcc gcttcatcaa tggcgggggct ttagataaca  183780 aactatcgcc taagagtcta gatagaatta aaactatcaa tactgaaggt ggtaattgga  183840
ttaaaggtat ccgaaatatc aatcaagaaa aggcaaagcc aaaagccaag cctactccta  183900
aggttgagcc taagcaacaa cccgaggtac aagccaccaa taccacgagt aacaccgata  183960
acactaatta ctttaaacgt attagtgaag gtctagctgg tttgcaaaaa tcaatcaatg  184020
gcgttaaaac accaaaggtt gaagtgaagg gtctagagaa catcagacca cctatcgatt  184080
acacctcgaa attcgataca atcatcgact tgcttaaacg taacgcagaa gggacagagg  184140
aaactaaacg ctcaatcctc agtatgttga aacgtaaacg caagagcgat gatgtggaag  184200
aagacgagta cgcaccgggc ttctttaagc gtatgattct taatcgacgt gctcgtaagt  184260
```

```
tgaaagagaa agagtatgtg gagaagaagg ctggtaagga agaaccttct gcatttcgtc    184320
aaaggtttga tagtatctct ggaattttga gaggtggtgt taatactggg tttgatttcc    184380
ttcgttctgg taagcgtggt gttgaggctt tcgttaagtc tgcggtaggg gcaagagaca    184440
tctacggtaa agatggtaaa gtagttctat ctggctctaa gttagagaag ggttactact    184500
acaccaaggt aaacgagaaa cttacacaaa tcttcaaact tgaggatatc aaaggcgctg    184560
tttatgattc tgaaggaaag gtaattcttt ctgaggagga cttaaagaat gctggtgagt    184620
tgtcgtacta taaagacagt cgttggtaca aactaacgga ggtcattggg ggtaaactcg    184680 gtggggtgt aaatgccatc acagggatgt ttggtaaggg cggagcaccg ttacgtgctg    184740
tcggtgataa gatcatcgct ggtgtgtttg gttaccctga tatttatgtt aaaggtgaga    184800 agacccccacg tttacgcgcc gagttcatgc gtaagggatt ttaccgtcta aatggttcag    184860
acggacctgt tgttaaagga ccatctgata tcaaaggggc agtttacgac atcaacaata    184920
aactcatcat tagtgaggag gaactagcct ccgatggttt tgagttagta gaccaagacg    184980
gaaatcctgt aagaactcgc ttccaacgtt tcaaccgcat ggtgtctagt caacatcgtc    185040
gtgtccgtaa attcatcggt gggaagatca catcgattaa aaacttccta gtaggtaaga    185100
agaaagagga tggtgaaggc gaagagaagg aaggattctt ttctagacag aaacgcgac    185160 tctcttcatt ctggaaaggt gatggcgaaa aagaagatac cgagaaacgt cgtggtatct    185220
tgagtcgcat cttcggacga gcaaaggatg tcgcttacgg cacttcagac gagtacaatg    185280
ttctcgttaa gatttacaac ttattgaata aacgtctacc tggtgagcca ggcgatgatc    185340
tcgaagaagg aaagagccac tttggtaaag cgaaaagcac tatcaaagat aaggtgagtg    185400
acttcaaaga gaaacaagca gcaaaaccag aaagacaacg tggtgtcaag aacttcttca    185460
agcgccgtgc taaattggct gagttgaaag ctaaacgcaa aatgcgtgaa gttaagaaa    185520 cggacacttt caaaaaggca agggacaaag ttgaagagct gaacgaaaac acagcttcga    185580
aacgtcgcta tgcaagaatg aaagcgaaca aggctaaacg aggttttatg gatcgtttaa    185640
gtcgtggtcg tcgtttaaca gaactcaaag ccaagcgcgc taaacgtagt tacgaaaggg    185700
accgtacacg tttaggtgaa acagccgcag ttctgaatgc gggtaaagaa gagatataca    185760
atccagtcaa gaagttcgtg gtgagtaata tccagaaagc taaacgcaag atggaagaga    185820
agttcgagaa acctcaggat aaatttgctc ctatgaaagg taagggtgct ttgaaagacc    185880
cacagcttga acttcttcgc cgcattgccg actcttctga ggcaggttgg attaaatcta    185940
tcgcagagtc tacagacgac tatgggatgg accaaggatt caagcgccgg gctatcggag    186000
acttcgctag gaagttcaag ggtggcctaa gtcgtttcta ccgtgactat gctcgtaagg    186060
acaccaatga ttttggtgag gagaaagtca aggataaaga gaagggacct aagaaagaag    186120
gtaaaggtaa gaaagaaggc ggcttgcttt ctaaattact tggtgggttg actggcggta    186180
tcggtgacct aggggattgg attaaaggca tcattgctgc taagatgggc ggtagtctat    186240
ttggcggcgg tattaaagaa ggtgccaaat ctttacttaa gtcgggtgct aagaaagtag    186300
ctggtcttgt tgcagggcaa ggattgcgca cagctggtgc tgcactatta tctggtgttg    186360
gtactgtgct tggcggtttg tccttacctg tggttcagg tgtggctgct gttggggcaa    186420
ttggttggtt tgcttaccgt aagttgacaa ggaaagaagc tggtcctttg ggacgacttc    186480
gcttggcaca atatggtgtg cgtgattacg acaactggaa ctctgaagat gctagtaaga    186540
ttcgctatct agaagacaac ctaaagcgtt ttgttacaat tacgcctagc ggtgccaccc    186600
ttaagggttt aacggctgag aaggccggag aactcgctat aggttatggt atcgataaag    186660
```

```
aaaaccaact tgaagtaaat gcttggcatt catggttcca aaatcgtttc atcccaatct   186720
atttactgtg gcaaggtagt atcaactcgg tatcaccaag cctaacagtt ctggatgtgg   186780
aagataagaa tcttgacgca gaaacacagt tgaagattct taatggtgtt cgcttaccgc   186840
ccaaccatcc gatctttgct gatcgtgccg atccattgaa ggccgatcgt gggtggttta   186900
agagtgctac tgatttcctt ggtttcacag aacagaatct tctttctggt gaagaggtag   186960
gtgatgtgac agctcgtgct attgaagagt tgcaagggaa agctaaacgc gagaaaaaaa   187020
ctgaacaaga ccgtgttaat aaagaagtcg gcgtgcgtaa gttcaatgaa ggtatgatgc   187080
aaaacaccaa accttcgccg atggattcac ctaaagcaca agaggctttg aagaatatgt   187140
acggggcaaa taaccgact  cgtaacttct cccagggat  ggataaagcc gctactggta   187200
actcggagaa agtgaatgtt ttagtacctg ctgttgaaaa acagggtata cctgctactg   187260
ttgaaattat tcgctttgcg atgtacggta ttgataagcc aacagatacc acattggagg   187320
ctttgagaaa gctggataaa attgcagcgg acaaaatcaa cattaaatct ggacaaatcg   187380
atgaccgttt ctacggtgaa gcgatgactc tagcggcagg gttcggagta gtcacttggg   187440
tttcagaaat taataagtta gatagacagc aatataaaga ctggttacgt gaacgttaca   187500
tccctgtctt tatagcttac aacaaggcca ttggtaatag cgtcggcatt ggtagtgttt   187560
tgaaccctat gccatcagaa gacgtgtatc gtgctatgaa ggcttagtg  gggactaagg   187620 tatttgcatc attaggccca gtaagtgtgc ttacaatgcc atctggtgtg aataaggttg   187680
gtacatacac cattattaag gatagtgcac caatcgacaa acttatcgag tcaattaagc   187740
cacccgagaa gcgtagtatg tcttcgacgg tcactgatgg tgtcgataag aaagttaaga   187800
aatcttacat ggatggattg acttacaaag agcgcgggga taagaacact tcagtgatag   187860
caagagaacg tcaaaaacaa atcgcagatg ctaataagca atacgatgag tataagacga   187920
ctactgcaca acaatcactg gctcctcgca tggaccctgc taaaatgact agtgacttgg   187980
ggacaggtca atatgccgag tttgcgaaga tgccactgaa gagccgtgaa gacgtcgcta   188040
ctttagttgg ccgaatcgca aaggcacaag gcgtagaccc taacttgatg atcacaacag   188100
cactagtgga gtcgtcacta aacccaacag ccaaggcaaa gacctcttcg gctgctggtt   188160
tattccaatt cattaataag acttgggatg aggtgatgag aaaacatgct aaccgtttgg   188220
gtattccagc gggaacgcgt gcaaccgacc ctgttgcggc aacactgttg gctagcgaat   188280
actttagaga gaatgggaaa attattagct ctaaggtgaa tcgtgatttg acgccagctg   188340
attactacat gggtcacttc ctaggtgcag gcggtgcagg aactttcttt agtgaaatgc   188400
aacgcaatcc aaatgctatc gcagcagaag tattaccatc ggctgctaag gcaaatctca   188460
atatcttcta tgactcttca actggcagag cgagaacttt aagtgaagtc tatgaattat   188520
tcaccaacaa gttcatctct cgtggtagtc agattggcag tttgactaga ggggagttca   188580
gttcatcttc aggcgtgcag attgggttac cttcccgtgc acctatcgat gacccattgc   188640
gtcgtgagga agcggttgtt tctaaagcga agcgtgactc tgaacaatct cgccgtgtgc   188700
gtgatggata tcgctcagta acaccgggcg gtgcggagtt tgaacttcaa tcgacagcac   188760
aagctaaaga gtacgtagct aaccaaaccg aagctgtttc aaaagaacag ccctctatga   188820
agctaagtga taaagagcgt tacgctactg cactggctga agtagaaagc ggtgtggagc   188880
cgacaaaacc aaaacgtgaa aatgtttttgt atgacaaatg gtttaaggac agcgcagagt   188940
atcaatccaa agacgctgtt gttcaaaata accaattgca ggcacagctg cgaattgtag   189000
```

```
agattcttca attcattagc gagaagtttg atttggcttt aaataatatg gggacaaaag   189060
tacctagcga cttaaatgtt gcagagaaca ctgcggctgc ccaattcagc cgtcagaaaa   189120
tcaccgtaga tttgagccaa acaaaaacca atgttgctag aaataaaaac gcttagtgtt   189180 aggggactc gttccccctt ctctatttaa tttcggaagg agacgttatg agtatgcaac    189240
caagaaccaa agaccttatg tgggttaatg gtctattcgg tttagcacct cgtgcaaggg   189300
attctcaatc ccgttctcaa cgtcgttaca gtaatctgca tttcaatttt gcagacacga   189360
ctattggtgg tagccaggct atcaactgtc caccgcaatt cactgccact tgcgatccac   189420 cttttcactgg gttatttgct aatccagaag gtcgtactga gggttctcgt agcgattact  189480
ccgacttatt tgcaggtgag cagaaccaag gtagttatcg aatgggttct ttctttttg    189540 aaagtattta cgataacgct catttgtac attgtcgttt cggtaaaccc aaatacaccg    189600
ggatgattaa cttctttgca aataactacg actctaactt agctcatttg gctaaaacgg   189660
gtgactacaa ctcttcgcg cgtaacctag gtgcgtgggc tggcgcagct gccatttata    189720
gtgtggtggg gcctttggct ttcgttacac tgttggcggt gccacaggtc cttaagttcg   189780
cccttggtcg taaaccgtcg aaatattact atctcaaacc aaccatgcac acttatcttc   189840
gtgctgtcca gtctatattg gatacacaag cattgcatta tcgcttgttg ccaatggctg   189900
agatattcgg gcgtgataag tacgagtatg agatgacaga agagcaacgt aatgaagttt   189960
atggtatgct cccagatatc tggaagtcga atggtaagtt cgatgtgtac aaggccatta   190020
accgttatca ggttctggct aactaccaag ctcgccaact caacgctatt tacgaagcgg   190080
catctgatgc tgacgatttg caaaaccgtc tacgtgctca tatgcgtcaa gcaaagacaa   190140
ccgctttgta taagaactat gctactgaga cgaaacgac ccttcaaaag ttggaagatt    190200
tgtataaggc taacccccgct taccaatcag agaacgttgt tccccctggt acagaagagt   190260
acgctaagca aatggttcag aactacgaca agcaacactt cgatgcggct agactgcaag   190320
aagaacagcg tgtcttacag atgaacacaa cacttgacca aaatgcagcc gagtacaaag   190380
tggctacttt ctgggaaggt atcgttgatg acgtatccgg tagtttctct gatatagcag   190440
agcaatccta ctctgagttg aaagatggtg gtcaatggat ttcatttatg atctccaaca   190500
aggaatctat ttctgattct ttcaccagtt caacacgcga acctgaaatt tcttccaagc   190560
ttaaaggtat agcttctagt gcaagaagta tagaagttag cacatctggc ggaaagacgg   190620 gattttgagtt tgtcgacgca gctatgactg tgtcgctga gtttgttaag ggtgcagctg   190680
atgcccttca tctaacaggt ttgatgtcgc tgtacggtgg ggcaatcatt gacttccctg   190740
aagtgtggga tgactcgaat gctgagattg gacagacaac cttaaacttc ccgttgcaat   190800
catggtcagg tagtgatttt gatttgtttc aaaatatcat cttccatta tcgttttggt    190860 tagcggctgc tatccctaac tcaacaggta gtcaatctta cacccacccc ttctatgtag   190920
aggcttactc tccgggtaag ttcatgattc gaaatggtat cattaccaat ttatcaatca   190980
ctcgcggcga aggtaatgtt ccatttaaag cagatggtaa aatgttaggc tgtaccttgt   191040
cagttactat taaagatttg tccaccgtga tgcacatgcc tttgattaac gacccgggta   191100
ttttcgatga cgactctatg ttcactgact atatgtcaat cttaggcagt gcgagtttgt   191160
ttgagatgac caacggtttc caaaagctga atatgaactt caacaaatgg cgtcaatcgt   191220
ggaagtctgc tgccatgact ggtaatgtga cttctagtgt gatgaactca gcacctgcac   191280
gggtactggc ttcggttatc gctggtggta actaccgcta gagacaaaaa aagaaagta   191340 ccctcgtaat gagggtactc ttttattttt ttatccgtta acagtgagaa tgacaactaa   191400
```

```
aaaggacact cattgtcaat cattcttctt taggtagtca gataacccag acacttcaat   191460
gcacccacgc aacggcattt cgccatcgtg atcgattgtc ggcatctggc aaatactttg   191520
tagattagtt attgaaattg ggaactccat tatgggaccc accccaaat ccggaagcgc    191580 cttagcgacg attgtggttt ctatttcata cgccactaac ttacaaccgt tagtccaacg   191640
tttcatccgt tcggagtttt ctaagtagta agacggtggt cgactaattg tttctttcgt   191700
tacaccttcc cacggcttaa tacgttttgc ttttgtaggg tctttaacgt aatgtggggt   191760
tgtagtgtgg atttgctcat ccaagtataa gaacaatccg tcctcttctc tttgaatcaa   191820
caaacaaatt tcggtttctt tcattttga tattccttgt tatccggcgt ctagataaaa     191880
gtacctcctt gtgtaggcaa ggaggtttaa cttatttctt tatggctatc agttcactga   191940
ttggttttct agacgatgct aaacaactaa tcgtgcgctt cgctggaaaa gcaactatct   192000
ctagtccctt gtacaactca cgcgtgatat cgttgtcatg attggatata gccaatggtg   192060
ccacagaacc ttttgaaagg gtagctaagt cctcttggtc cttcttagtg aatccctctg   192120
tgctgtaaga gacgaaattc gccgttgcac tcgatggaac ataaggcggg tcagaatata   192180
caacatcatt atctttaact tcagagaagg tctctctaaa accttgacat ttaaatgttg   192240
ccttcttagc cctctcgcca aagtaacgta tttcctcttc tgggaaatag ggttggttgt   192300
aagcaccaaa cccgacatta aacttaccct ttttgttata ccgacataac ccattaaaac   192360
aatgtcgatt caaatagata aataacagag ctttaaagta ggtatcggta gtctcgttga   192420
actcatctct taaccgaaga taaacctctt tctcgttcat atcgggagta aagaactctt   192480
tcaaatcact tatgaatttt tcatggtcgt ccttgataaa attataaaga ttaatcaagt   192540
cagggttgac atcacataaa agatattcat cgtagtcaag gtttaaaaaa acaacggccg   192600
aaccaacaaa tggctcaacg agtcgctcgc cagcaggcaa atagttttct agtttatcta   192660
ataaactata cttaccacct gcccacttta atggcgaacg gtgtctgagg actttagtca   192720
cttaccgcga tgttggcacg acgttcccag aagtcactaa tctgggcacg gtcagtcgga   192780
ttcaattcct caccctcaac gatgatactt tcgtatttga atgggatgat ttctttaacc   192840
cggtcagttg tcatgcggtc aacttccagc tctaccttaa cccaacctag agcttcaaag   192900
cccttgcctg agttgtagaa tacatcgact tcccacatgt actgctcacc actattgcga   192960
agtagcggtt caccacgatt agtgattggg atattgatac gcgttacacg gtgaatgttt   193020
tcagcgtaac gaatgtagct ttttgccacc ttagttggaa tagtgatgtt atcttcgatg   193080
ttatgaccat cgggatgttt cgtctttcc gtaaaggtag cactttcgcc ttcaacacga    193140
acacgtgtgc ggttaggtaa acgtttcagg aagatgtcga ggaaatggcg tttggtctta   193200
agcgccatta gttcatctaa cgtctcctgt gttacctgac accaaaacac atactcgtgt   193260
tcttcttcga ttgaacgctg gtcttcatcg agtagtccag ctaatggacc ttttctttct   193320
ccagacacgt taactcctta ttcagcagtt gccagtcctt tgatgtgctc catccacaaa   193380
gactgctgcg ccgacgtacg atgtcggtag ttcaaaccaa atgtgaattt gcgcggatcg   193440
tagttgttaa actgctcttc cttaagttca aggttaagag ccttgtctgc ctgtagacca   193500
accgcgatac gataaccttt ttcgttatag tgtttgtagt ttaccagaca gtagctgacg   193560
acgtcttttg cttcgtcttt gctaatttca atgtcgcgtg gtttcatgag aaactcatct   193620
tcgcgaagga tagcttcgtg atggattacc gccattgcgc gagtcatatg ttccatctta   193680
aaaccagtct gatgagcaat aagtgccatc gccaagtttt tcaatggggc aatgtcttta   193740
```

```
ttctgttggc ttaccacttc agccatcgca cccgctgtaa tagttttgtt cattttaaag   193800
ctttcctttt aacttagatt tgaataattt ggcattgttt gtgataacaa cgtcgcagtt   193860
gtcttaggct tcactttaga gccaatgtat gctagaattt tgtaatcggt agtagcaagt   193920
actttaattg catcatccga gcagaaagag aaataataag catattgctc attagggtca   193980
taggggtcga gataccaatt atcatagacc atcttagtga tgtccattaa atcagccgcc   194040
atagccttaa gactcatatt gtctttaagg tcatagaact gcaacaactc aaccaaataa   194100
cgctcacgac aagcgtattg acggtcactg tgtaactttg gccatagctt acggaaacat   194160
tcgaagtccg acatccgtgc agcggtcgac aagttacgtt ctattgatag ttgcgcagct   194220
cgtgtatccc acatcaagcc tgttatttgg tcgatgtatt ttgggatacc ccattcaatt   194280
gccttcgacg taatcgcatg tagtagtgct atttcttcag aagcattgaa aaaagtaccg   194340
agttcttcat taccagagag ggtgttaact aagccaaaga cccttgtga cattggggca    194400
tcacctttgg caaagtctag accttcttct gtaacaaaag cagccaatcc catctgttta   194460
ctctcatcag agtacccgag aatgttaagg aactcgctcc cagttgttaa caagtcattg   194520
gcttccgcct cactcaattt actcaagtca ttcgaaagac caagacgttg tcctgcccgt   194580
tttaaagctt cagggctatt gaaactagcc ccgtcttcaa aactaaccgt tgacttgaca   194640
tcatctggtt tgattttacg taaagggcta ttctcgccac ctaggatgtt tttggttttc   194700
tcccacatgc taggttcttc gacaggtgca gggcagtttg ctgttgtaaa gggcaaacct   194760
tctggtgcaa ctggcttact ggctaatttc agctcaccat cgaccacttt gtttgggtcg   194820
atagtttggt taaccacccc actctccact aatgtggagg tggagtctgt gacaggacgc   194880
acgtagtccg gtggggctac gcgcttgtca ggttgaacat tgggaagttc ttcacgcttc   194940
ccagagttga atatagttgg ttttacttta ctatccatcg cgttttacct taatgaactc   195000
taactcactc atatctatat ttaaactagc gtcgaatgta tcatcggact ctgtcgtcat   195060
ggtgatgttg attttcatct catggatgtt gagtgcttta actgcttggc agaatcgcat   195120
ccacgacaaa ccttcggtgt tacaaacgtc gcgtttaatg ttggagtact tgtcattacg   195180
atagtttcga atttgttcac agttaatagg gtcagataga tactgctcca ttaacttatg   195240
ccaaaccta ctagcgttaa acttgtctac caaccccag tatagtttac ctaaagggtg     195300
cttcatttca gagatggctt ttattggatt ttccaaataa ccatctaatc tagatgaaac   195360
acccgggttt ctatcgtcat cattacgact ttgattgata aatgataatg tagggttaaa   195420
tgagatagaa atcgatttt caatttcagc tatggttagt ttccgcttac acactaactc    195480
gactgtaact tgtttagact ttagtaatac tagtccggca actatacgtt tccaagttac   195540
ttccttaaca gaatcttctt tttgacttgt tcctcgaaca agagcaacag ttaatctatc   195600
acggagttct cgacgtctag cgggagtttg ttgacaaaat ctttcatctg atgtgaagtc   195660
attcatcaag cgttcccagt cttcggttc tttgactatt tgtgtagcca aagcccagaa     195720
tagatagcgt agcggaccac ctaactcaac agggtctagg ttttaccct tccctcgat     195780
gatatgtttt agattcataa tcacacccta tctggttctt gaacttatta aattcagcgg   195840
ctagtctaac agccatgata ccagcgtttc ttgggtattt cgacaatgat gaatctcttg   195900
gcaagtgttc tttgcatcga ctgtacagca caaagagtct tgttgggatt gtttcatagt   195960
cgtagccgtg gaaataacgg tcacgatata cttcttgttc ttcatattca aaattcctct   196020
tttgtttaat tgggtctttg ctcatatagt ttaagaaaga ctcgacgtaa tcgtttagct   196080
ccttgaagct accgaaacca ctctgtattt tcaaagggat ttctggctgc tcctcaaagc   196140
```

```
tagcgagttt gaaatggtag tatagtttgt cactctctaa tagtttagga gagttcaagc  196200
gccacgtgca ccatctaatt accattcttc ttatggataa catatatttg aaacctttt   196260 gcttctggga gtgattatgt ccgaagaaat taaagacaac gttaagaagg atgatgtctt  196320
aaccatgcta gccaaccta atttacagga tgagcaagct gtattagaat atgcccaacg   196380
aaaccgtcat gagctaatag agctattgaa gacttttgcc catagcggtg acaccaaaac  196440
catcaacgta attcgtggtc tattaaaaga catggatagt tcggtataca ccaaccgtcg  196500
aatccaagtc gagagcaaag atgctgatac caatgcggaa cttgcacgtc aggcggctat  196560
gcttcttgac caagcaggta tcggtgttcg tcgacatgat ggtgaagtgt cagattacgc  196620
acccgacttt gacatttctg ctatgccagt tattgacctc gatccttcag tgactagtaa  196680
ctcagatggt gttgtggaca tcgatgctat tgttgcgatg ggtctgagga agactcgcgg  196740
cgattcgtct gacgaagact aaacaaacca gcatcaacca attccaaagt aaaagccgta  196800
gcacagaact ttttggtttc agtgaaagga tttaccttat ccgcaatcat agcctcggcg  196860
gcttcttcca ttgtatctga acgaagtatg gcaggtgagt atacggtttt acccggcata  196920
cgacccctct cttcacttag ttctttgaca tggatatcaa tccacttgtg gaagtcgtaa  196980
ataaagacag cgtcgaagtt tgttttaata aactcgggtg tcaccttatc tataggttga  197040
aagataaggt caaccgatag cgtgcaacta ctatagaggt cttttagatt ctctaggtag  197100
attgcacgct cgtctttatt taacttgtat ggccaagtat tcacagttag tcttggtctt  197160
tctaagggtg tccccaccaa tgtcgctgca aacttagccc ctaactcaga gactaggcta  197220
aatagaaggt tggtcggccc agactgtttt aaagtctcga cgcttctatc atcccacatc  197280
ttctgccact cttcatcagt gattccgagc ttttttaaacc acacattagt aacgcgtgta  197340
cgatattctt tcatatcgat ttttgtgtat aagtgtggtc ggtgttctaa aattaaaccc  197400
agtcgagtgt cagctaaaga atcgatatcg actagaactc gttgctgcgt tatcattcca  197460
agttgttccc taagtgcata gcccgataga tagtcccaag agttgtgaca gctttagatt  197520
tcgttgcagc caacatactt tgctctaaac tacctttacc cgtcgctttg atttcagcat  197580
agatagcacg aagtagtttc aagttaccac cacgaccttg gataaattct ttagccgctg  197640
cctcgtaccc ctcagccatt aacaagtaag cttctgggaa agacattgag cttgctttcg  197700
aaacaccact acccgttacc tggtgtgtgt attggtcaac acggcggttg tgttctggta  197760
tacttgcctt cttaataatc gactgtgttt gtggacgcgt gattagtggc agaaccatat  197820
gctcgtgctc agtcaaaata gtcatacctg tcttagagtt agttaaccaa attctttctg  197880
agacaggtag acccatttct tttaatacat ctctggcgtg gtctgttgga acttggactg  197940
gtccaccaac aggtgcgtag aatgggatac cgtcgcccga aataatctca ttgagttttt  198000
catcagacat tgtttaaat aattgtctgt agagattacc gttagtttg ctggtatcgt    198060 agcggtccat ccactttaag atgtatgcct caatcttagc gcgtttaccc ggcttgaatt   198120
taaactcggc catgtgatta ttcctttata cgtttatgta ctgtaacata agaatcgagg  198180
atatccttgg cccattgttt gagtgagtcg atgtggtcaa cgcgttgcaa gcacttagtg  198240
gctttatcaa cagcgctatc aaaatccata gtagacattg tgcttggttt gttactacgg  198300
gtgatgcgag caaatagctt aatgcaaatc tcgccagtga ttttccgtac ttcggcgggt  198360
ttaggggatg aagacatccc ctttagtttg ttagccaaac gaacttcgcc gatatcacaa  198420
agaaaatcat acaattttcc aagtgcatca ttcatcttct tttttatcct tcttaacttt  198480
```

```
attgcgtgtt aggaacttag gatgccattt gtcagcagcc atttccaaca atgagtaaat    198540
tgttaaagtg tgaacaccaa agtgttttttg gtcttcttcg aacatccacc aatccacagt    198600
cttttcgtag atttcatccc agtcgtaacc gaggtctacg atgcgctgat agatatcttt    198660
agcttctagt cgcatatccg cagggatgcg aacagagttg tttaggtagt aagccaactg    198720
tgcagtaatg gtcatagcac gagcaagctt cttattctct tcgacatcgt tacgaattgt    198780
tgtacgttcg aatttaacat ccggtaggag gtcgagtgag tagaaacgat taccaatctt    198840
ctcaaaaccg tatgggtttt tcttaagcac ttcttttaaa tagtgccatt ctgaaagacc    198900
ttgtagaaga ccttcttctt gagagaagat aaggtcgatt ttaacaccag tcggaccaga    198960
cttagcacgc cattgtgtgt agcgtacaat cttaaggtca ttgtaagaca tcaaattacc    199020
acgtgcatct tgtttaggat acattggttc ttcgatacca gtgtctgggt tgtaactacc    199080
cggttgcttc aattcacctg atgatgaggc aatcatcagt gagttggtca tgtacgtcac    199140
ttgtttaccc ggaacgttgg caagcttaat cttaccttc atcgtatcga gtttacgctc    199200
agcattgtac ttgtccattt ggatatcatc agtcaactgt actgtaaagg caatggtgta    199260
ttcaccttgt ccagcaagac gtgcccaacg acccatcatt tgagctttgt ggttgttgtc    199320
tgtcatcgca atgtggtttg actcagattc accaacagaa gccttcatgg tctctttatc    199380
attagactta gaatgccatt cagataacga gtcaagactg tagtgccacg gtggtaacac    199440
tttctcttgt tcaccataga tgttaaagaa aggcgttgtc ttgaacccct tcttagcttt    199500
aaattgcttt tcgcgttctg gcgctttgtc acgcatccac gactcgtacc agtcagtacc    199560
gttaagtttc gaaatgttag acattgaaaa cttagggtct ttatcactag caggatttag    199620
tatttttgcg atagggacat ctagtgggtc gatatcccag aagttgtttc ggaatacgtt    199680
acaaatgaca gtattctgac gttgtgcctc tgctgattct tctgtatcgt agaaggaaga    199740
ccattctaaa cgatagcgat aaaacataca gaaagataaa tactgcatct taaatgtttt    199800
aaatacgtta ccacggccac caaagcccat gatacgagac atgccaccgt tcaagtaggt    199860
ggcaccgtct ttaccacgtt caaagtttcc aagcgcgata tcgaaaagtg gtagtacgtt    199920
ataacgaacg cgcattaatg tgccgttctc tacatcagtt ggggcagcca ttattactcc    199980
tgaatttgta aaggttgttg ctcttcagat gaaaagagtt ttaggtaaaa aatatatgt    200040 ctgtttctta tgaccgctta attacttatt ctgttcaagg attcttgtta tgaaaaccc    200100 attcctaccc atccgtcagc gactagttag ttatttaaac cgcggtacaa tcgtacctag    200160
tttaaatgat gtacaacaca acagtggtga gttgattgtt gatttgtcat cagaagacca    200220
agtccgtcta ccagacaaaa gccaccttat ggggttagcg tcatgggttg aacgcgaagg    200280
tttccttttc ttcgatgctt tgcaaatccc acatccggca ggctttaaag ctggcgaaca    200340
aaaactgtac ccgtatgtgc agtcactgaa cacgatgttc aactcattag tgttggtcga    200400
agacatgatt gattacgcca cacagacagt gtccaatctc ttgaatgacc ctgagaagct    200460
tgcatccaaa tccatcaaga gtgatatcaa ttcgttacac aatactttg accataaaag    200520 tatcacgatg ctggcggata tgtacaaacc attcttcgat aactctaagc agtctgaccg    200580
tgcaagtttt gctgagctgt ttaataacgc tcaagaactt acccgcaccg caaatgaatt    200640
agcgtatttg aatgatcgta tcggtggtgt cgattacgct aagaagatca atgctaagct    200700
agctcgtttg agtgagctat gtatcgagtt caatgaagaa tacccagatc acccagttcg    200760
ctctattctt gtcacacacc tagtatctcc tttagcatac tgggctgagt ttttggcggc    200820
gtatctttac aacgtcaacg tgttgaatgt ttgtttctct gagatagaag agaaactagc    200880
```

```
taagatgaaa aaagaaaaat aaaaaaagag gtactcgttt gagtacctct agttcttttt    200940
tttacccggc ttacgctact ttaacgctga ccgcttgtgg acctttctta ccgttctcga    201000
cgccaaagct gaccttctga ccttctttca aagttttgaa gccatcagtt tcgatagcag    201060
agaagtgaac gaacacatct ttaccattgt cttctggtgt gataaaacca aaacctttag    201120
cttcgttggc ttcagctgct gaagagcaaa gtcttgttgc agaggaaatt aactctaaca    201180
caattaagat taaagatttg tccgattctg taaatgaaga tgccgttcaa accaaagacg    201240
ccatcaaaca tcaattagga aatatcaagg aacaaaacaa agtacttgat aagttcaagg    201300
tatagagcac tcttgtggag gggttatgaa catcagtctc attttagcaa catcgagaaa    201360
tcaagtcatt ggtattgggg acaaactacc ttggaaacta ccagttgaca tggcgtggtt    201420
taagaagaat accatgggga agatggtcgt tcaaggaaga aagaccttcg acagtatcgg    201480
cagtccatta cctggacgtg aaaatgtcat cctcactagg gataaaaact tctcttaccc    201540
aatggttaca atatgccgaa ctttcgaagc agcgatgtca ttgatagaaa cacatcaagt    201600
tatcaacccg gatgcagaag tgatgattat tggcggtgct gagatatact ctctcttcga    201660
gcctgtggcg aacaaaatct acatgactag tgtcgatatc gatatacacg ataaagacgc    201720
tgtatttgcc cctgtcttcg atccagagcc atgggagatg gtttacgaag aagcatgggt    201780
gcaggataaa aagaatcctc actctggaac gttttatatc tttgaacgta ataagataa    201840 cagtcgttgg cttcggtcga cgactgtact ttattttta ccactttgaa ttttattata    201900
gaggtggtga cgaaatgaaa gaatacgtta tcttagaatt agaactatat cgattcgtcg    201960
gtatggaatt aacggggata gaaagattta aactaacccc gagaaaggat aaaatggtta    202020
tccttggtcg taacggcagt ggtaaaagcc gtttactatc tgccttatta gggcactctt    202080
taaataaact tgacttgatg gaaggtggct tttggaaaca aagggcttta atcgatgggg    202140
tcgagtatac gtttaaacag tacagacacg gcaaaggctt acggtgtgat atttactgcg    202200
gagacaaaga aatattgtcc ggggctaacc caactgtcta caatgacaag ataactgcat    202260
tagtcggata cgacaagaaa acacgtgagc ttttaggtgg gctagttaag ctgacaagaa    202320
tgtcaacacc tgaacggaag cattggttta gtcagttagc aaccagtgac ctatcaacgg    202380
cgcttaagta ttacaagtac ctaaaggaaa ctctacgtga cacaatcggt ggtattaagg    202440
taacagaaag atacgtagct gaccttaaac cgatggtcat ggagaccgaa gaagaataca    202500
aagacttatg cacgcgtgtc ggcgaactag aaaccgatta tcacattgtt gcagatcaat    202560
gggtcaagta ttcaaaggta gaatatgtta atgtagatga gttattggct gaggcggata    202620
aatgggctac taaatcacgc gggattaaca tcaatggttt agaaagctac gattactata    202680
ctcagttgat ttctgagctc agtgctgaac tgaagcaact agagaccaat attttaccgc    202740
ggtacaaaaa agaaatcaat gaagtcgata agcaattaag tgaacttcgt tactactcca    202800
atgatacaac taagttaaaa cttctgatag atagtcaaga agataagttg aaaaggcttg    202860
tatttgaaga aaactatttc gacggtgcct tggacgagta cagtcttagt gttctcgaat    202920
cactattaga gaaactcgac acttacgaaa aagaactcaa cgatttagtt attgagcaaa    202980
tctccacaga taaactcaaa gtattgaatg agaaacttga cgctaaaaaa cttgagcatc    203040
aaaacaaact catcgagatg aacaaagctt cagcattcat ccatgacatg acagctatga    203100
ttagtaagca tagtcatgcc aacgaagaag aatgtccgga gtgtaatcat cgtttcaaac    203160
cgggatttaa agcatttgat ttagaggcat caaaacgaca agttaaaaat gcctcaatta    203220
```

```
aagaagaagc gctaaaaggg gaaatcgcac agatatgttc agagattgag tttctaacca 203280
atgctgtaca aagaaccatg cgtttaatgg actacgtaca acgtctatat gctgttaatg 203340
gtttggctcc agtcatcggt gcaatgttgg aagatggtgg gatcaatgcc aacacgacgc 203400
cgtataagtg gtttaaagaa tatcgggtgg ggttaaataa aaccatccgt aaactccgta 203460
tagaagcaga gttagataaa ctgaataaag aatacgctgt agcgatggct gtatcaggaa 203520
aggatgttgg gttacttgaa tccagattgg aagagatgac taacaacgtt actaagacac 203580
agttgaaaat cgataagtta cgttctgaaa taactttggt gcaaaaccgt caacgtgaag 203640
cgcaggatgc tgagtacgct gagaccaaac ttgattcact tttaaagata atcgagaatt 203700
cgtctgagaa gcaagcaagt tataactttg ccaagtattt ggaaaaagaa aaagacgagt 203760
tatggtcttt actcagcact tcgaagagca gattgcagac attcgaagag acgagaaaag 203820
aattaaaata taacgaggag aaactagctc aactcaaaga aagaaaaacg gttaacgacg 203880
aactggttaa agcaatgtct ccaacagatg ggctattagc cgagtacttg tataagagca 203940
tctttgctat agccgattcg atgagtttgt tcatcgaaaa catcttcgag tacccgttag 204000
tagtcaaacc ttgtgatgta gacgaaggtg aacttgacta ccaattcccg atggtcgaag 204060
gtgagtctgg tgttacgagg gcagatatta gtcttggctc cgacgcgcaa caggagatta 204120
taaacgctac ctttgtgatg tcggcgatga aagctctgca cttacaacat catcctgtac 204180
tattcgatga acctggtcga gctcttgacc ctgggcataa agttagatac gcagactttt 204240
tatctgagta ttttaacagc gacatggtta gtcaggcctt tgtggtttca cataactcgg 204300
aaatatacac ccgcttcggt aatgttgatt tcatcgttat caatcctgat ggtgtagacc 204360
tcccagacac ttacaacgaa tgtgtggaga tacaatatgg ataatgttat cgagcaccca 204420
tcatcaaatc tacaacatct tattattgtt gctcttgggc aagagattaa taagatgtta 204480
gaagatacaa actaccccta ccaaaaagta aagaacgtgg ataacgttct cgttttttaac 204540 aaagaaggaa atgaacaatg cgtgaacaaa ttgtagaacg tctgaataaa gtatttgctg 204600
atctgaacat cgacctcaca ggtgtaacag atgagagcga cctaagtaat gatttgggtc 204660
tagactccct cgacaacgtg gagttaatca tgggtgtcga agaagagttt ggtatcgaaa 204720
tccctgacga agatagtgtg aatatcacta cttacggtca agttgtgaag tacatcgaag 204780
acaacttgta attcttctct gagggtccag gttttggacc ctcgtctttta tttaaaatga 204840 gcttatggaa gttataaaag tcgctaaatc gagaataaac tcgccatccg ttggtttccc 204900
agtggagata accgtggttg aaattatacc cgaacccacc cctgaggaaa agaagggtat 204960
gcataaggtc ggtaaacatt ataagaagtg gtggaataag gacaggtatt aatgtttggt 205020 tttttttaaag ttatcttaaa acgattgtat tgttttttata aacacaaagg tgatcatcac 205080
tggtcttatg cctaccaagt aaggcaatgg agaaaggggc gtaaacgagg aaagagcacc 205140
catcacagat atgaatataa gttaacatgt gagtgttgtg gaaaagaatc caagtggtta 205200
cgttggaaaa cctttgacga tgtcttttac aaaagcagac atcgtgctct tggaatctac 205260
gaggaaagtt aatttagtta tatgttatat tgatggtgct ttatgctaaa tgtagttgac 205320
gaggagacca tccacggtga tttgttcaaa gctaaagaag atgctttagt agtgacagtt 205380
aatattgtcg gtgccatggg taaagggata gcattgtcct gcaaacaaaa atatccaaca 205440
gtgtataaaa aatacaaaaa ggattgtgat gctggtttgt ttgattacaa caaaatcggt 205500
ttggtaaggg aggataaagc aataatactc ttcccaacca agaaggagtt ttggagggct 205560
gctgacccta aacacatcat ctatctttgt gggagattac cattagcttg caaggcgtgg 205620
```

```
ggtattactt ctatagccat accgccgcta ggtatggtta atgggtggtt aaaagaaaag    205680
gaaatagtag gtatagttaa tgccctaaag gagggttttg aagacacaga aataaaagca    205740
actttatact tacctagtaa tcttttagaa ttactatgag tattttcaca ttaatcaaga    205800
agttacaatt gaggaatctt aaaatgaata tcgacgctat gaagaaagca gctaagtttg    205860
ggttggactt tggaattaaa atcttcggtc tactcgttct ttttctaatc actatgtttc    205920
aggctaatgc ctatgccaac actaattgga ataaagtgaa agatgacatt agtctagcgg    205980
cttatttaac tgactttcca gctgaagagt tagcagctgt ggcttttgtg gagtcaagtt    206040
tcagagtgaa ggcgaaatcg cctggtagta gcgcaagtgg cttaacgcaa atcacctcgg    206100
ctacttggga ttacctattg gaaaagtacg ggccggattt caatattcga aagggcactt    206160
ccccatttga cccaagggca aactccatta tggcagcaat gtacctgact gagataaagg    206220
acattatgtc ataccgactt aagcgagaaa cgaccttaat agaaacctac cttgggtata    206280
aattctcacc ttaccgcgca gtcagaatgt tacaatccaa tccgagtaca ccacttttgg    206340 aatttttaccc tgaagccgcc gaaagaaacg aagcagtcta ctaccacaaa gatggtagct    206400
taaagacaat cgccgacgtt aagttaatgt ttaagaagcg tctaggtttt gctaagaaaa    206460
catacgggac ctcagctatc gctggtgtta ccgaactgaa gcattttgaa ttcatgccat    206520
ttcaatacgc catggaaaag ggtgtggtgg attgcatacc tgaaggagag atggatgagg    206580
aaactttgtt tagcaaaatt aaacgtaagg ctctggcaac tctaagtaat tccgtggaac    206640
ctattaatga tttaattgct tataaccta agccaacctc gggtcgtgaa tacaacgggg    206700
ttttaatttg atgaaattgt accgtgcaag aatacagcat tggagggaag tggataagat    206760
ggggttgcgt cttgttgacg tcacagtgaa gaccggacta aaacaatttg caccgacgtg    206820
ggatgctttg aaacaattca aagattctaa agaactgtc gacgacattg ccgtgtacga    206880
tgtgctctat atggagaaga tgaatgagct ttggcgtgta gcaccagaag aattcgacaa    206940
attaactaag gttgatactc tggtattagg ttgttattgt gatcaagaaa accacgatta    207000
ctgtcacgta gattcgttaa tttactgtat agaaaaaata tgtaaggata aaagatacc    207060 ctaccaatat atgggggtca ttaaaaaata aaagagtacc ctcgtaatga gggtactttc    207120
tttttttatt tatgggtttt ggcttctttc tttctgaata atgactgcta ccaaagcttc    207180
attttgctgt tgtagtttgt ctatttgctc ttcaagattt ttgattctaa catccttcgg    207240
gatgtagttg gtaatagcca gtcggcgcgc acgctcaagg tcagcttgtt gctgtgccgt    207300
caaatcattt tcaaataaat gatttgcttc gtagacatta gcatcgacac ctagtgttgc    207360
tttggcatgg tcagcgagct cggttttttaa agtactgata tcagtaccta atggcaataa    207420
cccaatctct aaagcgatga tttttatttc ataccctctg ttcttaaatc ccggatagtt    207480
aaggatgtaa gttgatggta cgtaaacagg taattcaccg cccgctttaa gagttacaat    207540
cgcagcctct aattcaacat cgcgtttgta ctcgtcttcc gtcaactgca acggttcgta    207600
gtattcagaa aagacctttt tacctagacg cgtcaattca tcaaagctac gaacctcttc    207660
gcaaacataa accaaacccg cttctaattt gaaaggttcg agtaactcga atagcccgt    207720 agcattaaca ggtggcaata gactcctgac tgtcattcaa ttatccttca atgttctcct    207780
gttgagtcgg gtgcatcatc actcggaatt caacgtttaa atattcgaac gcataaaact    207840
tgattttgtt gatttcaaca atagagaagt tgtgatccac tacgttgaaa gaatacaagc    207900
cttctgcgta acccatgcat tcaattagtt ttcgtaggaa ggtcgcagtc tctagacgca    207960
```

```
gccgtgaagt ctcatttgac ttaggtggca tgattgggta atctgggaat aattcgaaca   208020 gagtctttt  gccatctggg ttatcagcac ccgccactgc tgccgaagaa agcgacttgt   208080
agtggatagg tacaaaggcc aaataacgac catcgcgatt atttattcca tcagaaccta   208140
gctcttccac ggtttcgaag aaccagttgc tcttctcgac aaattttca  tatgggacta   208200 gtggtgaata agaagcacct tcgttagttt cattcagccc agttgacaat tcccaaaatg   208260
gtaggaaggt aaactcagtt gatgtgaaaa tttcagggaa tactttgatc caatcaccgc   208320
gaccataagc gctattggcc aagatataat cttgtaaagc acgtttaata cgtgttgggt   208380
tagcgcccgc agcaccatac acaatgacta accatgtcgt tgggtgtgta ctttctggat   208440
cttcacggtc atgccacgtg taggtgtaag aaatcaattg cgtatatgga acattgtccg   208500
ctagcaactt tacttttcg  tggtgttttg gaatggtgaa atcagctagc gcctctaaca   208560
cggaaggttt agtttgttgg aacacatcga tgttatcgat agggcttaca ggtacaatcg   208620
taaacccagt gtattgatat tcgaaagtgt cattggcaaa ccaaactgta attttgttct   208680
cttcggagtt ttcaagtatg aaactaatcc aagtagggaa ccaactaccg cgctcattaa   208740
ccattgtgcc aactgtcaaa tttcgaatct ttgcagagaa ctcgtttgtg attaatccac   208800
gagcagcttc ctctgactca ttaaggctat cgcctattgc agattcaaaa ataaattgac   208860
aaaccaagct gatagtgtta atgtgttcga taggcggttc tacgtccaac tcatcacgag   208920
ttgaatcaaa caccactaat tcagtatccg tagacttacc acggtagtag cgtttatcct   208980
tagtataact gattgactct tgagacaatt caccaacact agagataacg ccagcttggt   209040
tgttagaaaa gctactgatt ttacaaaaac catttaatga aaacataata aaaacactcc   209100
aagtgttgat aaaactgtga ggttaaataa tgtcagaaaa gctaaaggct ctattcacca   209160
cgattaacga gggttacacc tggttaacag aaggtagcac aaatggtgca aagacactat   209220
ctaaaattct atttgcattt accatcgtcc ttggtcttgt tacatggact attgcagaac   209280
gttactttgt cctactcgac gatgtcaaag taattgtcaa aacaaataat gacaagcaaa   209340
tagaaatcga caaattgaaa ttcgaaagag atcaatttgc tatcaaggcg gaaggcttaa   209400
gtcaaacatt aaacgattta atttccaagc accctactat tatagagaag gaggaagtta   209460
aagagccgca aaaagtgacc gttcctacat atgaagaagc gaaggagacg gctaagccga   209520
ccacaaagag agatgatatg caacggaggc gtcgtttaat agagataatt aatggctaag   209580
ggtatttatg ttgttaaaga aaattgtggc aatagtcact gcttttggag tgggcgggtg   209640
tagcgcacta ctccatccac ctccgtctga tgtggggaag cattctccta caccatctac   209700
ttcggttgaa caaccgatac gcactgcata caaaccaccg ttgagtgccg tgactttacc   209760
accagatatt gcgacatacc agaacatcgg agatgacgtg attgttctta agaactacgc   209820
taccgatctt aactggtaca tgttctatct attcagctac acacatgtga ttaaccaatt   209880
cgctatacag cgaggttggg agccacctaa aacggcaccg ctgtgtaaaa catttgcttg   209940
gccaaagcaa atggatgtcc ccttcttcga atacaaagag ggtatgtcgc tggaggactt   210000
ggatgttgag ttgactttgt ttatatctga agcgaaagct cgttaccaag agcaacagaa   210060
actatttgac gaggcggaga tgtggcagcg tcgtttgtgc atgtattaat aaccttcctt   210120
gtttgacaga gtgtaattac ttcggtagtt acctctgtct ttttttcttt ttttactgtg   210180
tcggtctttt atctgacaga tttgaaaatg atttcttgga gaacacgatg tcagaactat   210240
ttaacaagcc cactatccca tccacagtta cggggattga tttagaaaca aagggtacaa   210300
agctcaacgc tttcattctt gccctgggta gtgtcacatt cgatgtgaaa aaatatcagt   210360
```

```
tagtcgagtg ttctcgtttg gaactggacc cagaagacaa agaagccaaa gagttgttta   210420
cggaagatgc agatacccct cgttggtggg aagagtttga taaacatccg tggtcacctt   210480
ctgagttagc aaaaaagatt gcctggggtg ggactactcc acatcgcgaa ggtatcactt   210540
tctttgcaaa gatactggaa caactcaata aagaaatag tatctttact gcacgtggtc    210600
cagagttcga catgcgcgtt ctcgaggtga gttgtgtgcg ttacggcatc aatcacaatc   210660
tacgttttag taactttgat tcagaccgca cagcggaacg tatgttaaaa gctcttggtt   210720
gttctccgat tagtgaaaat gaactagaga agtacattcg ttgtacggat gctaatggtc   210780
cgctacactc agcacactac gatgcagcca aagaaggcta tcgtacaatg cgagcatatt   210840
ggttagtggc tatagctggt gcctatggac tagacacatt gaaagaagcg gttgcacgtt   210900
tggatgaagg gacttttgac cctgaggtct atggggagat ttgttttgag taaaatcaat   210960
tttgaaactg ctgtcgttta taccgacggt agttctatcg atggaaagca tcgacacgat   211020
actggcagcg gtagcggtat tcacggatac tgttacgata tacctccaac agaacaagcc   211080
aaactaatct tcgaaagaaa tggtgagaag tctttggagt gtcgcggtgt tttaactgaa   211140
gaagttccag aggcttttgg tgatatcgag tatcttcaaa taccaaaaaa tcaatattca   211200
caaaaaattg tttcggtaga agaactcgat ttaactcgcg tagaatgctc acacccaatc   211260
aaaggtggaa cgtcacaagt aggtgagttg ctcgcattca tcgacttgtt tgaaacggca   211320
ccattctctg ccaaagttta ccacatccac accgactcaa gttacctgaa agatggttac   211380
acccaatgga tggataactg gaaacgaaaa ggttgggtga atagttctgg ggctgttaag   211440
aacaaagaac tttggattcg tatcgatgcg attaaacaac gtgagagcaa aggcgagttt   211500
aaaataaact ggcataaaat taagggcac agtgatcgtt ttggaaatga gtctgcggac    211560
atgttggcag gcaaagcttc tggaaaagct atcaacatgg tcttaaacga tgaacatcgt   211620
gatgcgtata tccccgaatg ggatatcgga ccttacgtag ttggtgacga tactcttatt   211680
tacgaaacta agaagagaa acgtaacaaa gcgaaagaag ctaaaagcga caaaaagaat    211740
gcatcaaagt cagacaagcc aaaaaaggta aagacgaag agaaattcat ccccaaactc    211800
ttgcgtctga agtatcatta catgatgtcg aatggcgaag aaacagtcgt gaatgtcggg   211860
ggagaagagc tgtaccgtta cttggtggg gatcatgcta agatgaaaga cgatcgtctt     211920
cttctcggca agcccaacc tgacaacatg caggttctga cttttgtgaa agaccctgtg    211980
cgtatcttct ccgatatagc gacagtcgta tctgaccata tgtggaaaga tgtaccgatg   212040
atgtatcgtt ctgacctcgt tcttttgatg aatggtactt tcatgaatca agagaaattc   212100
aatcgacgtt tgctagacga ctacgatttc tcaaccttcc cgtacaatcg ttcattcaac   212160
gaattactat tcgatgagaa aaactgggta tcggttgctt gtaggccacc gggtctaagt   212220
tatcgtgcaa tggatgtggc tgactctatc acgaactggt atgtggagtt tgttgataat   212280
gatcgtaaga gtacagacac tgtatcggta ctagacatca cttctaagct ttacgatggc   212340
aagaagatga cagattggta tcgtgtcatc gacaagagcg ttcgtgttca aatgcctgtt   212400
ccaggcgacg aagagcgtaa agtggacttg atcctcacac ggaatatctc cttccctgac   212460
cgtaaccatt ttaacaaatt ggttaaagac gacccaaggg tttacattgt tgctcgtaag   212520
ttatcggata atggttttccg ttacttcgtt gttctggaaa ctaaggtcgg taatcaggta   212580
gtgtgttctt accatagttc tcttcgaatc cacgaataaa gagttatatg ttatcgtagt   212640
gatacaataa cagagggttc tttaaatggc tgataaatta cgtgttaaaa taccacgtat   212700
```

```
aatggttgat gctattggta agataaccga agatgcgtac tttaaattag actatcaaat    212760
gacacttgat agtctaaaaa tacaccctga ttcagttgac cgtgatatgc tgagagatga    212820
cttatctgaa atcatgcata acgtcatcgg aaacatgtta gctatcttgt ttgaggattt    212880
ggctctcctc atgctagaaa cgcaaacaga gtatggtaaa aggttcatcg attggaaaga    212940
tttaccaacg gctaataaat taaatcaact aacaatagat gaggatggtg gatatctaga    213000
cgccaaactc ggggaggtcg aagctgaatc tgccgacacc tctggcgaat atttaacaca    213060
tcattctaac atcctgggga caatgggtca cacttgccgt gaaatctatt atagttcttt    213120
ttattccaaa gaagacgata tggaatttcg taaaggggtt gctgatttag gcaatcacct    213180
tttagaccac ggtgccgtgt ctttcgacta cgattcgttg attaccgaaa tcattgatag    213240
agagataaat agtttccgtt cattagaatt gagaacttac gaagttgatg attttacact    213300
ggtatcggaa ttcaccccta aaattaacgg tgggtggatt gataatgtca atgataccga    213360
agtcgaatgg gggttgatag aacgtgagct agatgcagtt gcaagaactt ctggtgatat    213420
gtttgttctt gtcaatcatc acgatatcta cattggtgac catgtagata aaataaacga    213480
cttacctgtc gttgagtcta tcggtataat ggaggctaac taatggctgt aatccgaaat    213540
aataaactta ttaagggtga agctagagat atcctaatta agttaatcga agactgcgtt    213600
cttgaaatta tcgaggtgca tccgcgcatc gatgaagctg acctacaaga cactgtaggt    213660
cgggtaatat gggagctcat ctgggcttct gttgatggaa gagcagtgga ccgaaagtac    213720
atagagcgtc aggcaatgcc taagcgttcc agtgcgattt ggccgcttgt tctaaactcc    213780
atagaaatca ctgcaagaga gtttgtaaat catccagacg tccaggctga cctagatgac    213840
tactacgaag cgatggagca gattaaagat gactatggta tgtaattaaa agtaatattg    213900
gaaagagaaa taaattatgg caaatgtaat taaaggcaca gtgaagtggt tcaacgaagc    213960
taaaggtttt                                                          213970
```

VIBRIO ANGUILLARUM BACTERIOPHAGE VIB-ANP-1 AND USE THEREOF FOR INHIBITING PROLIFERATION OF VIBRIO ANGUILLARUM BACTERIA

CROSS-REFERENCE TO RELATED APPLICATIONS

This application is a U.S. National Phase Application of International Application No. PCT/KR2017/009076, filed Aug. 21, 2017, which claims priority to Korean Application No. 10-2016-0112908, filed Sep. 2, 2016, each of which are hereby incorporated by reference in their entirety.

REFERENCE TO SEQUENCE LISTING

The Sequence Listing submitted Mar. 1, 2019 as a text file named "08162_0049U1_Sequence_Listing.txt," created on Feb. 25, 2019, and having a size of 271,511 bytes is hereby incorporated by reference pursuant to 37 C.F.R. § 1.52(e)(5).

TECHNICAL FIELD

The present invention relates to a bacteriophage isolated from nature, which infects *Vibrio anguillarum* to thus kill *Vibrio anguillarum*, and a method for preventing and treating a *Vibrio anguillarum* infection using a composition including the same as an active ingredient. More particularly, the present invention relates to a Siphoviridae bacteriophage Vib-ANP-1 (Accession number: KCTC 13075BP) isolated from nature, which has the ability to specifically kill *Vibrio anguillarum* and which includes a genome expressed by SEQ. ID. NO: 1, and a method for preventing a *Vibrio anguillarum* infection and a treatment method after the *Vibrio anguillarum* infection using a composition including the bacteriophage as an active ingredient.

BACKGROUND ART

*Vibrio anguillarum*, belonging to the genus *Vibrio*, is a gram-negative bacillus, and is known as a representative fish pathogenic bacterium that causes vibriosis accompanied by hemorrhagic septicemia in olive flounder, salmonidae, eels, and various sea fishes. Although 23 serotypes of *Vibrio anguillarum* have been found to date, most *Vibrio anguillarum* pathogenic strains causing fish vibriosis are known to be of the O1 and O2 antigen types, which are a somatic antigen (O antigen).

*Vibrio anguillarum* cause serious economic damage in the aquaculture industry by causing vibriosis in various fishes. In particular, the outbreak of vibriosis in fish caused by a *Vibrio anguillarum* infection occurs frequently, resulting in great economic damage. Therefore, there is an urgent need to develop a method that is applicable for preventing and further treating a *Vibrio anguillarum* infection.

Antibiotics are extensively used for the inhibition and treatment of infections caused by *Vibrio anguillarum*. Recently, the effectiveness of antibiotics has been continuously decreasing due to the increase of antibiotic-resistant bacteria, and the development of effective methods other than antibiotics is required due to the increased number of regulations on the use of antibiotics in cultured fish. Especially, there is a great demand for environmentally friendly methods.

Recently, the use of bacteriophages as a countermeasure against bacterial diseases has attracted considerable attention. In particular, interest in bacteriophages is higher than ever due to the preference of environmentally friendly methods. Bacteriophages are very small microorganisms infecting bacteria and are usually simply called "phages". Once a bacteriophage infects bacteria, the bacteriophage is proliferated in the inside of the bacterial cell. After proliferation, the progeny of the bacteriophage destroys the bacterial cell wall and escapes from bacteria as the host, suggesting that the bacteriophage has the ability to kill bacteria.

The manner in which the bacteriophage infects bacteria is characterized by very high specificity thereof, so that the number of types of bacteriophages infecting a specific bacterium is limited. That is, a certain bacteriophage can infect only a specific bacterium, suggesting that a certain bacteriophage can kill only a specific bacterium and cannot harm other bacteria. Due to this bacteria specificity of bacteriophages, the bacteriophage confers antibacterial effects only upon target bacteria and does not affect commensal bacteria in the environment or in the intestines of fish. Conventional antibiotics, which have been widely used for bacterial treatment, influence many kinds of bacteria coincidentally. This causes problems such as environmental pollution or the disturbance of normal flora in animals. On the other hand, the use of bacteriophages does not disturb normal flora in animals, because the target bacterium is killed selectively. Hence, the bacteriophage may be utilized safely, which thus greatly lessens the probability of adverse actions in use compared to any other antibiotics.

Bacteriophages were first discovered by the English bacteriologist Twort in 1915 when he noticed that *Micrococcus* colonies melted and became transparent by something unknown. In 1917, the French bacteriologist d'Herelle discovered that *Shigella dysenteriae* in the filtrate of dysentery patient feces was melted by something, and further studied this phenomenon. As a result, he identified bacteriophages independently, and named them bacteriophages, which means "to eat bacteria". Since then, bacteriophages acting against such pathogenic bacteria as *Shigella, Salmonella Typhi*, and *Vibrio cholerae* have been continuously identified.

Owing to the unique ability of bacteriophages to kill bacteria, bacteriophages have attracted anticipation as an effective countermeasure against bacterial infection since their discovery, and there has been a lot of research related thereto. However, since penicillin was discovered by Fleming, studies on bacteriophages have continued only in some Eastern European countries and the former Soviet Union because the spread of antibiotics was generalized. Since 2000, the limitations of conventional antibiotics have appeared due to the increase in antibiotic-resistant bacteria, and the possibility of developing bacteriophages as a substitute for conventional antibiotics has been highlighted, so that bacteriophages are again attracting attention as antibacterial agents. In particular, recently, government regulations for the use of antibiotics have become more stringent around the world, and thus interest in bacteriophages is increasing and industrial applications therefor are increasingly arising.

As demonstrated above, bacteriophages tend to be highly specific for bacteria. Because of this specificity, bacteriophages frequently exhibit an antibacterial effect only for certain strains of bacteria, even though the bacteria belong to the same species. In addition, the different bacteriophages exhibit different antibacterial strengths against the same bacteria strain. Therefore, it is necessary to collect many kinds of bacteriophages that are useful to control specific bacteria efficiently. Hence, in order to develop the effective bacteriophage utilization method in response to *Vibrio anguillarum*, many kinds of bacteriophages that exhibit antibacterial action against *Vibrio anguillarum* must be acquired. Furthermore, the resulting bacteriophages need to be screened as to whether or not they are superior to others from the aspect of antibacterial strength and spectrum.

DISCLOSURE

Technical Problem

Therefore, the present inventors endeavored to develop a composition applicable for the prevention or treatment of a *Vibrio anguillarum* infection using a bacteriophage that is isolated from nature and can selectively kill *Vibrio anguillarum*, and further to establish a method for preventing or treating a *Vibrio anguillarum* infection using the composition. As a result, the present inventors isolated a bacteriophage suitable for this purpose from nature and secured the gene sequence of the genome that distinguishes the isolated bacteriophage from other bacteriophages. Then, the present inventors developed a composition including the bacteriophage as an active ingredient, and identified that this composition could be efficiently used to prevent and treat a *Vibrio anguillarum* infection, leading to the completion of the present invention.

Accordingly, it is an object of the present invention to provide a *Siphoviridae* bacteriophage Vib-ANP-1 (Accession number: KCTC 13075BP, deposited under the Budapest Treaty on the International Procedure at the Korean Collection for Type Cultures, Korea Research Institute of Bioscience and Biotechnology (KRIBB), 125 Gwahak-ro, Yuseong-gu, Daijeon 305-806, Republic of Korea; the deposit was made on Aug. 16, 2016) isolated from nature, which as the ability to specifically kill *Vibrio anguillarum* and which includes the genome expressed by SEQ. ID. NO: 1.

It is another object of the present invention to provide a composition applicable for preventing *Vibrio anguillarum* infection, which includes a bacteriophage Vib-ANP-1 infecting *Vibrio anguillarum* to thus kill *Vibrio anguillarum* as an active ingredient, and a method for preventing a *Vibrio anguillarum* infection using said composition.

It is another object of the present invention to provide a composition applicable for treating a *Vibrio anguillarum* infection, which includes a bacteriophage Vib-ANP-1 infecting *Vibrio anguillarum* to thus kill *Vibrio anguillarum* as an active ingredient, and a method for treating a *Vibrio anguillarum* infection using said composition.

It is another object of the present invention to provide a medicine bath agent (immersion agent) for preventing and treating a *Vibrio anguillarum* infection using said composition.

It is another object of the present invention to provide a feed additive effective upon farming by preventing and treating a *Vibrio anguillarum* infection using said composition.

Technical Solution

The present invention provides a Siphoviridae bacteriophage Vib-ANP-1 (Accession number: KCTC 13075BP) isolated from nature, which has the ability to specifically kill *Vibrio anguillarum* and which includes a genome expressed by SEQ. ID. NO: 1, and a method for preventing and treating *Vibrio anguillarum* infection using a composition including the same as an active ingredient.

The bacteriophage Vib-ANP-1 was isolated by the present inventors and then deposited at Korean Collection for Type Cultures, Korea Research Institute of Bioscience and Biotechnology on Aug. 16, 2016 (Accession number: KCTC 13075BP).

The present invention also provides a medicine bath agent and a feed additive applicable for the prevention or treatment of a *Vibrio anguillarum* infection, which include the bacteriophage Vib-ANP-1 as an active ingredient.

Since the bacteriophage Vib-ANP-1 included in the composition of the present invention kills *Vibrio anguillarum* efficiently, it is regarded effective in the prevention (prevention of infection) or treatment (treatment of infection) of diseases caused by *Vibrio anguillarum*. Therefore, the composition of the present invention can be utilized for the prevention and treatment of diseases caused by *Vibrio anguillarum*.

In this description, the term "prevention" or "prevent" indicates (i) to block a *Vibrio anguillarum* infection; and (ii) to inhibit the development of diseases caused by a *Vibrio anguillarum* infection.

In this description, the term "treatment" or "treat" indicates all actions that (i) suppress diseases caused by *Vibrio anguillarum*; and (ii) alleviate the pathological condition of the diseases caused by *Vibrio anguillarum*.

In this description, the term "isolate", "isolating", or "isolated" indicates actions which isolate bacteriophages from nature by applying diverse experimental techniques and which secure characteristics that can distinguish the target bacteriophage from others, and further includes the action of proliferating the target bacteriophage using bioengineering techniques so that the target bacteriophage is industrially applicable.

The pharmaceutically acceptable carrier included in the composition of the present invention is one that is generally used for the preparation of a pharmaceutical formulation, and examples thereof include lactose, dextrose, sucrose, sorbitol, mannitol, starch, acacia rubber, calcium phosphate, alginate, gelatin, calcium silicate, microcrystalline cellulose, polyvinyl pyrrolidone, cellulose, water, syrup, methylcellulose, methylhydroxybenzoate, propylhydroxybenzoate, talc, magnesium stearate, and mineral oil, but are not limited thereto. The composition of the present invention may additionally include lubricants, wetting agents, sweeteners, flavors, emulsifiers, suspending agents, and preservatives, in addition to the above ingredients.

In the composition of the present invention, the bacteriophage Vib-ANP-1 is included as an active ingredient. The bacteriophage Vib-ANP-1 is included at a concentration of $1 \times 10^1$ pfu/ml to $1 \times 10^{30}$ pfu/ml or $1 \times 10^1$ pfu/g to $1 \times 10^{30}$ pfu/g, and preferably at a concentration of $1 \times 10^4$ pfu/ml to $1 \times 10^{15}$ pfu/ml or $1 \times 10^4$ pfu/g to $1 \times 10^{15}$ pfu/g.

The composition of the present invention can be formulated according to a method that can be easily performed by those of ordinary skill in the art to which the present invention pertains using a pharmaceutically acceptable carrier and/or excipient in the form of a unit dose or in a multi-dose container. The formulation may be in the form of a solution, suspension, or emulsion in oil or a water-soluble medium, extract, powder, granule, tablet, or capsule. A dispersing agent or stabilizer may be additionally included.

The composition of the present invention may be prepared as a medicine bath agent and a feed additive according to the purpose of use, without limitation thereto.

For this purpose, bacteriophages that confer antibacterial activity against other bacterial species may be further included in the composition of the present invention in order to improve the effectiveness thereof. In addition, other kinds of bacteriophages that have antibacterial activity against *Vibrio anguillarum* may be further included in the composition of the present invention. These bacteriophages may be combined properly so as to maximize antibacterial effects, because their antibacterial activities against *Vibrio anguillarum* may be different from the aspects of antibacterial strength and spectrum.

Advantageous Effects

The method for preventing and treating *Vibrio anguillarum* infection using the composition including the bacteriophage Vib-ANP-1 as an active ingredient according to the present invention may have the advantage of very high specificity for *Vibrio anguillarum*, compared with the conventional methods based on chemical materials including conventional antibiotics. This means that the composition can be used for preventing or treating the *Vibrio anguillarum* infection without affecting other commensal bacteria that are useful and has fewer side effects according to the use thereof. In general, when chemical materials such as antibiotics are used, commensal bacteria are also damaged, thus weakening immunity in animals and entailing various side effects owing to the use thereof. Further, the composition of the present invention uses a bacteriophage isolated from nature as an active ingredient, and thus it is very environmentally friendly. Meanwhile, in the case of bacteriophages exhibiting antibacterial activity against the same species of bacteria, the antibacterial activities of the bacteriophages are different with regard to antibacterial strength and spectrum [the spectrum of the antibacterial activity of the bacteriophages applied to individual bacteria strains in terms of the strains of various bacteria belonging to *Vibrio anguillarum*. Typically, bacteriophages are usually effective only on some bacterial strains, even within the same species. That is to say, the antibacterial activity of bacteriophage may depend on the bacterial strain even for the same species of bacteria]. Accordingly, the present invention may provide antibacterial activity against *Vibrio anguillarum* different to that provided by other bacteriophages acting on *Vibrio anguillarum*. This provides significantly different applicability to industrial fields.

DESCRIPTION OF DRAWINGS

FIG. 1 is an electron micrograph showing the morphology of the bacteriophage Vib-ANP-1.

FIG. 2 is a photograph showing the results of an experiment on the ability of the bacteriophage Vib-ANP-1 to kill *Vibrio anguillarum*. Based on the center line of the plate culture medium, only the buffer containing no Bacteriophage Vib-ANP-1 is spotted on the left side thereof, and a solution containing Bacteriophage Vib-ANP-1 is spotted on the right side thereof. The clear zone observed in the right side is a plaque formed by lysis of the target bacteria due to the action of Bacteriophage Vib-ANP-1.

MODE FOR INVENTION

Hereinafter, the present invention will be described in more detail with reference to Examples. However, the Examples are merely examples of the present invention, and the scope of the present invention is not limited to the Examples.

Example 1

Isolation of Bacteriophage Capable of Killing *Vibrio anguillarum*

Samples were collected from nature to isolate the bacteriophage capable of killing *Vibrio anguillarum*. Meanwhile, the *Vibrio anguillarum* strains used for the bacteriophage isolation had been previously isolated and identified as *Vibrio anguillarum* by the present inventors.

The isolation procedure of the bacteriophage is described in detail hereinafter. The collected sample was added to an LB (Luria-Bertani) culture medium (tryptone, 10 g/L; yeast extract, 5 g/L; sodium chloride, 10 g/L) inoculated with *Vibrio anguillarum* at a ratio of 1/1,000, followed by shaking culture at 30° C. for 3 to 4 hours. Upon completion of the culture, centrifugation was performed at 8,000 rpm for 20 minutes and a supernatant was recovered. The recovered supernatant was inoculated with *Vibrio anguillarum* at a ratio of 1/1,000, followed by shaking culture at 30° C. for 3 to 4 hours. When the sample contained the bacteriophage, the above procedure was repeated a total of 5 times in order to sufficiently increase the number (titer) of the bacteriophages. After repeating the procedure 5 times, the culture solution was subjected to centrifugation at 8,000 rpm for 20 minutes. After the centrifugation, the recovered supernatant was filtered using a 0.45 µm filter. The obtained filtrate was used in a typical spot assay for examining whether or not a bacteriophage capable of killing *Vibrio anguillarum* was included therein.

The spot assay was performed as follows: LB culture medium was inoculated with *Vibrio anguillarum* at a ratio of 1/1,000, followed by shaking culture at 30° C. overnight. 3 ml ($OD_{600}$ of 1.5) of the culture solution of *Vibrio anguillarum* prepared above was spread on LA (Luria-Bertani Agar: tryptone, 10 g/L; yeast extract, 5 g/L; sodium chloride, 10 g/L; agar, 15 g/L) plate. The plate was left on a clean bench for about 30 minutes to dry the spread solution. After drying, 10 µl of the prepared filtrate was spotted onto the plate which *Vibrio anguillarum* was spread and then left for about 30 minutes to dry. After drying, the plate that was subjected to spotting was standing-cultured at 30° C. for one day, and then examined for the formation of a clear zone at the position at which the filtrate was dropped. In the case of the filtrate generating the clear zone, it is judged that the bacteriophage capable of killing *Vibrio anguillarum* is included therein. Through the above examination, the filtrate containing the bacteriophage having the ability to kill *Vibrio anguillarum* could be obtained.

The pure bacteriophage was isolated from the filtrate confirmed above to have the bacteriophage capable of killing *Vibrio anguillarum*. A conventional plaque assay was used for the isolation of the pure bacteriophage. In detail, a plaque formed in the course of the plaque assay was recovered using a sterilized tip, which was then added to the culture solution of *Vibrio anguillarum*, followed by culturing at 30° C. for 4 to 5 hours. After the culturing, centrifugation was performed at 8,000 rpm for 20 minutes to obtain a supernatant. The *Vibrio anguillarum* culture solution was added to the obtained supernatant at a volume ratio of 1/50, followed by culturing at 30° C. for 4 to 5 hours. In order to increase the number of bacteriophages, the above procedure was repeated at least 5 times. Then, centrifugation was performed at 8,000 rpm for 20 minutes to obtain the final supernatant. A plaque assay was further performed using the resulting supernatant. In general, the isolation of a pure bacteriophage is not completed through a single iteration of a procedure, so the above procedure was repeated using the resulting plaque formed above. After at least 5 repetitions of the procedure, the solution containing the pure bacteriophage was obtained. The procedure for the isolation of the pure bacteriophage was generally repeated until the generated plaques became similar to each other in size and morphology. In addition, the final isolation of the pure bacteriophage was confirmed using electron microscopy. Until the isolation of the pure bacteriophage was confirmed using the electron microscopy, the above procedure was repeated. The electron microscopy was performed according to a conventional method. Briefly, the solution containing the pure bacteriophage was loaded on a copper grid, followed by negative staining with 2% uranyl acetate and drying. The morphology thereof was then observed using a transmission electron microscope. The electron micrograph of the pure bacteriophage that was isolated is shown in FIG. 1. Based on the morphological characteristics, the novel bacteriophage above was confirmed to belong to the *Siphoviridae* bacteriophage.

The solution containing the pure bacteriophage confirmed above was subjected to the following purification process. The *Vibrio anguillarum* culture solution was added to the solution containing the pure bacteriophage at a volume ratio of 1/50 based on the total volume of the bacteriophage solution, followed by further culturing for 4 to 5 hours. After the culturing, centrifugation was performed at 8,000 rpm for 20 minutes to obtain a supernatant. This procedure was repeated a total of 5 times to obtain a solution containing sufficient numbers of the bacteriophage. The supernatant obtained from the final centrifugation was filtered using a 0.45 μm filter, followed by a conventional polyethylene glycol (PEG) precipitation process. Specifically, PEG and NaCl were added to 100 ml of the filtrate until reaching 10% PEG 8000/0.5 M NaCl, and then left at 4° C. for 2 to 3 hours. Thereafter, centrifugation was performed at 8,000 rpm for 30 minutes to obtain the bacteriophage precipitate. The resulting bacteriophage precipitate was suspended in 5 ml of a buffer (10 mM Tris-HCl, 10 mM $MgSO_4$, 0.1% Gelatin, pH 8.0). The resulting material was referred to as a bacteriophage suspension or bacteriophage solution.

As a result, the pure bacteriophage purified above was collected, was named the bacteriophage Vib-ANP-1, and was then deposited at Korean Collection for Type Cultures, Korea Research Institute of Bioscience and Biotechnology on Aug. 16, 2016 (Accession number: KCTC 13075BP).

Example 2

Separation and Sequence Analysis of Genome of Bacteriophage Vib-ANP-1

The genome of the bacteriophage Vib-ANP-1 was separated as follows. The genome was separated from the bacteriophage suspension obtained using the same method as in Example 1. First, in order to eliminate DNA and RNA of *Vibrio anguillarum* included in the suspension, 200 U of each of DNase I and RNase A was added to 10 ml of the bacteriophage suspension and then left at 37° C. for 30 minutes. After being left for 30 minutes, in order to inactivate the DNase I and RNase A activity, 500 μl of 0.5 M ethylenediaminetetraacetic acid (EDTA) was added thereto and then left for 10 minutes. In addition, the resulting mixture was further left at 65° C. for 10 minutes, and 100 μl of proteinase K (20 mg/ml) was then added thereto so as to break the outer wall of the bacteriophage, followed by reaction at 37° C. for 20 minutes. After that, 500 μl of 10% sodium dodecyl sulfate (SDS) was added thereto, followed by reaction at 65° C. for 1 hour. After the reaction for 1 hour, 10 ml of the solution of phenol:chloroform:isoamyl alcohol mixed at a component ratio of 25:24:1 was added to the reaction solution, followed by mixing well. In addition, the resulting mixture was subjected to centrifugation at 13,000 rpm for 15 minutes to separate layers. Among the separated layers, the upper layer was selected, and isopropyl alcohol was added thereto at a volume ratio of 1.5, followed by centrifugation at 13,000 rpm for 10 minutes to precipitate the genome. After collecting the precipitate, 70% ethanol was added to the precipitate, followed by centrifugation at 13,000 rpm for 10 minutes to wash the precipitate. The washed precipitate was recovered, vacuum-dried and then dissolved in 100 μl of water. This procedure was repeated to obtain a sufficient amount of the genome of the bacteriophage Vib-ANP-1.

Information on the sequence of the genome of the bacteriophage Vib-ANP-1 obtained above was secured by performing next-generation sequencing analysis using Illumina Mi-Seq equipment from Macrogen, Inc. The finally analyzed genome of the bacteriophage Vib-ANP-1 had a size of 213,970 bp and the sequence of the whole genome was expressed by SEQ. ID. NO: 1.

The homology (similarity) of the bacteriophage Vib-ANP-1 genomic sequence obtained above with previously reported bacteriophage genomic sequences was investigated using BLAST on the web. As a result of the BLAST investigation, bacteriophage sequences with homology of 50% or more were not confirmed.

Based upon this result, it is concluded that the bacteriophage Vib-ANP-1 must be a novel bacteriophage that has not been reported previously. Further, since the antibacterial strength and spectrum of bacteriophages typically depend on the type of bacteriophage, it is considered that the bacteriophage Vib-ANP-1 can provide antibacterial activity different from that of any other bacteriophages reported previously.

Example 3

Investigation of Ability of Bacteriophage Vib-ANP-1 to Kill *Vibrio anguillarum*

The ability of the isolated bacteriophage Vib-ANP-1 to kill *Vibrio anguillarum* was investigated. In order to investigate the killing ability, the formation of clear zones was observed using the spot assay in the same manner as described in Example 1. A total of 17 strains which had been isolated and identified as *Vibrio anguillarum* by the present inventors were used as *Vibrio anguillarum* for the investigation of killing ability. The bacteriophage Vib-ANP-1 had the ability to kill a total of 16 strains among 17 strains of *Vibrio anguillarum* as the experimental target. The representative experimental result is shown in FIG. 2. Meanwhile, the ability of the bacteriophage Vib-ANP-1 to kill *Edwardsiella tarda, Vibrio parahaemolyticus, Lactococcus garvieae, Streptococcus parauberis, Streptococcus iniae,* and *Aeromonas salmonicida* was also investigated in a separate experiment. As a result, the bacteriophage Vib-ANP-1 did not have the ability to kill these microorganisms.

Therefore, it is confirmed that the bacteriophage Vib-ANP-1 has the specific ability to kill *Vibrio anguillarum* and a broad antibacterial spectrum against *Vibrio anguillarum*, suggesting that the bacteriophage Vib-ANP-1 can be used as an active ingredient of the composition for preventing and treating *Vibrio anguillarum* infection.

Example 4

Experimental Example Regarding Prevention of *Vibrio anguillarum* Infection Using Bacteriophage Vib-ANP-1

100 μl of a bacteriophage Vib-ANP-1 solution at a level of $1\times10^8$ pfu/ml was added to a tube containing 9 ml of an LB culture medium. To another tube containing 9 ml of an LB culture medium, only the same amount of LB culture medium was further added. A *Vibrio anguillarum* culture solution was then added to each tube so that absorbance reached about 0.5 at 600 nm. After *Vibrio anguillarum* was added, the tubes were transferred to an incubator at 30° C., followed by shaking culture, during which the growth of *Vibrio anguillarum* was observed. As presented in Table 1, it was observed that the growth of *Vibrio anguillarum* was inhibited in the tube to which the bacteriophage Vib-ANP-1 solution was added, while the growth of *Vibrio anguillarum* was not inhibited in the tube to which the bacteriophage solution was not added.

TABLE 1

Growth inhibition of *Vibrio anguillarum*

| | $OD_{600}$ absorbance value | | |
|---|---|---|---|
| Classification | 0 minutes after culture | 60 minutes after culture | 120 minutes after culture |
| Bacteriophage solution is not added | 0.504 | 0.987 | 1.342 |
| Bacteriophage solution is added | 0.504 | 0.324 | 0.238 |

The above results indicate that the bacteriophage Vib-ANP-1 of the present invention not only inhibits the growth of *Vibrio anguillarum* but also has the ability to kill *Vibrio anguillarum*. Therefore, it is concluded that the bacteriophage Vib-ANP-1 can be used as an active ingredient of the composition for preventing a *Vibrio anguillarum* infection.

Example 5

Animal Experiment on Prevention of *Vibrio anguillarum* Infection Using Bacteriophage Vib-ANP-1

The preventive effect of the bacteriophage Vib-ANP-1 on olive flounder subjected to *Vibrio anguillarum* infection was investigated. A total of 2 groups of fifty juvenile olive flounder per group (body weight: 5 to 7 g and body length: 8 to 10 cm) was prepared and farmed separately in water tanks, and an experiment was performed for 14 days. The environment surrounding the water tanks was controlled, and the temperature in the laboratory where the water tanks were located was maintained constant. Over the whole experimental period from the $1^{st}$ day of the experiment, olive flounder in an experimental group (the group to which the bacteriophage was administered) was fed with a feed containing the bacteriophage Vib-ANP-1 at $1\times10^8$ pfu/g according to a conventional feeding method. In contrast, olive flounder in a control group (the group to which the bacteriophage was not administered) was fed with the same feed as in the experimental group except that the bacteriophage Vib-ANP-1 was not contained according to the same method as in the experimental group. From the seventh day after the experiment started, the feed to be provided was contaminated with *Vibrio anguillarum* at a level of $1\times10^8$ cfu/g for two days and thereafter provided respectively twice a day so as to induce a *Vibrio anguillarum* infection. From the ninth day after the experiment started (the second day after the *Vibrio anguillarum* infection was induced), vibriosis pathogenesis was examined in all test animals on a daily basis. The vibriosis pathogenesis was examined by measuring a body darkening index. The measurement of the body darkening index was performed using a conventional method for measuring a dark coloration (DC) score (0: normal, 1: slight darkening, 2: strong darkening). The results are shown in Table 2.

TABLE 2

Result of measurement of body darkening index (mean)

| | DC score (mean) | | | | | |
|---|---|---|---|---|---|---|
| Days | D9 | D10 | D11 | D12 | D13 | D14 |
| Control group (bacteriophage is not administered) | 0.76 | 0.80 | 0.80 | 0.96 | 1.12 | 1.20 |
| Experimental group (bacteriophage is administered) | 0.24 | 0.08 | 0.04 | 0 | 0 | 0 |

From the above results, it is confirmed that the bacteriophage Vib-ANP-1 of the present invention could be very effective in inhibiting *Vibrio anguillarum* infection.

Example 6

Example of Treatment of Infectious Diseases of *Vibrio anguillarum* Using Bacteriophage Vib-ANP-1

The treatment effect of the bacteriophage Vib-ANP-1 on olive flounder suffering from vibriosis caused by *Vibrio anguillarum* was investigated. A total of 2 groups of sixty juvenile olive flounder per group (body weight: 5 to 7 g and body length: 8 to 10 cm) was prepared and farmed separately in water tanks, and an experiment was performed for 14 days. The environment surrounding the water tanks was controlled, and the temperature in the laboratory where the water tanks were located was maintained constant. From the fifth day after the experiment started, the feed contaminated with *Vibrio anguillarum* at a level of $1\times10^8$ cfu/g was provided twice a day for three days according to a conventional feeding method. olive flounder subjects showing clinical symptoms of vibriosis were observed in both water tanks from the last day of the procedure in which the feed contaminated with *Vibrio anguillarum* was provided. From the next day after the feed contaminated with *Vibrio anguillarum* was provided for three days (the eighth day after the experiment started), olive flounder in an experimental group (the group to which the bacteriophage was administered) was fed with a feed containing the bacteriophage Vib-ANP-1 ($1\times10^8$ pfu/g) according to a conventional feeding method. In contrast, olive flounder in a control group (the group to which the bacteriophage was not administered) was fed with the same feed as in the experimental group except that the bacteriophage Vib-ANP-1 was not contained according to the same method as in the experimental group.

From the third day after the forced infection of *Vibrio anguillarum* (the eighth day after the experiment started), vibriosis pathogenesis was examined in all test animals on a daily basis. The vibriosis pathogenesis caused by *Vibrio anguillarum* was examined by measuring a body darkening index as in Example 5. The results are shown in Table 3.

TABLE 3

Result of measurement of body darkening index (mean)

| | DC score (mean) | | | | | | |
|---|---|---|---|---|---|---|---|
| Days | D8 | D9 | D10 | D11 | D12 | D13 | D14 |
| Control group (bacteriophage is not administered) | 0.87 | 0.97 | 1.00 | 1.13 | 1.20 | 1.23 | 1.33 |
| Experimental group (bacteriophage is administered) | 0.90 | 0.80 | 0.77 | 0.70 | 0.43 | 0.20 | 0.13 |

From the above results, it is confirmed that the bacteriophage Vib-ANP-1 of the present invention could be very effective in the treatment of infectious diseases caused by *Vibrio anguillarum*.

Example 7

Preparation of Feed Additives and Feeds

Feed additives were prepared using a bacteriophage Vib-ANP-1 solution so that a bacteriophage Vib-ANP-1 was contained in an amount of $1 \times 10^8$ pfu per 1 g of the feed additives. The method of preparing the feed additives was as follows: Maltodextrin (50%, w/v) was added to the bacteriophage solution and the resulting mixture was then freeze-dried. Finally, the dried mixture was ground into fine powders. In the above-described preparation procedure, the drying procedure can be replaced with drying under a reduced pressure, drying with heat, or drying at room temperature. In order to prepare the control for comparison, the feed additive that did not contain the bacteriophage but contained a buffer (10 mM Tris-HCl, 10 mM $MgSO_4$, 0.1% Gelatin, pH 8.0) used to prepare the bacteriophage solution was prepared.

The two kinds of feed additives that were prepared above were each mixed with a raw fish-based moist pellet at a weight ratio of 250, thus preparing two kinds of final feeds.

Example 8

Preparation of Medicine Bath Agent

The method of preparing a medicine bath agent was as follows: The medicine bath agent was prepared using a bacteriophage Vib-ANP-1 solution so that a bacteriophage Vib-ANP-1 was contained in an amount of $1 \times 10^8$ pfu per 1 ml of the medicine bath agent. In the method of preparing the medicine bath agent, the bacteriophage Vib-ANP-1 solution was added so that the bacteriophage Vib-ANP-1 was contained in an amount of $1 \times 10^8$ pfu per 1 ml of a buffer used to prepare the bacteriophage solution, and mixing was sufficiently performed. In order to prepare the control for comparison, the buffer used to prepare the bacteriophage solution was used as the medicine bath agent that did not contain the bacteriophage.

The two prepared kinds of medicine bath agents were diluted with water at a volume ratio of 1,000, resulting in the final medicine bath agent.

Example 9

Confirmation of Feeding Effect on Olive Flounder Farming

Improvement in the feeding result upon olive flounder farming was investigated using the feed and the medicine bath agents prepared in Examples 7 and 8. In particular, the investigation was focused on mortality. A total of 1,000 juvenile olive flounder was divided into two groups, each including 500 olive flounder (group A; fed with the feed and group B; treated with the medicine bath agent), and an experiment was performed for four weeks. Each group was divided into sub-groups each including 250 olive flounder, and the sub-groups were classified into a sub-group to which the bacteriophage Vib-ANP-1 was applied (sub-group-①) and a sub-group to which the bacteriophage was not applied (sub-group-②). In the present experiment, the target olive flounder was the juvenile (body weight: 5 to 7 g and body length: 8 to 10 cm), and the juvenile olive flounder of the experimental sub-groups were farmed in separate water tanks placed apart from each other at a certain space interval. The sub-groups were classified and named as shown in Table 4.

TABLE 4

Sub-group classification and expression in olive flounder feeding experiment

| | Sub-group classification and expression | |
|---|---|---|
| Application | Bacteriophage Vib-ANP-1 is applied | Bacteriophage is not applied |
| Group fed with feed | A-① | A-② |
| Group treated with medicine bath agent | B-① | B-② |

In the case of provision of the feeds, the feeds prepared in Example 7 were provided according to a conventional feeding method as classified in Table 4. The treatment using the medicine bath agent was performed according to a conventional treatment method using a medicine bath agent as classified in Table 4 using the medicine bath agent prepared as described in Example 8. The results are shown in Table 5.

TABLE 5

Mortality of olive flounder in feeding experiment

| Group | Dead olive flounder/total olive flounder of experiment (No.) | Mortality (%) |
|---|---|---|
| A-① | 8/250 | 3.2 |
| A-② | 43/250 | 17.2 |
| B-① | 10/250 | 4.0 |
| B-② | 55/250 | 22.0 |

The above results indicate that the provision of the feed prepared according to the present invention and the treatment using the medicine bath agent prepared according to the present invention were effective in improving the feeding result in the farming of olive flounder. Therefore, it is concluded that the composition of the present invention could be efficiently applied to improving the results of animal feeding.

While the present invention has been particularly shown and described with reference to exemplary embodiments thereof, those skilled in the art will appreciate that the specific description is only a preferred embodiment, and that the scope of the present invention is not limited thereto. It is therefore intended that the scope of the present invention be defined by the claims appended hereto and their equivalents.

Name of Depositary Authority: Korea Research Institute of Bioscience and Biotechnology
Accession number: KCTC 13075BP
Accession date: 20160816

The invention claimed is:

1. A feed additive composition comprising maltodextrin and $1\times10^4$ pfu/ml to $1\times10^{15}$ pfu/ml or $1\times10^4$ pfu/g to $1\times10^{15}$ pfu/g of *Siphoviridae* bacteriophage Vib-ANP-1 that has a specific antibacterial activity against *Vibrio anguillarum* and a 213.97 kb size of genome expressed by a nucleotide sequence of SEQ ID NO:1, and is deposited as accession number of KCTC 13075BP.

2. The feed additive composition of claim 1, wherein the composition suppresses diseases caused by *Vibrio anguillarum*, or alleviates the pathological condition of the diseases caused by *Vibrio anguillarum*.

3. A method for suppressing diseases caused by *Vibrio anguillarum*, or alleviating the pathological condition of the diseases caused by *Vibrio anguillarum*, wherein the method comprises a step of administering to an animal other than a human a composition comprising maltodextrin and $1\times10^4$ pfu/ml to $1\times10^{15}$ pfu/ml or $1\times10^4$ pfu/g to $1\times10^{15}$ pfu/g of *Siphoviridae* bacteriophage Vib-ANP-1 (Accession number: KCTC 13075BP), that has a specific antibacterial activity against *Vibrio anguillarum* and a 213.97 kb size of genome encoded by the nucleotide sequence of SEQ ID NO:1.

* * * * *